US008937068B2

(12) United States Patent
Seipelt et al.

(10) Patent No.: US 8,937,068 B2
(45) Date of Patent: Jan. 20, 2015

(54) PYRIDOPYRAZINE DERIVATIVES AND THEIR USE

(75) Inventors: Irene Seipelt, Offenbach (DE); Eckhard Claus, Frankfurt (DE); Eckhard Guenther, Maintal (DE); Tilmann Schuster, Grossostheim (DE); Michael Czech, Frankfurt (DE); Emmanuel Polymeropoulos, Frankfurt (DE)

(73) Assignee: Zentaris GmbH, Frankfurt (DE)

( * ) Notice: Subject to any disclaimer, the term of this patent is extended or adjusted under 35 U.S.C. 154(b) by 693 days.

(21) Appl. No.: 11/558,493

(22) Filed: Nov. 10, 2006

(65) Prior Publication Data

US 2007/0123494 A1 May 31, 2007

Related U.S. Application Data

(60) Provisional application No. 60/735,707, filed on Nov. 11, 2005.

(51) Int. Cl.
| A61K 31/4985 | (2006.01) |
| C07D 471/04 | (2006.01) |
| C07D 519/00 | (2006.01) |
| A61K 45/06 | (2006.01) |

(52) U.S. Cl.
CPC ............... A61K 45/06 (2013.01); C07D 471/04 (2013.01); A61K 31/4985 (2013.01)
USPC .......................................... 514/249; 544/350

(58) Field of Classification Search
CPC ............................ C07D 471/04; C07D 519/00
USPC ............................................................ 544/350
See application file for complete search history.

(56) References Cited

U.S. PATENT DOCUMENTS

| 3,180,868 | A | 4/1965 | Osdene et al. |
| 3,209,004 | A | 9/1965 | Santilli et al. |
| 4,082,845 | A | 4/1978 | Saari et al. |
| 5,480,883 | A | 1/1996 | Spada et al. |
| 2004/0092521 | A1 | 5/2004 | Altenbach et al. |
| 2004/0102360 | A1 | 5/2004 | Barnett et al. |
| 2004/0266777 | A1 | 12/2004 | Claus et al. |
| 2005/0032803 | A1 | 2/2005 | Claus et al. |
| 2005/0165028 | A1 | 7/2005 | Norman et al. |
| 2005/0256118 | A1 | 11/2005 | Altenbach et al. |
| 2005/0256309 | A1 | 11/2005 | Altenbach et al. |
| 2005/0272728 | A1 | 12/2005 | Altenbach et al. |
| 2005/0272736 | A1 | 12/2005 | Altenbach et al. |

FOREIGN PATENT DOCUMENTS

| EP | 0 735 025 B1 | 7/1998 |
| EP | 1 661 889 A1 | 5/2006 |
| GB | 1184848 | 3/1970 |
| JP | 50-53394 | 5/1975 |
| JP | 2006-137723 | 6/2006 |
| WO | WO 95/15758 | 6/1995 |
| WO | WO 99/17759 | 4/1999 |
| WO | WO 99/32111 | 7/1999 |
| WO | WO 99/43681 | 9/1999 |
| WO | WO 00/12497 | 3/2000 |
| WO | WO 00/35435 A1 | 6/2000 |
| WO | WO 00/37141 A1 | 6/2000 |
| WO | WO 01/81346 A2 | 11/2001 |
| WO | WO 02/06213 A2 | 1/2002 |
| WO | WO 02/055079 A2 | 7/2002 |
| WO | WO 02/090355 A1 | 11/2002 |
| WO | WO 03/024448 A2 | 3/2003 |
| WO | WO 03/064421 A1 | 8/2003 |
| WO | WO 03/064431 A2 | 8/2003 |
| WO | WO 03/068223 A1 | 8/2003 |
| WO | WO 03/084473 A2 | 10/2003 |
| WO | WO 03/086394 A1 | 10/2003 |
| WO | WO 03/086403 A1 | 10/2003 |
| WO | WO 2004/005472 A1 | 1/2004 |
| WO | WO 2004/017950 A2 | 3/2004 |
| WO | WO 2004/030635 A2 | 4/2004 |
| WO | WO 2004/055003 A1 | 7/2004 |
| WO | WO 2004/104002 A1 | 12/2004 |
| WO | WO 2004/104003 A1 | 12/2004 |
| WO | WO 2004/108702 A1 | 12/2004 |
| WO | WO 2005/007099 A2 | 1/2005 |
| WO | WO 2005/021513 A1 | 3/2005 |

(Continued)

OTHER PUBLICATIONS

Yap et al. "Targeting the PI3K-AKT-mTOR pathway:progress, pitfalls, and promises." 2008, Current Opinion in Pharmacology, 8, 393-412.*
Romina Marone et al.; "Targeting phosphoinositide 3-kinase—Moving towards therapy"; Biochimica et Biophysica Acta 1784 (2008), pp. 159-185.
Reinhard Wetzker et al.; "Phosphoinositide 3-Kinases as Targets for Therapeutic Intervention"; Curre/It Pharmaceutical Design, 2004,10, pp. 1915-1922.
Thomas Rückle et al.; "PI3γ inhibition: towards an 'aspirin of the 21st century'?"; Nature Reviews, Drug Discovery vol. 5, Nov. 2006 pp. 903-918.
Jeffrey A. Engelman et al.; "The evolution of phosphatidylinositol 3-kinases as regulators of growth and metabolism"; Nature Reviews, Genetics, vol. 7, Aug. 2006, pp. 606-619.
U.S. Appl. No. 13/770,470, filed Feb. 19, 2013, Claus, et al.
U.S. Appl. No. 13/542,101, filed Jul. 5, 2012, Gerlach, et al.
U.S. Appl. No. 13/523,968, filed Jun. 15, 2012, Claus, et al.
Brader, et al., Tumori 90:2-8 (2004), Phosphoinositide 3-Kinase Signalling Pathways in Tumor Progression, Invasion and Angiogenesis.
Engleman, et al., Nature 7:606 (2006), The Evolution of Phosphatidylinositol 3-Kinases As Regulators of Growth and Matabolism.
Franke, et al., Oncogene 22:8983-8998 (2003), PI3K/AKT and Apoptosis: Size Matters.

(Continued)

Primary Examiner — Brian McDowell
(74) Attorney, Agent, or Firm — Oblon, Spivak, McClelland, Maier & Neustadt, L.L.P.

(57) ABSTRACT

Pyridopyrazine compounds which are suitable for the treatment or prevention of physiological and/or pathophysiological states mediated and/or modulated by signal transduction pathways and/or enzymes in mammals and in particular in humans. A compound according to the general formula (I)

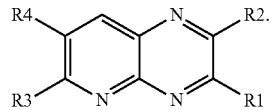

22 Claims, No Drawings

(56) References Cited

FOREIGN PATENT DOCUMENTS

| | | |
|---|---|---|
| WO | WO 2005/023771 A1 | 3/2005 |
| WO | WO 2005/023807 A2 | 3/2005 |
| WO | WO 2005/056547 A2 | 6/2005 |
| WO | WO 2005/061519 A1 | 7/2005 |
| WO | WO 2005/103029 A1 | 11/2005 |
| WO | WO 2005/123698 A1 | 12/2005 |
| WO | WO 2005/123733 A1 | 12/2005 |
| WO | WO 2006/002047 A2 | 1/2006 |
| WO | WO 2006/012396 A1 | 2/2006 |
| WO | WO 2006/014580 A1 | 2/2006 |
| WO | WO 2006/017326 A1 | 2/2006 |
| WO | WO 2006/017468 A2 | 2/2006 |
| WO | WO 2006/020561 A2 | 2/2006 |
| WO | WO 2006/021448 A1 | 3/2006 |
| WO | WO 2006/024666 A1 | 3/2006 |
| WO | WO 2006/059103 A2 | 6/2006 |
| WO | WO 2006/074147 A2 | 7/2006 |
| WO | WO 2006/081178 A2 | 8/2006 |
| WO | WO 2006/081179 A1 | 8/2006 |
| WO | WO 2006/081182 A2 | 8/2006 |
| WO | WO 2006/081264 A1 | 8/2006 |
| WO | WO 2006/091395 A2 | 8/2006 |
| WO | WO 2006/128129 A2 | 11/2006 |
| WO | WO 2006/128172 A2 | 11/2006 |
| WO | WO 2007/023186 A1 | 3/2007 |
| WO | WO 2007/044729 A2 | 4/2007 |
| WO | WO 2007/054556 A1 | 5/2007 |

OTHER PUBLICATIONS

Vivanco, et al., Nature Reviews Cancer 2:489-501 (2002), The Phosphatidylinositol 3-Kinase-AKT Pathway in Human Cancer.
Dario R. Alessi, et al. "Mechanism of Activation of Protein Kinase B by Insulin and IGF-1", The EMBO Journal, vol. 15, No. 23, 1996, pp. 6541-6551.
Khaled All, et al. "Essential Role for the p110β Phosphoinositide 3-Kinase in the Allergic Response", Letters to Nature, vol. 43, Oct. 21, 2004, pp. 1007-1011.
C.M. Atkinson, et al. "Cinnolines and Other Heterocyclic Types in Relation to the Chemotherapy of Trypanosomiasis. Part XI. Some Reactions of Simple Quinoxaline Derivatives", 1955.
Brydon L. Bennett, et al. "SP600125, An Anthrapyrazolone Inhibitor of Jun N-Terminal Kinase", PNAS, vol. 98, No. 24, Nov. 20, 2001, pp. 13681-13686.
Andrey Bondev, et al. "Differential Regulation of Lipid and Protein Kinase Activities of Phosphoinositide 3-Kinase γ In Vitro", Biological Chemistry, vol. 380, Nov. 1999, pp. 1337-1340.
Tzvetanka Bondeva, et al. "Bifurcation of Lipid and Protein Kinase Signals of PI3K γ to the Protein Kinases PKB and MAPK", Science, vol. 282, Oct. 9, 1998, pp. 293-296.
Richard J. Brown, et al. "Synthesis and Properties of Axially-Chiral N-(2,6-Disubstituted) phenyl Triazolones", Tetrahedron, vol. 60, 2004, pp. 4361-4375.
Ian G. Campbell, et al. "Mutation of the PIK3CA Gene in Ovarian and Breast Cancer", Cancer Research, vol. 64, Nov. 1, 2004, pp. 7678-7681.
Arlindo L. Castelhano, et al. "Glucokinase-Activating Ureas", Bioorganic & Medicinal Shemistry Letters, vol. 15, 2005, pp. 1501-1504.
Daniela Catarzi, et al. "Tricyclic Heteroaromatic Systems. Synthesis and $A_1$ and $A_{2a}$ Adenosine Binding Activities of Some 1-Aryl-1, 4-Dihydro-3-Methyl[1]Benzopyrano[2,3-c]Pyrazol-4-Ones, 1-Aryl-4,9-Dihydro-3Methyl-1H-Pyrazolo[3,4-b]Quinolin-4-Ones, and 1-Aryl-1H-IMIDAZO[4,5-b]Quinoxalines", Journal of Medicinal Chemistry, vol. 38, 1995, pp. 1330-1336.
Gary G. Chiang, et al. "Determination of the Catalytic Activities of Mtor and Other Members of the Phosphoinositide-3-Kinase-Related Kinase Family", Methods in Molecular Biology, vol. 281, pp. 125-141.
Michael A. Crackower, et al. "Regulation of Myocadial Contractility and Cell Size by Distinct PI3K-PTEN Signaling Pathways", Cell, vol. 110, Sep. 20, 2002, pp. 737-749.

Mircea Darabantu, et al. "Synthesis of New Polyaza Heterocycles. Part 42: Diazines", Tetrahedraon, vol. 61, 2005, pp. 2897-2905.
Stephen P. Davies, et al. "Specificity and Mechanism of Action of Some Commonly Used Protein Kinase Inhibitors", Biochem. J., vol. 351, 2000, pp. 95-105.
Helen Davies, et al. "Mutations of the Braf Gene in Human Cancer", Letters to Nature, Jun. 9, 2002, pp. 1-6.
Ritu Dhand, et al. "PI 3-Kinase Is a Dual Specificity Enzyme: Autoregulation by an Intrinsic Protein-Serine Kinase Activity", The EMBO Journal, vol. 13, No. 3, 1994, pp. 522-533.
M.S.A. El-Gaby, et al. "Some Nucleophilic Reactions With 6-Benzoyl-2,3-Dichloroquinoxaline: Synthesis of Tetrazolo[1,5-a]Quinoxaline, 2-Methylidene-1, 3-Dithiolo[4,5-b] Quinoxalines, Quinoxalino[2,3-b] Quinoxlines and Pyrazolo[1',5':1,2] Imidazolo[4,5-b]-Quinoxalines", Indian Journal of Chemistry, vol. 40B, Mar. 2001, pp. 195-200.
Robert D. Elliott, et al. "The Isomeric Pyridopyrazines From the Reaction of Some Tetraaminopyridines With Pyruvaldehyde and Benzil", The Journal of Organic Chemistry, vol. 33, No. 6, 1968, pp. 2393-2397.
Ola A. El-Sayed, et al. "Synthesis of Some Novel Quinoline-3-Carboxylic Acids and Pyrimidoquinoline Derivatives As Potential Antimicrobial Agents", Arch. Pharm. Pharm. Med. Chem., vol. 9, 2002, pp. 403-410.
Emma Ford, et al. "Regioselective Substitution of 2,3-Dichloro-6-Amino-Quinoxaline", Tetrahedron Letters, vol. 41, 2000, pp. 3197-3198.
H. Friess, et al. "Pancreatic Cancer: The Potential Clinical Relevance of Alterations in Growth Factors and Their Receptors", Journal of Molecular Medicine, vol. 74, 1996, pp. 35-42.
Rudolph Gotz, et al. "Essential Role of Bag-1 in Differentiation and Survival of Hematopoietic and Neuronal Cells", Nat. Neuroscience, vol. 8, No. 9, Sep. 2005, pp. 1169-1178.
Ariamala Gopalsamy, et al. "Pyrazolo[1,5-a] Pyrimidin-7-YL Phenyl Amides As Novel Anti-Proliferative Agents: Parallel Synthesis for Lead Optimization of Amide Region", Bioorganic &Medicinal Chemistry Letters, vol. 15, 2005, pp. 1591-1594.
S. Goswami, et al. "Simple and Effiecient Synthesis of 2,7-Difunctionalized-1,8-Naphthyridines", Molecules, vol. 10, 2005, pp. 929-936.
Rebecca J. Gum, et al. "Acquisition of Sensitivity of Stress-Activated Protein Kinases to the p38 Inhibitor, SB 203580, by Alteration of One or More Amino Acids Within the ATP Binding Pocket", The Journal of Biological Chemistry, vol. 273, No. 25, Jun. 19, 1998, pp. 15605-15610.
Wei He, et al. "Potent Quinoxaline-Based Inhibitors of PDGF Receptor Tyrosine Kinase Activity. Part 2: The Synthesis and Biological Activities of RPR127963 an Orally Bioavailable Inhibitor", Bioorganic and Medicinal Chemistry Letters, vol. 13, 2003, pp. 3097-3100.
Xungui He, et al. "Synthesis and Biological Evaluation of Bis and Monocarbonate Prodrugs of 10- Hydroxycamptothecins", Bioorganic and Medicinal Chemistry, vol. 12, 2004, pp. 4003-4008.
Gottfried Heinisch, et at. "Synthesis of N-Aryl-N'-Heteroaryl-Substituted Urea and Thiourea Derivatives and Evaluation of Their Anticonvulsant Activity", Arch. Pharm. Pharm. Med. Chem., vol. 330, 1997, pp. 207-210.
Corey R. Hopkins, et al. "An Improved Method for the Synthesis of 6-Substituted-5H-Pyrrolo[2,3-b] Pyrazines Via Palladium-Catalyzed Heteroannulation Using Microwave Heating", Tetrahedron Letters, vol. 45, 2004, pp. 8631-8633.
Rika Hoshino, et al. "Constitutive Activation of the 41-/43-kDa Mitogen-Activated Protein Kinase Signaling Pathway in Human Tumors", Oncogene, vol. 18, 1999, pp. 813-822.
Eugen Muller, et al. "Methoden Der Organischen Chemie (Houben-Weyl)", 1981, pp. 1-11.
S. Gobec, et al. "Houben-Weyl Methods of Molecular Transformation", Science of Synthesis, vol. 16, 1981, pp. 1-25.
M. Bohle, et al. "Hetarenes IV. Six Member and Larger Heteroringswith Maximum Unsaturation", Methods of Organic Chemistry(Houben-Weyl), vol. E9, Dec. 18, 1997, pp. 1-8.
"Methoden Der Organischen Chemie (Houben-Weyl)", Dec. 3, 1992, pp. 1-4.

(56) References Cited

OTHER PUBLICATIONS

John W. Huffman, et al. "Enantioselective Synthesis of 1-Methoxy- and 1-Deoxy-2'-Methyl-$\Delta^8$-Tetrahydrocannabinols: New Selective Ligands for the CB$_2$ Receptor", Bioorganic & Medicinal Chemistry, vol. 14, 2006, pp. 247-262.

Gregory Hughes, et al. "Ethynyl Π-Extended 2,5-Diphenyl-1,3,4-Oxadiazoles and 2-Phenyl 5-(2-Thienyl)-1,3,4-Oxadiazoles: Synthesis, X-Ray Crystal Structures and Optical Properties", Org. Biomol. Chem., vol. 2, 2004, pp. 3363-3367.

Alessio Innocenti, et al. "Carbonic Anhydrase Inhibitors: The First On-Resin Screening of a 4- Sulfamoylphenylthiourea Library", Journal of Medicinal Chemistry, vol. 47, 2004, pp. 5224-5229.

Roy Katso, et al. "Cellular Function of Phosphoinositide 3-Kinases: Implications for Development, Immunity, Homeostasis, and Cancer", Annu. Rev. Cell Dev. Biol., vol. 17, 2001, pp. 615-675.

Samir N. Khleif, et al. "A Phase I Vaccine Trial With Peptides Reflecting RAS Oncogene Mutations of Solid Tumors", Journal of Immunotherapy, vol. 22, No. 2, 1999, pp. 155-165.

C.L. Leese, et al. "Polyazanaphthalenes. Part I. Some Derivatives of 1:4:5-Triazanaphthalene and Quinoxaline", Japanese Chem. Society,1955, pp. 303-309.

Douglas A. Levin, et al. "Frequent Mutation of the PIK3CA Gene in Ovarian and Breast Cancer", Clinical Cancer Research, vol. 11, No. 8, Apr. 15, 2005, pp. 2875-2878.

Timothy S. Lewis, et al. "Signal Transduction Through Map Kinase Cascades", 1998.

Jing Li, et al. "PTEN, A Putative Protein Tyrosine Phosphatase Gene Mutated in Human Brain, Breast, and Prostate Cancer", Science, vol. 275, Mar. 28, 1997.

Tony Liu, et al. "Mechanistic Studies of $LA^{3+}$-and $ZN^{2+}$-Catalyzed Methanolysis of Aryl Phosphate and Phosphorothioate Triesters. Development of Artificial Phosphotriesterase Systems", OBC, vol. 3, 2005, pp. 1525-1533.

Yiling Lu, et al. "Targeting PI3K-AKT Pathway for Cancer Therapy", Rev. Exp. Clin. Hematol. vol. 7.2, Jun. 2003, pp. 205-228.

Ying Lu, et al. "Design, Synthesis, and Evaluation of 2-Alkoxydihyrocinnamates As PPAR Agonists", Bioorganic & Medicinal Chemistry Letters, vol. 16, 2006, pp. 915-919.

Yen-Ying Ma, et al. PIK3CA as an Oncogene in Cervical Cancer, Oncogene, vol. 19, 2000, pp. 2739-2744.

Lisheng Mao, et al. "Facile Synthesis of 2,3-Distributed Quinoxalines by Suzuki-Miyaura Coupling", Synthesis, No. 15, 2004, pp. 2535-2539.

Chris Marshall, "How Do Small GTPASE Signal Transduction Pathways Regulate Cell Cycle Entry", Current Opinion in Cell Biology, vol. 11, 1999, pp. 732-736.

Kenji Matsuno, et al. "Potent and Selective Inhibitors of PDGF Receptor Phosphorylation. 2. Synthesis, Structure Activity Relationship, Improvement of Aqueous Solubility, and Biological Effects of 4-[4-(Substituted (Thio) Carbamoyl)-1-Piperazinyl]-6,7-Dimethoxyquinazoline Derivatives", Journal of Medicinal Chemistry, vol. 45, No. 2002, pp. 4513-4523.

F. McPhillips, et al. "Association of C-RAF Expression With Survival and Its Targeting With Antisense Oligonucleotides in Ovarian Cancer", British Journal of Cancer, vol. 85, No. 11, 2001, pp. 1753-1758.

W. Mederski, et al. "A General Synthesis of 1-Aryl Carbamoyl-2-Alkyl-4-Aryl Substituted Semicarbazides As Nonbasic Factor Xa Inhibitors", Bioorganic and Medicinal Chemistry Letters, vol. 13 ,2003, pp. 3715-3718.

John Mendelsohn, et al. "The EGF Receptor Family as Targets for Cancer Therapy", Oncogene, vol. 19, 2000, pp. 6550-6565.

Jaromir Mindl, et al. "Kinetics and Mechanism of Hyrolysis of Aryl N-Methoxycarbamates and Their Derivatives", Collection Czechoslovak Chem. Commun. vol. 48, 1983, pp. 900-905.

Juan F. Miravet, et al. "Reactive Organogels: Self-Assembled Support for Functional Materials", Organic Letters, vol. 7, No. 22, 2005, pp. 4791-4794.

Gary A. Molander, et al. "Suzuki-Miyaura Cross-Coupling Reactions of Potassium Alkenyltrifluorocarborates", Journal of Organic Chemistry, vol. 67, No. 24, 2002, pp. 8424-8429.

Sarah M. Moore, et al. "The Presence of a Constitutively Active Phosphoinositide 3-Kinase in Small Cell Lung Cancer Cells Mediates Anchorage-Independent Proliferation Via a Protein Kinase B and $p70^{s6k}$—Dependent Pathway[1]", Cancer Research, vol. 58, Nov. 15, 1998, pp. 5239-5247.

Michael R. Myers, et al. "Potent Quinoxaline-Based Inhibitors of PDGF Receptor Tyrosine Kinase Activity. Part 1: SAR Exploration and Effective Bioisosteric Replacement of a Phenyl Substituent", Bioorganic and Medicinal Chemistry Letters, vol. 13, 2003, pp. 3091-3095.

A. Nagel, et al. "Nuclear and Magnetic Resonance Data of Pyrido [2,3-b] Pyrazines and Their σ- Adducts With Amide Ion and Water", Journal of Heterocyclic Chemistry, vol. 16, 1979, pp. 301-304.

Charles O. Okafor, et al. "Synthesis of Analogues of the 2,3,6,-Triazaphenothiazine Ring System", Journal of Heterocyclic Chemistry, vol. 20, 1983, pp. 199-203.

Klaus Okkenhaug, et al. "PI3K in Lymphocyte Development, Differentiation and Activation", Immunology, vol. 3, Apr. 2003, pp. 317-330.

T.S. Osdene, et al. The Synthesis of Compounds With Potential Anti-Folic Acid Activity. Part IV. 3: 6-Diaminopyrido(2:3) Pyrazine., J. Chem. Soc., 1955, pp. 2032-2035.

Emma R. Parmee, et al. "4-Amino Cyclohexylglycine Analogues As Potent Dipeptidyl Peptidase IV Inhibitors", Bioorganic and Medicinal Chemistry Letters, vol. 14, 2004, pp. 43-46.

Enrico Patrucco, et al. "PI3K γ Modulated the Cardiac Response to Chronic Pressure Overload by Distinct Kinase-Dependent and -Independent Effects", Cell, vol. 118, Aug. 6, 2004, pp. 375-387.

Graham S. Poindexter, et al. "Dihydropyridine Neuropeptide Y Y$_1$ Receptor Antagonists 2: Bioisoteric Urea Replacements", Bioorganic and Medicinal Chemistry, vol. 12, 2004, pp. 507-521.

Ulf R. Rapp, et al. "BCL-2 Proteins: Master Switches at the Intersection of Death Signaling and the Survival Control by RAF Kinases", Biochimica Et Biophysica Acta, vol. 1644, 2004, pp. 149-158.

Jean-Marie Receveur, et al. "4-Acylamino- and 4-Ureidobenzamides as Melanin-Concentrating Hormone (MCH) Receptor 1 Antagonists", Bioorganic and Medicinal Chemistry Letters, vol. 14, 2004, pp. 5075-5080.

Adam R. Renslo, et al. "Self Complimentary Cavitands", Journal of the American Chemical Society, vol. 121, 1999, pp. 7459-7460.

Pablo Rodriguez-Vicana, et al. "Phosphatidylinositol-3-OH Kinase as a Direct Target of RAS", Nature, vol. 70, Aug. 18, 1994, pp. 527-532.

M. Sako, "Product Class 20: Pyridopyrazines", Science of Synthesis, vol. 16, No. 20, 2004, pp. 1269- 1290.

Yardena Samuels, et al. "High Frequency of Mutations of the PIK3CA Gene in Human Cancers", Science, vol. 304, Apr. 23, 2004.

Satoshi Sasaki, et al. "Discovery of a Thieno[2,3-d] Pyraimidine-2,4-Dione Bearing a p-methoxyureidophenyl Moiety at the 6-Position: A Highly Potent and Orally Bioavailable Non-peptide Antagonist for the Human Luteinizing Hormone-Releasing Hormone Receptor", Journal of Medicinal Chemistry, vol. 46, 2003, pp. 113-124.

Judith S. Sebolt-Leopold et al. "Targeting the Mitogen-Activated Protein Kinase Cascade to Treat Cancer", Nature Reviews, vol. 4, Dec. 2004, pp. 937-947.

Laleh Shayesteh, et al. "PIK3CA Is Implicated as an Oncogene in Ovarian Cancer", Nature Genetics, vol. 21, Jan. 1999, pp. 99-102.

Joachim K. Seydel, et al. "Synthesis and Quantitative Structure-Activity Relationships of Anticonvulsant 2,3,6-Triaminopyridines", Journal of Medicinal Chemistry, vol. 37, 1994, pp. 3016-3022.

Takeshi Shiota, et al. "Regioselective Reactions of Organozinc Reagents With 2,4-Dichloroquinoline and 5,7-Dichloropyrazolo[1,5-a] Pyrimidine", Journal of Organic Chemistry, vol. 64, 1999, pp. 453-457.

V. Sirivatanauksorn, et al. "Molecular Pattern of Ductal Pancreatic Cancer", Langenbeck's Arch Surg., vol. 383, 1998, pp. 105-115.

(56) References Cited

OTHER PUBLICATIONS

Peter A. Steck, et al. "Identification of a Candidate Tumour Suppressor Gene, MMAC1, at Chromosome 10q23.3 That Is Mutated in Multiple Advanced Cancers", Nature Genetics, vol. 15, Apr. 1997, pp. 356-362.

Pierre Sujobert, et al. "Essential Role for the p110δ Isoform in Phosphoinositide 3-Kinase Activation and Cell Proliferation in Acute Myeloid Leukemia", Blood, vol. 106, No. 3, Aug. 2005, pp. 1063-1066.

Jason W. Szewczyk, et al. "SAR Studies: Designing Potent and Selective LXR Agonists", Bioorganic and Medicinal Chemistry Letters, vol. 16, 2006, pp. 3055-3060.

Teruo Tanaka, et al. "Syntheses of Pyrido[2,3-b]pyrazine Derivatives", Yakugaku Zasshi, vol. 95, No. 9, 1975, pp. 1092-1097 (with partial English Translation).

Rajendra P. Tangallapally, et al. Synthesis and Evaluation of Nitrofuranylamides as Novel Antituberculosis Agents, Journal of Medicinal Chemistry, vol. 47, 2004, pp. 5276-5283.

Edward C. Taylor, et al. Pterdines. 52. A Convienient Synthesis of 6-Formylpterin, Synthetic Communications, vol. 16, No. 17, 1987, pp. 1865-1868.

Carroll Temple, et al. "Synthesis of Potential Antimalarial Agents. II. 6,8-Disubstituted Pyrido[2,3-b] Pyrazines", Journal of Medicinal Chemistry, vol. 11, Nov. 1968, pp. 1216-1218.

Carroll Temple, et al. "Potential Antimitotic Agents. Synthesis of Some Ethyl Benzopyrazin-7- Ylcarbamates, Ethyl Pyrido 3,4-b]pyrazine-7-Ylcarbamates, and Ethyl Pyrido[3,4-e]-As-Triazin-7-Ylcarbamates", Journal of Medicinal Chemistry, vol. 33, 1990, pp. 3044-3050.

Carroll Temple, et al. "Antimitotic Agents. Chiral Isomers of Ethyl [5-Amino-1,2-Dihydro-3-(4- Hydroxyhpenyl)-2-Methylpyrido[3,4-b] Pyrazin-7-YL] Carbamate", Journal of Medicinal Chemistry, vol. 35, 1992, pp. 988-993.

Andrew M. Thompson, et al. "3-(3,5-Dimethoxyphenyl)-1,6-Naphthyridine-2,7-Diamines and Related 2- Urea Derivatives Are Potent and Selective Inhibitors of the FGF Receptor-1 Tyrosine Kinase", Journal of Medicinal Chemistry, vol. 43, 2000, pp. 4200-4211.

Jakob Troppmair, et al. "RAF and the Road to Cell Survival: A Tale of Bad Spells, Ring Bearers and Detours", Biochemical Pharmacology, vol. 66, 2003, pp. 1341-1345.

Bart Vanhaesebroeck, et al. "Autophosphorylation of p110 δ Phosphoinositide 3-Kinase: A New Paradigm for the Regulation of Lipid Kinases In Vitro and In Vivo", The EMBO Journal, vol. 18, No. 5, 1999, pp. 1292-1302.

Bart Vanhaesebroeck, et al. "Synthesis and Function of 3-Phosphorylated Inositol Lipids", Annuual Reviews Biochem., vol. 70, 2001, pp. 535-602.

Quingmin Wang et al. "A Convenient Synthesis of Novel N'-Tert-Butyl-N'-Substituted Benzoyl-N-(Substituted Phenyl) Aminocarbonylhydrazines and Their Derivatives", Synthetic Communications, vol. 34, No. 2, 2004, pp. 255-264.

Caroline R. Weinstein-Oppenheimer, et al. "The RAF Signal Transduction Cascade as a Target for Chemotherapeutic Intervention in Growth Factor-Responsive Tumors", Pharmacology & Therapeutics, vol. 88, 2000, pp. 229-279.

Reinhard Wetzker, et al. "Phosphoinositide 3-Kinases as Targets for Therapeutic Intervention", Current Pharmaceutical Design, vol. 10, 2004, pp. 1915-1922.

Ho Bum Woo, et al. "Synthesis of Novel Curcumin Mimics With Asymmetrical Units and Their Anti-Angiogenic Activity", Bioorganic and Medicinal Chemistry Letters, vol. 15, 2005, pp. 3782-3786.

Matthias P. Wymann, et al. "Structure and Function of Phosphoinositide 3-Kinases",Biochimica Et Biophysica Acta, vol. 1436, 1998, pp. 127-150.

Guichun Yang, et al. "Synthesis of Methyl N-Aryl Oxamate Using Soluble Polymer Support", Synthetic Communications, vol. 36, 2000, pp. 611-619.

Jingjun Yin, et al. "PD-Catalyzed N-Arylation of Heteroarylamines", Organic Letters, vol. 4, No. 20, 2002, pp. 3481-3484.

Bu-Bing Zeng, et al. "Nitroxyl (HNO) Release From New Functionalized N-Hydroxyurea-Derived Acyl Nitroso-9,10-Dimethylanthracene Cycloadducts", Bioorganic & Medicinal Chemistry Letters, vol. 14, 2004, pp. 5565-5568.

Andrey Bondev, et al. "Differential Regulation of Lipid and Protein Kinase Activities of Phosphoinositide 3-Kinaseγ in Vitro", Biological Chemistry, vol. 380, Nov. 1999, pp. 1337-1340.

Tzvetanka Bondeva, et al. "Bifurcation of Lipid and Protein Kinase Signals of PI3Kγ to the Protein Kinases PKB and MAPK", Science, vol. 282, Oct. 9, 1998, pp. 293-296.

Robert H. Bradbury, et al. "New Non-Peptide Endothelin-A Receptor Antagonists: Synthesis, Biological Properties, and Structure-Activity Relationships of 5-(Dimethylamino)-N-Pyridyl-, N-pyrimidinyl-, N-Pyridazinyl-, and -N-Pyrazinyl-1-Naphthalenesulfonamides", Journal of Medicinal Chemistry, vol. 40, No. 6, 1997, pp. 996-1004.

Richard J. Brown, at al. "Synthesis and Properties of Axially-Chiral N-(2,6-Disubstituted) Phenyl Triazolones", Tetrahedron, vol. 60, 2004, pp. 4361-4375.

Ian G. Campbell, at al. "Mutation of the PIK3CA Gene in Ovarian and Breast Cancer", Cancer Research, vol. 64, Nov. 1, 2004, pp. 7678-7681.

Adindo L. Castelhano, et al. "Glucokinase-Activating Ureas", Bioorganic & Medicinal Shemistry Letters, vol. 15, 2005, pp. 1501-1504.

Daniela Catarzi, et al. "Tricyclic Heteroaromatic Systems. Synthesis and $A_1$ and $A_{2a}$, Adenosine Binding Activities of Some 1-Aryl-1,4-Dihydro-3-Methyl[1]Benzopyrano[2,3-c]Pyrazol-4-Ones,1-Aryl-4,9-Dihydro-3-Methyl-1H-Pyrazolo[3,4-b]Quinoline-4-Ones, and 1-Aryl-1H-Imidazo[4,5-b]Quinoxalines", Journal of Medicinal Chemistry, vol. 38, 1995, pp. 1330-1336.

Hwai Wen Chang, et al. "Transformation of Chicken Cells by the Gene Encoding the Catalytic Subunit of PI 3-Kinase", Science, vol. 276, Jun. 20, 1997, pp. 1848-1850.

F. Chang, et al. "Involvement of PI3K/Akt Pathway in Cell Cycle Progression, Apoptosis, and Neoplastic Transformation: A Target for Cancer Chemotherapy", Leukemia, vol. 17, 2003, pp. 590-603.

F. Chang, et al. "Signal Transduction Mediated by the RAS/RAF/MEK/ERK Pathway From Cytokine Receptors to Transcription Factors: Potential Targeting for Therapeutic Intervention", Leukemia, vol. 17, 2003, pp. 1263-1293.

Jiong J. Chen, et al. "Pyrido[2,3-b] Pyrazines From Pyrazine C-Nucleosides: An Unusual Intramolecular Rearrangement", Journal of the American Chemical Society, vol. 118, 1996, pp. 8953-8954.

Jing Chen, et al. "RAF-1 Promotes Cell Survival by Antagonizing Apoptosis Signal-Regulating Kinase 1 Through a MEK-ERK Independent Mechanism", PNAS, vol. 98, No. 14, Jul. 3, 2001, pp. 7783-7788.

Jie-Fei Cheng, et al. "Discovery and Structure-Activity Relationship of Coumarin Derivatives As TNF-α Inhibitors" Bioorganic & Medicinal Chemistry Letters, vol. 14, 2004, pp. 2411-2415.

(56) References Cited

OTHER PUBLICATIONS

Gary G. Chiang, et al. "Determination of the Catalytic Activities of Mtor and Other Members of the Phosphoinositide-3-Kinase-Related Kinase Family", Methods in Molecular Biology, vol. 281, pp. 125-141 (2004).

Michael A. Crackower, at al. "Regulation of Myocadial Contractility and Cell Size by Distinct PI3K-PTEN Signaling Pathways", Cell, vol. 110, Sep. 20, 2002, pp. 737-749.

Natalie A. Dales, et al. "Design and Synthesis of Unsymmetrical Peptidyl Urea Inhibitors of Aspartic Peptidases", Letters vol. 3, No. 15, 2001, pp. 2313-2316.

Gerd Dannhardt, et al. "A Novel Series of 2-Carboxytetrahydroquinolines Provides New Insights Into the Eastern Region of Glycine Site NMDA Antagonists", Arch. Pharm. Pharm. Med. Chem., vol. 333, 2000, pp. 267-274.

* cited by examiner

PYRIDOPYRAZINE DERIVATIVES AND THEIR USE

CROSS-REFERENCE TO RELATED APPLICATION

This application claims priority to U.S. 60/735,707, filed Nov. 11, 2005, which is hereby incorporated by reference in its entirety.

TECHNICAL FIELD

The present invention relates to pyridopyrazine derivatives with new biological action and their use for the treatment of physiological and/or pathophysiological states mediated and/or modulated by signal transduction pathways in mammals and in particular in humans.

PRIOR ART

The signal transduction cascades ras-Raf-Mek-Erk and PI3K-Akt play a central role in cell growth, cell proliferation, apoptosis, adhesion, migration and glucose metabolism. Consequently, the fundamental involvement in the pathogenesis of diseases such as cancer, neurodegeneration and inflammatory diseases is proven both for the ras-Raf-Mek-Erk and for the PI3K-Akt signal pathway. The individual components of these signal cascades are therefore important therapeutic points of attack for intervention in various disease processes (Weinstein-Oppenheimer C. R. et al. 2000, Chang F. et al. 2003, Katso R. et al 2001 and Lu Y. et al 2003).

The molecular and biochemical properties of both signal pathways are first described separately hereinafter.

A plurality of growth factors, cytokines and oncogenes transduce their growth-promoting signals via the activation of G-protein coupled ras which leads to the activation of serine threonine kinase Raf and to the activation of mitogen-activated protein kinase kinase 1 and 2 (MAPKK1/2 or Mek1/2) and results in the phosphorylation and activation of MAPK 1 and 2—also known as extracellular signal regulated kinase (Erk1 and 2). Compared to other signal pathways, the ras-Raf-Mek-Erk signal pathway combines a large number of proto-oncogenes, including ligands, tyrosine kinase receptors, G-proteins, kinases and nuclear transcription factors. Tyrosine kinases such as, for example, EGFR (Mendelsohn J. et al., 2000) frequently mediate constitutively active signals to the downstream ras-Raf-Mek-Erk signal pathway in tumour events caused by overexpression and mutation. Ras mutations are mutated in 30% of all human tumours (Khleif S. N. et al., 1999, Marshall C., 1999), the highest incidence of 90% being found in pancreatic carcinomas (Friess H. et al., 1996, Sirivatanauksorn V. et al., 1998). For c-Raf a deregulated expression and/or activation has been described in various tumours (Hoshino R. et al., 1999, McPhillips F. et al., 2001). B-Raf point mutants were detected in 66% of all human malignant melanomas, 14% of all ovarian carcinomas and 12% of all carcinomas of the colon (Davies H. et al., 2002). It is therefore not surprising that Erk1/2 is primarily involved in many cellular processes such as cell growth, cell proliferation and cell differentiation (Lewis T. S. et al., 1998, Chang F. et al., 2003).

In addition, the members of the Raf kinases also have Mek-Erk-indepedent anti-apoptotic functions whose molecular steps have not yet been fully described. Ask1, Bcl-2, Akt and Bag1 have been described as possible interaction partners for the Mek-Erk-independent Raf activity (Chen J et al., 2001, Troppmaier J. et al., 2003, Rapp U. R. et al., 2004, Gotz R. et al., 2005). It is assumed nowadays that both Mek-Erk-dependent and Mek-Erk-independent signal transduction mechanisms control the activation of the upstream ras and Raf stimuli.

The isoenzymes of the phosphatidylinositol 3-kinases (PI3Ks) function predominantly as lipid kinases and catalyse the D3 phosphorylation of the second-messenger lipids PtdIns (phosphatidylinositol) to PtdIns(3)P, PtdIns(3,4)$P_2$, PtdIns(3,4,5)$P_3$ phosphatidylinositol phosphates. The class I PI3Ks are composed structurally of the catalytic (p110alpha, beta, gamma, delta) and the regulatory (p85alpha, beta or p101gamma) subunits. Furthermore, the class II (PI3K-C2alpha, PI3K-C2beta) and class III (Vps34p) enzymes belong to the family of the PI3 kinases (Wymann M. P. et al., 1998, VanHaesebroeck B. et al., 2001). The PIP increase triggered by the PI3Ks activates the proliferative ras-Raf-Mek-Erk signal pathway via the coupling of ras on the one hand (Rodriguez-Viciana P. et al., 1994) and on the other hand stimulates the anti-apoptotic signal pathway by recruiting Akt to the cell membrane and consequent overactivation of this kinase (Alessi D. R. et al., 1996, Chang H. W. et al., 1997, Moore S. M. et al., 1998). Consequently, the activation of PI3Ks fulfils at least two crucial mechanisms for tumour formation, namely the activation of cell growth and cell differentiation and the inhibition of apoptosis. In addition, PI3K also have protein-phosphorylating properties (Dhand et al., 1994, Bondeva T. et al., 1998, Bondev A. et al., 1999, Van-Haesebroeck B. et al., 1999) which can trigger a PI3Ks-intrinsically regulating serine autophosphorylation for example. In addition, it is known that PI3Ks also have kinase-independent regulating effector properties, e.g. during control of cardiac contraction (Crackower M. A. et al., 2002, Patrucco et al., 2004). It is furthermore proven that PI3Kdelta and PI3Kgamma are specifically expressed on hematopoietic cells and therefore constitute potential points of attack for isoenzyme-specific PI3Kdelta and PI3Kgamma inhibitors in the treatment of inflammatory diseases such as rheumatism, asthma and allergies and in the treatment of B and T cell lymphomas (Okkenhaug K. et al., 2003, Ali K. et al., 2004, Sujobert P. et al., 2005). PI3Kalpha, which was recently identified as a proto-oncogene (Shayesteh L. et al., 1999, Ma Y. Y. et al., 2000, Samuels Y. et al., 2004, Campbell I. G. et al., 2004, Levine D. A., 2005) is considered to be an important target in the treatment of tumour diseases. The importance of PI3K species as a target for the development of active substances is therefore extremely diverse (Chang F. & Lee J. T. et al, 2003).

The kinases related to PI3K (PIKK), which include the serine/threonine kinases mTOR, ATM, ATR, h-SMG-1 and DNA-PK (Chiang G. G. et al 2004) are also of great interest. Their catalytic domains have a high sequence homology to the catalytic domains of PI3Ks.

In addition, the loss of the tumour suppressor protein PTEN (Li J. et al., 1997, Steck P. A. et al., 1997)—whose function is the reversion of the phosphorylation initiated by the PI3K—contributes to an overactivation of Akt and its downstream cascade components and thereby emphasise the causal importance of PI3K as a target molecule for tumour therapy.

Various inhibitors of individual components of the ras-Raf-Mek-Erk and PI3K-Akt signal pathways have already been published and patented.

The present state of development in the field of kinase inhibitors, in particular of the ras-Raf-Mek-Erk and PI3K-Akt pathway, is described in the reviews of J. S. Sebolt-Leopold et al., 2004, and R. Wetzker et al., 2004. These publications contain comprehensive listings of the published patent specifications which describe the synthesis and use of low-molecular ras-Raf-Mek-Erk- and PI3K inhibitors.

The kinase inhibitor Bay 43-9006 (WO 99/32111, WO 03/068223) which is already undergoing clinical trials, shows a relatively non-specific inhibition pattern of serine/threonine and of tyrosine kinases such as Raf, VEGFR2/3, Flt-3, PDGFR, c-Kit and other kinases. Great importance is attached to this inhibitor in angiogenesis-induced advanced tumour diseases (e.g. in renal cell carcinoma) and also in melanomas having a high B-Raf mutation rate. The clinical effect of Bay 43-9006 is currently also being determined in patients presenting with refractory solid tumours in combination with, for example, Docetaxel. Mild side effects and promising anti-tumoral effects have been described so far. No inhibition of the kinases in the PI3K-Akt signal pathway has been described for Bay 43-9006.

The Mek1/2 inhibitor PD0325901 (WO 02/06213) is currently undergoing a Phase I clinical trial. The precursor substance CI-1040 (WO 00/35435, WO 00/37141) was striking because of its high Mek specificity and target affinity. However, this compound proved to be metabolically unstable in Phase I/II trials. No clinical data are available yet for the current successor substance PD0325901. However, no interaction with Erk1 or Erk2 nor any PI3K-Akt signal pathway inhibiting function or its simultaneous modulation has yet been disclosed for this Mek inhibitor.

Patent specifications WO 04/104002 and WO 04/104003 describe pyrido[2,3-b]pyrazines, which can be substituted in the 6- or 7-position with urea, thiourea, amidine or guanidine groups. These compounds possess properties as inhibitors or modulators of kinases, in particular of tyrosine and serine/threonine kinases, and a use as a medicament is specified. However, no use of these compounds as modulators of lipid kinases, alone or in combination with tyrosine and serine/threonine kinases has been described.

In addition, patent specification WO 99/17759 describes pyrido[2,3-b]pyrazines which, among other things, carry alkyl-, aryl- and heteroaryl-substituted carbamates in the 6-position. These compounds are to be used to modulate serine threonine protein kinases.

Patent specification WO 05/007099 describes, among other things, urea-substituted pyrido[2,3-b]pyrazines as inhibitors of the serine/threonine kinase PKB. A use in the treatment of cancer diseases is specified for these compounds. However, no specific examples of urea-substituted pyridopyrazines with these biological properties are given.

Further examples of pyrido[2,3-b]pyrazines substituted with urea in the 6- and 7-position are given in patent specification WO 05/056547. The compounds in this patent specification are described as inhibitors of protein kinases, in particular GSK-3, Syk and JAK-3. A use in the treatment of proliferative diseases is given for these compounds among other things. No use of these compounds as modulators of lipid kinases, alone or in combination with serine/threonine kinases is described.

The patent application WO 04/005472 describes, among other things pyrido[2,3-b]pyrazines substituted with carbamate in the 6-position which inhibit the growth of bacteria as antibacterial substances. No antitumour effect is described.

Certain diphenyl quinoxalines and pyrido[2,3-b]pyrazines with special alkylpyrrolidine, alkylpiperidine or alkyl sulfonamides group at a phenyl ring which can additionally also bear urea or carbamate substitutions in the 6- or 7-position are described in patent specifications WO 03/084473, WO 03/086394 and WO 03/086403 as inhibitors of the activity of the serine/threonine kinase Akt. A use in the treatment of cancer diseases is specified for these compounds. No defined indication of a biological effect is given for the pyrido[2,3-b]pyrazine compounds described therein as examples.

Patent specification WO 03/024448 describes amide and acrylamide-substituted pyrido[2,3-b]pyrazines which can also contain carbamates as additional substituents and can be used as histone deacetylase inhibitors for the treatment of cell proliferation diseases.

In another publication (Temple C. et al. 1990) the synthesis of a 6-ethylcarbamate-substituted pyrido[2,3-b]pyrazine derivative is described as one example. No antitumour effect is disclosed or made obvious.

The synthesis of further derivatives of 6-ethylcarbamate-substituted pyrido[2,3-b]pyrazine is described in a publication by R. D. Elliott (J. Org. Chem. 1968). No biological effect of these compounds is described or disclosed.

The publication by C. Temple (1968) describes the synthesis and investigation of 6-ethylcarbamate-substituted pyrido [2,3-b]pyrazines as potential antimalarial drugs. No antitumour effect is disclosed or made obvious.

The PI3K inhibitors published so far are undergoing preclinical trials. ICOS disclosed a PI3K inhibitor IC87114 with high PI3Kdelta isoenzyme specificity (WO 01/81346). For PI103 (WO 04/017950) Yamanouchi/Piramed describe a selectivity versus the PI3Kalpha isoform. In addition, a research environment which has attracted a great deal of attention exists in the early development of PI3K inhibitors (see the review of R. Wetzker et al., 2004).

Inhibitors of the SAPK signal pathway, either of Jnk or of p38 have been described in the literature (Gum R. J., 1998, Bennett B. L. et al 2001, Davies S. P. et al 2000). However, no PI3K-inhibiting function and also no specific inhibition of Erk1 or Erk2 or simultaneous inhibition of SAPKs, Erk1, Erk2, or PI3Ks is disclosed for these SAPK inhibitors.

DESCRIPTION OF THE INVENTION

The object of the present invention is to provide new compounds which can be used for the treatment or prevention of physiological and/or pathophysiological states in mammals, in particular in humans, which are mediated by signal transduction pathways selected from the group consisting of: "ras-Raf-Mek-Erk signal transduction pathway, PI3K-Akt signal transduction pathway and/or SAPK signal transduction pathway". A further object of the invention is to provide new compounds for the aforesaid uses by modulation of said signal transduction pathways. It is further the object of the present invention to provide new compounds which can be used for the treatment or prevention of physiological and/or pathophysiological states in mammals, in particular in humans, which are mediated by enzymes selected from the group consisting of: "ATM, ATR, mTOR, DNA-PK, hSMG-1". A further object of the invention is to provide new compounds for the aforesaid uses by modulation of said enzymes.

The inventive object was surprisingly achieved in one aspect by preparing a compound according to the general formula (I)

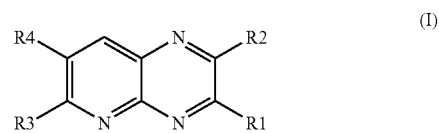

wherein the substituents R1, R2, R3, R4 have the following meaning:

R1 and R can be independently of one another
(i) hydrogen
(ii) hydroxyl
(iii) halogen
(iv) alkyl, wherein the alkyl group is saturated and can consists of 1 to 8 C atoms,
(v) unsubstituted or substituted aryl, wherein the alkyl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O—(CH$_2$)$_n$—O, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, aryl or heteroaryl, n can have the value 1, 2 or 3 and the alkyl-, cycloalkyl-, heterocyclyl-, aryl-, heteroaryl-, alkyl-cycloalkyl-, alkyl-heterocyclyl-, alkyl-aryl- and alkyl-heteroaryl substituents for their part can in turn be substituted,
(vi) unsubstituted or substituted heteroaryl, wherein the heteroaryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-aryl, S-heteroaryl, OH, $OCF_3$, O-alkyl, O-cycloalkyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, aryl or heteroaryl, and the alkyl-, cycloalkyl-, heterocyclyl-, aryl- and heteroaryl substituents for their part can in turn be substituted,
(vii) OR5, wherein R5 can be alkyl, cycloalkyl, heterocyclyl, aryl, heteroaryl, alkyl-cycloalkyl, alkyl-heterocyclyl, alkyl-aryl or alkyl-heteroaryl, and the alkyl-, cycloalkyl-, heterocyclyl-, aryl-, heteroaryl-, alkyl-cycloalkyl, alkyl-heterocyclyl, alkyl-aryl or alkyl-heteroaryl substituents for their part can in turn be substituted,
(viii) SR6, wherein R6 can be alkyl, cycloalkyl, heterocyclyl, aryl, heteroaryl, alkyl-cycloalkyl, alkyl-heterocyclyl, alkyl-aryl or alkyl-heteroaryl and the alkyl-, cycloalkyl-, heterocyclyl-, aryl- and heteroaryl-, alkyl-cycloalkyl-, alkyl-heterocyclyl-, alkyl-aryl- or alkyl-heteroaryl substituents for their part can in turn be substituted,
(ix) NR7R8, wherein R7 and R8 independently of one another can be hydrogen, alkyl, cycloalkyl, heterocyclyl, aryl, heteroaryl, alkyl-cycloalkyl, alkyl-heterocyclyl, alkyl-aryl or alkyl-heteroaryl and the alkyl-, cycloalkyl-, heterocyclyl-, aryl- and heteroaryl-, alkyl-cycloalkyl, alkyl-heterocyclyl, alkyl-aryl or alkyl-heteroaryl substituents for their part can in turn be substituted,
or R7 and R8 together mean cycloalkyl or heterocyclyl, wherein cycloalkyl and heterocyclyl for their part can in turn be substituted.

R3 and R4 can independently of one another mean hydrogen or NR9R10 assuming that if R3=NR9R110, R4=H, and if R4=NR9R110, R3=H,
wherein R9 can be hydrogen, alkyl, cycloalkyl, heterocyclyl, aryl, heteroaryl, alkyl-cycloalkyl, alkyl-heterocyclyl, alkyl-aryl or alkyl-heteroaryl and the alkyl-, cycloalkyl-, heterocyclyl-, aryl- and heteroaryl-, alkyl-cycloalkyl, alkyl-heterocyclyl, alkyl-aryl or alkyl-heteroaryl substituents for their part can in turn be substituted,
and R10:
can mean —C(Y)NR11R12, wherein Y=O, S and R11 and R12 can be independently of one another
(i) hydrogen,
(ii) unsubstituted or substituted alkyl wherein the alkyl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)

NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_2$NH-alkyl-aryl, SO$_3$H, SO$_2$O-alkyl, SO$_2$O-aryl, SO$_2$O-alkyl-aryl, cycloalkyl, heterocyclyl, aryl or heteroaryl, (iii) unsubstituted or substituted cycloalkyl, wherein the cycloalkyl group can be substituted with one or more, the same or different F, Cl, Br, I, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, alkyl, or aryl, (iv) unsubstituted or substituted heterocyclyl, wherein the heterocyclyl group can be substituted with one or more, the same or different OH, O-alkyl, O-aryl, NH$_2$, NH-alkyl, NH-aryl, alkyl, alkyl-aryl or aryl, (v) unsubstituted or substituted aryl, wherein the aryl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O—(CH$_2$)$_n$—O, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_2$NH-alkyl, SO$_2$NH-aryl, SO$_2$NH-heteroaryl, SO$_2$NH-alkyl-aryl, SO$_3$H, SO$_2$O-alkyl, SO$_2$O-aryl, SO$_2$O-alkyl-aryl, alkyl, cycloalkyl, heterocyclyl, aryl or heteroaryl, and n can have the value 1, 2 or 3, (vi) unsubstituted or substituted heteroaryl, wherein the heteroaryl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH$_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO$_2$-alkyl, NHSO$_2$-cycloalkyl, NHSO$_2$-heterocyclyl, NHSO$_2$-aryl, NHSO$_2$-heteroaryl, NHSO$_2$-alkyl-aryl, NHSO$_2$-alkyl-heteroaryl, NO$_2$, SH, S-alkyl, S-aryl, S-heteroaryl, OH, OCF$_3$, O-alkyl, O-cycloalkyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO$_3$H, OSO$_2$-alkyl, OSO$_2$-cycloalkyl, OSO$_2$-heterocyclyl, OSO$_2$-aryl, OSO$_2$-heteroaryl, OSO$_2$-alkyl-aryl, OSO$_2$-alkyl-heteroaryl, OP(O)(OH)$_2$, C(O)-alkyl, C(O)-aryl, C(O)-heteroaryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO$_2$NH$_2$, SO$_2$NH-alkyl, SO$_2$NH-aryl, SO$_2$NH-heteroaryl, SO$_2$NH-alkyl-aryl, SO$_3$H, SO$_2$O-alkyl, SO$_2$O-aryl, SO$_2$O-alkyl-aryl, alkyl, cycloalkyl, heterocyclyl, aryl or heteroaryl, (vii) —C(O)—R17, wherein R17 can be alkyl, aryl or heteroaryl and the alkyl and aryl substituents for their part can in turn be substituted, (viii) or R11 and R12 together can mean cycloalkyl or heterocyclyl, can mean —C(Y)NR13R14 wherein Y═NH and R13 and R14 can be independently of one another, (i) hydrogen, (ii) unsubstituted or substituted aryl, wherein the aryl group can be substituted with one or more, the same or different F, Cl, Br, I, CF$_3$, CN, NH$_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHSO$_2$-alkyl, NHSO$_2$-cycloalkyl, NHSO$_2$-aryl, NHSO$_2$-heteroaryl, NO$_2$, SH, S-alkyl, S-cycloalkyl, S-heterocyclyl, S-aryl, S-heteroaryl, OH, OCF$_3$, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OSO$_2$-alkyl, OSO$_2$-cycloalkyl, OSO$_2$-aryl, OSO$_2$-heteroaryl, C(O)-alkyl, C(O)-aryl, CO$_2$H, CO$_2$-alkyl, CO$_2$-cycloalkyl, CO$_2$-heterocyclyl, CO$_2$-aryl, CO$_2$-heteroaryl, CO$_2$-alkyl-cycloalkyl, CO$_2$-alkyl-heterocyclyl, CO$_2$-alkyl-aryl, CO$_2$-alkyl-heteroaryl, C(O)—NH$_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, SO$_2$-alkyl, SO$_2$-aryl, SO$_2$NH$_2$, SO$_3$H, alkyl, cycloalkyl, heterocyclyl, aryl or heteroaryl, (iii) unsubstituted or substituted cycloalkyl, wherein the cycloalkyl group can be substituted with one or more, the same or different F, Cl, Br, I, $NH_2$, NH-alkyl, NH-cycloalkyl, NH-heterocyclyl, NH-aryl, NH-heteroaryl, NH-alkyl-aryl, NH-alkyl-heteroaryl, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-cycloalkyl, $NHSO_2$-aryl, $NHSO_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, $CO_2H$, $CO_2$-alkyl, $CO_2$-cycloalkyl, $CO_2$-heterocyclyl, $CO_2$-aryl, $CO_2$-heteroaryl, $C(O)-NH_2$, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, $C(O)N(alkyl)_2$, alkyl, or aryl, (iv) unsubstituted or substituted heterocyclyl, wherein the heterocyclyl group can be substituted with one or more, the same or different OH, O-alkyl, O-aryl, $NH_2$, NH-alkyl, NH-aryl, alkyl, or aryl, (v) unsubstituted or substituted aryl, wherein the aryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, $NH-alkyl-NH_2$, NH-alkyl-OH, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, $O-(CH_2)_n-O$, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, $C(O)-NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, $C(O)N(alkyl)_2$, $C(O)N(cycloalkyl)_2$, $C(O)N(aryl)_2$, $C(O)N(heteroaryl)_2$, SO-alkyl, SO-aryl, $SO_2$-alkyl, $SO_2$-aryl, $SO_2NH_2$, $SO_2NH$-alkyl, $SO_2NH$-aryl, $SO_2NH$-heteroaryl, $SO_3H$, $SO_2O$-alkyl, $SO_2O$-aryl, $SO_2O$-heteroaryl, alkyl, cycloalkyl, heterocyclyl, aryl or heteroaryl, and n can have the value 1, 2 or 3, (vi) unsubstituted or substituted heteroaryl, wherein the heteroaryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-aryl, NH-alkyl-heteroaryl, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-aryl, OH, $OCF_3$, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, $C(O)-NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, $C(O)N(alkyl)_2$, $C(O)N(cycloalkyl)_2$, $C(O)N(aryl)_2$, $C(O)N(heteroaryl)_2$, $SO_2$-alkyl, $SO_2$-aryl, $SO_2NH_2$, $SO_2NH$-alkyl, $SO_2NH$-aryl, $SO_2NH$-heteroaryl, $SO_3H$, $SO_2O$-alkyl, $SO_2O$-aryl, $SO_2O$-heteroaryl, alkyl, cycloalkyl, heterocyclyl, aryl or heteroaryl, (vii) or R13 and R14 together can mean cycloalkyl or heterocyclyl, can mean —C(NR15)R16, wherein R15=H and R16 can be
(i) unsubstituted or substituted alkyl, wherein the alkyl group can be substituted with one or more, the same or different F, Cl, Br, I, $CF_3$, $NH_2$, NH-alkyl, NH-cycloalkyl, NH-heterocyclyl, NH-aryl, NH-heteroaryl, NH-alkyl-aryl, NH-alkyl-heteroaryl, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-cycloalkyl, $NHSO_2$-aryl, $NHSO_2$-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, C(O)-alkyl, C(O)-aryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, $C(O)-NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, $C(O)N(alkyl)_2$, $C(O)N(cycloalkyl)_2$, $C(O)N(aryl)_2$, $C(O)N(heteroaryl)_2$, SO-alkyl, SO-aryl, $SO_2$-alkyl, $SO_2$-aryl, $SO_2NH_2$, $SO_3H$, alkyl, cycloalkyl, heterocyclyl, aryl or heteroaryl, (ii) unsubstituted or substituted cycloalkyl, wherein the cycloalkyl group can be substituted with one or more, the same or different F, Cl, Br, I, $NH_2$, NH-alkyl, NH-cycloalkyl, NH-heterocyclyl, NH-aryl, NH-heteroaryl, NH-alkyl-aryl, NH-alkyl-heteroaryl, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-cycloalkyl, $NHSO_2$-aryl, $NHSO_2$-heteroaryl, OH, O-alkyl, O-cycloalkyl, O-heterocyclyl, O-aryl, O-heteroaryl, O-alkyl-aryl, O-alkyl-heteroaryl, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, $CO_2H$, $CO_2$-alkyl, $CO_2$-cycloalkyl, $CO_2$-heterocyclyl, $CO_2$-aryl, $CO_2$-heteroaryl, $C(O)-NH_2$, C(O)NH-alkyl, C(O)NH-cycloalkyl, C(O)NH-heterocyclyl, C(O)NH-aryl, C(O)NH-heteroaryl, C(O)NH-alkyl-aryl, C(O)NH-alkyl-heteroaryl, $C(O)N(alkyl)_2$, alkyl, or aryl, (iii) unsubstituted or substituted heterocyclyl, wherein the heterocyclyl group can be substituted with one or more, the same or different OH, O-alkyl, O-aryl, $NH_2$, NH-alkyl, NH-aryl, alkyl or aryl, (iv) unsubstituted or substituted aryl, wherein the aryl group can be substituted with one or more, the same or different F, Cl, Br, I, $CF_3$, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, $NH-alkyl-NH_2$, NH-alkyl-OH, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, $O-(CH_2)_n-O$, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, $C(O)N(alkyl)_2$, $C(O)N(cycloalkyl)_2$, $C(O)N(aryl)_2$, $C(O)N(heteroaryl)_2$, SO-alkyl, SO-aryl, $SO_2$-alkyl, $SO_2$-aryl, $SO_2NH_2$, $SO_2NH$-alkyl, $SO_2NH$-aryl, $SO_2NH$-heteroaryl, $SO_3H$, $SO_2O$-alkyl, $SO_2O$-aryl, $SO_2O$-heteroaryl, alkyl, cycloalkyl, heterocyclyl, aryl or heteroaryl, and n can have the value 1, 2 or 3, (v) unsubstituted or substituted heteroaryl, wherein the heteroaryl group can be substituted with one or more, the same or different F, Cl, Br, I, $CF_3$, $NH_2$, NH-alkyl, NH-cycloalkyl, NH-heterocyclyl, NH-aryl, NH-heteroaryl, NH-alkyl-aryl, NH-alkyl-heteroaryl, $N(alkyl)_2$, NHC(O)-alkyl, NHC(O)-cycloalkyl, NHC(O)-heterocyclyl, NHC(O)-aryl, NHC(O)-heteroaryl, $NHSO_2$-alkyl, $NHSO_2$-aryl, $NHSO_2$-heteroaryl, $NO_2$, SH, S-alkyl, S-aryl, OH, $OCF_3$, O-alkyl, O-cycloalkyl, O-heterocyclyl, O-aryl, O-heteroaryl, OC(O)-alkyl, OC(O)-cycloalkyl, OC(O)-heterocyclyl, OC(O)-aryl, OC(O)-heteroaryl, $OSO_2$-alkyl, $OSO_2$-cycloalkyl, $OSO_2$-aryl, $OSO_2$-heteroaryl, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, $C(O)N(alkyl)_2$, $C(O)N(cycloalkyl)_2$, $C(O)N(aryl)_2$, $C(O)N(heteroaryl)_2$, $SO_2$-alkyl, $SO_2$-aryl, $SO_2NH_2$, $SO_2NH$-alkyl, $SO_2NH$-aryl, $SO_2NH$-heteroaryl, $SO_3H$, $SO_2O$-alkyl, $SO_2O$-aryl, $SO_2O$-heteroaryl, alkyl, cycloalkyl, heterocyclyl, aryl or heteroaryl;

which can be used for the production of a medicament for the treatment or prevention of physiological and/or pathophysiological states in mammals mediated by signal transduction pathways selected from the group consisting of: the "ras-Raf-Mek-Erk signal transduction pathway, the PI3K-Akt signal transduction pathway and/or the SAPK signal transduction pathway.

In a preferred embodiment, compounds according to the general formula (I) are prepared, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH═CH2; —CH═CH—CH3, —C(═CH2)-CH3), propinyl (—CH2-C≡CH, —C≡C—CH3), butenyl, butinyl, pentenyl, pentinyl, hexenyl, hexinyl, heptenyl, heptinyl, octenyl, octinyl" which can be used for the production of a medicament for the treatment or prevention of physiological and/or pathophysiological states in mammals mediated by signal transduction pathways selected from the group consisting of: the "ras-Raf-Mek-Erk signal transduction pathway, the PI3K-Akt signal transduction pathway and/or the SAPK signal transduction pathway.

In a further preferred embodiment, compounds according to the general formula (I) are prepared for the aforementioned use, wherein the heterocyclyl group is selected from the group consisting of: "tetrahydrofuryl, tetrahydropyranyl, pyrrolidinyl, piperidinyl, piperazinyl, morpholinyl".

In a further preferred embodiment, compounds according to the general formula (I) are prepared for the aforementioned use, wherein the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl, acridinyl".

In a further preferred embodiment compounds according to the general formula (I) are prepared for the aforementioned use, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH═CH2; —CH═CH—CH3, —C(═CH2)-CH3), propinyl (—CH2-C≡CH, —C≡C—CH3), butenyl, butinyl, pentenyl, pentinyl, hexenyl, hexinyl, heptenyl, heptinyl, octenyl, octinyl" and/or wherein the heterocyclyl group is selected from the group consisting of: "tetrahydrofuryl, tetrahydropyranyl, pyrrolidinyl, piperidinyl, piperazinyl, morpholinyl" and/or the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl, acridinyl".

The inventive object was surprisingly achieved in a further aspect by preparing pyridopyrazine compounds selected from the group consisting of:

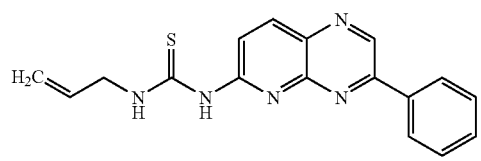

Compound 1

1-Allyl-3-(3-phenyl-pyrido[2,3-b]pyrazin-6-yl)-thiourea

Compound 2

1-(2-Methyl-allyl)-3-(3-naphth-2-yl-pyrido[2,3-b]pyrazin-6-yl)-thiourea

-continued

Compound 3

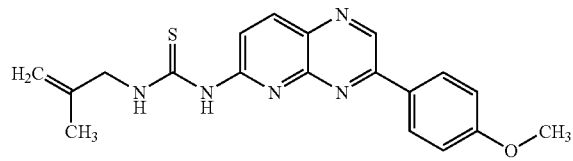

1-[3-(4-Methoxy-phenyl)-pyrido[2,3-b]pyrazin-6-yl)-
3-(2-methyl-allyl)-thiourea

Compound 4

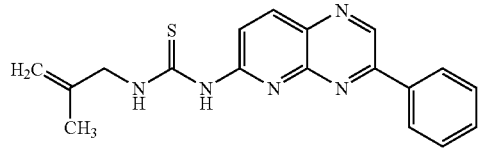

1-(2-Methyl-allyl)-3-(3-phenyl-pyrido[2,3-b]pyrazin-
6-yl)-thiourea

Compound 5

1-Allyl-3-(3-naphth-2-yl-pyrido[2,3-b]pyrazin-6-yl)-thiourea

Compound 6

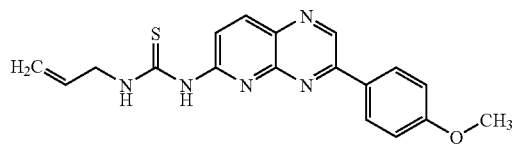

1-Allyl-3-(3-naphth-2-yl-pyrido[2,3-b]pyrazin-6-yl)-thiourea

Compound 7

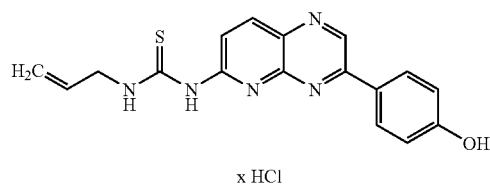

x HCl

1-Allyl-3-(3-(4-hydroxy-phenyl)-pyrido[2,3-b]pyrazin-6-yl)-
thiourea Hydrochloride Compound 8

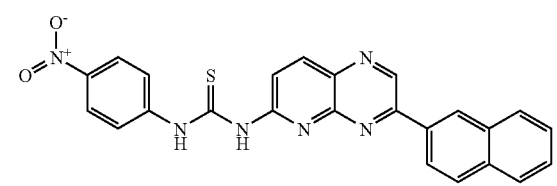

1-(3-Naphth-2-yl-pyrido[2,3-b]pyrazin-6-yl)-3-(4-nitro-phenyl)-thiourea

Compound 9

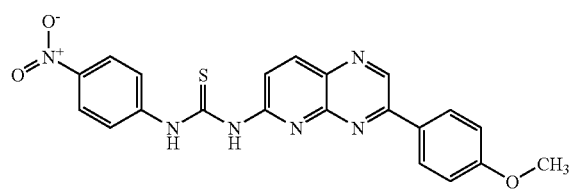

1-[3-(4Methoxy-phenyl)-pyrido[2,3-b]pyrazin-6-yl)-3-(4-nitro-
phenyl)-thiourea

Compound 10

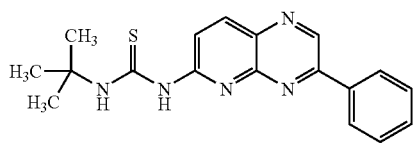

1-tert-Butyl-3-(3-phenyl-pyrido[2,3-b]pyrazin-6-yl)-thiourea

Compound 11

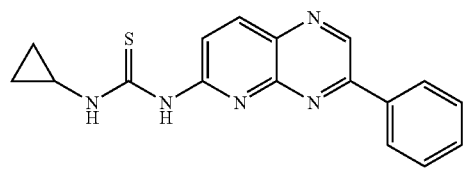

1-Cyclopropyl-3-(3-phenyl-pyrido[2,3-b]pyrazin-6-yl)-
thiourea

Compound 12

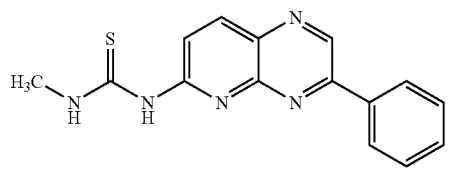

1-Methyl-3-(3-phenyl-pyrido[2,3-b]pyrazin-6-yl)-thiourea

Compound 13

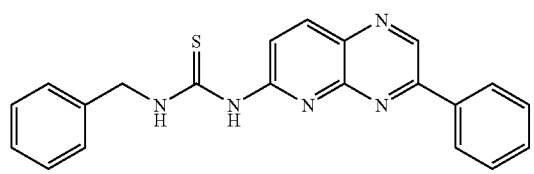

1-Benzyl-3-(3-phenyl-pyrido[2,3-b]pyrazin-6-yl)-thiourea

Compound 14

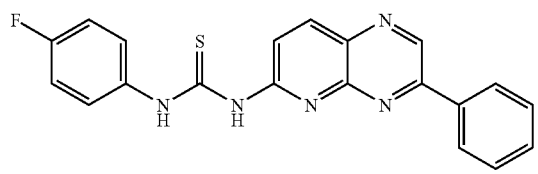

1-(4-Fluoro-phenyl)-3-(3-phenyl-pyrido[2,3-b]pyrazin-6-yl)-
thiourea

-continued

Compound 15

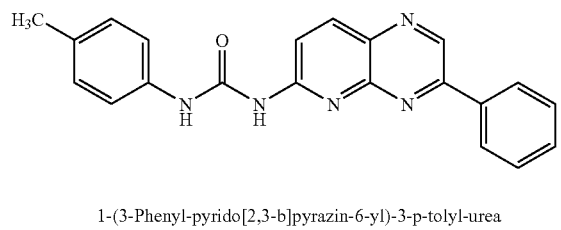

1-(3-Phenyl-pyrido[2,3-b]pyrazin-6-yl)-3-p-tolyl-urea

Compound 16

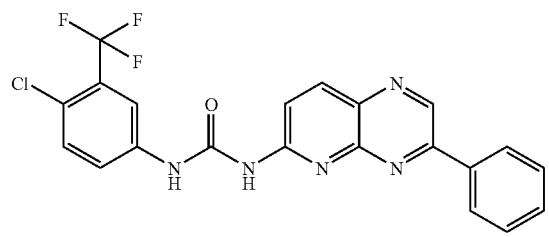

1-(4-Chloro-3-trifluoromethyl-phenyl)-3-(3-phenyl-pyrido[2,3-b]pyrazin-6-yl)-urea Compound 17

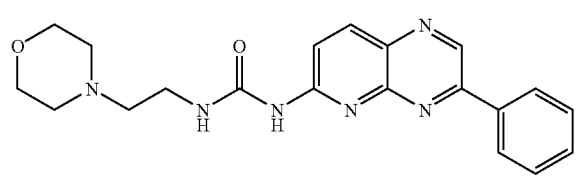

1-(2-Morpholin-4-yl-ethyl)-3-(3-phenyl-pyrido[2,3-b]pyrazin-6-yl)-urea

Compound 18

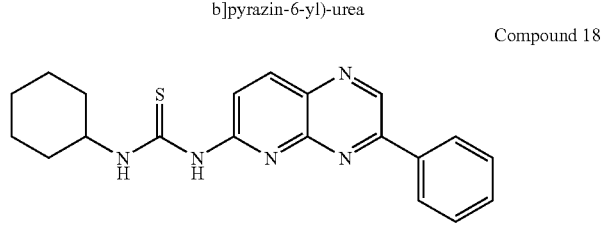

1-Cyclohexyl-3-(3-phenyl-pyrido[2,3-b]pyrazin-6-yl)-thiourea

Compound 19

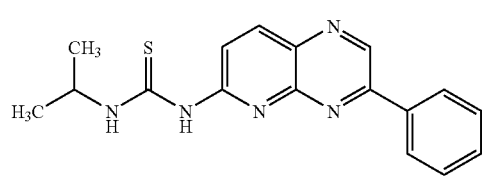

1-Isopropyl-3-(3-phenyl-pyrido[2,3-b]pyrazin-6-yl)-thiourea

Compound 20

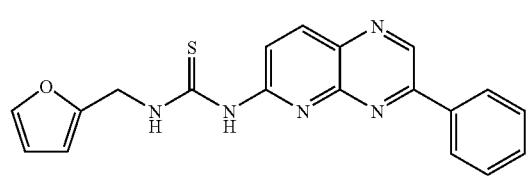

1-Furan-2-ylmethyl-3-(3-phenyl-pyrido[2,3-b]pyrazin-6-yl)-thiourea

Compound 21

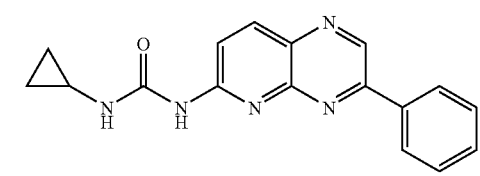

1-Cyclopropyl-3-(3-phenyl-pyrido[2,3-b]pyrazin-6-yl)-urea

Compound 22

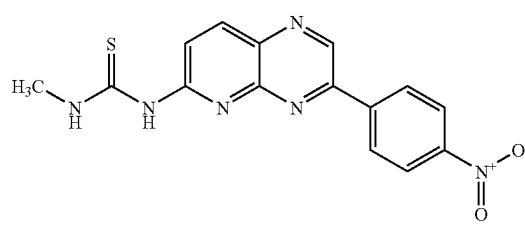

1-Methyl-3-[3-(4-nitro-phenyl)-pyrido[2,3-b]pyrazin-6-yl]-thiourea

Compound 23

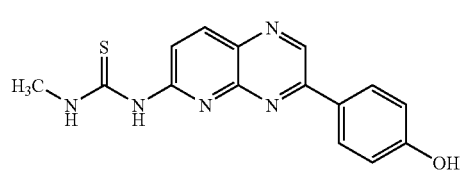

1-[3-(4-Hydroxy-phenyl)-pyrido[2,3-b]pyrazin-6-yl]-3-methyl-thiourea

Compound 24

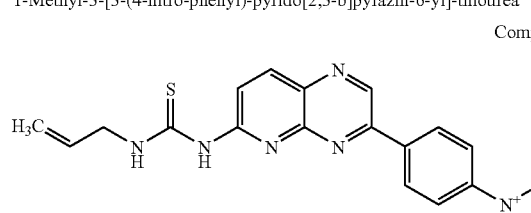

1-Allyl-3-[3-(4-nitro-phenyl)-pyrido[2,3-b]pyrazin-6-yl]-thiourea

Compound 25

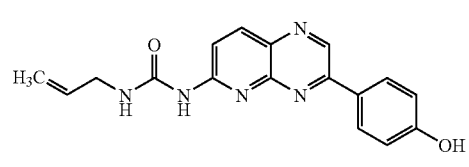

1-Allyl-3-[3-(4-hydroxy-phenyl)-pyrido[2,3-b]pyrazin-6-yl]-urea

Compound 26

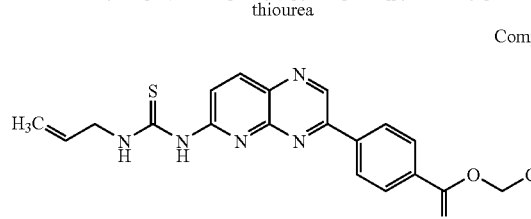

4-[6-(3-Allyl-thioureido)-pyrido[2,3-b]pyrazin-3-yl]-benzoic acid-ethyl-ester

-continued

Compound 27

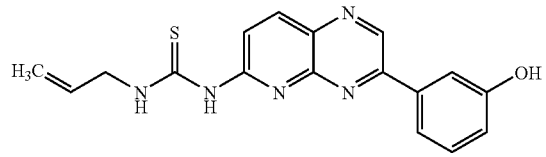

1-Allyl-3-[3-(3-hydroxy-phenyl)-pyrido[2,3-b]pyrazin-6-yl]-thiourea

Compound 28

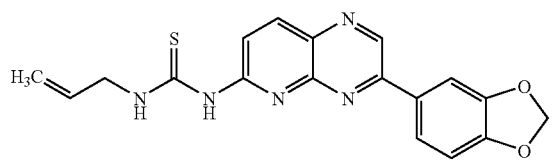

1-Allyl-3-(3-benzo[1,3]dioxol-5-yl-pyrido[2,3-b]pyrazin-6-yl]-thiourea

Compound 29

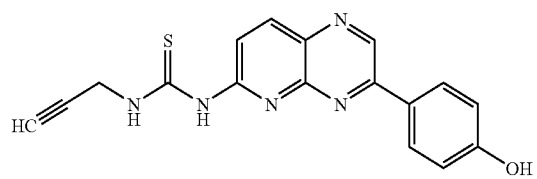

1-[3-(4-Hydroxy-phenyl)-pyrido[2,3-b]pyrazin-6-yl]-3-prop-2-inyl-thiourea

Compound 30

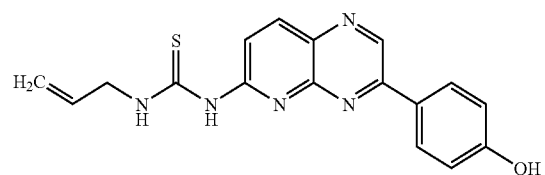

1-Allyl-3-[3-(4-hydroxy-phenyl)-pyrido[2,3-b]pyrazin-6-yl]-thiourea

Compound 31

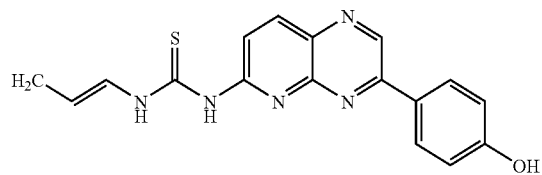

1-[3-(4-Hydroxy-phenyl)-pyrido[2,3-b]pyrazin-6-yl]-3-((E)-propenyl)-thiourea

Compound 32

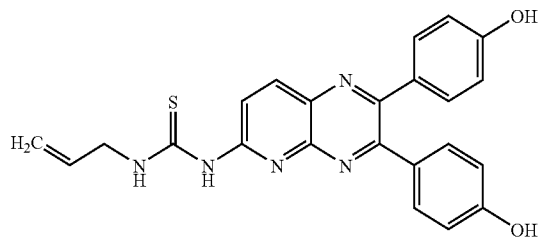

1-Allyl-3-[2,3-bis-(4-hydroxy-phenyl)-pyrido[2,3-b]pyrazin-6-yl]-thiourea

Compound 33

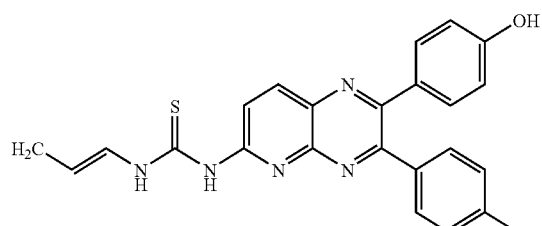

1-[2,3-Bis-(4-hydroxy-phenyl)-pyrido[2,3-b]pyrazin-6-yl]-3-((E)-propenyl)-thiourea Compound 34

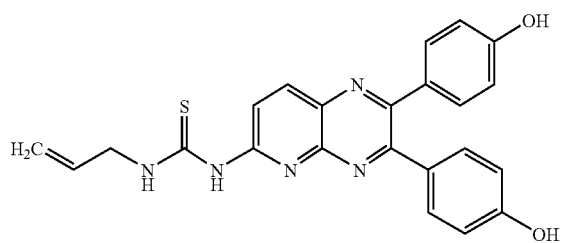

1-Allyl-3-[2-(4-hydroxy-phenyl)-pyrido[2,3-b]pyrazin-6-yl]-thiourea

Compound 35

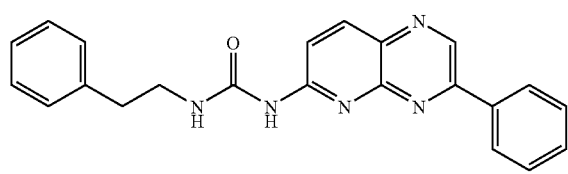

1-Phenylethyl-3-(3-phenyl-pyrido[2,3-b]pyrazin-6-yl)-urea

Compound 36

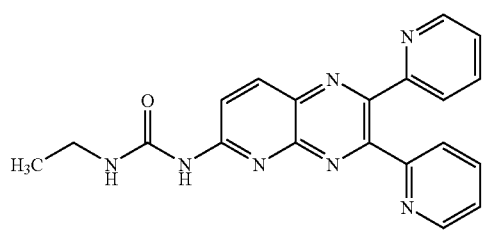

1-(2,3-Di-pyridin-2-yl-pyrido[2,3-b]pyrazin-6-yl)-3-ethyl-urea

-continued

Compound 37

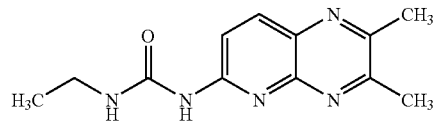

1-(2,3-Dimethyl-pyrido[2,3-b]pyrazin-6-yl)-3-ethyl-urea

Compound 38

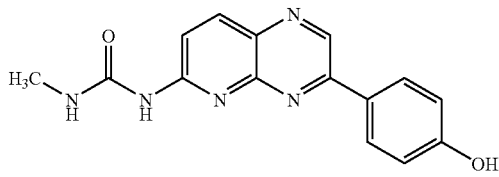

1-[3-(4-Hydroxy-phenyl)-pyrido[2,3-b]pyrazin-6-yl]-3-methyl-urea

Compound 39

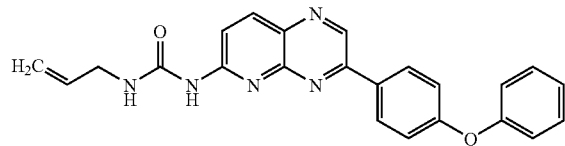

1-Allyl-3-[3-(4-phenoxy-phenyl)-pyrido[2,3-b]pyrazin-6-yl]-urea

Compound 40

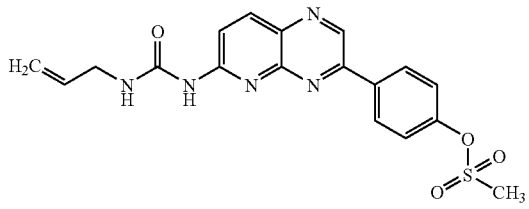

Methane sulfonic acid-4-[6-(3-allyl-ureido)-pyrido[2,3-b]pyrazin-3-yl]-phenyl-ester Compound 41

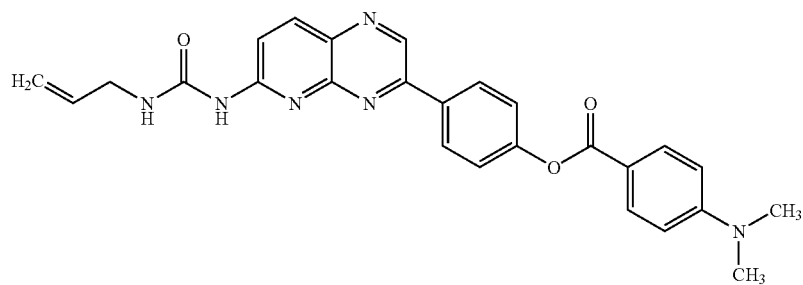

4-Dimethylamino-benzoic acid-4-[6-(3-allyl-ureido)-pyrido[2,3-b]pyrazin-3-yl]-phenyl-ester Compound 42

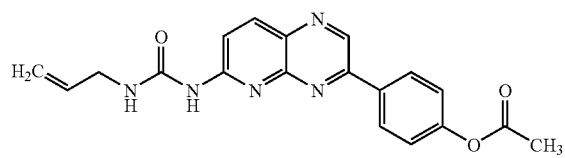

Acetic acid-4-[6-(3-allyl-ureido)-pyrido[2,3-b]pyrazin-3-yl]-phenyl-ester

Compound 43

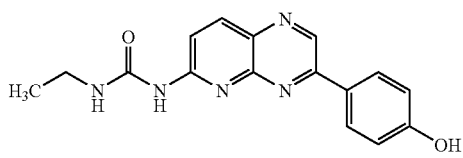

1-Ethyl-3-[3-(4-hydroxy-phenyl)-pyrido[2,3-b]pyrazin-6-yl]-urea

Compound 44

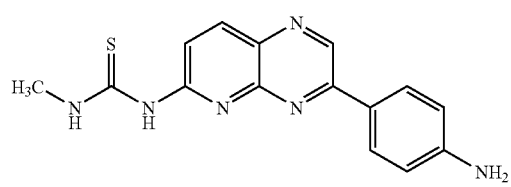

1-[3-(4-Amino-phenyl)-pyrido[2,3-b]pyrazin-6-yl]-3-methyl-thiourea

Compound 45

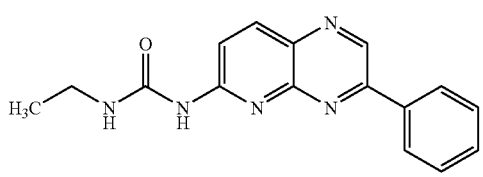

1-Ethyl-3-(3-phenyl-pyrido[2,3-b]pyrazin-6-yl)-urea

Compound 46

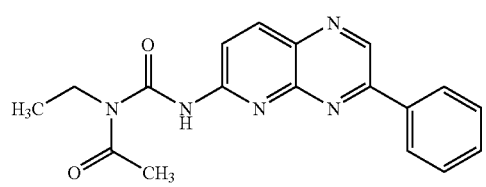

1-Acetyl-1-ethyl-3-(3-phenyl-pyrido[2,3-b]pyrazin-6-yl)-urea

Compound 47

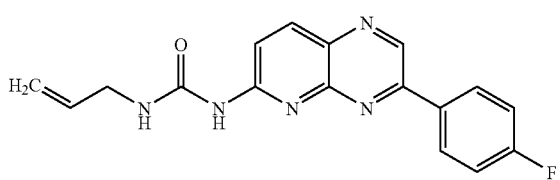

1-Allyl-3-[3-(4-fluoro-phenyl)-pyrido[2,3-b]pyrazin-6-yl]-urea

-continued

Compound 48

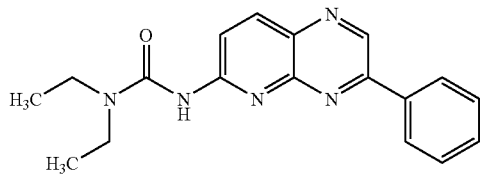

1,1-Diethyl-3-(3-phenyl-pyrido[2,3-b]pyrazin-6-yl)-urea

Compound 49

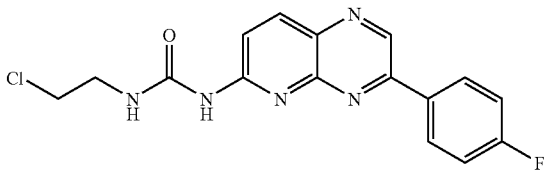

1-(2-Chloro-ethyl)-3-[3-(4-fluoro-phenyl)-pyrido[2,3-b]pyrazin-6-yl]-urea

Compound 50

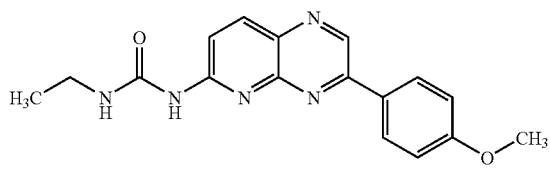

1-Ethyl-3-[3-(4-methoxy-phenyl)-pyrido[2,3-b]pyrazin-6-yl]-urea

Compound 51

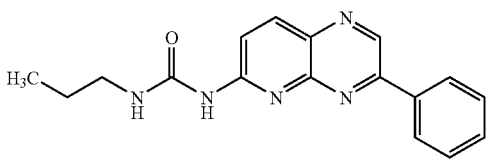

1-(3-Phenyl-pyrido[2,3-b]pyrazin-6-yl)-3-propyl-urea

Compound 52

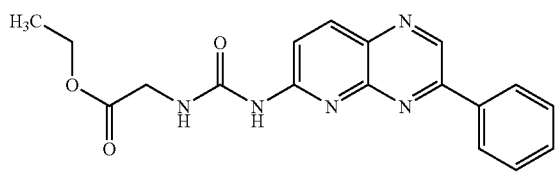

[3-(3-Phenyl-pyrido[2,3-b]pyrazin-6-yl)-ureido]-acetic acid-ethyl-ester

Compound 53

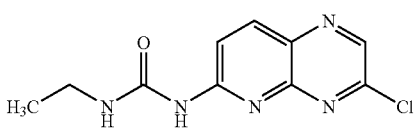

1-(3-Chlorooo-pyrido[2,3-b]pyrazin-6-yl)-3-ethyl-urea

Compound 54

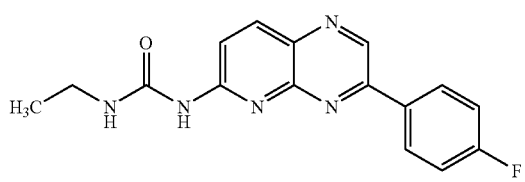

1-Ethyl-3-[3-(4-fluoro-phenyl)-pyrido[2,3-b]pyrazin-6-yl]-urea

Compound 55

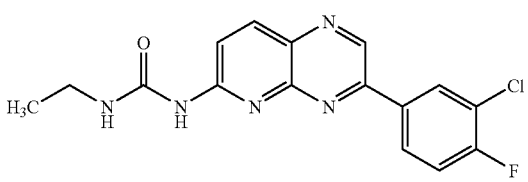

1-[3-(3-Chloro-4-fluoro-phenyl)-pyrido[2,3-b]pyrazin-6-yl]-3-ethyl-urea

Compound 56

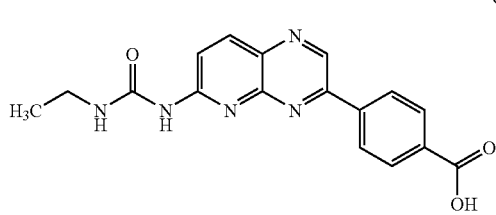

4-[6-(3-Ethyl-ureido)-pyrido[2,3-b]pyrazin-3-yl]-benzoic acid

Compound 57

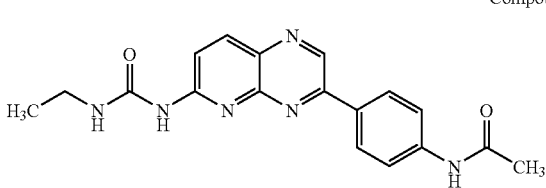

N-{4-[6-(3-Ethyl-ureido)-pyrido[2,3-b]pyrazin-3-yl]-phenyl}-acetamide

Compound 58

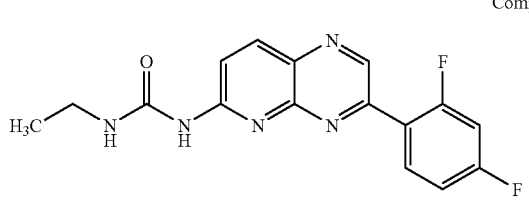

1-[3-(2,4-Difluoro-phenyl)-pyrido[2,3-b]pyrazin-6-yl]-3-ethyl-urea

Compound 59

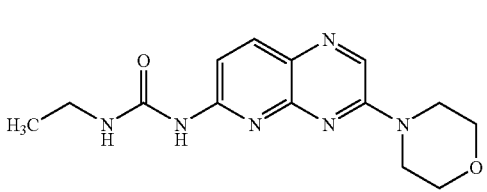

1-Ethyl-3-(3-morpholin-4-yl-pyrido[2,3-b]pyrazin-6-yl)-urea

-continued

Compound 60

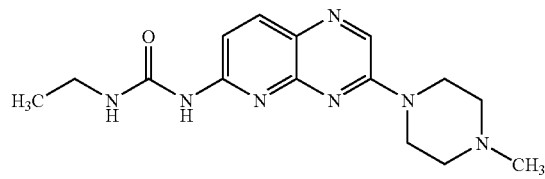

1-Ethyl-3-[3-(4-methyl-piperazin-1-yl)-pyrido[2,3-b]pyrazin-6-yl]-urea

Compound 61

1-Ethyl-3-[3-(2-hydroxy-phenyl)-pyrido[2,3-b]pyrazin-6-yl]-urea

Compound 62

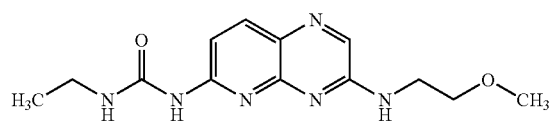

1-Ethyl-3-[3-(2-methoxy-ethylamino)-pyrido[2,3-b]pyrazin-6-yl]-urea

Compound 63

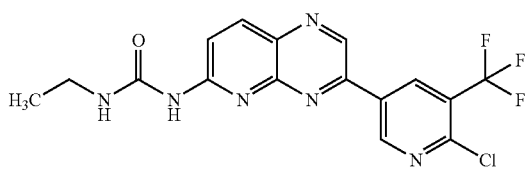

1-[3-(4-Chloro-3-trifluoromethyl-phenyl)-pyrido[2,3-b]pyrazin-6-yl]-3-ethyl-urea Compound 64

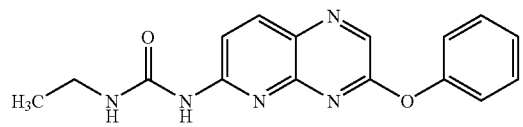

1-Ethyl-3-(3-phenoxy-pyrido[2,3-b]pyrazin-6-yl)-urea

Compound 65

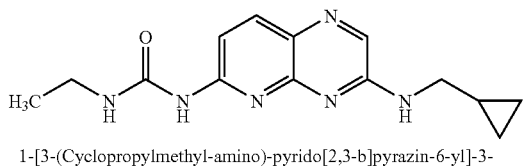

1-[3-(Cyclopropylmethyl-amino)-pyrido[2,3-b]pyrazin-6-yl]-3-ethyl-urea

Compound 66

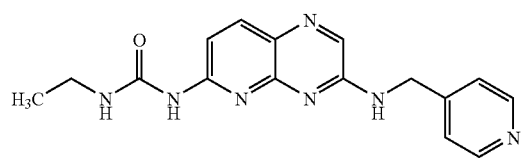

1-Ethyl-3-{3-[(pyridin-4-ylmethyl)-amino]-pyrido[2,3-b]pyrazin-6-yl}-urea

Compound 67

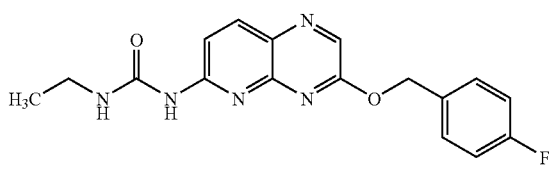

1-Ethyl-3-[3-(4-fluoro-benzyloxy)-pyrido[2,3-b]pyrazin-6-yl]-urea

Compound 68

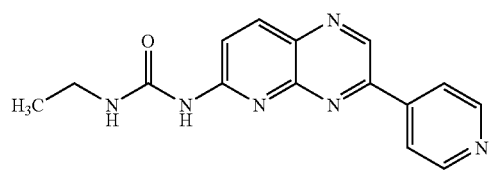

1-Ethyl-3-(3-pyridin-4-yl-pyrido[2,3-b]pyrazin-6-yl)-urea

Compound 69

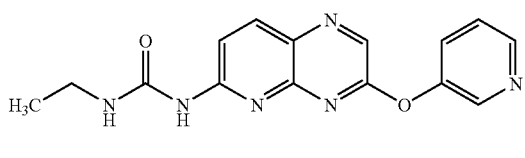

1-Ethyl-3-[3-pyridin-3-yloxy)-pyrido[2,3-b]pyrazin-6-yl]-urea

Compound 70

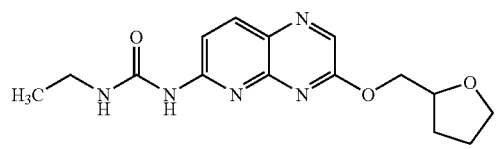

1-Ethyl-3-[3-(tetrahydro-furan-2-ylmethoxy)-pyrido[2,3-b]pyrazin-6-yl]-urea

Compound 71

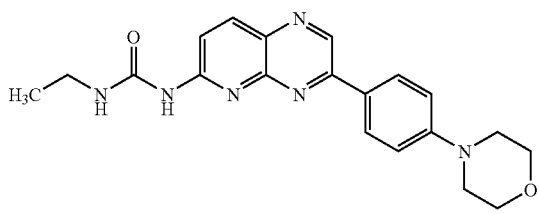

1-Ethyl-3-[3-(4-morpholin-4-yl-phenyl)-pyrido[2,3-b]pyrazin-6-yl]-urea

-continued

Compound 72

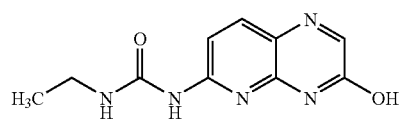

1-Ethyl-3-(3-hydroxy-pyrido[2,3-b]pyrazin-6-yl)-urea

Compound 73

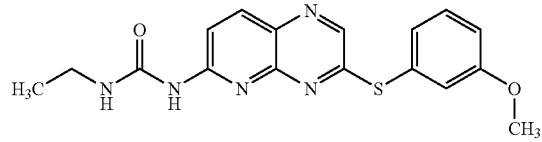

1-Ethyl-3-[3-(3-methoxy-phenylsulfanyl)-pyrido[2,3-b]pyrazin-6-yl]-urea

Compound 74

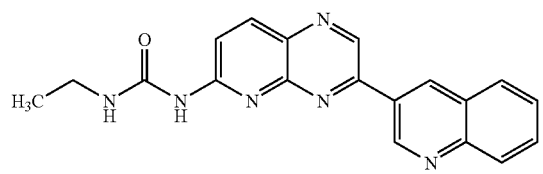

1-Ethyl-3-(3-quinolin-3-yl-pyrido[2,3-b]pyrazin-6-yl)-urea

Compound 75

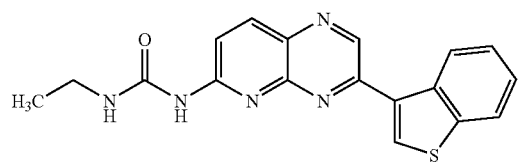

1-(3-Benzo[b]thiophen-3-yl-pyrido[2,3-b]pyrazin-6-yl)-3-ethyl-urea

Compound 76

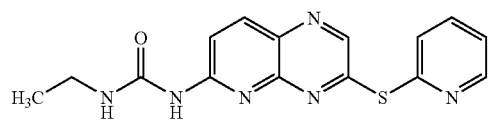

1-Ethyl-3-[3-(pyridin-2-ylsulfanyl)-pyrido[2,3-b]pyrazin-6-yl]-urea

Compound 77

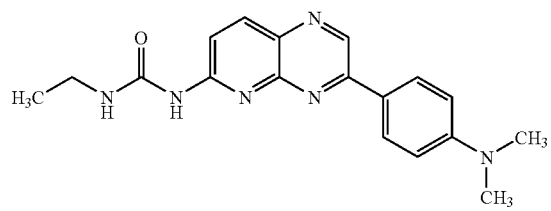

1-[3-(4-Dimethylamino-phenyl)-pyrido[2,3-b]pyrazin-6-yl]-3-ethyl-urea

Compound 78

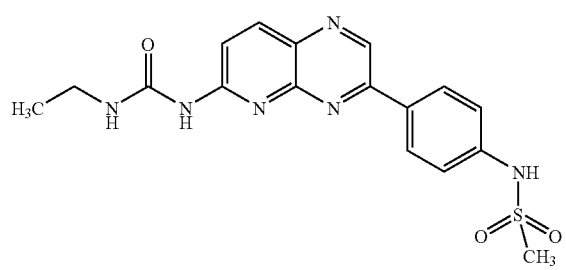

N-{4-[6-(3-Ethyl-ureido)-pyrido[2,3-b]pyrazin-3-yl]-phenyl}-methansulfonamide

Compound 79

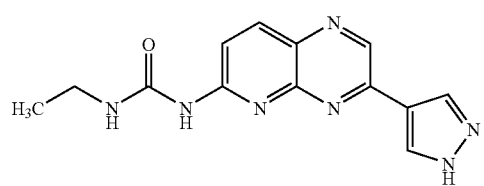

1-Ethyl-3-[3-(1H-pyrazol-4-yl)-pyrido[2,3-b]pyrazin-6-yl]-urea

Compound 80

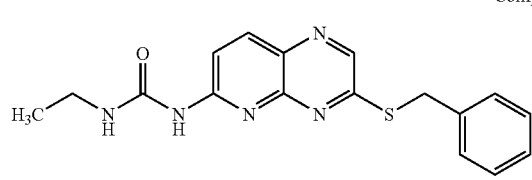

1-(3-Benzylsulfanyl-pyrido[2,3-b]pyrazin-6-yl)-3-ethyl-urea

Compound 81

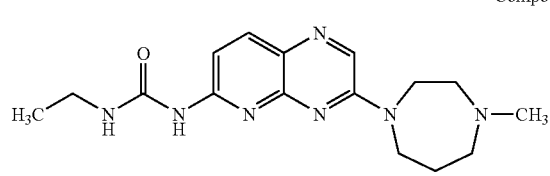

1-Ethyl-3-[3-(4-methyl-[1,4]diazepan-1-yl)-pyrido[2,3-b]pyrazin-6-yl]-urea

Compound 82

1-[3-(4-Amino-phenyl)-pyrido[2,3-b]pyrazin-6-yl]-3-ethyl-urea

Compound 83

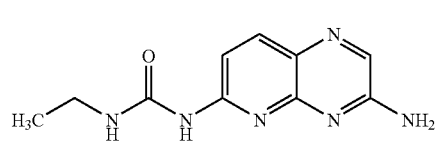

1-(3-Amino-pyrido[2,3-b]pyrazin-6-yl)-3-ethyl-urea

-continued

Compound 84

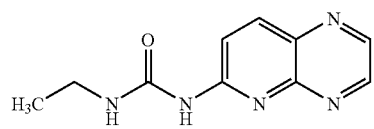

1-Ethyl-3-pyrido[2,3-b]pyrazin-6-yl-urea

Compound 85

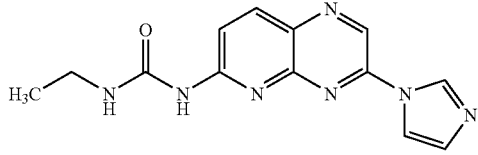

1-Ethyl-3-(3-imidazol-1-yl-pyrido[2,3-b]pyrazin-6-yl)-urea

Compound 86

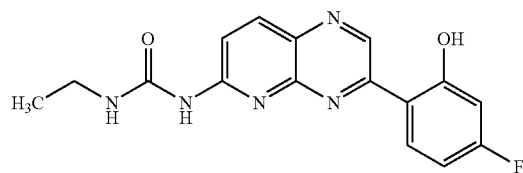

1-Ethyl-3-[3-(4-fluoro-2-hydroxy-phenyl)-pyrido[2,3-b]pyrazin-6-yl]-

Compound 87

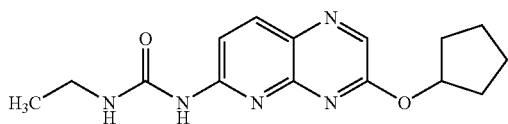

1-(3-Cyclopentyloxy-pyrido[2,3-b]pyrazin-6-yl)-3-ethyl-urea

Compound 88

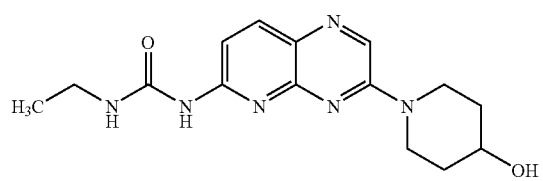

1-Ethyl-3-[3-(4-hydroxy-piperidin-1-yl)-pyrido[2,3-b]pyrazin-6-yl]-urea

Compound 89

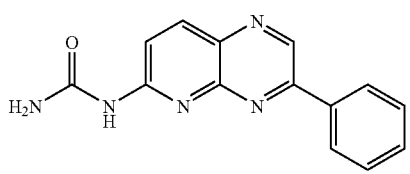

(3-Phenyl-pyrido[2,3-b]pyrazin-6-yl)-urea

Compound 90

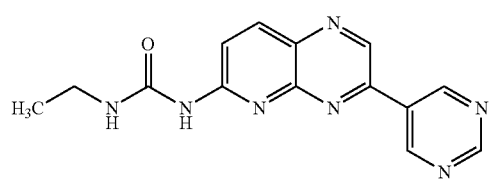

1-Ethyl-3-(3-pyrimidin-5-yl-pyrido[2,3-b]pyrazin-6-yl)-urea

Compound 91

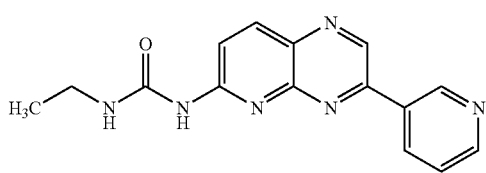

1-Ethyl-3-(3-pyridin-3-yl-pyrido[2,3-b]pyrazin-6-yl)-urea

Compound 92

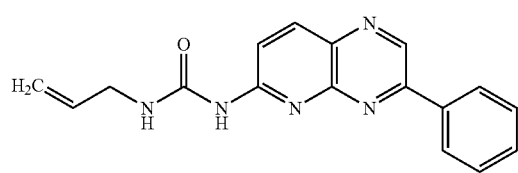

1-Allyl-3-(3-phenyl-pyrido[2,3-b]pyrazin-6-yl)-urea

Compound 93

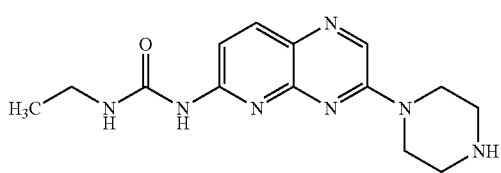

1-Ethyl-3-(3-piperazin-1-yl-pyrido[2,3-b]pyrazin-6-yl)-urea

Compound 94

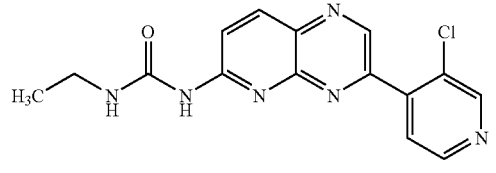

1-[3-(3-Chloro-pyridin-4-ylmethyl)-pyrido[2,3-b]pyrazin-6-yl]-3-ethyl-urea

Compound 95

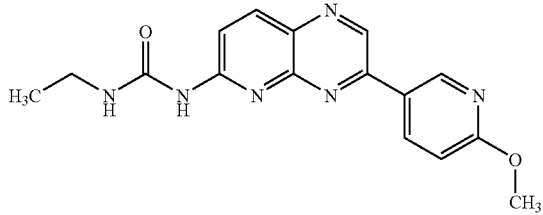

1-Ethyl-3-[3-(6-methoxy-pyridin-3-yl)-pyrido[2,3-b]pyrazin-6-yl]-urea

-continued

Compound 96

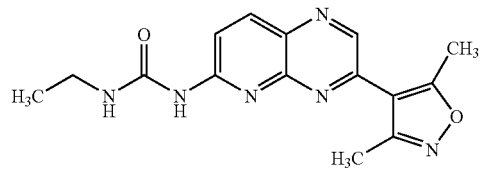

rido[2,3-b]pyrazin-6-yl]-3-ethyl-

Compound 97

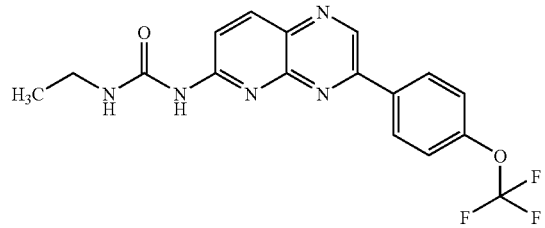

1-Ethyl-3-[3-(4-trifluoromethoxy-phenyl)pyrido[2,3-b]pyrazin-6-yl]-urea

Compound 98

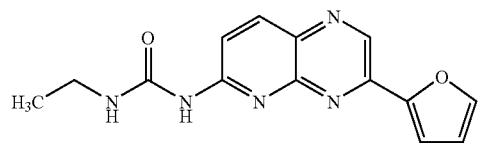

1-Ethyl-3-(3-furan-2-yl-pyrido[2,3-b]pyrazin-6-yl)-urea

Compound 99

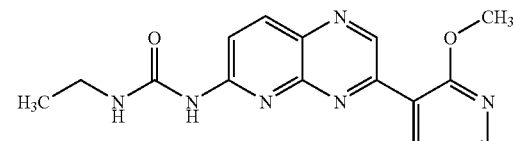

1-Ethyl-3-[3-(2-methoxy-pyridin-3-yl)-pyrido[2,3-b]pyrazin-6-yl]-urea

Compound 100

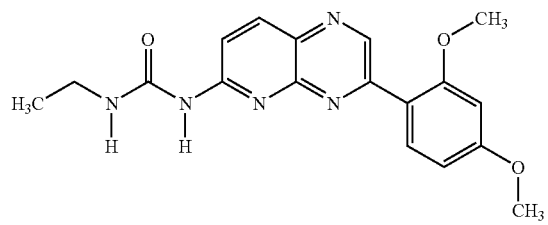

1-[3-(2,4-Dimethoxy-phenyl)-pyrido[2,3-b]pyrazin-6-yl]-3-ethyl-urea

Compound 101

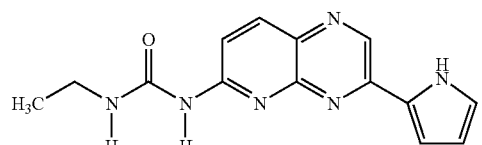

2,3-b]pyrazin-6-yl]-urea

Compound 102

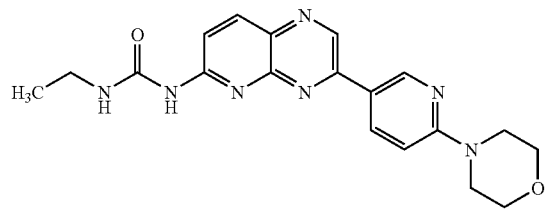

1-Ethyl-3-[3-(6-morpholin-4-yl-pyridin-3-yl)-pyrido[2,3-b]pyrazin-6-yl]-urea

Compound 103

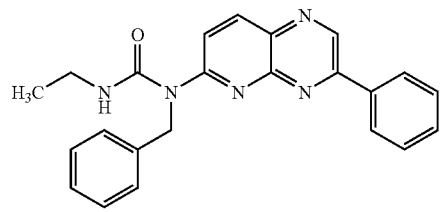

1-Benzyl-3-ethyl-1-(3-phenyl-pyrido[2,3-b]pyrazin-6-yl)-urea

Compound 104

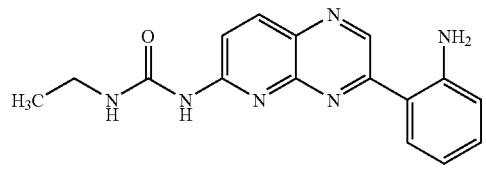

1-[3-(2-Amino-phenyl)-pyrido[2,3-b]pyrazin-6-yl]-3-ethyl-urea

Compound 105

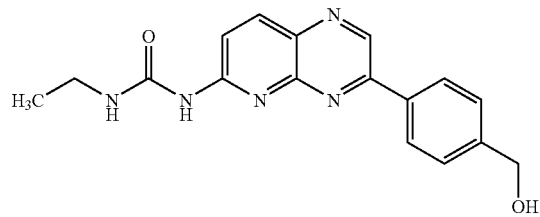

1-Ethyl-3-[3-(4-hydroxymethyl-phenyl)-pyrido[2,3-b]pyrazin-6-yl]-urea

-continued

Compound 106

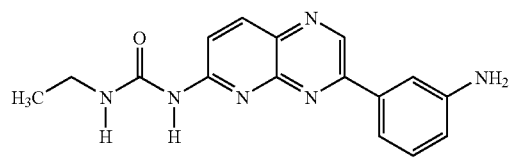

1-[3-(3-Amino-phenyl)-pyrido[2,3-b]pyrazin-6-yl]-
3-ethyl-urea

Compound 107

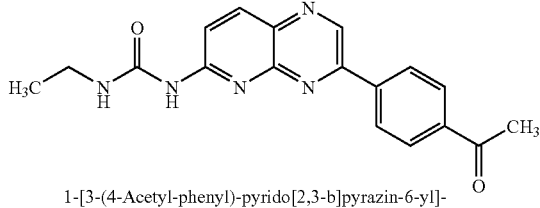

1-[3-(4-Acetyl-phenyl)-pyrido[2,3-b]pyrazin-6-yl]-
3-ethyl-urea

Compound 108

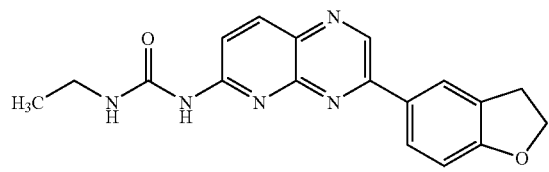

1-[3-(2,3-Dihydro-benzofuran-5-yl)-pyrido[2,3-b]pyrazin-6-
yl]-3-ethyl-urea

Compound 109

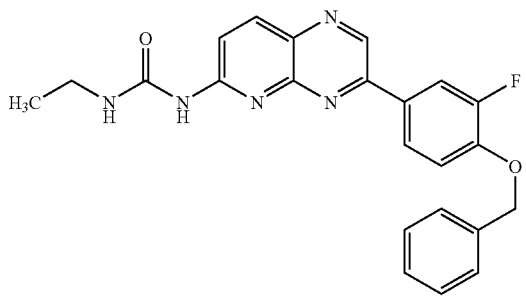

1-[3-(4-Benzyloxy-3-fluoro-phenyl)-pyrido[2,3-b]pyrazin-6-
yl]-3-ethyl-urea

Compound 110

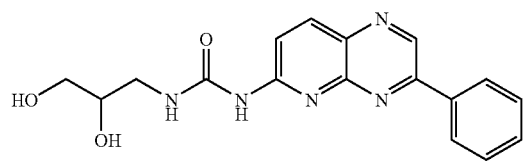

1-(2,3-Dihydroxy-propyl)-3-(3-phenyl-pyrido[2,3-b]pyrazin-
6-yl)-urea

Compound 111

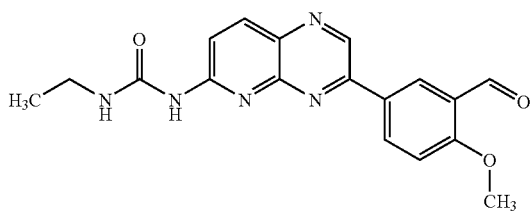

1-Ethyl-3-[3-(3-formyl-4-methoxy-phenyl)-pyrido[2,3-b]pyrazin-
6-yl]-urea

Compound 112

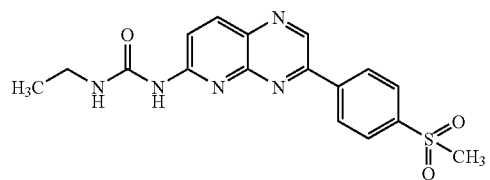

1-Ethyl-3-[3-(4-methansulfonyl-phenyl)-pyrido[2,3-b]pyrazin-
6-yl]-urea

Compound 113

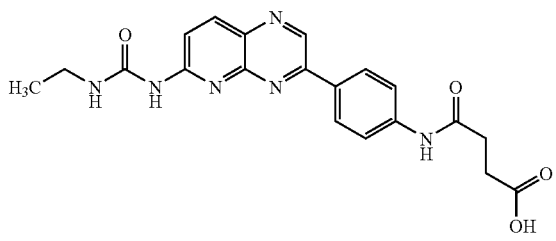

N-{4-[6-(3-Ethyl-ureido)-pyrido[2,3-b]pyrazin-3-yl]-phenyl}-
succinamid acid

Compound 114

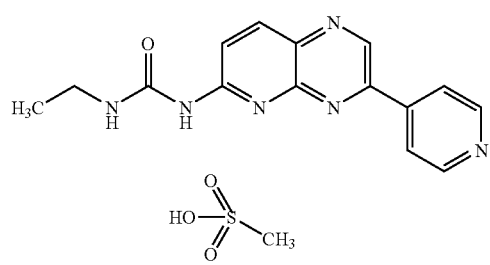

1-Ethyl-3-(3-pyridin-4-yl-pyrido[2,3-b]pyrazin-6-yl)-urea
Methane sulfonic acid salt (free base)

Compound 115

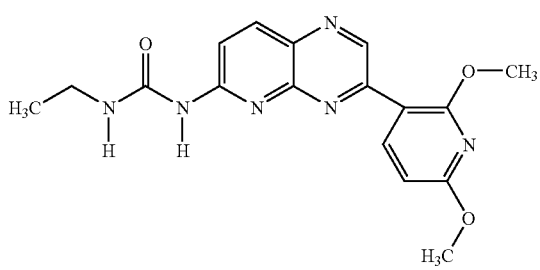

1-[3-(2,6-Dimethoxy-pyridin-3-yl)-pyrido[2,3-b]pyrazin-6-yl]-
3-ethyl-urea

-continued

Compound 116

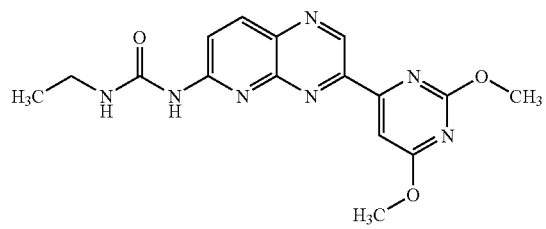

1-[3-(2,6-Dimethoxy-pyrimidin-4-yl)-pyrido[2,3-b]pyrazin-6-yl]-3-ethyl-urea

Compound 117

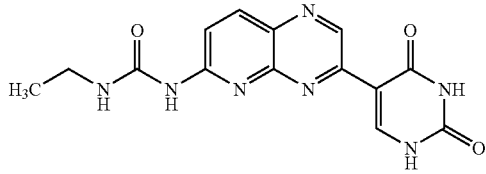

1-[3-(2,4-Dioxo-1,2,3,4-tetrahydro-pyrimidin-5-yl)-pyrido[2,3-b]pyrazin-6-yl]-3-ethyl-urea Compound 188

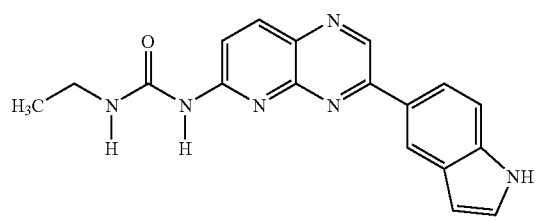

1-Ethyl-3-[3-(1H-indol-5-yl)-pyrido[2,3-b]pyrazin-6-yl]-urea

Compound 119

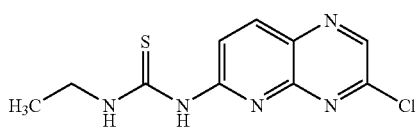

1-(3-Chloro-pyrido[2,3-b]pyrazin-6-yl)-3-ethyl-thiourea

Compound 120

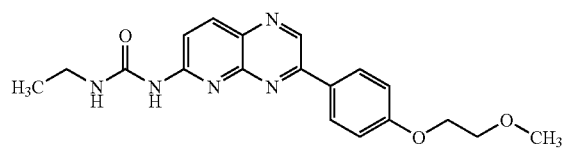

1-Ethyl-3-{3-[4-(2-methoxy-ethoxy)-phenyl]-pyrido[2,3-b]pyrazin-6-yl}-urea

Compound 121

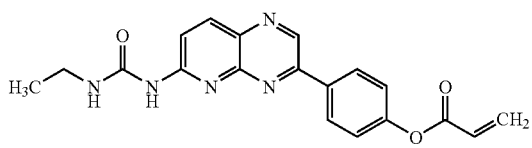

Acrylic acid-4-[6-(3-ethyl-ureido)-pyrido[2,3-b]-pyrazin-3-yl]phenyl-ester

Compound 122

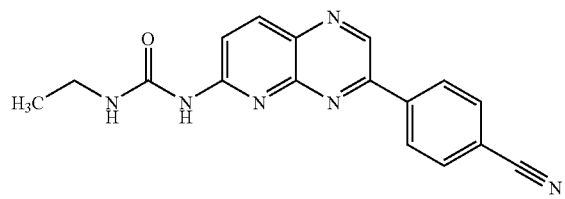

1-[3-(4-Cyano-phenyl)-pyrido[2,3-b]pyrazin-6-yl]-3-ethyl-urea

Compound 123

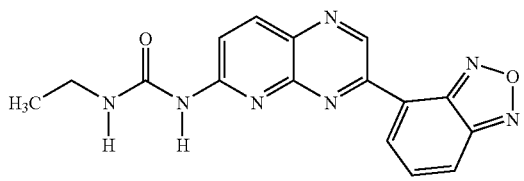

1-(3-Benzo[1,2,5]oxadiazol-4-yl-pyrido[2,3-b]pyrazin-6-yl)-3-ethyl-urea

Compound 124

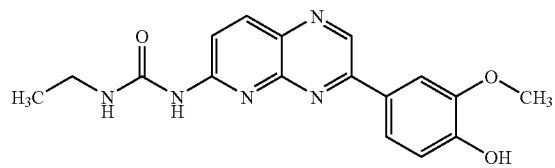

1-Ethyl-3-[3-(4-hydroxy-3-methoxy-phenyl)-pyrido[2,3-b]pyrazin-6-yl]-urea

Compound 125

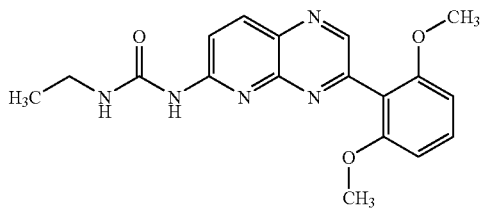

1-[3-(2,6-Dimethoxy-phenyl)-pyrido[2,3-b]pyrazin-6-yl]-3-ethyl-urea

-continued

Compound 126

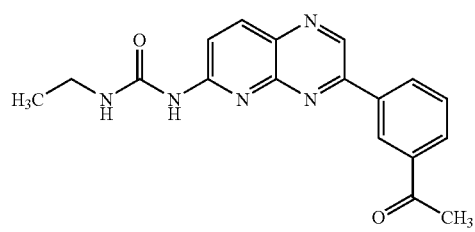

1-[3-(3-Acetyl-phenyl)-pyrido[2,3-b]pyrazin-6-yl]-3-ethyl-urea

Compound 127

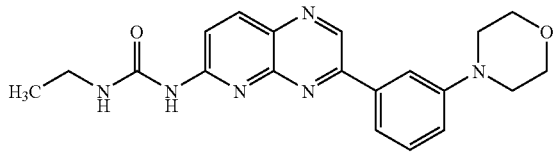

1-Ethyl-3-[3-(3-morpholin-4-yl-phenyl)-pyrido[2,3-b]pyrazin-6-yl]-urea

Compound 128

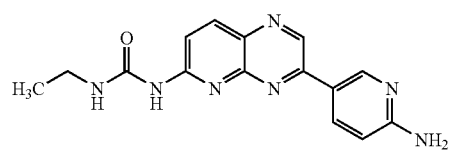

1-[3-(6-Amino-pyridin-3-yl)-pyrido[2,3-b]pyrazin-6-yl]-3-ethyl-urea

Compound 129

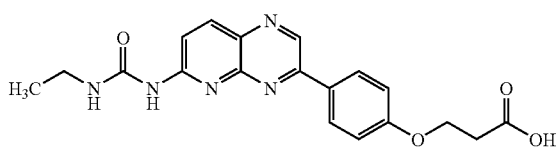

3-{4-[6-(3-Ethyl-ureido)-pyrido[2,3-b]-pyrazin-3-yl]-phenoxy}-propionic acid

Compound 130

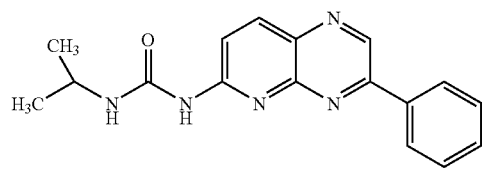

1-Isopropyl-3-(3-phenyl-pyrido[2,3-b]pyrazin-6-yl)-urea

Compound 131

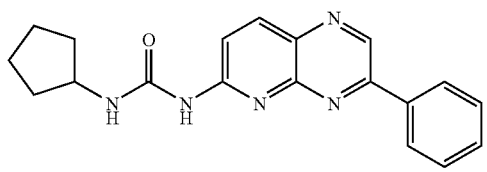

1-Cyclopentyl-3-(3-phenyl-pyrido[2,3-b]pyrazin-6-yl)-urea

Compound 132

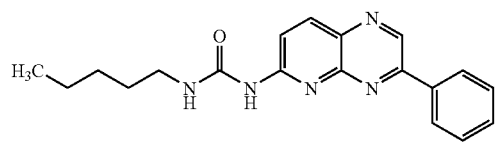

1-Pentyl-3-(3-phenyl-pyrido[2,3-b]pyrazin-6-yl)-urea

Compound 133

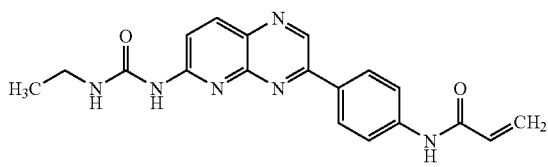

N-{4-[6-(3-Ethyl-ureido)-pyrido[2,3-b]pyrazin-3-yl]-phenyl}-acrylamide

Compound 134

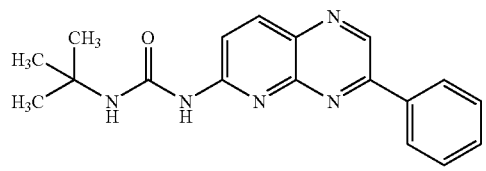

1-tert-Butyl-3-(3-phenyl-pyrido[2,3-b]pyrazin-6-yl)-urea

Compound 135

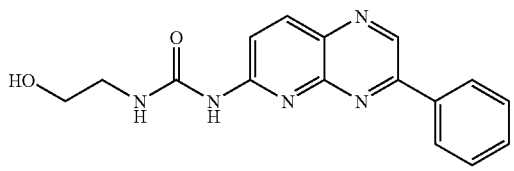

1-(2-Hydroxy-ethyl)-3-(3-phenyl-pyrido[2,3-b]pyrazin-6-yl)-urea

Compound 136

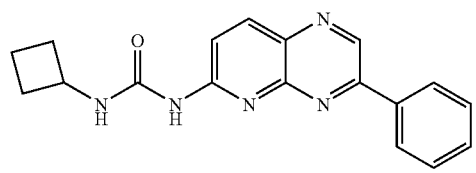

1-Cyclobutyl-3-(3-phenyl-pyrido[2,3-b]pyrazin-6-yl)-urea

Compound 137

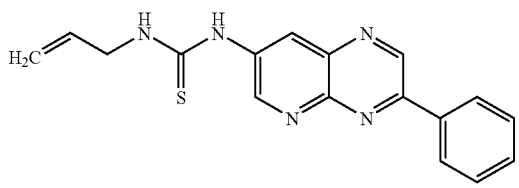

1-Allyl-3-[3-(4-nitro-phenyl)-pyrido[2,3-b]pyrazin-7-yl]-thiourea

-continued

Compound 138

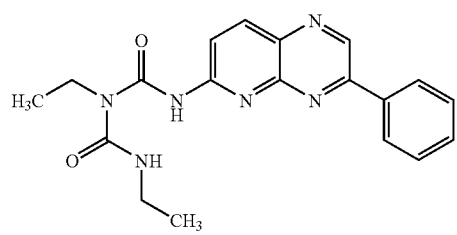

1-Ethyl-1-(Ethylcarbamoyl)-3-(3-phenyl-pyrido[2,3-b]pyrazin-6-yl)-urea

Compound 139

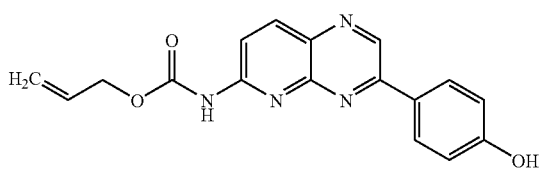

[3-(4-Hydroxy-phenyl)-pyrido[2,3-b]pyrazin-6-yl]-carbamic acid-allyl-ester

Compound 140

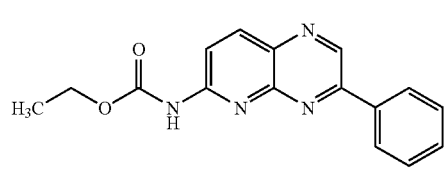

(3-Phenyl-pyrido[2,3-b]pyrazin-6-yl)-carbamic acid-ethyl-ester

Compound 141

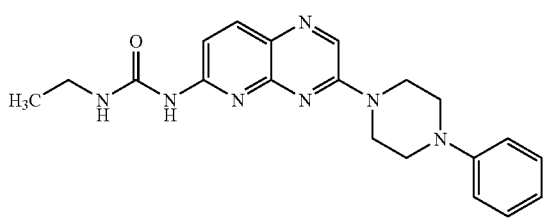

1-Ethyl-3-[3-(4-phenyl-piperazin-1-yl)-pyrido[2,3-b]pyrazin-6-yl]-urea

Compound 142

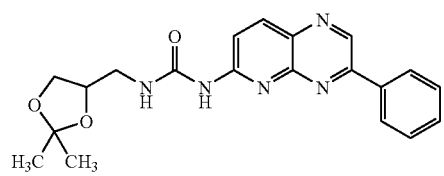

thyl)-3-(3-phenyl-pyrido[2,3-

Compound 143

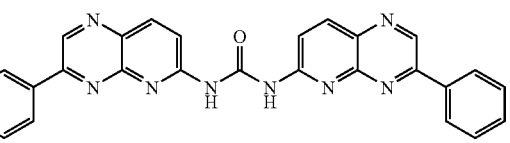

1,3-Bis-(3-phenyl-pyrido[2,3-b]pyrazin-6-yl)-urea

Compound 144

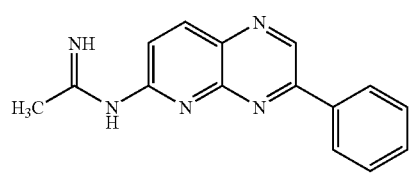

N-(3-Phenyl-pyrido[2,3-b]pyrazin-6-yl)-acetamidine

Compound 145

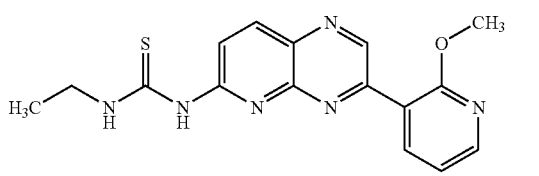

1-Ethyl-3-[3-(2-methoxy-pyridin-3-yl)-pyrido[2,3-b]pyrazin-6-yl]-thiourea

Compound 146

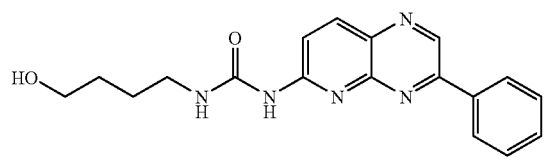

1-(4-Hydroxy-butyl)-3-(3-phenyl-pyrido[2,3-b]pyrazin-6-yl)-urea

Compound 147

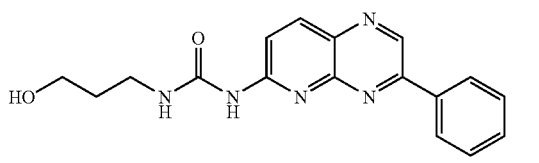

1-(3-Hydroxy-propyl)-3-(3-phenyl-pyrido[2,3-b]pyrazin-6-yl)-urea

Compound 148

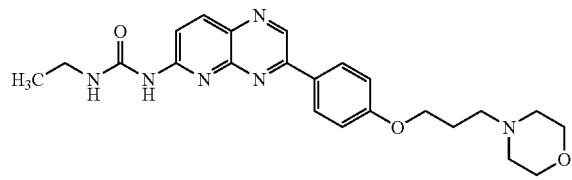

1-Ethyl-3-{3-[4-(3-morpholin-4-yl-propoxy)-phenyl]-pyrido[2,3-b]pyrazin-6-yl}-urea Compound 149

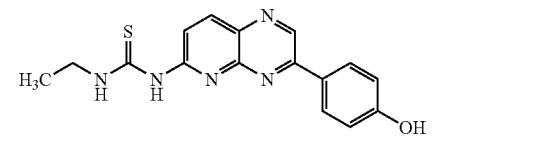

1-Ethyl-3-[3-(4-hydroxy-phenyl)-pyrido[2,3-b]pyrazin-6-yl]-thiourea

-continued

Compound 150

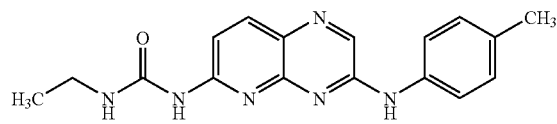

1-Ethyl-3-(3-p-tolylamino-pyrido[2,3-b]pyrazin-6-yl)-urea

Compound 151

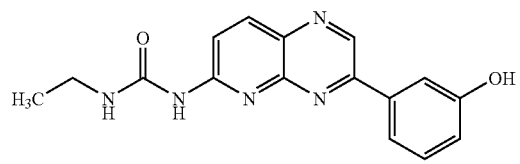

1-Ethyl-3-[3-(3-hydroxy-phenyl)-pyrido[2,3-b]pyrazin-6-yl]-urea

Compound 152

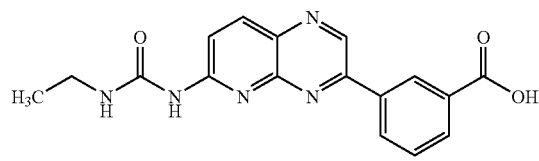

3-[6-(3-Ethyl-ureido)-pyrido[2,3-b]pyrazin-3-yl]-benzoic acid

Compound 153

1-[3-(3,4-Dimethoxy-phenyl)-pyrido[2,3-b]pyrazin-6-yl]-3-ethyl-urea

Compound 154

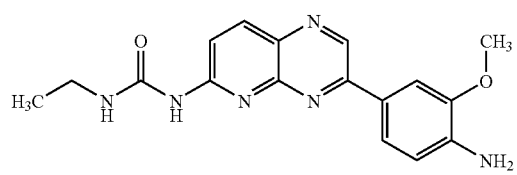

1-[3-(4-Amino-3-methoxy-phenyl)-pyrido[2,3-b]pyrazin-6-yl]-3-ethyl-urea

Compound 155

3-[6-(3-Ethyl-ureido)-pyrido[2,3-b]-pyrazin-3-yl]-benzamide

Compound 156

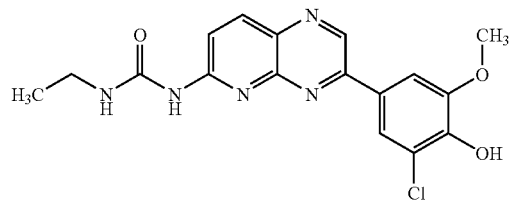

1-[3-(3-Chloro-4-hydroxy-5-methoxy-phenyl)-pyrido[2,3-b]pyrazin-6-yl]-3-ethyl-urea Compound 157

1-Ethyl-3-(3-m-tolyamino-pyrido-[2,3-b]pyrazin-6-yl)-urea

Compound 158

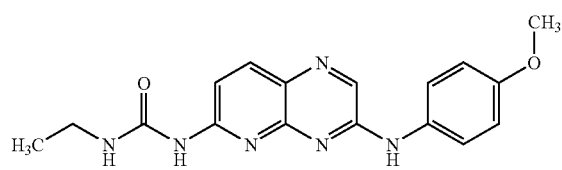

1-Ethyl-3-[3-(4-methoxy-phenylamino)-pyrido[2,3-b]pyrazin-6-yl]-urea

Compound 159

1-[3-(4-Chloro-phenylamino)-pyrido[2,3-b]pyrazin-6-yl]-3-ethyl-urea

Compound 160

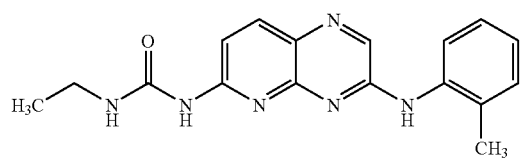

1-Ethyl-3-(3-o-tolyamino-pyrido-[2,3-b]-pyrazin-6-yl)-urea

Compound 161

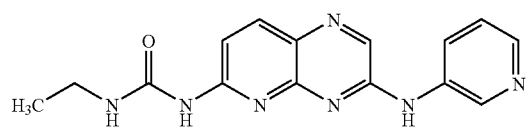

1-Ethyl-3-[3-(pyridin-3-ylamino)-pyrido-[2,3-b]pyrazin-6-yl]-urea

Compound 162

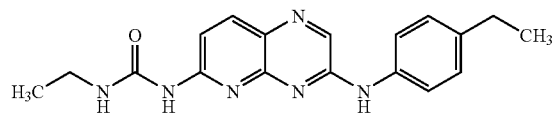

1-Ethyl-3-[3-(4-ethyl-phenylamino)-pyrido[2,3-b]pyrazin-6-yl]-urea

Compound 163

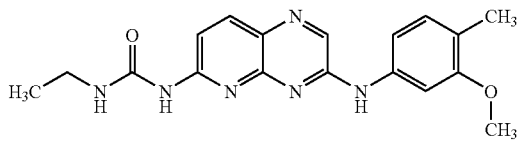

1-Ethyl-3-[3-(3-methoxy-4-methyl-phenylamino)-pyrido[2,3-b]pyrazin-6-yl]-urea

Compound 164

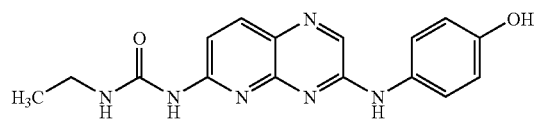

1-Ethyl-3-[3-(4-hydroxy-phenylamino)-pyrido[2,3-b]pyrazin-6-yl]-urea

Compound 165

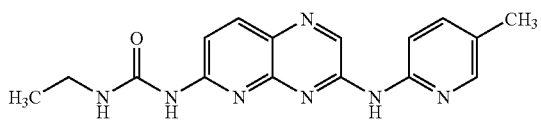

1-Ethyl-3-[3-(5-methyl-pyridin-2-yl-amino)-pyrido[2,3-b]pyrazin-6-yl]-urea

Compound 166

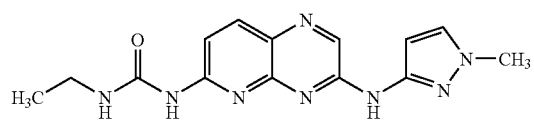

1-Ethyl-3-[3-(1-methyl-1H-pyrazol-3-ylamino)-pyrido[2,3-b]pyrazin-6-yl]-urea

Compound 167

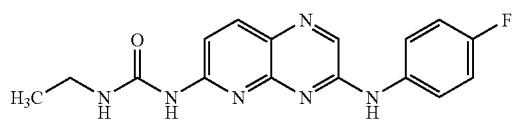

1-Ethyl-3-[3-(4-fluoro-phenylamino)-pyrido[2,3-b]pyrazin-6-yl]-urea

Compound 168

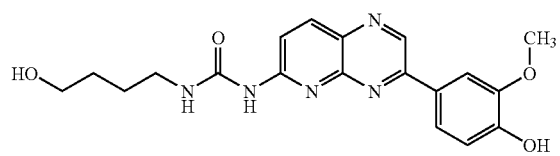

1-(4-Hydroxy-butyl)-3-[3-(4-hydroxy-3-methoxy-phenyl)-pyrido[2,3-b]pyrazin-6-yl]-urea Compound 169

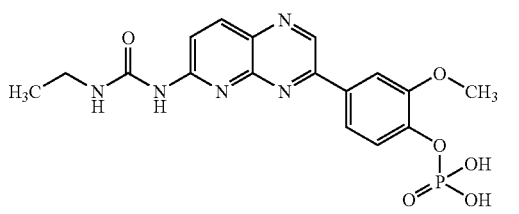

Phosphoric acid-mono-{4-[6-(3-ethyl-ureido)-pyrido-[2,3-b]pyrazin-3-yl]-2-methoxy-phenyl}-ester Compound 170

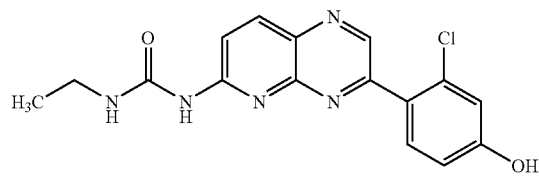

1-[3-(2-Chloro-4-hydroxy-phenyl)-pyrido[2,3-b]pyrazin-6-yl]-3-ethyl-urea

Compound 171

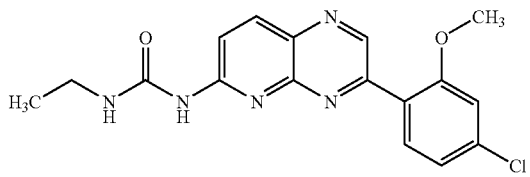

1-[3-(4-Chloro-2-methoxy-phenyl)-pyrido[2,3-b]pyrazin-6-yl]-3-ethyl-urea

Compound 172

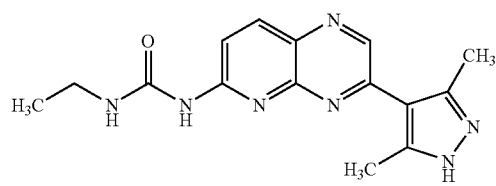

1-[3-(3,5-Dimethyl-1H-pyrazol-4-yl)-pyrido[2,3-b]pyrazin-6-yl]-3-ethyl-urea

Compound 173

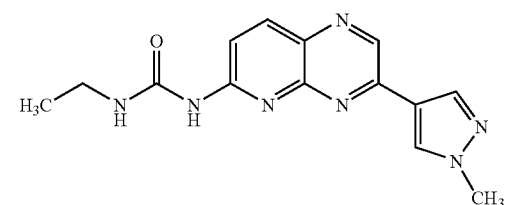

1-Ethyl-3-[3-(1-methyl-1H-pyrazol-4-yl)-pyrido[2,3-b]pyrazin-6-yl]-urea

-continued

Compound 174

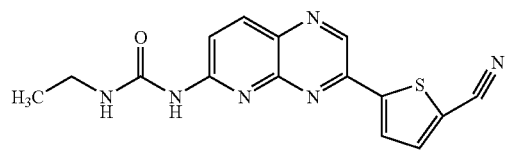

1-[3-(5-Cyano-thiophen-2-yl)-pyrido[2,3-b]pyrazin-
6-yl]-3-ethyl-urea

Compound 175

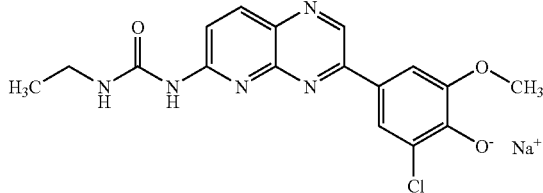

Sodium 2-chloro-4-[6-(3-ethyl-ureido)-pyrido[2,3-b]pyrazin-
3-yl]-6-methoxy-phenolate Compound 176

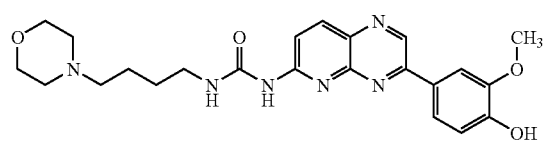

1-[3-(4-Hydroxy-3-methoxy-phenyl)-pyrido[2,3-b]pyrazin-
6-yl]-3-(4-morpholin-4-yl-butyl)-urea Compound 177

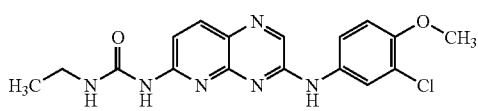

1-[3-(3-Chloro-4-methoxy-phenylamino)-pyrido[2,3-
b]pyrazin-6-yl]-3-ethyl-urea

Compound 178

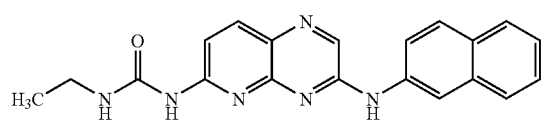

1-Ethyl-3-[3-(naphthalin-2-ylamino)-pyrido[2,3-b]pyrazin-
6-yl]-urea

Compound 179

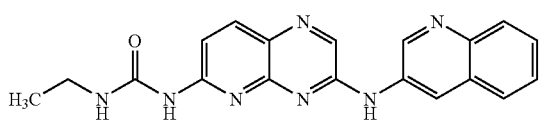

1-Ethyl-3-[3-(quinolin-3-ylamino)-pyrido[2,3-b]pyrazin-
6-yl]-urea

Compound 180

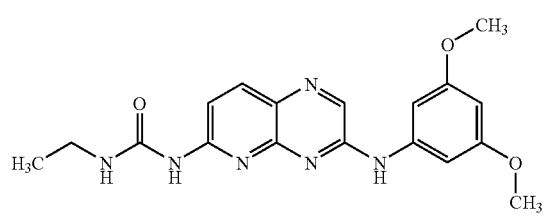

1-[3-(3,5-Dimethoxy-phenylamino)-pyrido[2,3-b]pyrazin-
6-yl]-3-ethyl-urea

Compound 181

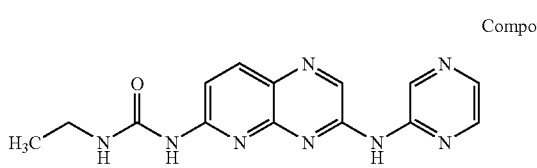

1-Ethyl-3-[3-(pyrazin-2-ylamino)-pyrido[2,3-b]pyrazin-
6-yl]-urea

Compound 182

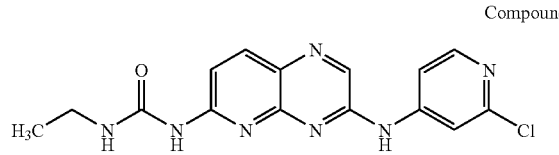

1-Ethyl-3-[3-(3-isopropoxy-phenylamino)-pyrido[2,3-b]pyrazin-
6-yl]-urea

Compound 183

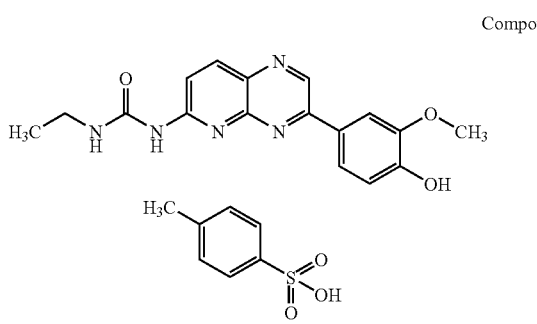

1-Ethyl-3-[3-(4-hydroxy-3-methoxy-phenyl)-pyrido[2,3-
b]pyrazin-6-yl]-urea p-Toluolsulfonat Compound 184

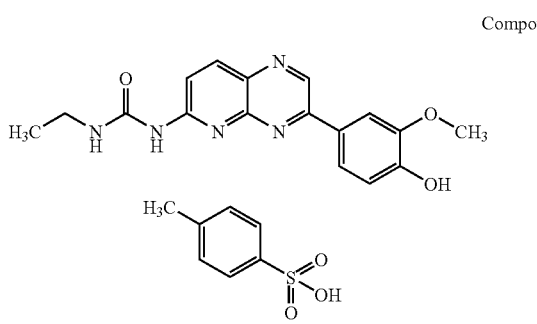

1-[3-(2-Chloro-pyridin-4-ylamino)-pyrido[2,3-b]-pyrazin-
6-yl]-3-ethyl-urea

Compound 185

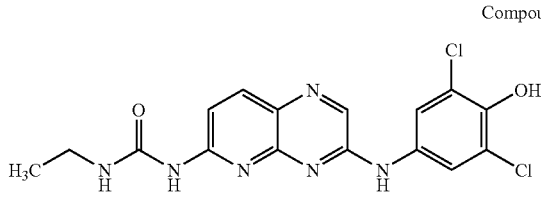

1-[3-(3,5-Dichloro-4-hydroxy-phenylamino)-pyrido[2,3-b]pyrazin-
6-yl]-3-ethyl-urea Compound 186

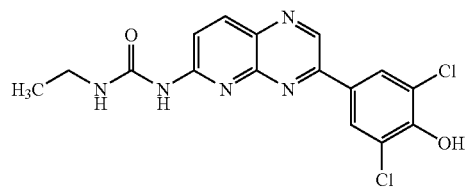

1-[3-(3,5-Dichloro-4-hydroxy-phenyl)-pyrido[2,3-b]pyrazin-6-yl]-3-ethyl-urea

Compound 187

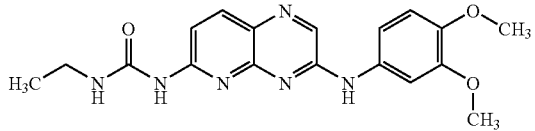

1-[3-(3,4-Dimethoxy-phenylamino)-pyrido[2,3-b]pyrazin-6-yl]-3-ethyl-urea

Compound 188

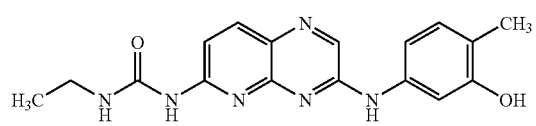

1-Ethyl-3-[3-(3-hydroxy-4-methyl-phenylamino)-pyrido[2,3-b]pyrazin-6-yl]-urea

Compound 189

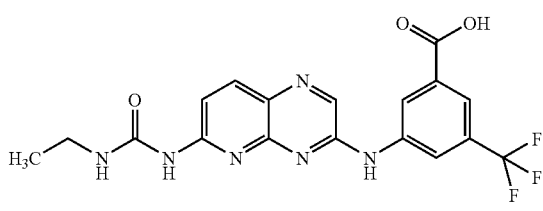

3-[6-(3-Ethyl-ureido)-pyrido[2,3-b]-pyrazin-3-ylamino]-5-trifluoromethyl-benzoic acid Compound 190

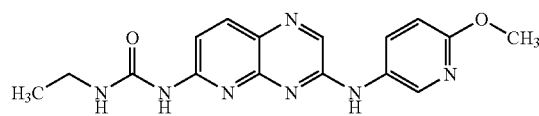

1-Ethyl-3-[3-(6-methoxy-pyridin-3-ylamino)-pyrido[2,3-b]pyrazin-6-yl]-urea

Compound 191

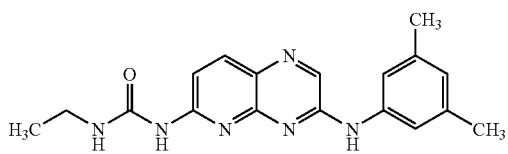

1-[3-(3,5-Dimethyl-phenylamino)-pyrido[2,3-b]pyrazin-6-yl]-3-ethyl-urea

Compound 192

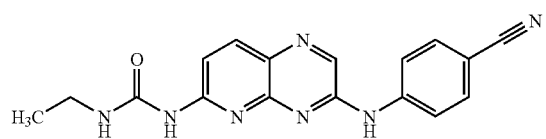

1-[3-(4-Cyano-phenylamino)-pyrido[2,3-b]pyrazin-6-yl]-3-ethyl-urea

Compound 193

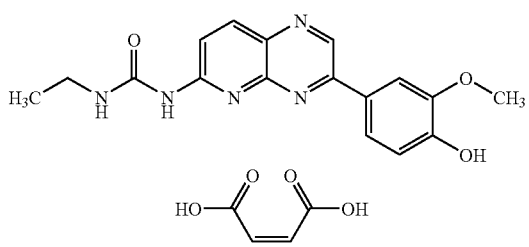

phenyl)-pyrido[2,3-b]pyrazin-6-yl]-urea (Z)-but-2-endicarbonic acid salt

Compound 194

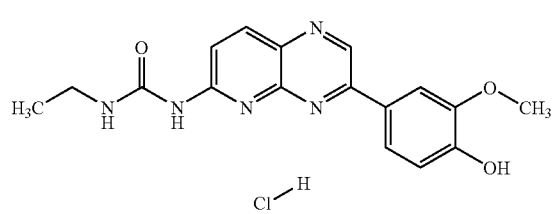

1-Ethyl-3-[3-(4-hydroxy-3-methoxy-phenyl)pyrido[2,3-b]pyrazin-6-yl]-urea Hydrochloride Compound 195

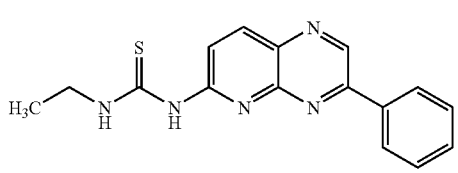

1-Ethyl-3-(3-phenyl-pyrido[2,3-b]pyrazin-6-yl)-thiourea

-continued

Compound 196

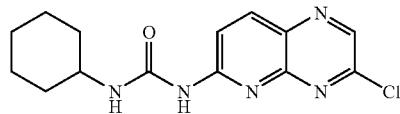

1-(3-Chloro-pyrido[2,3-b]pyrazin-
6-yl)-3-cyclohexyl-urea

Compound 197

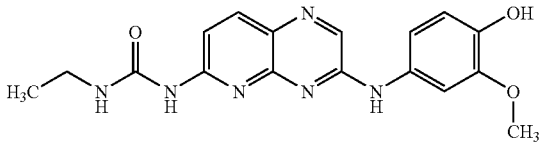

1-Ethyl-3-[3-(4-hydroxy-3-methoxy-phenylamino)-pyrido[2,3-
b]pyrazin-6-yl]-urea

Compound 198

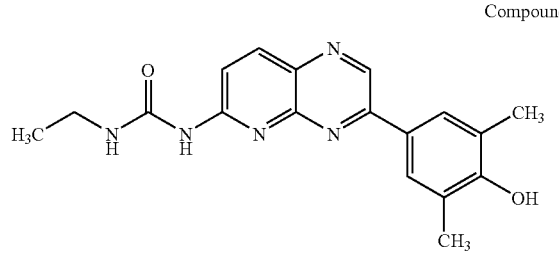

1-Ethyl-3-[3-(4-hydroxy-3,5-dimethyl-phenyl)-pyrido[2,3-
b]pyrazin-6-yl]-urea

Compound 199

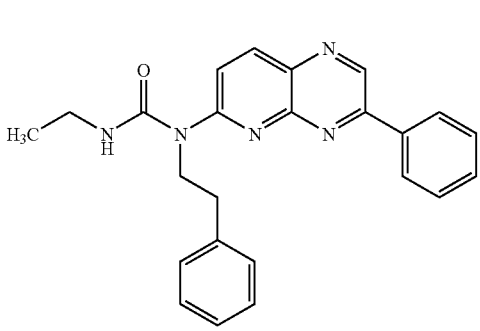

3-Ethyl-1-phenethyl-1-(3-phenyl-pyrido[2,3-b]pyrazin-
6-yl)-urea

Compound 200

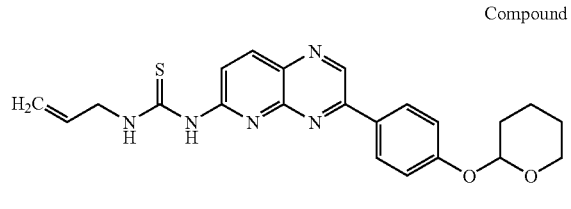

1-Allyl-3-{3-[4-(tetrahydro-pyran-2-yloxy)-phenyl]-pyrido[2,3-
b]pyrazin-6-yl}-thiourea Compound 201

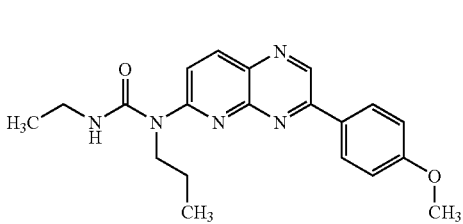

3-Ethyl-1-[3-(4-methoxy-phenyl)-pyrido[2,3-
b]pyrazin-6-yl]-1-propyl-urea

Compound 202

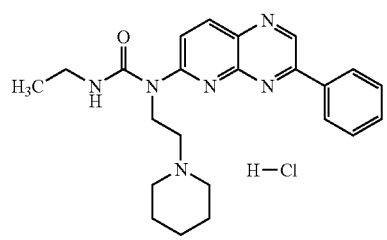

3-Ethyl-1-(3-phenyl-pyrido[2,3-b]pyrazin-6-yl)-
1-(2-piperazin-1-yl-ethyl)-urea Hydrochloride Compound 203

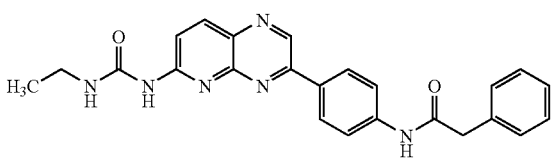

N-{4-[6-(3-Ethyl-ureido)-pyrido[2,3-b]pyrazin-3-yl]-
phenyl}-2-phenyl acetamide

Compound 204

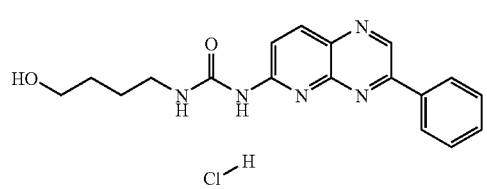

1-(4-Hydroxy-butyl)-3-(3-phenyl-pyrido[2,3-b]pyrazin-
6-yl)-urea Hydrochloride

Compound 205

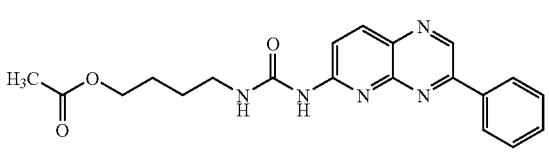

Acetic acid-4-[3-(3-phenyl-pyrido[2,3-b]pyrazin-
6-yl)-ureido]-butyl ester

Compound 206

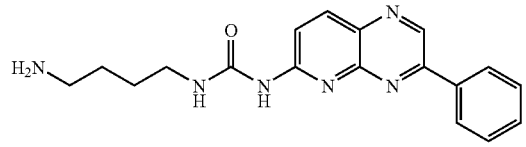

1-(4-Amino-butyl)-3-(3-phenyl-pyrido[2,3-b]pyrazin-6-yl)-urea

Compound 207

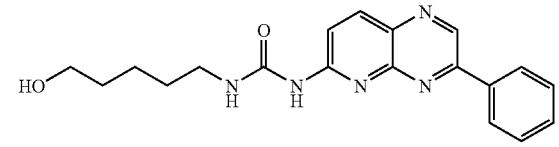

1-(5-Hydroxy-pentyl)-3-(3-phenyl-pyrido[2,3-b]pyrazin-6-yl)-urea

Compound 208

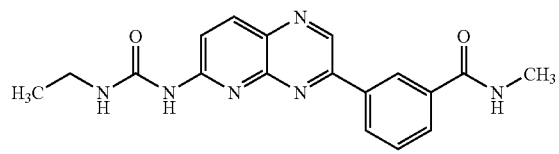

3-[6-(3-Ethyl-ureido)-pyrido[2,3-b]-pyrazin-3-yl]-N-methyl-benzamide

Compound 209

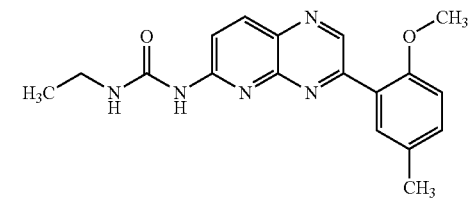

1-Ethyl-3-[3-(2-methoxy-5-methyl-phenyl)-pyrido[2,3-b]pyrazin-6-yl]-urea

Compound 210

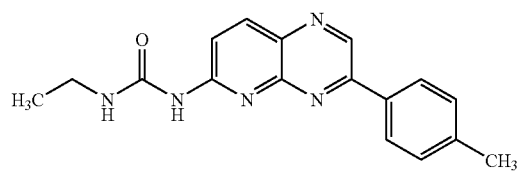

1-Ethyl-3-(3-p-tolyl-pyrido[2,3-b] pyrazin-6-yl)-urea

Compound 211

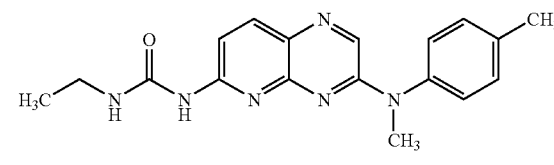

1-Ethyl-3-[3-(methyl-p-tolyl-amino)-pyrido[2,3-b]pyrazin-6-yl]-urea

Compound 212

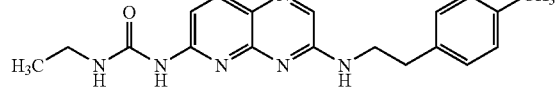

1-Ethyl-3-[3-(2-p-tolyl-ethylamino)-pyrido[2,3-b]pyrazin-6-yl]-urea

Compound 213

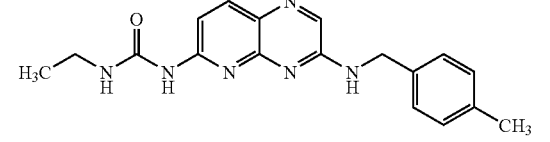

1-Ethyl-3-[3-(4-methyl-benzylamino)-pyrido[2,3-b]pyrazin-6-yl]-urea

Compound 214

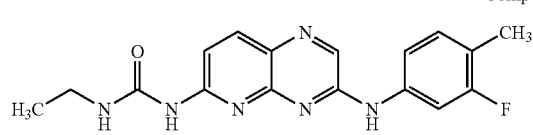

1-Ethyl-3-[3-(3-fluoro-4-methyl-phenyl-amino)-pyrido[2,3-b]pyrazin-6-yl]-urea

Compound 215

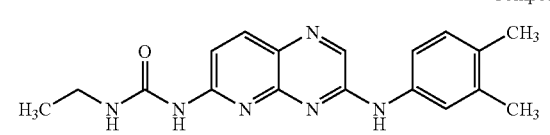

1-[3-(3,4-Dimethyl-phenylamino)-pyrido[2,3-b]pyrazin-6-yl]-3-ethyl-urea

Compound 216

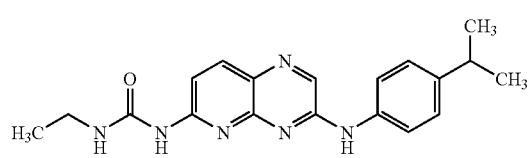

1-Ethyl-3-[3-(4-isopropyl-phenylamino)-pyrido[2,3-b]pyrazin-6-yl]-urea

Compound 217

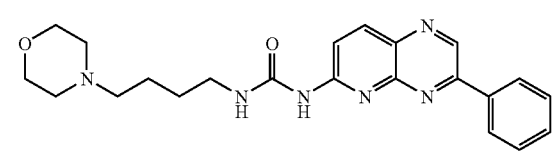

1-(4-Morpholin-4-yl-butyl)-3-(3-phenyl-pyrido[2,3-b]pyrazin-6-yl)-urea

Compound 218

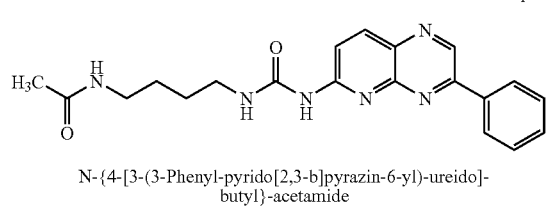

N-{4-[3-(3-Phenyl-pyrido[2,3-b]pyrazin-6-yl)-ureido]-butyl}-acetamide

Compound 219

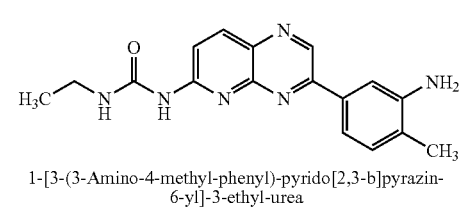

1-[3-(3-Amino-4-methyl-phenyl)-pyrido[2,3-b]pyrazin-6-yl]-3-ethyl-urea

-continued

Compound 220

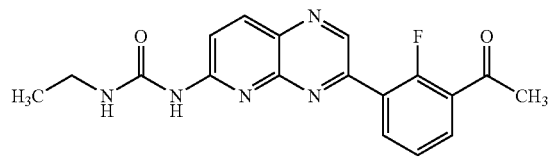

1-[3-(3-Acetyl-2-fluoro-phenyl)-pyrido[2,3-b]pyrazin-6-yl]-3-ethyl-urea

Compound 221

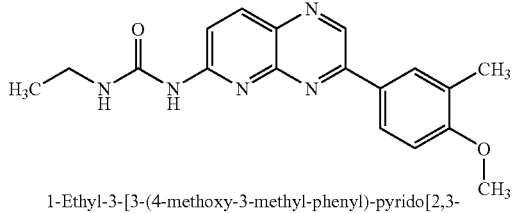

1-Ethyl-3-[3-(4-methoxy-3-methyl-phenyl)-pyrido[2,3-b]pyrazin-6-yl]-urea

Compound 222

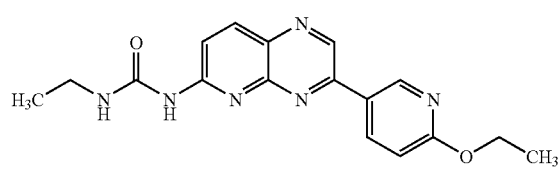

1-[3-(6-Ethoxy-pyridin-3-yl)-pyrido[2,3-b]pyrazin-6-yl]-3-ethyl-urea

Compound 223

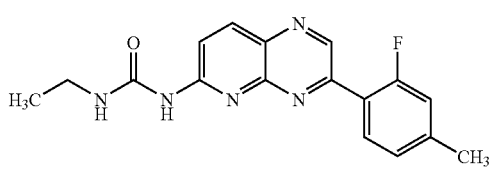

1-Ethyl-3-[3-(2-fluoro-4-methyl-phenyl)-pyrido[2,3-b]pyrazin-6-yl]-urea

Compound 224

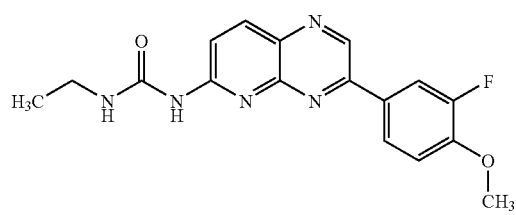

1-Ethyl-3-[3-(3-fluoro-4-methoxy-phenyl)-pyrido[2,3-b]pyrazin-6-yl]-urea

Compound 225

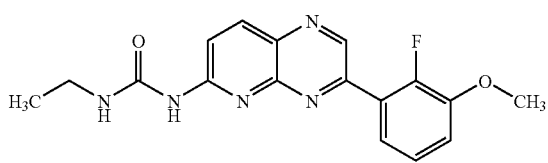

1-Ethyl-3-[3-(2-fluoro-3-methoxy-phenyl)-pyrido[2,3-b]pyrazin-6-yl]-urea

Compound 226

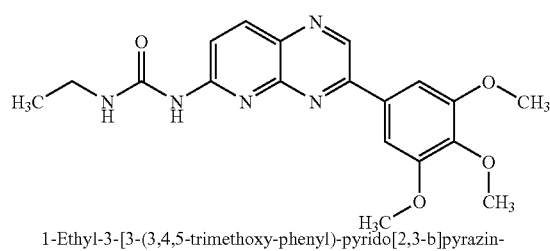

1-Ethyl-3-[3-(3,4,5-trimethoxy-phenyl)-pyrido[2,3-b]pyrazin-6-yl]-urea

Compound 227

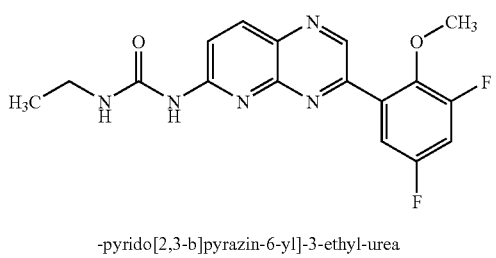

-pyrido[2,3-b]pyrazin-6-yl]-3-ethyl-urea

Compound 228

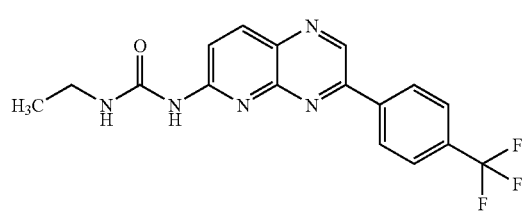

1-Ethyl-3-[3-(4-trifluoromethyl-phenyl)-pyrido[2,3-b]pyrazin-6-yl]-urea

Compound 229

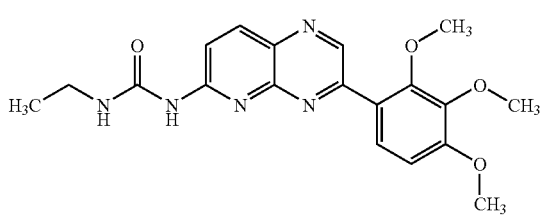

1-Ethyl-3-[3-(2,3,4-trimethoxy-phenyl)-pyrido[2,3-b]pyrazin-6-yl]-urea

Compound 230

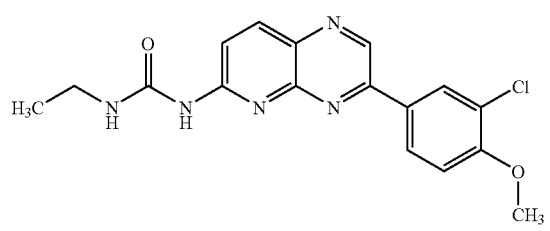

pyrido[2,3-b]pyrazin-6-yl]-3-ethyl-urea

Compound 231

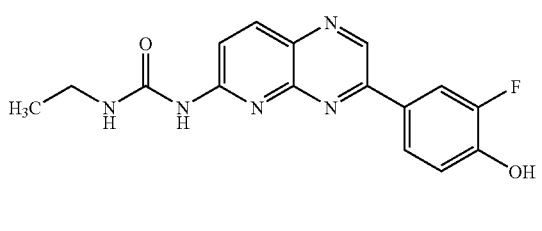

1-Ethyl-3-[3-(3-fluoro-4-hydroxy-phenyl)-pyrido[2,3-b]pyrazin-6-yl]-urea

-continued

Compound 232

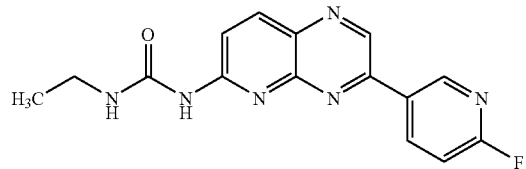

1-Ethyl-3-[3-(6-fluoro-pyridin-3-yl)-pyrido[2,3-b]pyrazin-6-yl]-urea

Compound 233

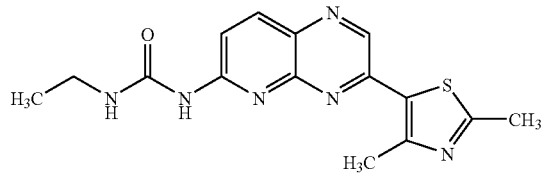

1-[3-(2,4-Dimethyl-thiazol-5-yl)-pyrido[2,3-b]pyrazin-6-yl]-3-ethyl-urea

Compound 234

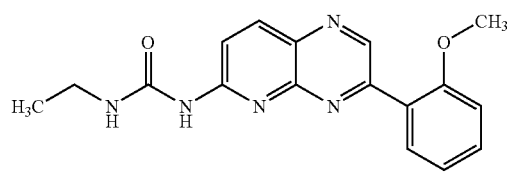

1-Ethyl-3-[3-(2-methoxy-phenyl)-pyrido[2,3-b]pyrazin-6-yl]-urea

Compound 235

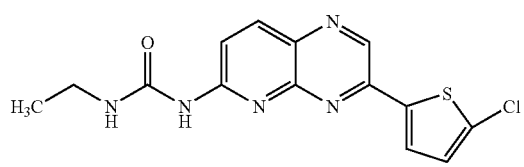

1-[3-(2-Chloro-pyridin-4-yl)-pyrido[2,3-b]pyrazin-6-yl]-3-ethyl-urea

Compound 236

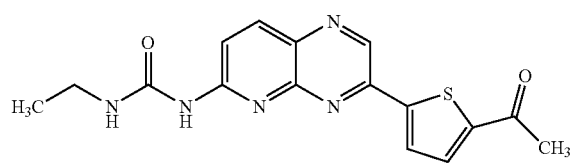

1-[3-(5-Acetyl-thiophen-2-yl)-pyrido[2,3-b]pyrazin-6-yl]-3-ethyl-urea

Compound 237

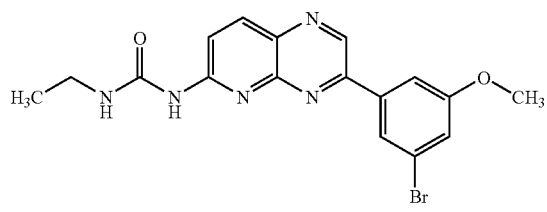

1-[3-(5-Chloro-thiophen-2-yl)-pyrido[2,3-b]pyrazin-6-yl]-3-ethyl-urea

Compound 238

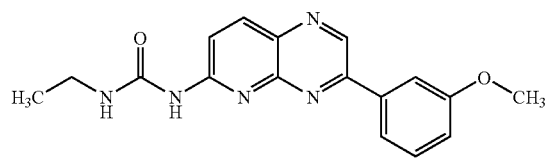

1-Ethyl-3-[3-(3-methoxy-phenyl)-pyrido[2,3-b]pyrazin-6-yl]-urea

Compound 239

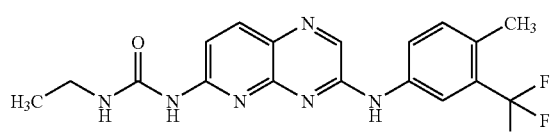

1-[3-(3-Bromo-5-methoxy-phenyl)-pyrido[2,3-b]pyrazin-6-yl]-3-ethyl-urea

Compound 240

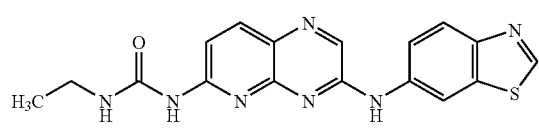

1-[3-(Benzothiazol-6-ylamino)-pyrido[2,3-b]pyrazin-6-yl]-3-ethyl-urea

Compound 241

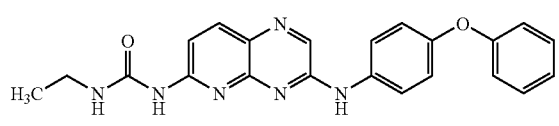

1-Ethyl-3-[3-(4-methyl-3-trifluoromethyl-phenylamino)-pyrido[2,3-b]pyrazin-6-yl]-urea Compound 242

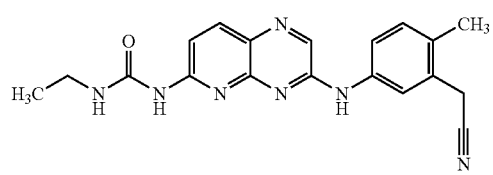

1-[3-(3-Cyano-4-methyl-phenylamino)-pyrido[2,3-b]pyrazin-6-yl]-3-ethyl-urea

Compound 243

1-Ethyl-3-[3-(4-phenoxy-phenylamino)-pyrido[2,3-b]pyrazin-6-yl]-urea

-continued

Compound 244

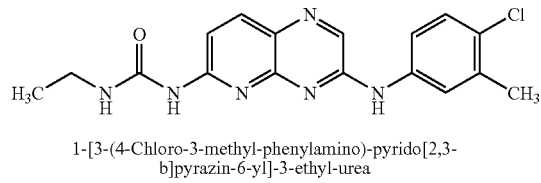

1-[3-(4-Chloro-3-methyl-phenylamino)-pyrido[2,3-b]pyrazin-6-yl]-3-ethyl-urea

Compound 245

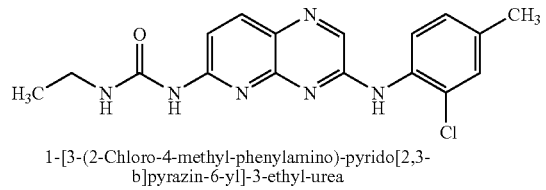

1-[3-(2-Chloro-4-methyl-phenylamino)-pyrido[2,3-b]pyrazin-6-yl]-3-ethyl-urea

Compound 246

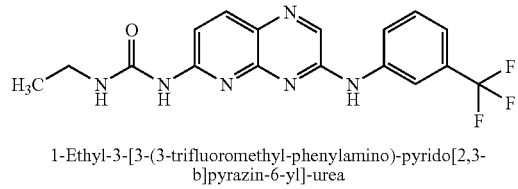

1-Ethyl-3-[3-(3-trifluoromethyl-phenylamino)-pyrido[2,3-b]pyrazin-6-yl]-urea

Compound 247

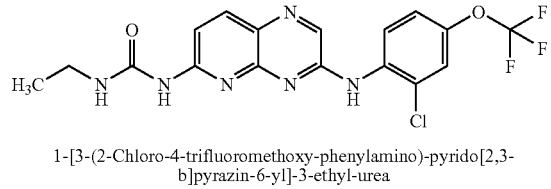

1-[3-(2-Chloro-4-trifluoromethoxy-phenylamino)-pyrido[2,3-b]pyrazin-6-yl]-3-ethyl-urea Compound 248

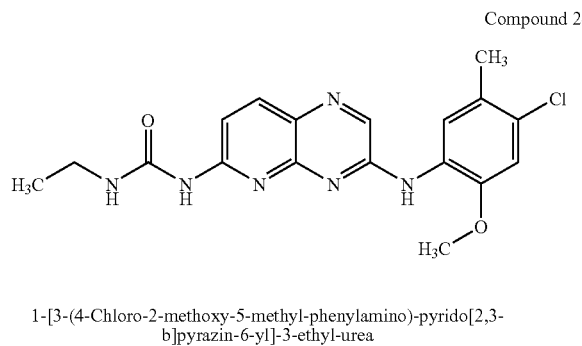

1-[3-(4-Chloro-2-methoxy-5-methyl-phenylamino)-pyrido[2,3-b]pyrazin-6-yl]-3-ethyl-urea Compound 249

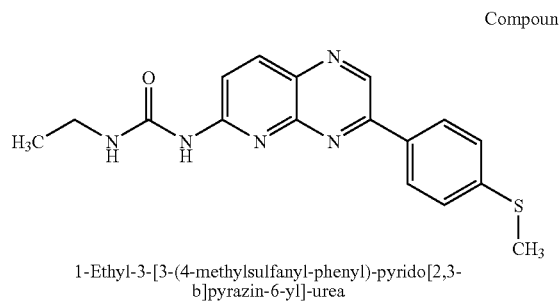

1-Ethyl-3-[3-(4-methylsulfanyl-phenyl)-pyrido[2,3-b]pyrazin-6-yl]-urea

Compound 250

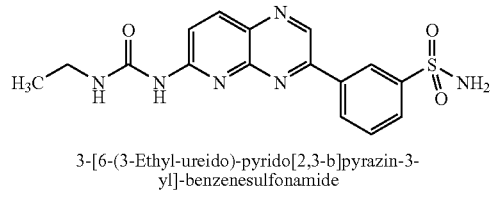

3-[6-(3-Ethyl-ureido)-pyrido[2,3-b]pyrazin-3-yl]-benzenesulfonamide

Compound 251

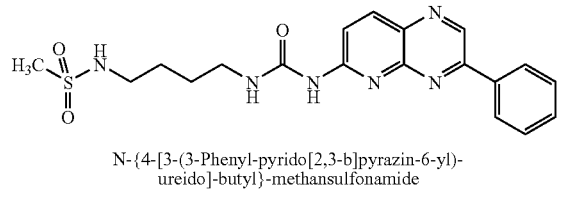

N-{4-[3-(3-Phenyl-pyrido[2,3-b]pyrazin-6-yl)-ureido]-butyl}-methansulfonamide

Compound 252

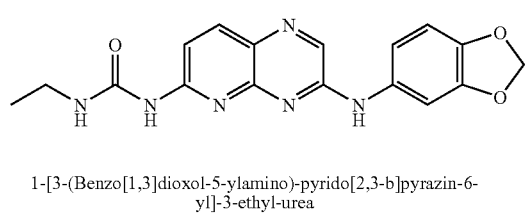

1-[3-(Benzo[1,3]dioxol-5-ylamino)-pyrido[2,3-b]pyrazin-6-yl]-3-ethyl-urea

Compound 253

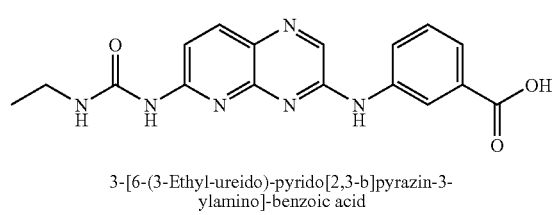

3-[6-(3-Ethyl-ureido)-pyrido[2,3-b]pyrazin-3-ylamino]-benzoic acid

Compound 254

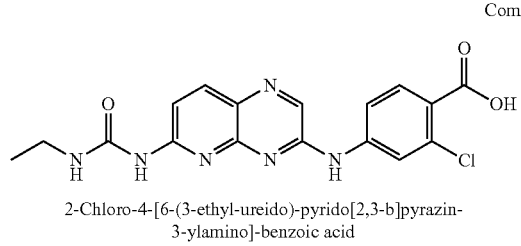

2-Chloro-4-[6-(3-ethyl-ureido)-pyrido[2,3-b]pyrazin-3-ylamino]-benzoic acid

Compound 255

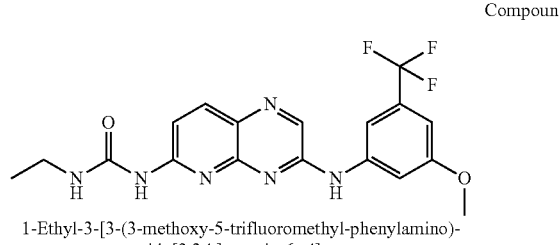

1-Ethyl-3-[3-(3-methoxy-5-trifluoromethyl-phenylamino)-pyrido[2,3-b]pyrazin-6-yl]-urea -continued Compound 256

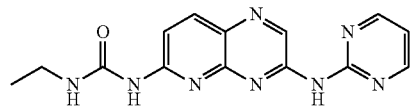

1-Ethyl-3-[3-(pyrimidin-2-ylamino)-pyrido[2,3-b]pyrazin-6-yl]-urea

Compound 257

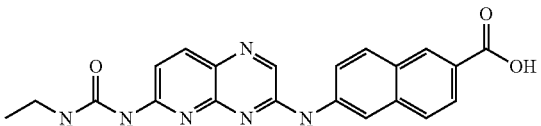

6-[6-(3-Ethyl-ureido)-pyrido[2,3-b]pyrazin-3-ylamino]-naphthalin-2-carbonic acid Compound 258

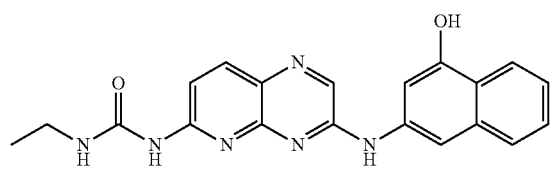

1-Ethyl-3-[3-(4-hydroxy-quinolin-2-ylamino)-pyrido[2,3-b]pyrazin-6-yl]-urea

Compound 259

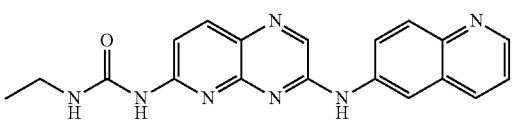

1-Ethyl-3-[3-(quinonil-6-ylamino)-pyrido[2,3-b]pyrazin-6-yl]-urea

Compound 260

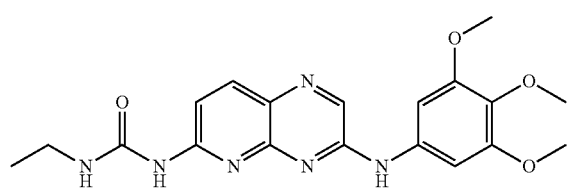

1-Ethyl-3-[3-(3,4,5-trimethoxy-phenylamino)-pyrido[2,3-b]pyrazin-6-yl]-urea

Compound 261

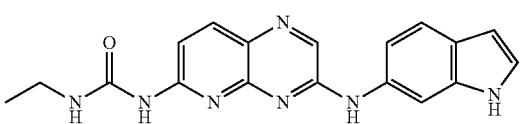

1-Ethyl-3-[3-(1H-indol-6-ylamino)-pyrido[2,3-b]pyrazin-6-yl]-urea

Compound 262

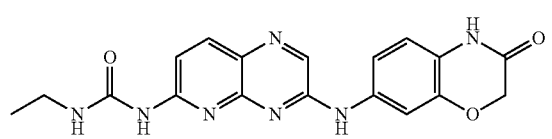

1-Ethyl-3-[3-(3-oxo-3,4-dihydro-2H-benzo[1,4]oxazin-7-ylamino)-pyrido[2,3-b]pyrazin-6-yl]-urea Compound 263

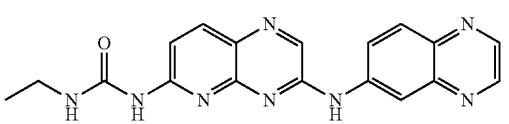

1-Ethyl-3-[3-(quinoxalin-6-ylamino)-pyrido[2,3-b]pyrazin-6-yl]-urea

Compound 264

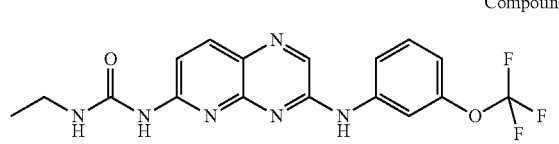

1-Ethyl-3-[3-(3-trifluoromethoxy-phenylamino)-pyrido[2,3-b]pyrazin-6-yl]-urea

Compound 265

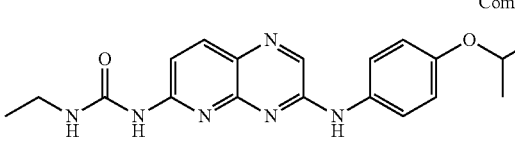

1-Ethyl-3-[3-(4-isopropoxy-phenylamino)-pyrido[2,3-b]pyrazin-6-yl]-urea

Compound 266

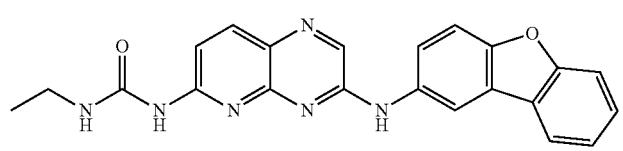

1-[3-(Dibenzofuran-2-ylamino)-pyrido[2,3-b]pyrazin-6-yl]-3-ethyl-urea

Compound 267

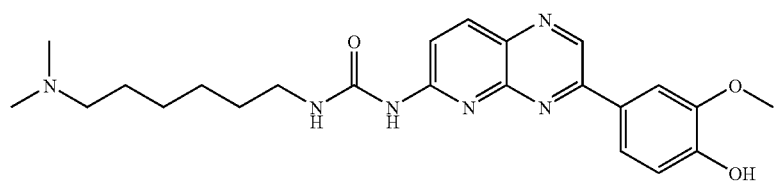

1-(6-Dimethylamino-hexyl)-3-[3-(4-hydroxy-3-methoxy-phenyl)-pyrido[2,3-b]pyrazin-6-yl]-urea Compound 268

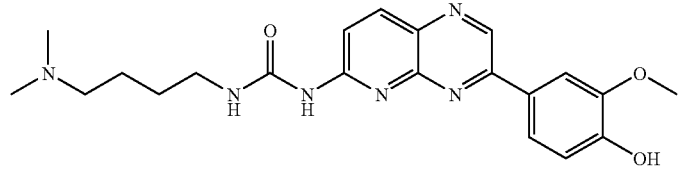

1-(4-Dimethylamino-butyl)-3-[3-(4-hydroxy-3-methoxy-phenyl)-pyrido[2,3-b]pyrazin-6-yl]-urea Compound 269

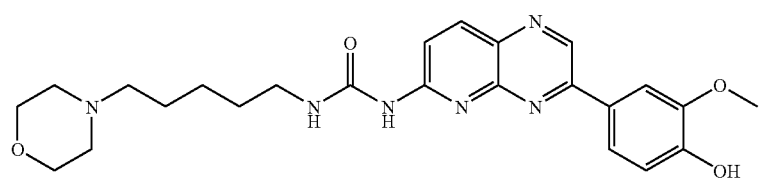

1-[3-(4-Hydroxy-3-methoxy-phenyl)-pyrido[2,3-b]pyrazin-6-yl]-3-(5-morpholin-4-yl-pentyl)-urea which can be used for the production of a medicament for the treatment or prevention of physiological and/or pathophysiological states in mammals mediated by signal transduction pathways selected from the group consisting of: the "ras-Raf-Mek-Erk signal transduction pathway, the PI3K-Akt signal transduction pathway and/or the SAPK signal transduction pathway.

In order to avoid ambiguities: when chemical structure and chemical name of the explicit compounds shown above erroneously do not match one another, the chemical structure shall unambiguously define the particular explicit compound.

The afore-mentioned generic compounds having the general formula (I) and preferred embodiments as well as the explicitly specified pyridopyrazine compounds 1 to 269 are hereinafter designated jointly as "compounds according to the invention".

The expressions and terms specified to explain the compounds according to the invention having the general formula (I), the preferred embodiments and compounds 1 to 269 basically have the following meanings unless specified otherwise in the description and the claims:

In the context of this invention, the expression "alkyl" encompasses acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Preferred alkyl radicals are methyl, ethyl, n-propyl, 2-propyl, n-butyl, sec-butyl, tert-butyl, n-pentyl, iso-pentyl, neo-pentyl, n-hexyl, 2-hexyl, n-heptyl, n-octyl, n-nonyl, n-decyl, n-undecyl, n-dodecyl, ethylenyl (vinyl), ethynyl, propenyl (—CH$_2$CH═CH$_2$; —CH═CH—CH$_3$, —C(═CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl, octadienyl and octynyl.

For the purposes of this invention, the expression "cycloalkyl" means cyclic nonaromatic hydrocarbons having 1 to 3 rings with 3 to 20, preferably 3 to 12 carbon atoms, which may be saturated or unsaturated, more preferably ($C_3$-$C_8$)cycloalkyl. The cycloalkyl radical may also be part of a bi- or polycyclic system, where, for example, the cycloalkyl radical is fused to an aryl, heteroaryl or heterocyclyl radical as defined herein by any possible and desired ring member(s).

The bonding to the compounds of the general formula (I) can be effected via any possible ring member of the cycloalkyl radical. Preferred cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The expression "heterocyclyl" represents a 3- to 14-membered, preferably 3-, 4-, 5-, 6-, 7- or 8-membered, cyclic organic radical which contains at least 1 heteroatom, optionally 2, 3, 4 or 5 heteroatoms, especially nitrogen, oxygen and/or sulphur, the heteroatoms being the same or different and the cyclic radical being saturated or unsaturated but not aromatic. The heterocyclyl radical may also be part of a bi- or polycyclic system, where, for example, the heterocyclyl radical is fused to an aryl, heteroaryl or cycloalkyl radical as defined herein by any possible and desired ring member(s). The bonding to the compounds of the general formula (I) can be effected via any possible ring member of the heterocyclyl radical. Preferred heterocyclyl radicals are tetrahydrofuryl, pyrrolidinyl, imidazolidinyl, thiazolidinyl, tetrahydropyranyl, piperidinyl, piperazinyl, morpholinyl, thiapyrrolidinyl, oxapiperazinyl, oxapiperidinyl and oxadiazolyl.

In the context of this invention, the expression "aryl" means aromatic hydrocarbons having 3 to 14 carbon atoms, preferably 5 to 14 carbon atoms, more preferably 6 to 14 carbon atoms. The aryl radical may also be part of a bi- or polycyclic system, where, for example, the aryl radical is fused to a heterocyclyl, heteroaryl or cycloalkyl radical as defined herein by any possible and desired ring member(s), for example to tetrahydrofuran, tetrahydrothiophene, pyrrolidine, imidazolidine, thiazolidine, tetrahydropyran, dihydropyran, piperidine, furan, thiophene, imidazole, thiazole, oxazole, isoxazole. The bonding to the compounds of the general formula (I) can be effected via any possible ring member of the aryl radical. Preferred aryl radicals are phenyl, biphenyl, naphthyl and anthracenyl, but likewise indanyl, indenyl or 1,2,3,4-tetrahydronaphthyl.

The expression "heteroaryl" represents a 5-, 6- or 7-membered cyclic aromatic radical which contains at least 1 heteroatom, if appropriate also 2, 3, 4 or 5 heteroatoms, especially nitrogen, oxygen and/or sulphur, the heteroatoms being the same or different. The number of nitrogen atoms is preferably 0 to 3, that of oxygen and sulphur atoms preferably 0 or 1. The heteroaryl radical may also be part of a bi- or polycyclic system, where, for example, the heteroaryl radical is fused to a heterocyclyl, aryl or cycloalkyl radical as defined herein by any possible and desired ring member(s). The bonding to the compounds of the general formula (I) can be effected via any possible ring member of the heteroaryl radical. Preferred heteroaryl radicals are pyrrolyl, furyl, thienyl, thiazolyl, isothiazolyl, oxazolyl, oxadiazolyl, isoxazolyl, pyrazolyl, imidazolyl, triazole, tetrazole, pyridinyl, pyrimidinyl, pyridazinyl, pyrazinyl, triazinyl, phthalazinyl, indolyl, indazolyl, indolizinyl, quinolinyl, isoquinolinyl, quinoxalinyl, quinazolinyl, pteridinyl, carbazolyl, phenazinyl, phenoxazinyl, phenothiazinyl, and acridinyl.

For the purposes of the present invention, the expressions "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_4$-alkyl radical.

In connection with "alkyl", "cycloalkyl", "heterocyclyl", "aryl", "heteroaryl", alkyl-cycloalkyl", "alkyl-heterocyclyl", "alkyl-aryl" and "alkyl-heteroaryl" the term substituted is understood in the sense of this invention unless defined explicitly above in the description and the claims as the substitution of one or more hydrogen groups by F, Cl, Br, I, CN, $CF_3$, $NH_2$, NH-alkyl, NH-aryl, $N(alkyl)_2$, $NO_2$, SH, S-alkyl, OH, $OCF_3$, O-alkyl, O-aryl, $OSO_3H$, $OP(O)(OH)_2$, CHO, $CO_2H$, $SO_3H$ or alkyl. The substituents can be the same or different and the substitutions can take place in any arbitrary and possible position of the alkyl, cycloalkyl, heterocyclyl, aryl and heteroaryl group.

In the context of this invention, the expression "halogen" encompasses the halogen atoms fluorine, chlorine, bromine and iodine.

Multiply substituted groups are to be understood as those which are multiply, e.g. doubly, triply, substituted either at different or at the same atoms, for example, triply substituted at the same C atoms as in the case of $CF_3$, —$CH_2CF_3$ or at different positions as in the case of —CH(OH)—CH═CH—$CHCl_2$. The multiple substitution can take place with the same or different substituents.

Insofar as the compounds according to the invention have at least one centre of asymmetry, they can be present in the form of their racemates, in the form of the pure enantiomers and/or diastereomers or in the form of mixtures of these enantiomers and/or diastereomers. The mixtures can be present in any arbitrary mixture ratio of the stereoisomers.

Thus, for example, the compounds according to the invention which have one or a plurality of centres of chirality and which occur as their racemates can be separated into their optical isomers, that is enantiomers or diastereomers, by methods known per se. The separation can be performed by column separation at chiral phases or by recrystallisation from an optically active solvent or by using an optically active acid or base or by derivatisation with an optically active reagent, such as for example, an optically active alcohol and subsequent separation of the residue.

The inventive compounds may be present in the form of their double bond isomers as "pure" E or Z isomers, or in the form of mixtures of these double bond isomers.

As far as possible, the compounds according to the invention can be present in the form of tautomers.

If they possess a sufficiently basic group, such as for example, a primary, secondary or tertiary amine, the compounds according to the invention can be converted into their physiologically compatible salts using inorganic and organic acids. The pharmaceutically acceptable salts of the compounds according to the invention are preferably formed with hydrochloric acid, bromic acid, sulphuric acid, phosphoric acid, methane sulfonic acid, p-toluene sulfonic acid, carbonic acid, formic acid, acetic acid, trifluoroacetic acid, sulfoacetic acid, oxalic acid, malonic acid, maleic acid, succinic acid, tartaric acid, racemic acid, malic acid, embonic acid, mandelic acid, fumaric acid, lactic acid, citric acid, glutamic acid or asparaginic acid. The salts formed include, among others, hydrochloride, hydrobromide, sulfate, hydrogen sulfate, phosphate, methane sulfonate, tosylate, carbonate, hydrogen carbonate, formiate, acetate, triflate, sulfoacetate, oxalate, malonate, maleate, succinate, tartrate, malate, embonate, mandelate, fumarate, lactate, citrate, glutaminate and aspartate. The stoichiometry of the salts of the compounds according to the invention which are formed can be integer or non-integer multiples of one.

If they contain a sufficiently acidic group, such as the carboxy group, for example, the compounds according to the invention can be converted into their physiologically compatible salts using inorganic and organic bases. Possible inorganic bases are, for example, sodium hydroxide, potassium hydroxide, calcium hydroxide, possible organic bases are ethanol amine, diethanol amine, triethanol amine, cyclohexylamine, dibenzylethylene diamine and lysine. The stoichiometry of the salts of the compounds according to the invention which are formed can be integer or non-integer multiples of one.

Likewise preferred are solvates and in particular hydrates of the compounds according to the invention, which can be obtained, for example, by crystallisation from a solvent or from aqueous solution. In this context, one, two, three or an arbitrary number of solvate or water molecules can combine with the compounds according to the invention to form solvates and hydrates.

It is known that chemical substances form solids which are present in various states of order, which are designated as polymorphous forms or modifications. The various modifications of a polymorphous substance can differ strongly in respect of their physical properties. The compounds according to the invention can be present in various polymorphous forms, in which case certain modifications can be metastable.

The compounds according to the invention can likewise be present in the form of any prodrugs such as, for example, esters, carbonates, carbamates, ureas, amides or phosphates, wherein the actually biologically active form is only released by catabolism.

It is further known that chemical substances are converted to metabolites in the body which optionally can likewise induce the desired biological effect, possibly even in a more distinct form.

Corresponding prodrugs and metabolites of the compounds according to the invention should also be considered as pertaining to the invention.

It was now surprisingly and advantageously determined that the compounds according to the invention can act simultaneously or have a modulating or inhibiting effect on two or more signal transduction pathways or enzymes. In this context, it has been found that the compounds according to the invention can act or have a modulating or inhibiting effect with high selectivity.

Such a simultaneous, for example, dual modulation or inhibition of two or more signal transduction pathways, e.g. the ras-Raf-Mek-Erk signal pathway, the PI3K-Akt signal pathway and/or the SAPK signal pathway, more especially Erk1/Erk2 and/or PI3K and/or Jnk and/or p38, is advantageous compared with merely single modulation or inhibition of a signal transduction pathway since synergistic therapeutic effects can be brought about, such as for example, intensified apoptosis and faster and more efficient tumour regression.

The surprising advantageous effects of the compounds according to the invention allow multiple therapy approaches to be pursued in physiological and/or pathophysiological states or clinical pictures which are sensitive for the treatment or modulation of, or are mediated by, two or more signal transduction pathways.

It was further surprisingly and advantageously determined that the compounds according to the invention can also act with high selectivity or have a modulating or inhibiting effect on the PI3K-Akt signal transduction pathway or enzymes thereof and that the multiple mechanisms of action and therapy approaches described above can also be used with this signal pathway or enzymes.

It was further surprisingly and advantageously determined that the compounds according to the invention can also act with high selectivity or have a modulating or inhibiting effect on the SAPK signal transduction pathway or enzymes thereof and that the multiple mechanisms of action and therapy approaches described above can also be used with this signal pathway or enzymes.

It was further surprisingly and advantageously determined that the compounds according to the invention can also act with high selectivity or have a modulating or inhibiting effect on enzymes such as ATM, ATR, mTOR, DNA-PK and/or hSMG-1 and that the multiple mechanisms of action and therapy approaches described above can also be used with this signal pathway or enzymes.

The term "modulation" is understood according to the invention as follows: "activation, partial activation, inhibition, partial inhibition". In this case, it is within the specialist knowledge of the average person skilled in the art to measure and determine such activation, partial activation, inhibition, partial inhibition by means of the usual methods of measurement and determination. Thus, a partial activation can be measured and determined in relation to a complete activation; likewise, a partial inhibition in relation to a complete inhibition.

The terms "inhibiting, inhibition and/or retardation" are understood as follows according to the invention: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The terms "modulation" and "inhibiting, inhibition and/or retardation" in connection with "enzymes" and/or "kinases" within the scope of this invention relate both to the inactive form (enzymatically inactive) and/or active form (enzymatically active) of the respective enzyme and/or kinase. This means within the scope of this invention that the compound according to the invention can have a modulating effect on the inactive form, active form or both forms of the enzyme and/or kinase.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the signal transduction pathway or pathways selected from the group consisting of: the "ras-Raf-Mek-Erk signal transduction pathway, the PI3K-Akt signal transduction pathway and/or the SAPK signal transduction pathway.

In a further aspect, the inventive object was surprisingly achieved by preparing the compounds according to the invention which can be used to produce a medicament for the treatment or prevention of physiological and/or pathophysiological states in mammals, mediated by enzymes selected from the group consisting of: "ATM, ATR, mTOR, DNA-PK, hSMG-1".

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of one or more enzymes selected from the group consisting of: "ATM, ATR, mTOR, DNA-PK, hSMG-1".

In a preferred embodiment, the compounds according to the invention are prepared for use to produce a medicament for the treatment or prevention of physiological and/or pathophysiological states in mammals mediated by the ras-Raf-Mek-Erk signal transduction pathway, the PI3K-Akt signal transduction pathway and/or use to produce a medicament for the treatment or prevention of physiological and/or pathophysiological states in mammals, wherein the treatment or prevention is effected by modulation of the ras-Raf-Mek-Erk signal transduction pathway and the PI3K-Akt signal transduction pathway.

In a further aspect, the inventive object was surprisingly achieved by preparing the compounds according to the invention which can be used to produce a medicament for the treatment or prevention of physiological and/or pathophysiological states in mammals, mediated by the PI3K-Akt signal transduction pathway.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the PI3K-Akt signal transduction pathway.

In a preferred embodiment, the compounds according to the invention are prepared for use to produce a medicament for the treatment and/or prevention of physiological and/or pathophysiological states in mammals mediated by the SAPK signal transduction pathway and the PI3K-Akt signal transduction pathway and/or to produce a medicament for the treatment or prevention of physiological and/or pathophysiological states in mammals, wherein the treatment or prevention is effected by modulation of the SAPK signal transduction pathway and the PI3K-Akt signal transduction pathway.

In a further aspect, the inventive object was surprisingly achieved by preparing the compounds according to the invention which can be used to produce a medicament for the treatment or prevention of physiological and/or pathophysiological states in mammals, mediated by the SAPK signal transduction pathway.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the SAPK signal transduction pathway.

In a preferred embodiment, the compounds according to the invention are prepared for the uses described above, wherein the modulation of the ras-Raf-Mek-Erk signal transduction pathway is effected by modulation of one or more enzymes selected from the group consisting of: "tyrosine kinase, serine/threonine kinase, receptor tyrosine kinase, cytoplasmic tyrosine kinase, cytoplasmic serine/threonine kinase" and preferably selected from the group consisting of: "Erk, Erk1, Erk2".

In a further preferred embodiment, the compounds according to the invention are prepared for the uses described above, wherein the modulation of the P13K-Akt signal transduction pathway is effected by modulation of one or more enzymes selected from the group consisting of: "PI3K, PI3Kalpha, PI3Kbeta, PI3Kgamma, PI3Kdelta, PI3K-C2alpha, PI3K-C2beta, PI3K-Vps34p".

In a further preferred embodiment, the compounds according to the invention are prepared for the uses described above, wherein the modulation of the SAPK signal transduction pathway is effected by modulation of one or more enzymes selected from the group consisting of: "tyrosine kinase, serine/threonine kinase, receptor tyrosine kinase, cytoplasmic tyrosine kinase, cytoplasmic serine/threonine kinase" and is preferably selected from the group consisting of: "Jnk, Jnk1, Jnk2, Jnk3, p38, p38alpha, p38beta, p38gamma, p38delta".

In a further aspect, the inventive object was surprisingly achieved by preparing the compounds according to the invention according to the aspects, preferred embodiments and uses described above which can be used to produce a medicament for the treatment or prevention of physiological and/or pathophysiological states in mammals, wherein the treatment or prevention is effected by modulation of two or more enzymes.

In a further preferred embodiment, the compounds according to the invention are prepared for the uses described above, wherein in the treatment or prevention effected by modulation of two or more enzymes, at least one enzyme is selected from the group consisting of: "Erk, Erk1, Erk2" and at least one enzyme is selected from the group consisting of: "PI3K, PI3Kalpha, PI3Kbeta, PI3Kgamma, PI3Kdelta, PI3K-C2alpha, PI3K-C2beta, PI3K-Vps34p".

In a further preferred embodiment, the compounds according to the invention are prepared for the uses described above, wherein in the treatment or prevention effected by modulation of two or more enzymes at least one enzyme is selected from the group consisting of: "Jnk, Jnk1, Jnk2, Jnk3, p38, p38alpha, p38beta, p38gamma, p38delta" and at least one enzyme is selected from the group consisting of: "PI3K, PI3Kalpha, PI3Kbeta, PI3Kgamma, PI3Kdelta, PI3K-C2alpha, PI3K-C2beta, PI3K-Vps34p".

In a further preferred embodiment, the compounds according to the invention are prepared for the uses described above, wherein in the treatment or prevention effected by modulation of two or more enzymes, at least one enzyme is selected from the group consisting of: "Erk, Erk1, Erk2" and at least one enzyme is selected from the group consisting of: "ATM, ATR, mTOR, DNA-PK, hSMG-1".

In a further preferred embodiment, the compounds according to the invention are prepared for the uses described above, wherein in the treatment or prevention effected by modulation of two or more enzymes, at least one enzyme is selected from the group consisting of: "Jnk, Jnk1, Jnk2, Jnk3, p38, p38alpha, p38beta, p38gamma, p38delta" and at least one enzyme is selected from the group consisting of: "ATM, ATR, mTOR, DNA-PK, hSMG-1".

In a further preferred embodiment, the compounds according to the invention are prepared for the uses described above, wherein in the treatment or prevention effected by modulation of two or more enzymes, at least one enzyme is selected from the group consisting of: "PI3K, PI3Kalpha, PI3Kbeta, PI3Kgamma, PI3Kdelta, PI3K-C2alpha, PI3K-C2beta, PI3K-Vps34p" and at least one enzyme is selected from the group consisting of: "ATM, ATR, mTOR, DNA-PK, hSMG-1".

In a further preferred embodiment, the compounds according to the invention are prepared for the uses described above, wherein the modulation is an inhibition.

The compounds according to the invention can be administered within the scope of this invention to all known mammals, in particular, humans, for the treatment and/or prevention.

In another preferred embodiment, the compounds according to the invention are prepared for the uses described above, wherein the mammal is selected from the group consisting of: "human, domesticated animal, cattle, pet, beef cattle, cow, sheep, pig, goat, horse, pony, donkey, hinny, mule, hare, rabbit, cat, dog, guinea pig, hamster, rat, mouse" and is preferably a human.

The compounds according to the invention can be used within the scope of this invention for the treatment and/or prevention of all known physiological and/or pathophysiological states.

In a preferred embodiment, the compounds according to the invention are prepared for the uses described above, wherein the physiological and/or pathophysiological states are selected from the group consisting of: "malignant tumours, benign tumours, inflammatory diseases, inflammations, pain, rheumatic diseases, arthritic diseases, HIV infections, neurological or neurodegenerative diseases, rheumatism, arthritis, AIDS, ARC (AIDS related complex), Kaposi's sarcoma, tumours originating from the brain and/or nervous system and/or meninges, dementia, Alzheimer's disease, hyperproliferative diseases, psoriasis, endometriosis, scarring, benign prostatahyperplasia (BPH), diseases of the immune system, autoimmune diseases, immunodeficiency diseases, colon tumour, gastric tumour, intestinal tumour, pulmonary tumour, pancreatic tumour, ovarian tumour, prostatic tumour, leukaemia, melanoma, hepatic tumour, renal tumour, head tumour, throat tumour, glioma, breast tumour, uterine cancer, endometrial cancer, cervico-uterine carcinoma, brain tumour, adeno-acanthoma, cancer of the bladder, gastric tumour, colorectal tumour, oesophageal cancer, gynecological tumour, ovarian tumour, cancer of the thyroid, lymphoma, chronic leukaemia, acute leukaemia, restenosis, diabetes, diabetic nephropathy, fibrotic diseases, cystic fibrosis, malignant nephrosclerosis, thrombotic microangiopathy syndrome, organ transplant rejection, glomerulopathy, metabolic diseases, solid/fixed tumours, rheumatic arthritis, diabetic retinopathy, asthma, allergies, allergic diseases, chronic obstructive pulmonary diseases, inflammatory bowel disease, fibrosis, atherosclerosis, heart diseases, cardiovascular diseases, diseases of the myocardium, vascular diseases, angiogenetic diseases, kidney diseases, rhinitis, Grave's disease, focal ischaemia, cardiac failure, ischaemia, cardiac hypertrophia, renal failure, cardiac myocytic malfunction, high blood pressure, vasoconstriction, stroke, anaphylactic shock, platelet agglutination, skeletomuscular atrophy, obesity, overweight, glucosis homeostasis, congestive cardiac insufficiency, angina, heart attack, cardiac infarction, hyperglycaemia, hypoglycaemia, hypertension".

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament comprises at least one further pharmacologically active substance.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered with at least one further pharmacologically active substance before and/or during and/or after treatment.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered before and/or during and/or after treatment with radiation therapy and/or surgery.

The compounds according to the invention can be administered within the scope of this invention with all known pharmacologically active substances in a combination therapy as described.

In a preferred embodiment, the compounds according to the invention are prepared for the uses described above, wherein the further pharmacologically active substance is selected from the group consisting of: "DNA topoisomerase I and/or II inhibitors, DNA intercalators, alkylating agents, microtubuli destabilisors, hormone and/or growth factor receptor agonists and/or antagonists, antibodies against growth factors and their receptors, kinase inhibitors, antimetabolites".

In a preferred embodiment, the compounds according to the invention are prepared for the uses described above, wherein the further pharmacologically active substance is selected from the group consisting of: "asparaginase, bleomycin, carboplatin, carmustin, chlorambucil, cisplatin, colaspase, cyclophosphamide, cytarabine, dacarbazine, dactinomycin, daunorubicin, doxorubicin(adriamycin), epirubicin, etoposide, 5-fluorouracil, hexamethylmelamine, hydroxurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifene, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinylestradiol, 5-fluorodeoxyuridin, 5-fluorodeoxyuridin monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbin, epothilone, gemcitabine, Taxotere, BCNU, CCNU, DTIC, 5-fluorouarcil, Herceptin, Avastin, Erbitux, Sorafenib, Gleevec, Iressa, Tarceva, rapamycin, actinomycin D".

In a further aspect of the present invention, the inventive object was surprisingly achieved by preparing the pyridopyrazine selected from the group consisting of:

Compound 38

1-[3-(-Hydroxy-phenyl)-pyrido[2,3-b]pyrazin-6-yl]-3-methyl-urea

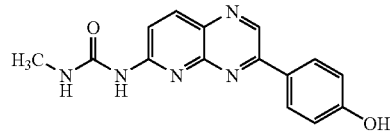

Compound 39

1-Allyl-3-[3-(4-phenoxy-phenyl)-pyrido[2,3-b]pyrazin-6-yl]-urea

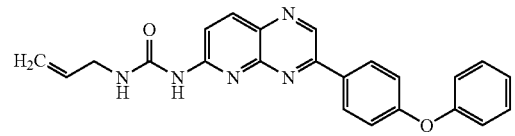

Compound 40

Methane sulfonic acid-4-[6-(3-allyl-ureido)-pyrido[2,3-b]pyrazin-3-yl]-phenyl-ester

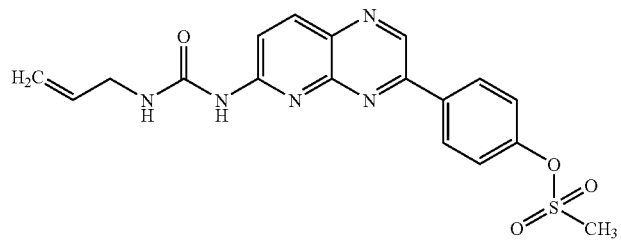

Compound 41

4-Dimethylamino-benzoic acid-4-[6-(3-allyl-ureido)-pyrido[2,3-b]pyrazin-3-yl]-phenyl-ester

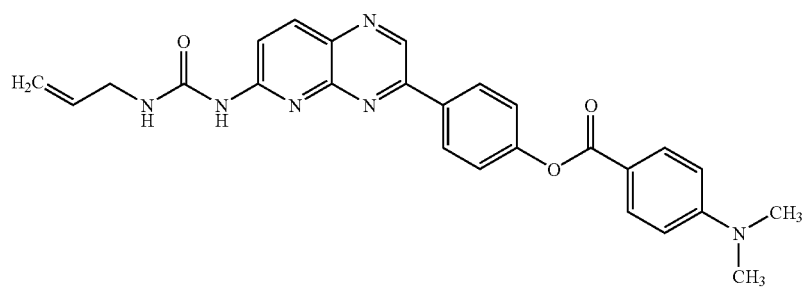

Compound 42

Acetic acid-4-[6-(3-allyl-ureido)-pyrido[2,3-b]pyrazin-3-yl]-phenyl-ester

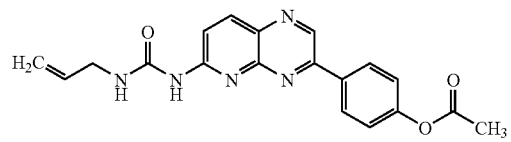

Compound 44

1-[3-(4-Amino-phenyl)-pyrido[2,3-b]pyrazin-6-yl]-3-methyl-thiourea

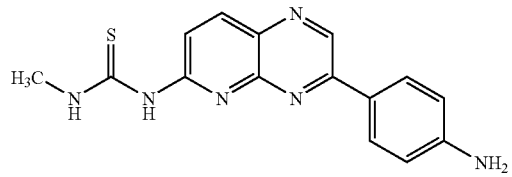

Compound 46

1-Acetyl-1-ethyl-3-(3-phenyl-pyrido[2,3-b]pyrazin-6-yl)-urea

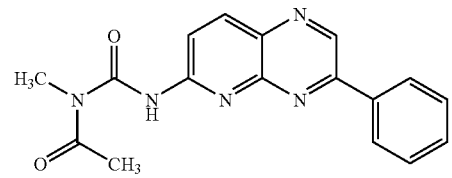

Compound 48

1,1-Diethyl-3-(phenyl-pyrido[2,3-b]pyrazin-6-yl)-urea

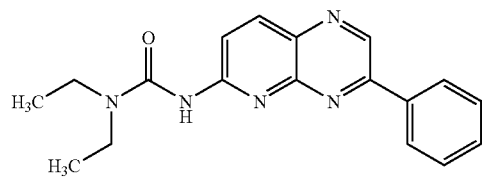

Compound 50

1-Ethyl-3-[3-(4-methoxy-phenyl)-pyrido[2,3-b]pyrazin-6-yl]urea

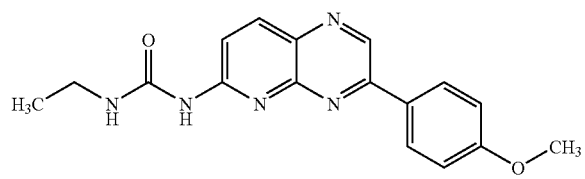

Compound 52

[3-(3-Phenyl-pyrido[2,3-b]pyrazin-6-yl)-ureido]-acetic acid-ethyl-ester

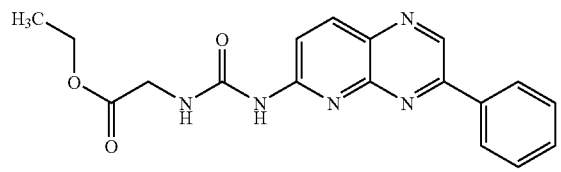

Compound 54

1-Ethyl-3-[3-(4-fluoro-phenyl)-pyrido[2,3-b]pyrazin-6-yl]-urea

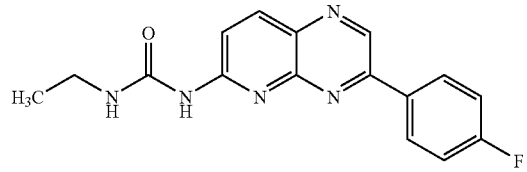

Compound 43

1-Ethyl-3-[3-(4-hydroxy-phenyl)-pyrido[2,3-b]pyrazin-6-yl]-urea

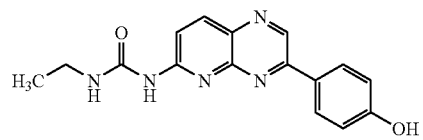

Compound 45

1-Ethyl-3-(3-phenyl-pyrido[2,3-b]pyrazin-6-yl)-urea

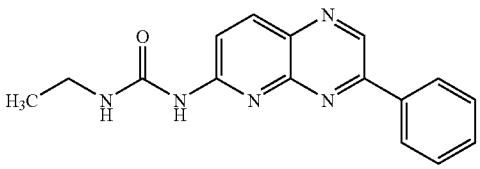

Compound 47

1-Allyl-3-[3-(4-fluoro-phenyl)-pyrido[2,3-b]pyrazin-6-yl]-urea

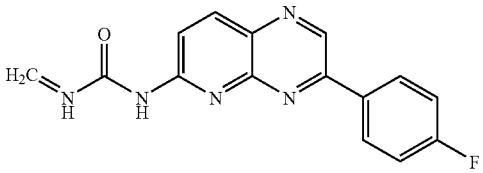

Compound 49

1-(2-Chloro-ethyl)-3-[3-(4-fluoro-phenyl)-pyrido[2,3-b]pyrazin-6-yl]-urea

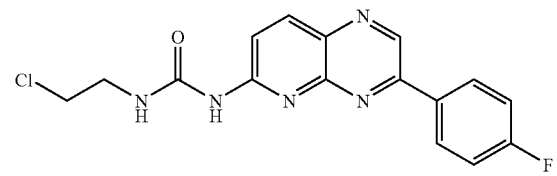

Compound 51

1-(3-Phenyl-pyrido[2,3-b]pyrazin-6-yl)-3-propyl-urea

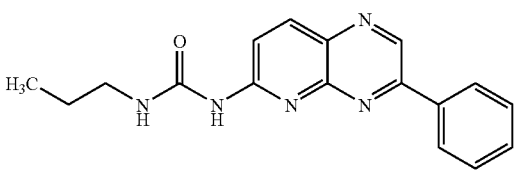

Compound 53

1-(3-Chloroo-pyrido[2,3-b]pyrazin-6-yl)-3-ethyl-urea

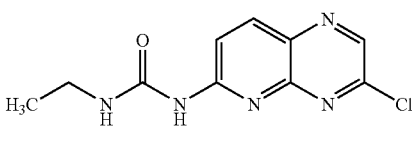

Compound 55

1-[3-(3-Chloro-4-fluoro-phenyl)-pyrido[2,3-b]pyrazin-6-yl]-3-ethyl-urea

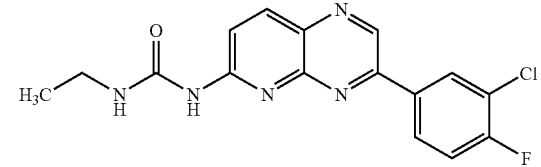

-continued

Compound 56
4-[6-(3-Ethyl-ureido)-pyrido[2,3-b]pyrazin-3-yl]-benzoic acid
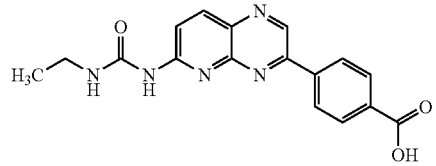

Compound 57
N-{4-[6-(3-Ethyl-ureido)-pyrido[2,3-b]pyrazin-3-yl]-phenyl}-acetamide
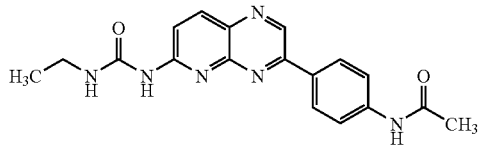

Compound 58
1-[3-(2,4-Difluoro-phenyl)-pyrido[2,3-b]pyrazin-6-yl]-3-ethyl-urea
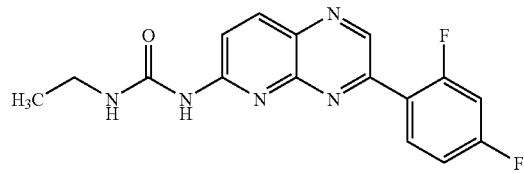

Compound 59
1-Ethyl-3-(3-morpholin-4-yl-pyrido[2,3-b]pyrazin-6-yl-urea
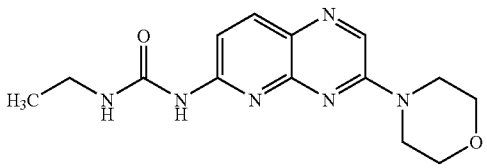

Compound 60
1-Ethyl-3-[3-(4-methyl-piperazin-1-yl)-pyrido[2,3-b]pyrazin-6-yl]-urea
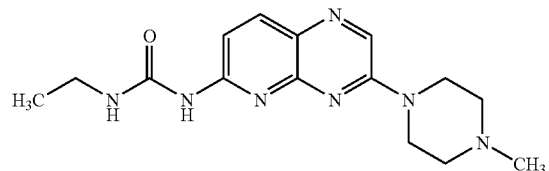

Compound 61
1-Ethyl-3-[3-(2-hydroxy-phenyl)-pyrido[2,3-b]pyrazin-6-yl]-urea
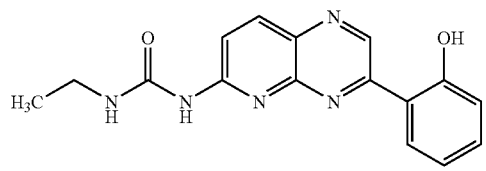

Compound 62
1-Ethyl-3-[3-(2-methoxy-ethylamino)-pyrido[2,3-b]pyrazin-6-yl]-urea
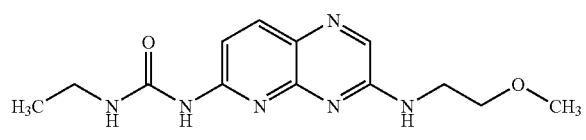 [SMILES: CCNC(=O)Nc1ccc2ncc(NCCOC)nc2n1]

Compound 63
1-[3-(4-Chloro-3-trifluoromethyl-phenyl)pyrido[2,3-b]pyrazin-6-yl]-3-ethyl-urea
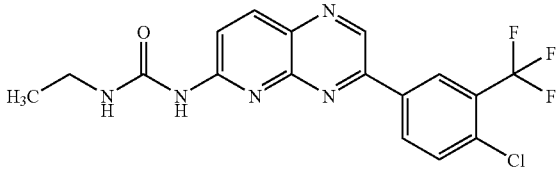

Compound 64
1-Ethyl-3-(3-phenoxy-pyrido[2,3-b]pyrazin-6-yl)-urea
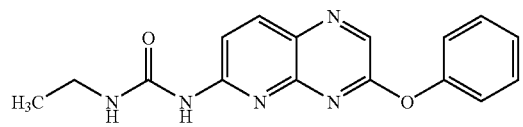

Compound 65
1-[3-(Cyclopropylmethyl-amino)-pyrido[2,3-b]pyrazin-6-yl]-3-ethyl-urea
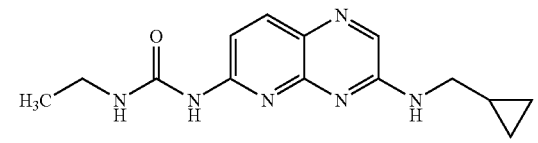 [SMILES: CCNC(=O)Nc1ccc2ncc(NCC3CC3)nc2n1]

Compound 66
1-Ethyl-3-{3-[(pyridin-4-ylmethyl)-amino]-pyrido[2,3-b]pyrazin-6-yl}-urea
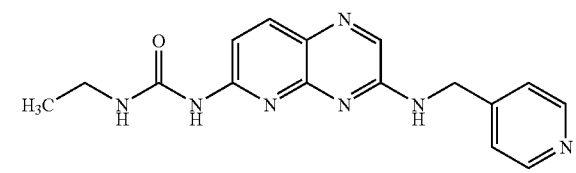 [SMILES: CCNC(=O)Nc1ccc2ncc(NCc3ccncc3)nc2n1]

Compound 67
1-Ethyl-3-[3-(4-fluoro-benzloxy)-pyrido[2,3-b]pyrazin-6-yl]-urea
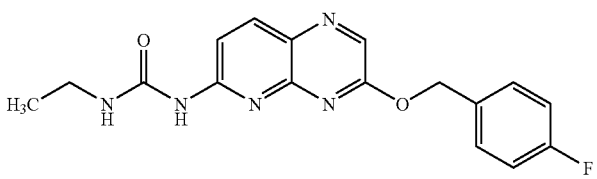

Compound 68
1-Ethyl-3-(3-pyridin-4-yl-pyrido[2,3-b]pyrazin-6-yl)-urea
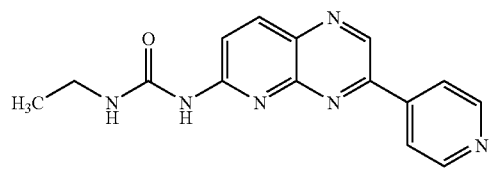

Compound 69
1-Ethyl-3-[3-(pyridin-3-yloxy)-pyrido[2,3-b]pyrazin-6-yl]-urea
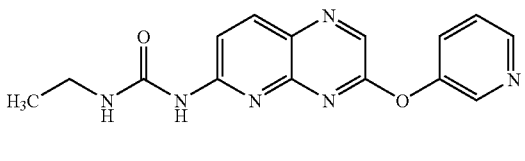

Compound 70

1-Ethyl-3-[3-(tetrahydro-furan-2-ylmethoxy)-pyrido[2,3-b]pyrazin-6-yl]-urea

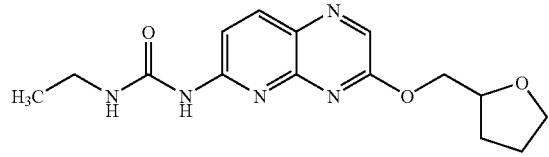

Compound 71

1-Ethyl-3-[3-(4-morpholin-4-yl-phenyl)-pyrido[2,3-b]pyrazin-6-yl]-urea

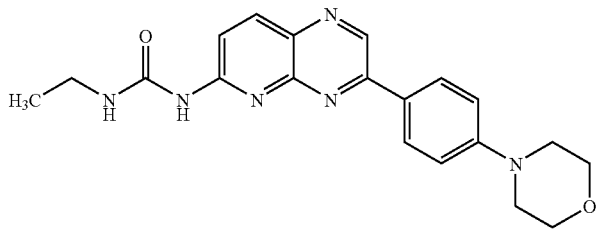

Compound 72

1-Ethyl-3-(3-hydroxy-pyrido[2,3-b]pyrazin-6-yl)-urea

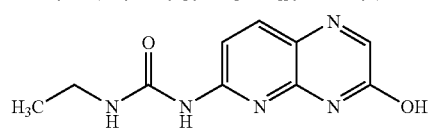

Compound 73

1-Ethyl-3-[3-(3-methoxy-phenylsulfanyl)-pyrido[2,3-b]pyrazin-6-yl]-urea

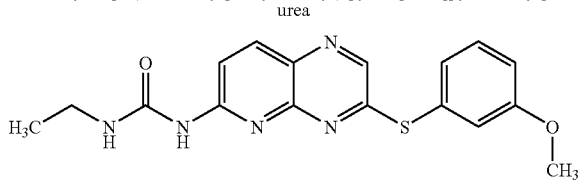

Compound 74

1-Ethyl-3-(3-quinolin-3-yl-pyrido[2,3-b]pyrazin-6-yl)-urea

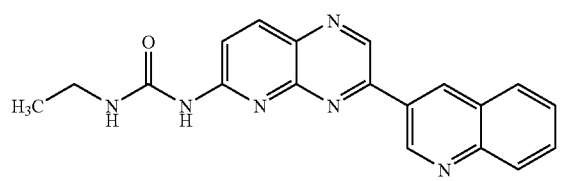

Compound 75

1-(3-Benzo[b]thiophen-3-yl-pyrido[2,3-b]pyrazin-6-yl)-3-ethyl-urea

Compound 76

1-Ethyl-3-[3-(pyridin-2-ylsulfanyl)-pyrido[2,3-b]pyrazin-6-yl]-urea

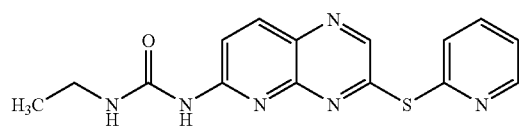

Compound 77

1-[3-(4-Dimethylamino-phenyl)-pyrido[2,3-b]pyrazin-6-yl]-3-ethyl-urea

Compound 78

N-{4-[6-(3-Ethyl-ureido)-pyrido[2,3-b]pyrazin-3-yl]-phenyl}-methansulfonamide

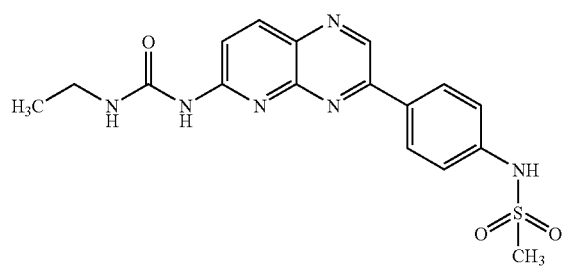

Compound 79

1-Ethyl-3-[3-(1H-pyrazol-4-yl)-pyrido[2,3-b]pyrazin-6-yl]-urea

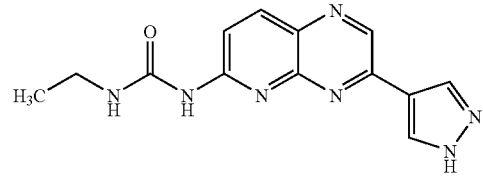

Compound 80

1-(3-Benzylsulfanyl-pyrido[2,3-b]pyrazin-6-yl)-3-ethyl-urea

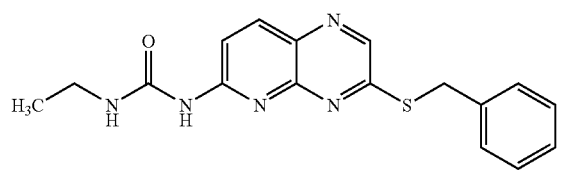

Compound 81

1-Ethyl-3-[3-(4-methyl-[1,4]diazepan-1-yl)-pyrido[2,3-b]pyrazin-6-yl]-urea

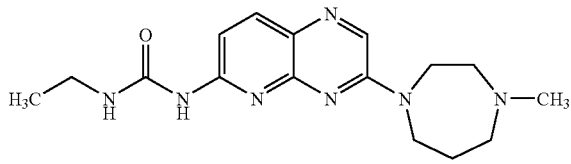

-continued

Compound 82

1-[3-(4-Amino-phenyl)-pyrido[2,3-b]pyrazin-6-yl]-3-ethyl-urea

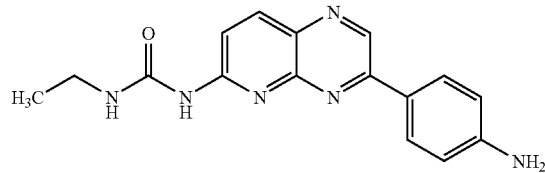

Compound 83

1-(3-Amino-pyrido[2,3-b]pyrazin-6-yl)-3-ethyl-urea

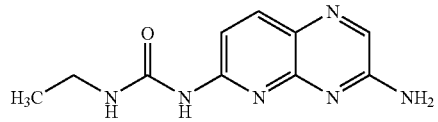 [SMILES: CCNC(=O)Nc1ccc2ncc(N)nc2n1]

Compound 84

1-Ethyl-3-pyrido[2,3-b]pyrazin-6-yl-urea

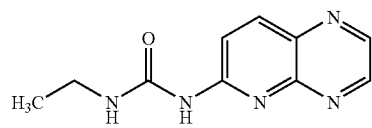

Compound 85

1-Ethyl-3-(3-imidazol-1-yl-pyrido[2,3-b]pyrazin-6-yl)-urea

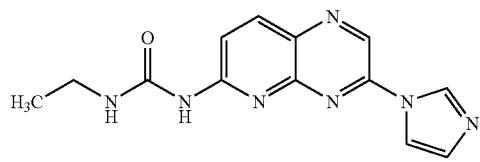

Compound 86

1-Ethyl-3-[3-(4-fluoro-2-hydroxy-phenyl)-pyrido[2,3-b]pyrazin-6-yl]-urea

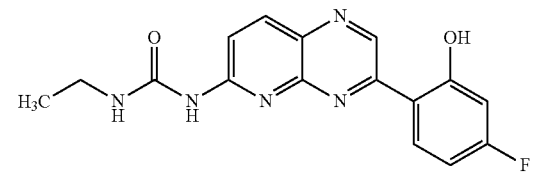

Compound 87

1-(3-Cyclopentyloxy-pyrido[2,3-b]pyrazin-6-yl)-3-ethyl-urea

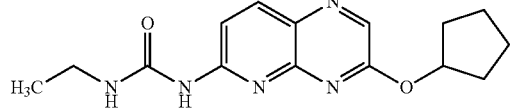

Compound 88

1-Ethyl-3-[3-(4-hydroxy-piperidin-1-yl)-pyrido[2,3-b]pyrazin-6-yl]-urea

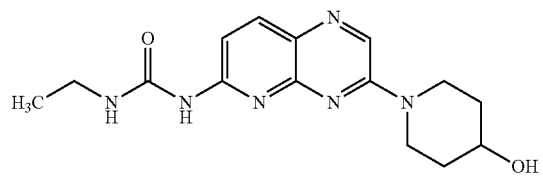

Compound 89

(3-Phenyl-pyrido[2,3-b]pyrazin-6-yl)-urea

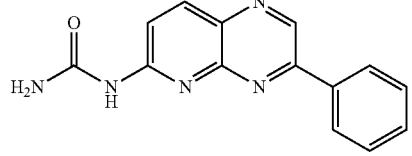

Compound 90

1-Ethyl-3-(3-pyrimidin-5-yl-pyrido[2,3-b]pyrazin-6-yl)-urea

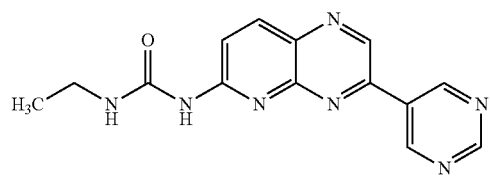

Compound 91

1-Ethyl-3-(3-pyridin-3-yl-pyrido[2,3-b]pyrazin-6-yl)-urea

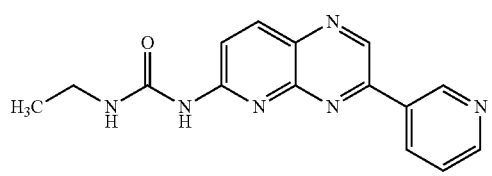

Compound 92

1-Allyl-3-(3-phenyl-pyrido[2,3-b]pyrazin-6-yl)-urea

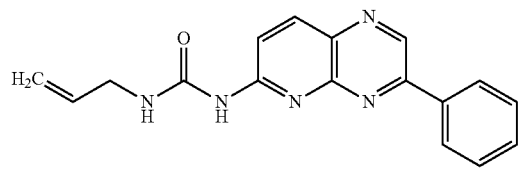

Compound 93

1-Ethyl-3-(3-piperazin-1-yl-pyrido[2,3-b]pyrazin-6-yl)-urea

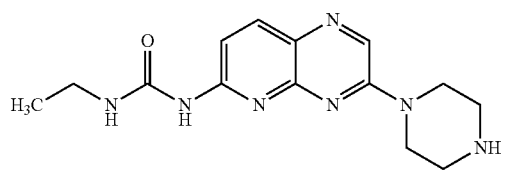

Compound 94
1-[3-(3-Chloro-pyridin-4-ylmethyl)-pyrido[2,3-b]pyrazin-6-yl]-3-ethyl-urea

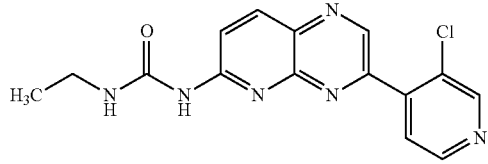

Compound 95
1-Ethyl-3-[3-(6-methoxy-pyridin-3-yl)-pyrido[2,3-b]pyrazin-6-yl]-urea

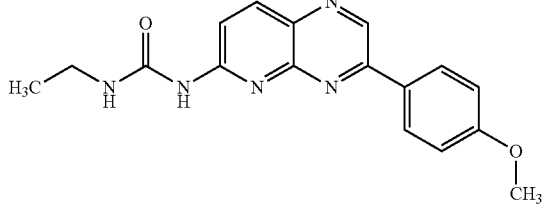

Compound 96
1-[3-(3,5-Dimethyl-isoxazol-4-yl)-pyrido[2,3-b]pyrazin-6-yl]-3-ethyl-urea

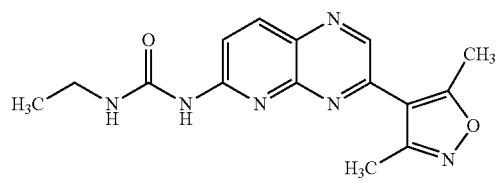

Compound 97
1-Ethyl-3-[3-(4-trifluoromethoxy-phenyl)-pyrido[2,3-b]pyrazin-6-yl]-urea

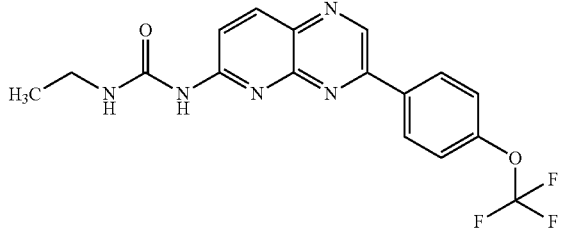

Compound 98
1-Ethyl-3-(3-furan-2-yl-pyrido[2,3-b]pyrazin-6-yl)-urea

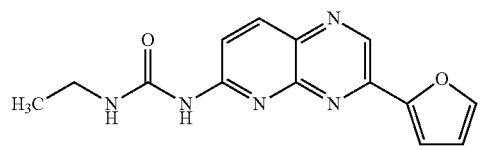

Compound 99
1-Ethyl-3-[3-(2-methoxy-pyridin-3-yl)-pyrido[2,3-b]pyrazin-6-yl]-urea

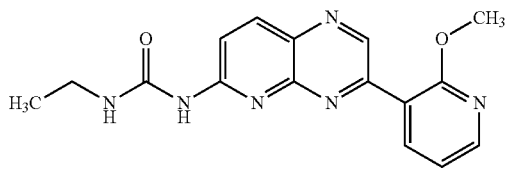

Compound 100
1-[3-(2,4-Dimethoxy-phenyl)-pyrido[2,3-b]pyrazin-6-yl]-3-ethyl-urea

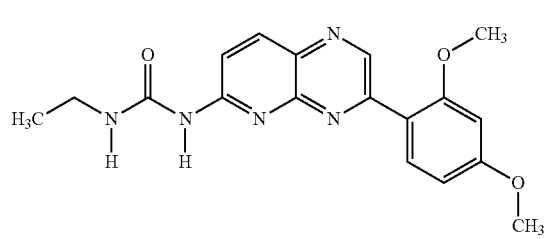

Compound 101
1-Ethyl-3-[3-(1H-pyrrol-2-yl)-pyrido[2,3-b]pyrazin-6-yl]-urea

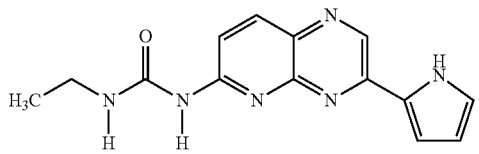

Compound 102
1-Ethyl-3-[3-(6-morpholin-4-yl-pyridin-3-yl)-pyrido[2,3-b]pyrazin-6-yl]-urea

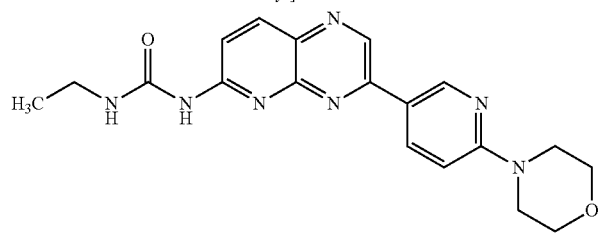

Compound 103
1-Benzyl-3-ethyl-1-(3-phenyl-pyrido[2,3-b]pyrazin-6-yl)-urea

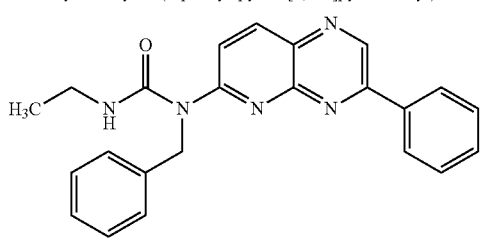

-continued

Compound 104
1-[3-(2-Amino-phenyl)-pyrido[2,3-b]pyrazin-6-yl]-3-ethyl-urea
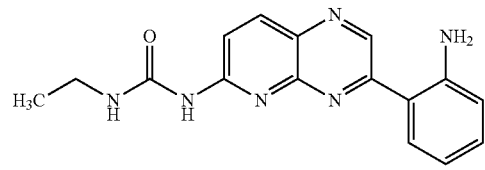

Compound 105
1-Ethyl-3-[3-(4-hydroxymethyl-phenyl)pyrido[2,3-b]pyrazin-6-yl]-urea
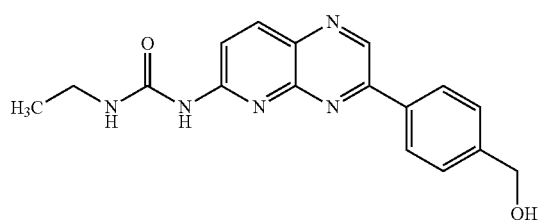

Compound 106
1-[3-(3-Amino-phenyl)-pyrido[2,3-b]pyrazin-6-yl]-3-ethyl-urea
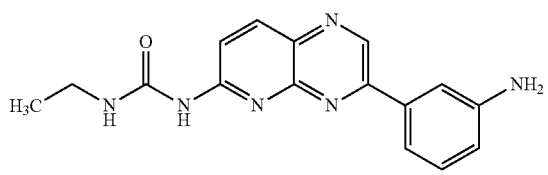

Compound 107
1-[3-(4-Acetyl-phenyl)-pyrido[2,3-b]pyrazin-6-yl]-3-ethyl-urea
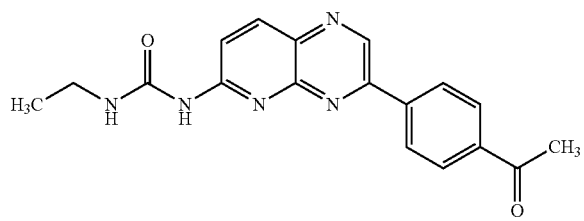

Compound 108
1-[3-(2,3-Dihydro-benzofuran-5-yl)-pyrido[2,3-b]pyrazin-6-yl]-3-ethyl-urea
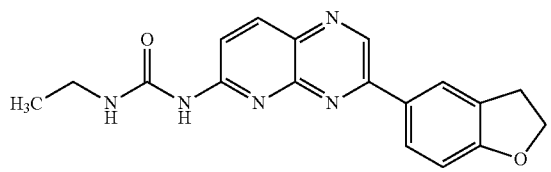

Compound 109
1-[3-(4-Benzyloxy-3-fluoro-phenyl)-pyrido[2,3-b]pyrazin-6-yl]-3-ethyl-urea
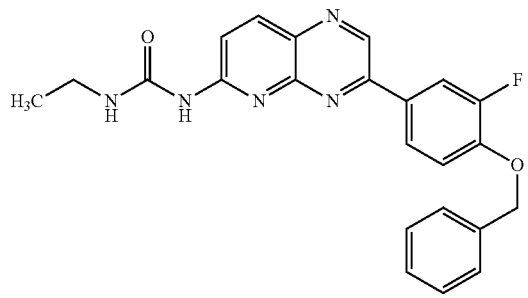

Compound 110
1-(2,3-Dihydroxy-propyl)-3-(3-phenyl-pyrido[2,3-b]pyrazin-6-yl)-urea
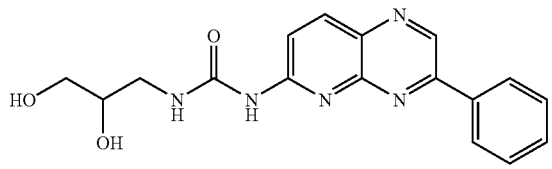

Compound 111
1-Ethyl-3-[3-(3-formyl-4-methoxy-phenyl)-pyrido[2,3-b]pyrazin-6-yl]-urea
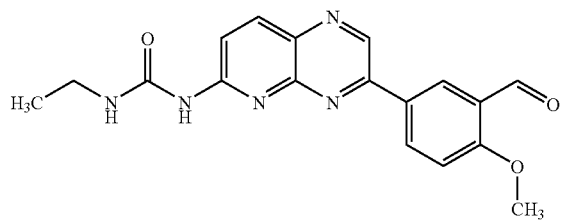

Compound 112
1-Ethyl-3-[3-(4-methansulfonyl-phenyl)-pyrido[2,3-b]pyrazin-6-yl]-urea
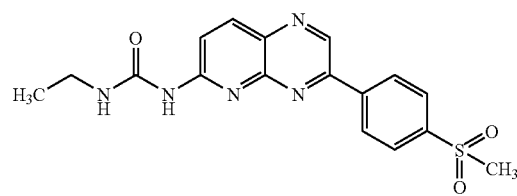

Compound 113
N-{4-[6-(3-Ethyl-ureido)-pyrido[2,3-b]pyrazin-3-yl]-pheny}-succinamid acid
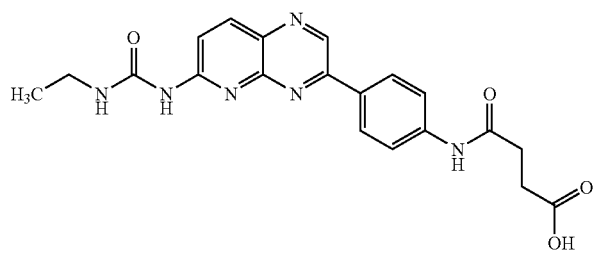

-continued

Compound 115

1-Ethyl-3-(3-pyridin-4-yl-pyrido[2,3-b]pyrazin-6-yl]-urea Methane sulfonic acid salt (free base)

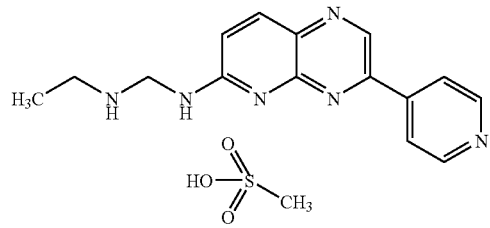

Compound 115

1-[3-(2,6-Dimethoxy-pyridin-3-yl)pyrido[2,3-b]pyrazin-6-yl]-3-ethyl-urea

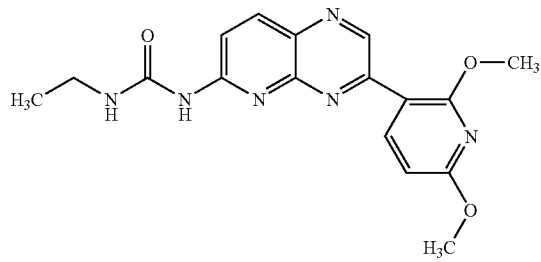

Compound 116

1-[3-(2,6-Dimethoxy-pyrimidin-4-yl)-pyrido[2,3-b]pyrazin-6-yl]-3-ethyl-urea

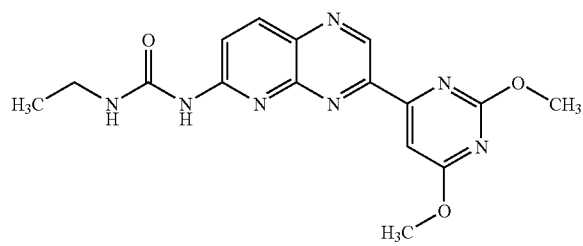

Compound 117

1-[3-(2,4-Dioxo-1,2,3,4-tetrahydro-pyrimidin-5-yl)-pyrido[2,3-b]pyrazin-6-yl]-3-ethyl-urea

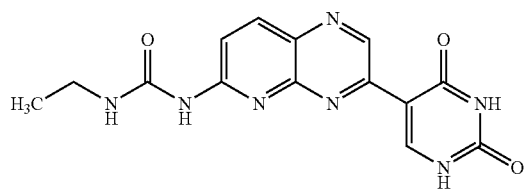

Compound 118

1-Ethyl-3-[3-(1H-indo-5-yl)-pyridol[2,3-b]pyrazin-6-yl]-urea

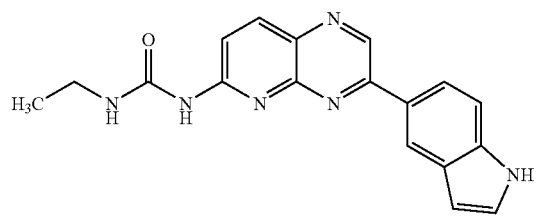

Compound 119

1-(3-Chloro-pyrido[2,3-b]pyrazin-6-yl)-3-ethyl-thiourea

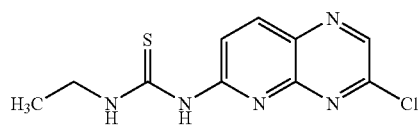

Compound 120

1-Ethyl-3-{3-[4-(2-methoxy-ethoxy)-phenyl]-pyrido[2,3-b]pyrazin-6-yl}-urea

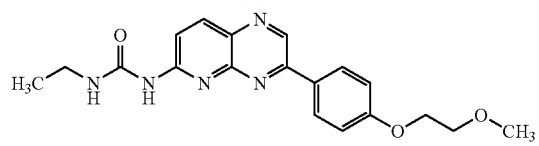

Compound 121

Acrylic acid-4-[6-(3-ethyl-ureido)-pyrido[2,3-b]-pyrazin-3-yl]-phenyl-ester

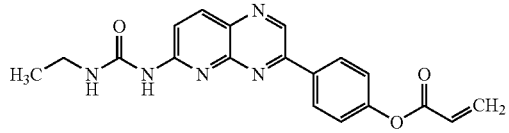

Compound 122

1-[3-(4-Cyano-phenyl)-pyrido[2,3-b]pyrazin-6-yl]-3-ethyl-urea

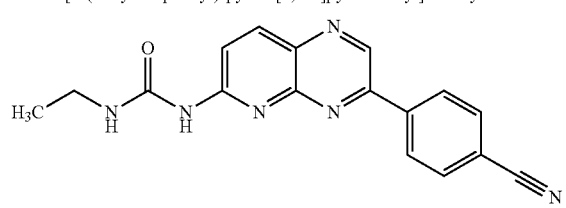

Compound 123

1-(3-Benzo[1,2,5]oxadiazol-4-yl-pyrido[2,3-b]pyrazin-6-yl)-3-ethyl-urea

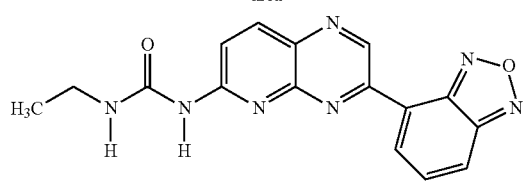

-continued

Compound 124

1-Ethyl-3-[3-(4-hydroxy-3-methoxy-phenyl)-pyrido[2,3-b]pyrazin-6-yl]-urea

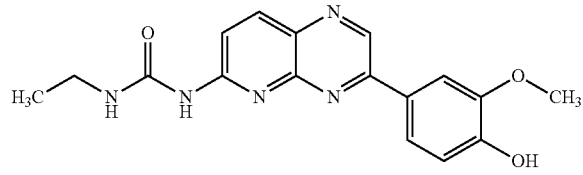

Compound 125

1-[3-(2,6-Dimethoxy-phenyl)-pyrido[2,3-b]pyrazin-6-yl]-3-ethyl-urea

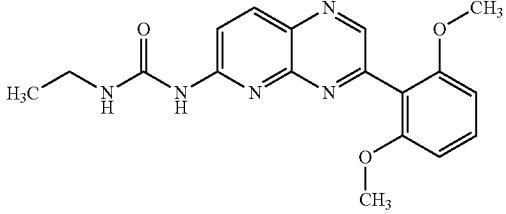

Compound 126

1-[3-(3-Acetyl-phenyl)-pyrido[2,3-b]pyrazin-6-yl]-3-ethyl-urea

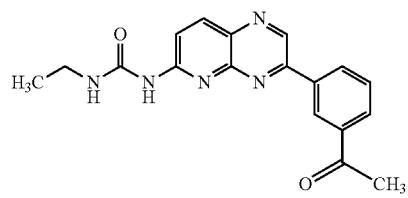

Compound 127

1-Ethyl-3-[3-(3-morpholin-4-yl-phenyl)-pyrido[2,3-b]pyrazin-6-yl]-urea

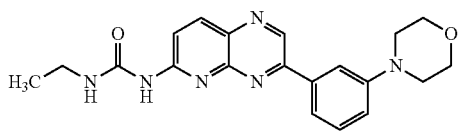

Compound 128

1-[3-(6-Amino-pyridin-3-yl)-pyrido[2,3-b]pyrazin-6-yl]-3-ethyl-urea

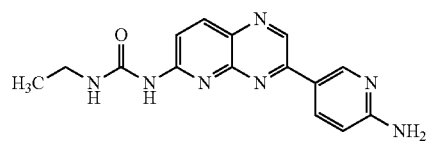

Compound 129

3-{4-[6-(3-Ethyl-ureido)-pyrido[2,3-b]-pyrazin-3-yl]-phenoxy}-propionic acie

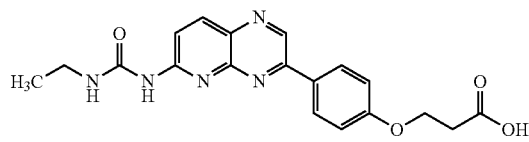

Compound 130

1-Isopropyl-3-(3-phenyl-pyrido[2,3-b]pyrazin-6-yl)-urea

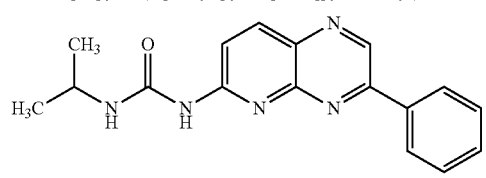

Compound 131

1-Cyclopentyl-3-(3-phenyl-pyrido[2,3-b]pyrazin-6-yl-urea

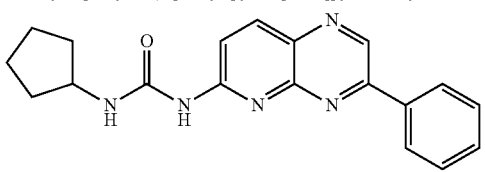

Compound 132

1-Pentyl-3-(3-phenyl-pyrido[2,3-b]pyrazin-6-yl)-urea

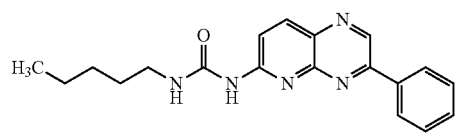

Compound 133

N-{4-[6-(3-Ethyl-ureido)-pyrido[2,3-b]pyrazin-3-yl]-phenyl}-acrylamide

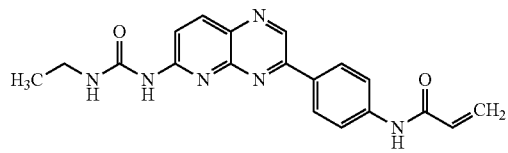

Compound 134

1-tert-Butyl-3-(3-phenyl-pyrido[2,3-b]pyrazin-6-yl)-urea

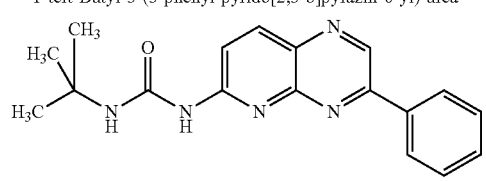

Compound 135

1-(2-Hydroxy-ethyl)-3-(3-phenyl-pyrido[2,3-b]pyrazin-6-yl)-urea

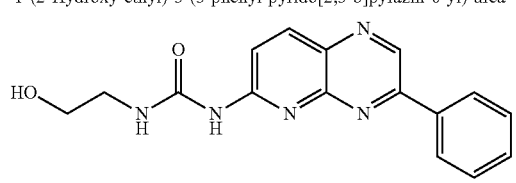

Compound 136

1-Cyclobutyl-3-(3-phenyl-pyrido[2,3-b]pyrazin-6-yl)-urea

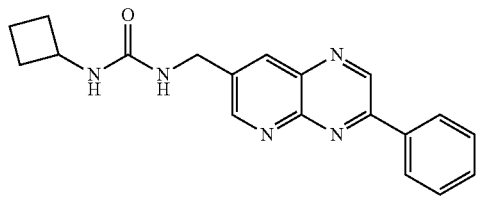

Compound 137

1-Allyl-3-[3-(4-nitro-phenyl)-pyrido[2,3-b]pyrazin-7-yl]-thiourea

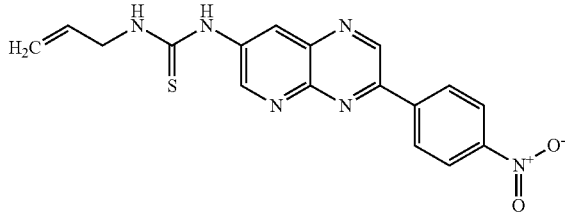

Compound 138

1-Ethyl-1-(Ethylcarbamoyl)-3-(3-phenyl-pyrido[2,3-b]pyrazin-6-yl)-urea

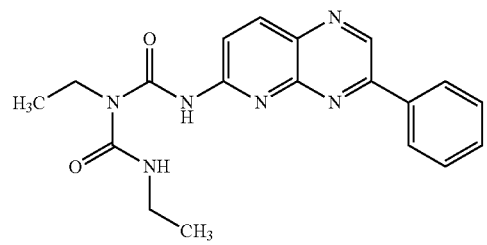

Compound 139

[3-(4-Hydroxy-phenyl)-pyrido[2,3-b]pyrazin-6-yl]carbamic acid-allyl-ester

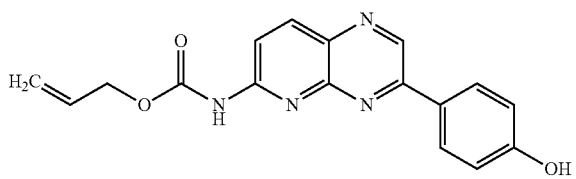

Compound 140

(3-Phenyl-pyrido[2,3-b]pyrazin-6-yl)-carbamic acid-ethyl-ester

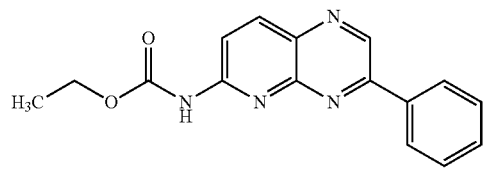

Compound 141

1-Ethyl-3-[3-(4-phenyl-piperazin-1-yl)-pyrido[2,3-b]pyrazin-6-yl]-urea

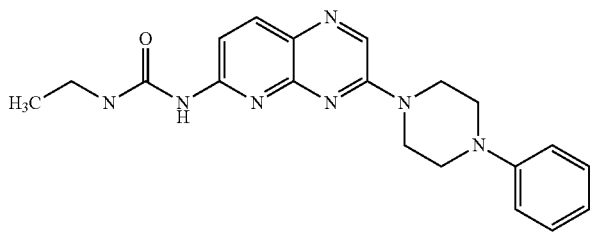

Compound 142

1-(2,2-Dimethyl-[1,3]dioxolan-4-ylmethyl)-3-(3-phenyl-pyrido[2,3-b]pyrazin-6-yl)-urea

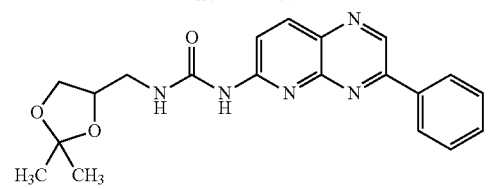

Compound 143

1,3-Bis-(3-phenyl-pyrido[2,3-b]pyrazin-6-yl)-urea

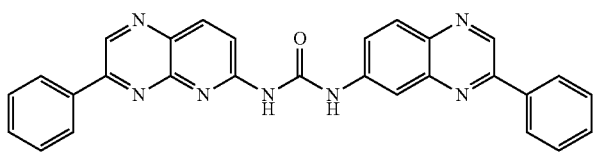

Compound 144

N-(3-Phenyl-pyrido[2,3-b]pyrazin-6-yl)-acetamidine

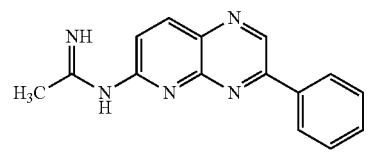

Compound 145

1-Ethyl-3-[3-(2-methoxy-pyridin-3-yl)-pyrido[2,3-b]pyrazin-6-yl]-thiourea

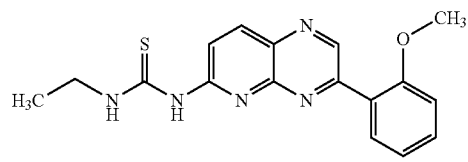

Compound 146

1-(4-Hydroxy-butyl)-3-(3-phenyl-pyrido[2,3-b]pyrazin-6-yl)-urea

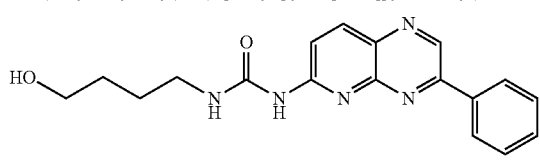

Compound 147

1-(3-Hydroxy-propyl)-3-(3-phenyl-pyrido[2,3-b]pyrazin-6-yl)-urea

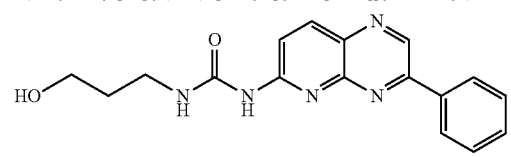

Compound 148

1-Ethyl-3-{3-[4-(3-morpholin-4-yl-propoxy)-phenyl]-pyrido[2,3-b]pyrazin-6-yl}-urea

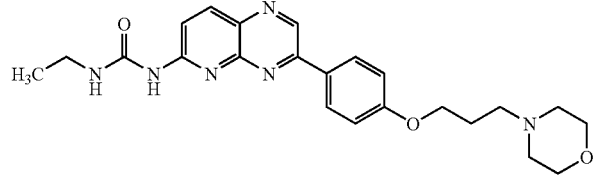

Compound 149

1-Ethyl-3-[3-(4-hydroxy-phenyl)-pyrido[2,3-b]pyrazin-6-yl]-thiourea

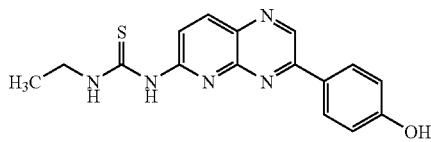

Compound 150

1-Ethyl-3-(3-p-tolylamino-pyrido[2,3-b]pyrazin-6-yl)-urea

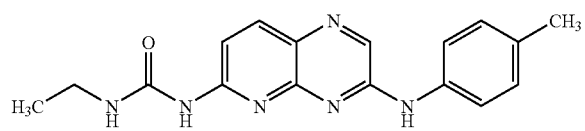 [SMILES: CCNC(=O)Nc1ccc2ncc(Nc3ccc(C)cc3)nc2n1]

Compound 151

1-Ethyl-3-[3-(3-hydroxy-phenyl)-pyrido[2,3-b]pyrazin-6-yl]-urea

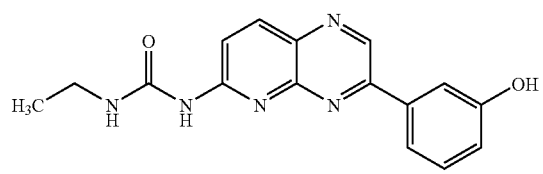

Compound 152

3-[6-(3-Ethyl-ureido)-pyrido[2,3-b]pyrazin-3-yl]-benzoic acid

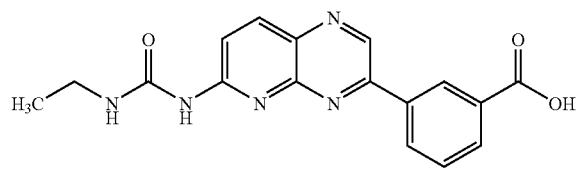

Compound 153

1-[3-(3,4-Dimethoxy-phenyl)-pyrido[2,3-b]pyrazin-6-yl]-3-ethyl-urea

Compound 154

1-[3-(4-Amino-3-methoxy-phenyl)-pyrido[2,3-b]pyrazin-6-yl]-3-ethyl-urea

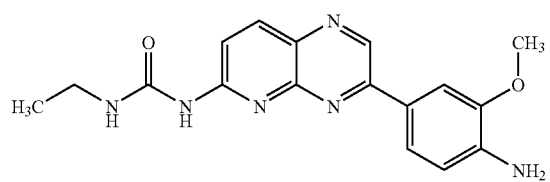

Compound 155

3-[6-(3-Ethyl-ureido)-pyrido[2,3-b]-pyrazin-3-yl]-benzamide

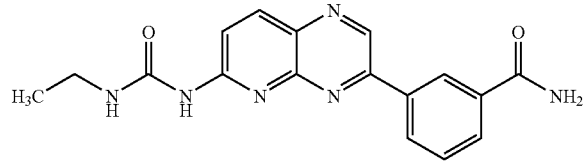

Compound 156

1-[3-(3-Chloro-4-hydroxy-5-methoxy-phenyl)-pyrido[2,3-b]pyrazin-6-yl]-3-ethyl-urea

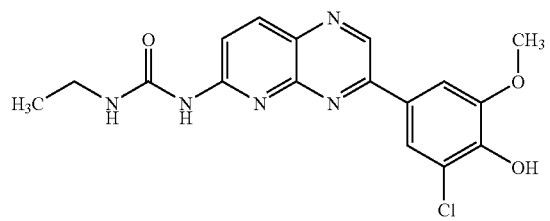

Compound 157

1-Ethyl-3-(3-m-tolylamino-pyrido-[2,3-b]pyrazin-6-yl)-urea

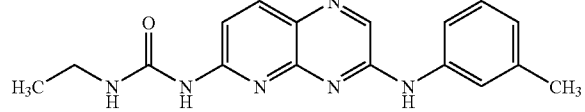

Compound 158

1-Ethyl-3-[3-(4-methoxy-phenylamino)-pyrido[2,3-b]pyrazin-6-yl]-urea

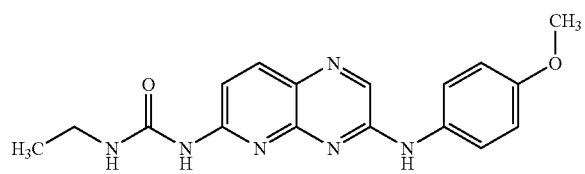 [SMILES: CCNC(=O)Nc1ccc2ncc(Nc3ccc(OC)cc3)nc2n1]

Compound 159

1-[3-(4-Chloro-phenylamino)-pyrido-[2,3-b]pyrazin-6-yl]-3-ethyl-urea

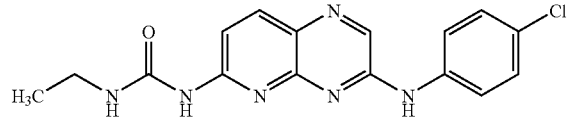 [SMILES: CCNC(=O)Nc1ccc2ncc(Nc3ccc(Cl)cc3)nc2n1]

Compound 160
1-Ethyl-3-(3-o-tolylamino-pyrido[2,3-b]-pyrazin-6-yl)-urea
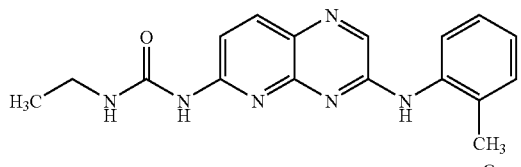

Compound 161
1-Ethyl-3-[3-(pyridin-3-ylamino)-pyrido-[2,3-b]pyrazin-6-yl-urea
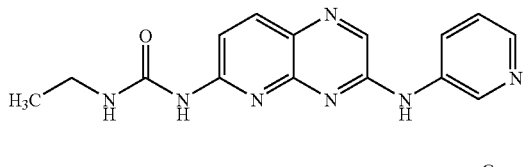

Compound 162
1-Ethyl-3-[3-(4-ethyl-phenylamino)-pyrido[2,3-b]pyrazin-6-yl]urea
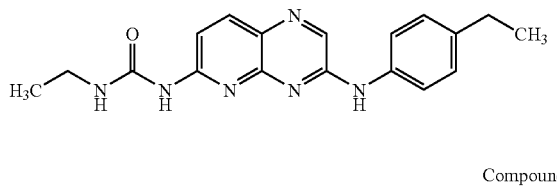

Compound 163
1-Ethyl-3-[3-(-methoxy-4-methyl-phenylamino)-pyrido[2,3-b]pyrazin-6-yl]-urea
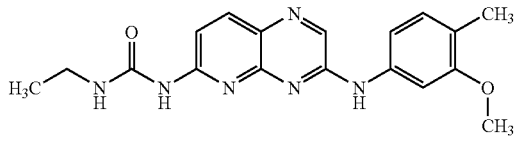

Compound 164
1-Ethyl-3-[3-(4-hydroxy-phenylamino)-pyrido[2,3-b]pyrazin-6-yl]-urea
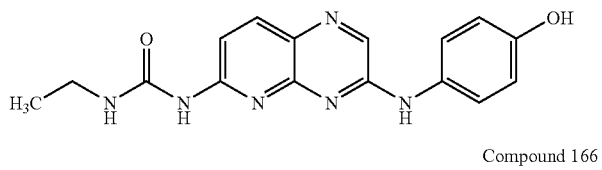

Compound 165
1-Ethyl-3-[3-(5-methyl-pyridin-2-yl-amino)-pyrido[2,3-b]pyrazin-6-yl]-urea
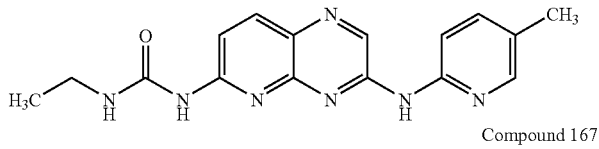

Compound 166
1-Ethyl-3-[3-(1-methyl-1H-pyrazol-3-ylamino)-pyrido[2,3-b]pyrazin-6-yl]-urea
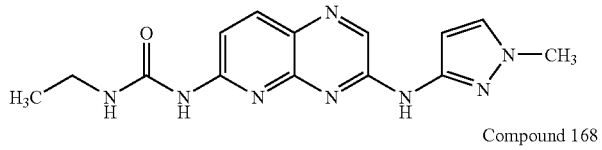

Compound 167
1-Ethyl-3-[3-(4-fluoro-phenylamino)-pyrido[2,3-b]pyrazin-6-yl-urea
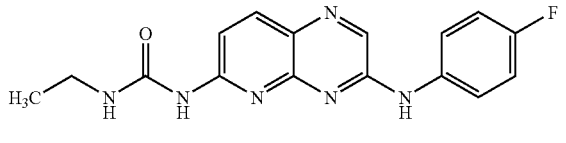 [SMILES: CCNC(=O)Nc1ccc2ncc(Nc3ccc(F)cc3)nc2n1]

Compound 168
1-(4-Hydroxy-butyl)-3-[3-(4-hydroxy-3-methoxy-phenyl)-pyrido[2,3-b]pyrazin-6-yl]-urea
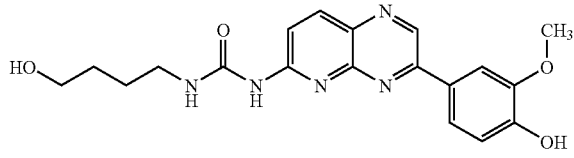

Compound 169
Phosphoric acid-mono-{4-[6-(3-ethyl-ureido)-pyrido-[2,3-b]pyrazin-3-yl]-2-methoxy-phenyl}-ester
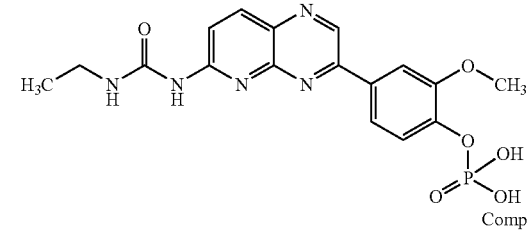

Compound 170
1-[3-(2-Chloro-4-hydroxy-phenyl)-pyrido[2,3-b]pyrazin-6-yl]-3-ethyl-urea
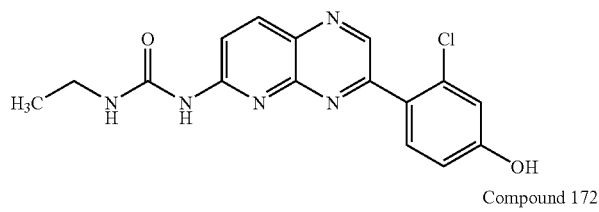

Compound 171
1-[3-(4-Chloro-2-methoxy-phenyl)-pyrido[2,3-b]pyrazin-6-yl]-3-ethyl-urea Compound 172
1-[3-(3,5-Dimethyl-1H-pyrazol-4-yl)-pyrido[2,3-b]pyrazin-6-yl]-3-ethyl-urea
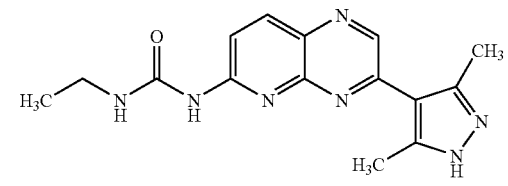

Compound 173
1-Ethyl-3-[3-(1-methyl-1H-pyrazol-4-yl)-pyrido[2,3-b]pyrazin-6-yl]-urea Compound 174

1-[3-(5-Cyano-thiophen-2-yl)-pyrido[2,3-b]pyrazin-6-yl]-3-ethyl-urea

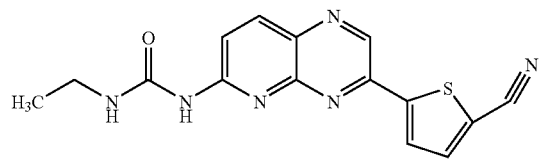

Compound 175

Sodium 2-chloro-4-[6-(3-ethyl-ureido)-pyrido[2,3-b]pyrazin-3-yl]-6-methoxy-phenolate

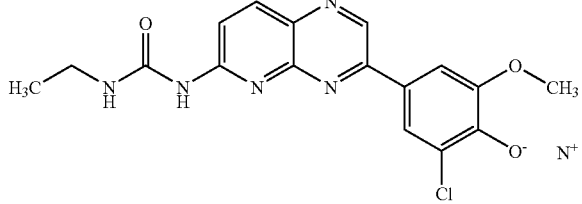

Compound 176

1-[3-(4-Hydroxy-3-methoxy-phenyl)-pyrido[2,3-b]pyrazin-6-yl]-3-(4-morpholin-4-yl-butyl)-urea

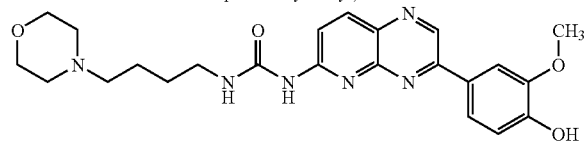

Compound 177

1-[3-(3-Chloro-4-methoxy-phenylamino)-pyrido[2,3-b]pyrazin-6-yl]-3-ethyl-urea

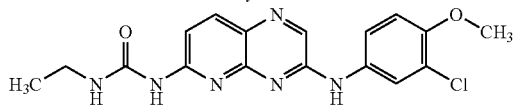

Compound 178

1-Ethyl-3-[3-(naphthalin-2-ylamino)-pyrido[2,3-b]pyrazin-6-yl]-urea

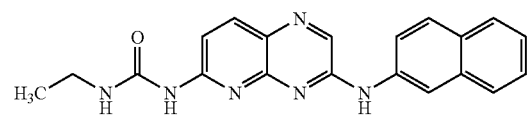

Compound 179

1-Ethyl-3-[3-(Quinolin-3-ylamino)-pyrido[2,3-b]pyrazin-6-yl]-urea

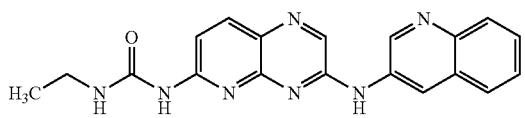

Compound 180

1-[3-(3,5-Dimethoxy-phenylamino)-pyrido[2,3-b]pyrazin-6-yl]-3-ethyl-urea

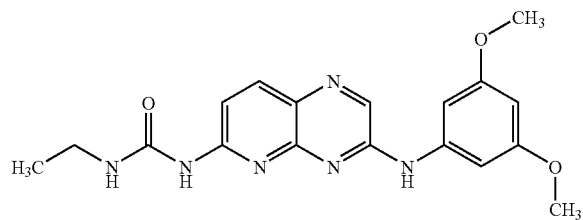 [SMILES: CCNC(=O)Nc1ccc2ncc(Nc3cc(OC)cc(OC)c3)nc2n1]

Compound 181

1-Ethyl-3-[3-(pyrazin-2-ylamino)-pyrido[2,3-b]pyrazin-6-yl]-urea

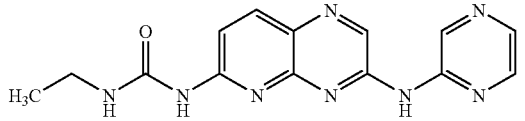 [SMILES: CCNC(=O)Nc1ccc2ncc(Nc3cnccn3)nc2n1]

Compound 182

1-Ethyl-3-[3-(3-isopropoxy-phenylamino)-pyrido[2,3-b]pyrazin-6-yl]-urea

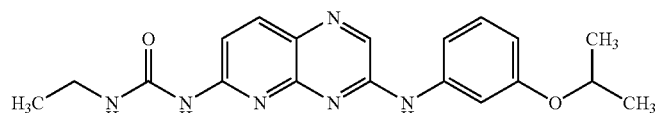

Compound 183

1-Ethyl-3-[-3-(4-hydroxy-3-methoxy-phenyl)-pyrido[2,3-b]pyrazin-6-yl]-urea p-Toluolsulfonat

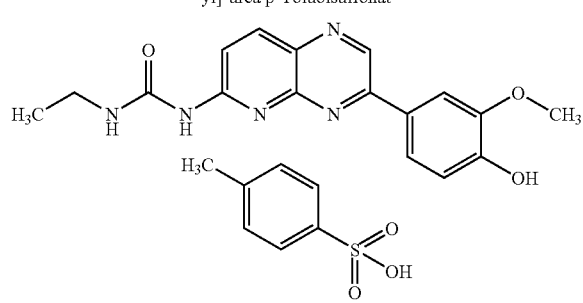

Compound 184

1-[3-(2-Chloro-pyridin-4-ylamino-pyrido[2,3-b]prazin-6-yl]-3-ethyl-urea

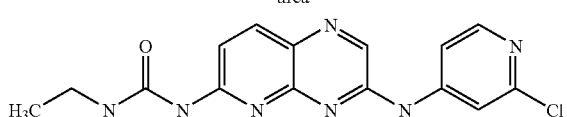

-continued

Compound 185

1-[3-(3,5-Dichloro-4-hydroxy-phenylamino)-pyrido[2,3-b]pyrazine-6-yl]-3-ethyl-urea

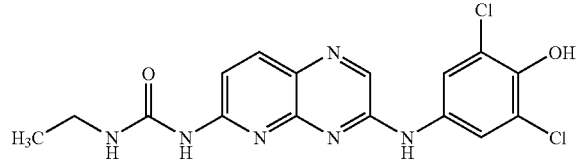 [SMILES: CCNC(=O)Nc1ccc2ncc(Nc3cc(Cl)c(O)c(Cl)c3)nc2n1]

Compound 186

1-[3-(3,5-Dichloro-4-hydroxy-phenyl)-pyrido[2,3-b]pyrazine-6-yl]-3-ethyl-urea

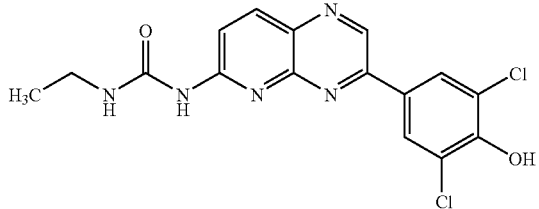

Compound 187

1-[3-(3,4-Dimethoxy-phenylamino)-pyrido[2,3-b]pyrazine-6-yl]-3-ethyl-urea

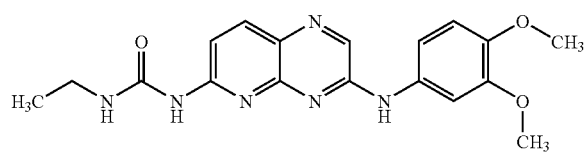 [SMILES: CCNC(=O)Nc1ccc2ncc(Nc3ccc(OC)c(OC)c3)nc2n1]

Compound 188

1-Ethyl-3-[3-(3-hydroxy-4-methyl-phenylamino)-pyrido[2,3-b]pyrazin-6-yl]-urea

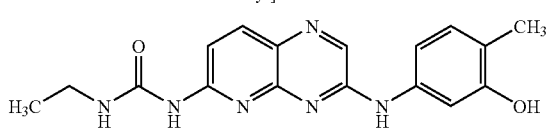

Compound 189

3-[6-(3-Ethyl-ureido)-pyrido[2,3-b]-pyrazin-3-ylamino]-5-trifluoromethyl-benzoic acid

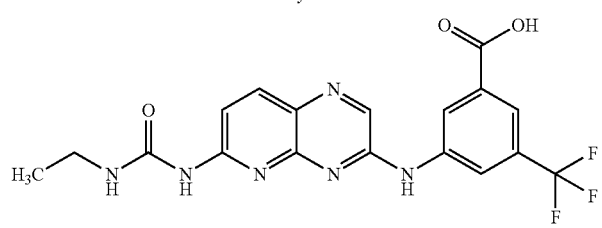

Compound 190

1-Ethyl-3-[3-(6-methoxy-pyridin-3-ylamino)-pyrido[2,3-b]pyrazin-6-yl]-urea

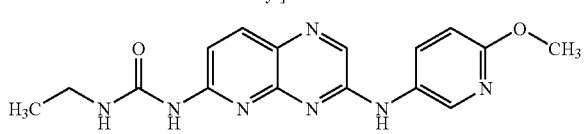

Compound 191

1-[3-(3,5-Dimethyl-phenylamino)-pyrido[2,3-b]pyrazin-6-yl]-3-ethyl-urea

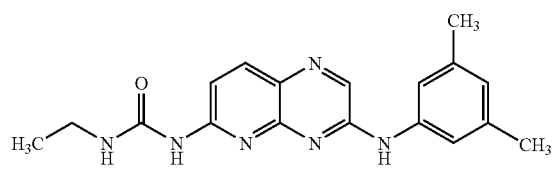

Compound 192

1-[3-(4-Cyano-phenylamino)-pyrido-[2,3-b]pyrazin-6-yl]-3-ethyl-urea

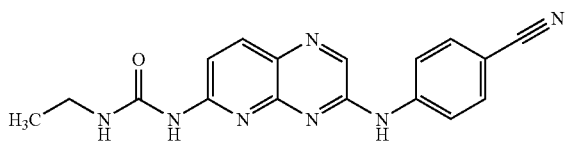

Compound 193

1-Ethyl-3-[3-(4-hydroxy-3-methoxy-phenyl)-pyrido[2,3-b]pyrazin-6-yl]-urea (Z)-but-2-endicarbonic acid salt

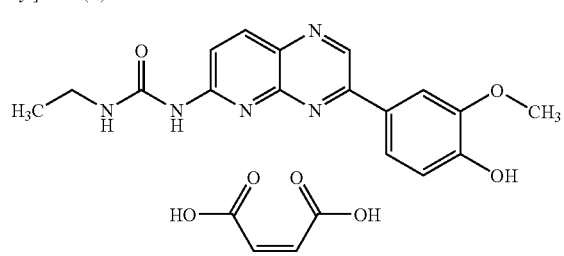

Compound 194

1-Ethyl-3-[3-(4-hydroxy-3-methoxy-phenyl)-pyrido[2,3-b]pyrazin-6-yl]-urea Hydrochloride

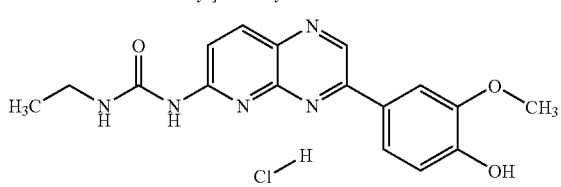

Compound 195

1-Ethyl-3-(3-phenyl-pyrido[2,3-b]pyrazin-6-yl)-thiourea

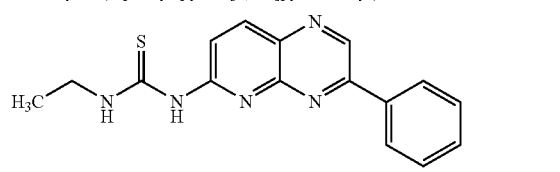

Compound 196

1-(3-Chloro-pyrido[2,3-b]pyrazin-6-yl)-3-cyclohexyl-urea

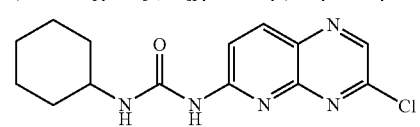

-continued

Compound 197

1-Ethyl-3-[3-(4-hydroxy-3-methoxy-phenylamino)-pyrido[2,3-b]pyrazin-6-yl]-urea

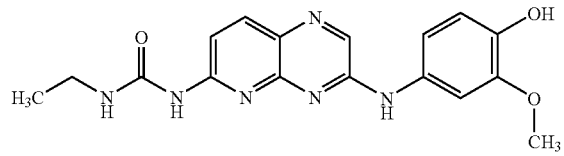

Compound 198

1-Ethyl-3-[3-(4-hydroxy-3,5-dimethyl-phenyl)-pyrido[2,3-b]pyrazin-6-yl]-urea

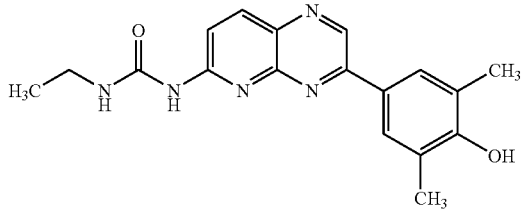

Compound 199

3-Ethyl-1-phenethyl-1-(3-phenyl-pyrido[2,3-b]pyrazin-6-yl)urea

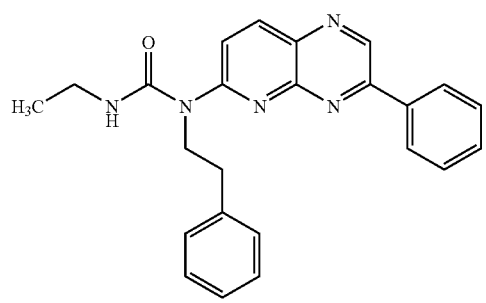

Compound 200

1-Allyl-3-{3-[4-(tetranydro-pyran-2-yloxy)-phenyl]-pyrido[2,3-b]pyrazin-6-yl}-thiourea

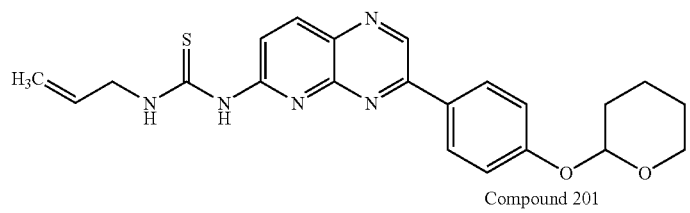

Compound 201

3-Ethyl-1-[3-(4-methoxy-phenyl)-pyrido[2,3-b]pyrazin-6-yl]-1-propyl-urea

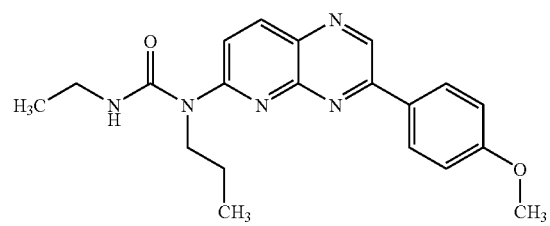

Compound 202

3-Ethyl-1-(3-phenyl-pyrido[2,3-b]pyrazin-6-yl)-1-(2-piperidin-1-yl-ethyl)-urea Hydrochloride

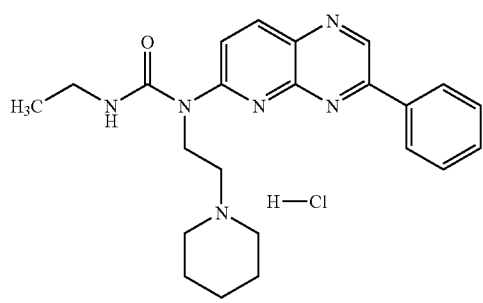

Compound 203

N-{4-[6-(3-Ethyl-ureido)-pyrido[2,3-b]pyrazin-3-yl]-phenyl}-2-phenyl acetamide

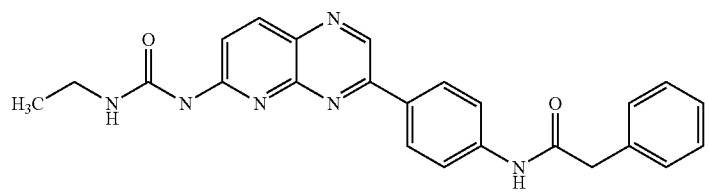

-continued

Compound 204

1-(4-Hydroxy-butyl)-3-(3-phenyl-pyrido[2,3-b]pyrazin-6-yl)-urea Hydrochloride

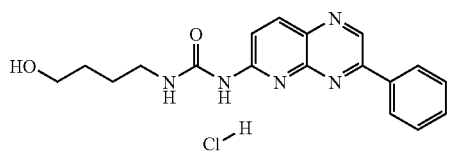

Compound 205

Acetic acid-4-[3-(3-phenyl-pyrido[2,3-b]pyrazin-6-yl)-ureido]-butyl ester

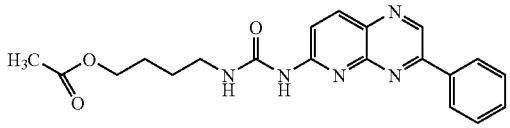

Compound 206

1-(4-Amino-butyl)-3-(3-phenyl-pyrido[2,3-b]pyrazin-6-yl)-urea

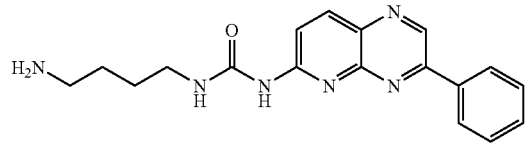

Compound 207

1-(5-Hydroxy-pentyl)-3-(3-phenyl-pyrido[2,3-b]pyrazin-6-yl)-urea

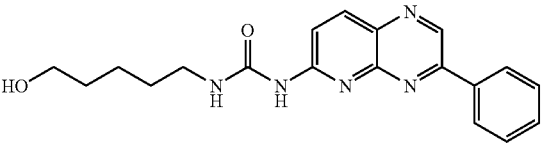

Compound 208

3-[6-(3-Ethyl-ureido)-pyrido[2,3-b]-pyrazin-3-yl]-N-methyl-benzamide

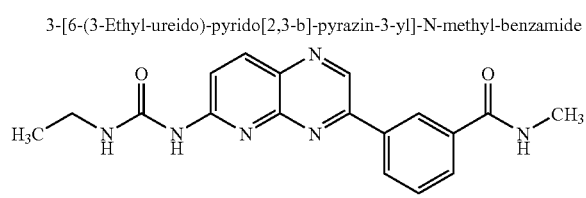

Compound 209

1-Ethyl-3-[3-(2-methoxy-5-methyl-phenyl)-pyrido[2,3-b]pyrazin-6-yl]-urea

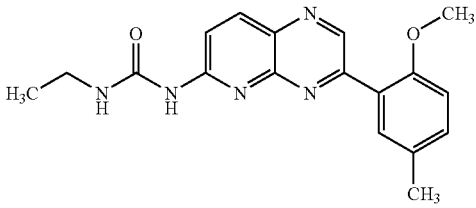

Compound 210

1-Ethyl-3-(3-p-tolyl-pyrido[2,3-b]pyrazin-6-yl)-urea

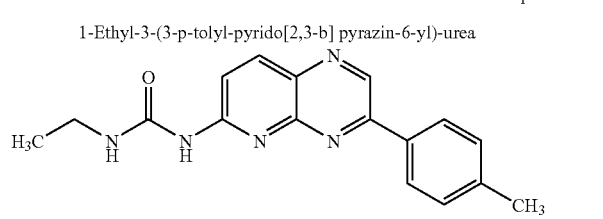

Compound 211

1-Ethyl-3-[3-(methyl-p-tolyl-amino)-pyrido[2,3-b]pyrazin-6-yl]-urea

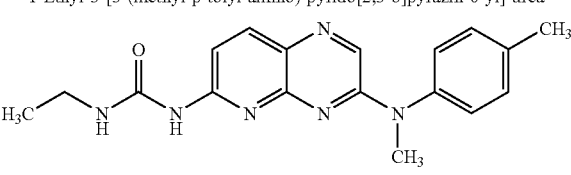

Compound 212

1-Ethyl-3-[3-(2-p-tolyl-ethylamino)-pyrido[2,3-b]pyrazin-6-yl]-urea

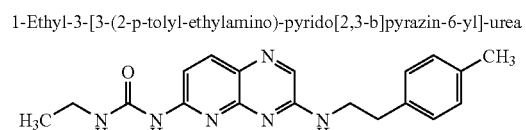

Compound 213

1-Ethyl-3-[3-(4-methyl-benzylamino)-pyrido[2,3-b]pyrazin-6-yl]-urea

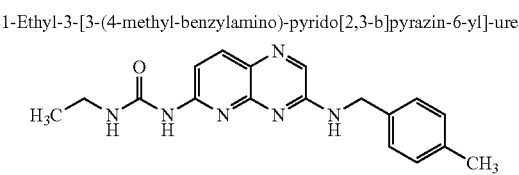

Compound 214

1-Ethyl-3-[3-(3-fluoro-4-methyl-phenyl-amino)-pyrido[2,3-b]pyrazin-6-yl]-urea

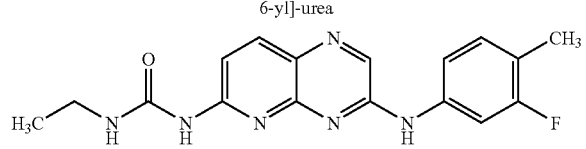

Compound 215

1-[3-(3,4-Dimethyl-phenylamino)-pyrido[2,3-b]pyrazin-6-yl]-3-ethyl-urea

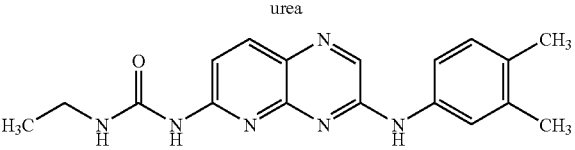

Compound 216

1-Ethyl-3-[3-(4-isopropyl-phenylamino)-pyrido[2,3-b]pyrazin-6-yl]-urea

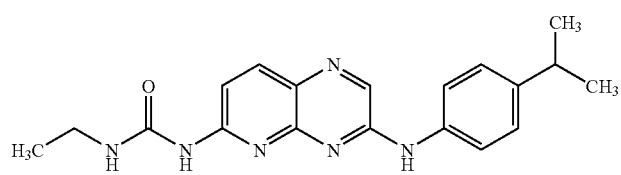

Compound 217
1-(4-Morpholin-4-yl-butyl)-3-(3-phenyl-pyrido[2,3-b]pyrazin-6-yl-urea

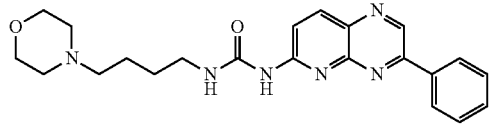

Compound 218
N-{4-[3-(3-Phenyl-pyrido[2,3-b]pyrazin-6-yl)-ureido]-butyl}-acetamide

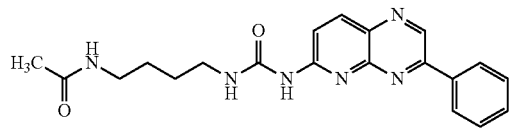

Compound 219
1-[3-(3-Amino-4-methyl-phenyl)-pyrido[2,3-b]pyrazin-6-yl]-3-ethyl-urea

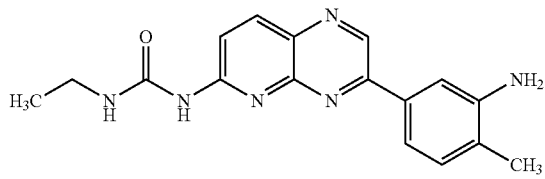

Compound 220
1-[3-(3-Acetyl-2-fluoro-phenyl)-pyrido[2,3-b]pyrazin-6-yl]-3-ethyl-urea

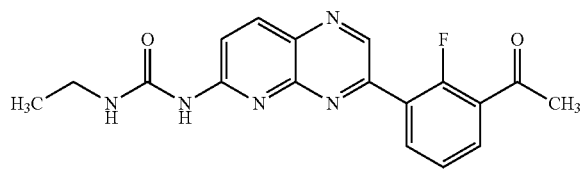

Compound 221
1-Ethyl-3-[3-4-methoxy-3-methyl-phenyl)-pyrido[2,3-b]pyrazin-6-yl]-urea

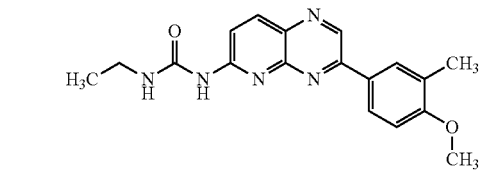

Compound 222
1-[3-(6-Ethoxy-pyridin-3-yl)-pyrido[2,3-b]pyrazin-6-yl]-3-ethyl-urea

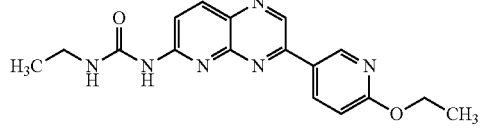

Compound 223
1-Ethyl-3-[3-2-fluoro-4-methyl-phenyl)-pyrido[2,3-b]pyrazin-6-yl-urea

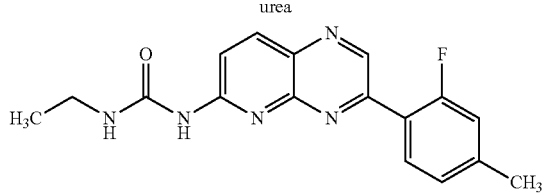

Compound 224
1-Ethyl-3-[3-(3-fluoro-4-methoxy-phenyl)-pyrido[2,3-b]pyrazin-6-yl]-urea

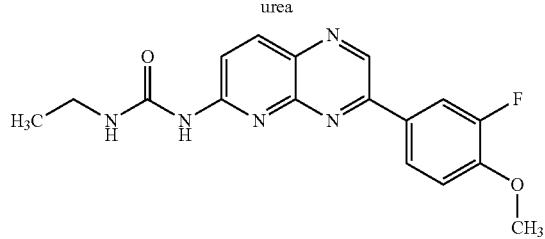

Compound 225
1-Ethyl-3-[3-(2-fluoro-3-methoxy-phenyl)-pyrido[2,3-b]pyrazin-6-yl]-urea

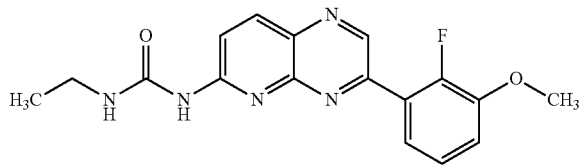

Compound 226
1-Ethyl-3-[3-(3,4,5-trimethoxy-phenyl)-pyrido[2,3-b]pyrazin-6-yl]-urea

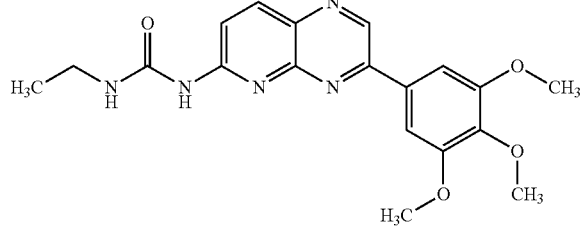

Compound 227
1-[3-(3,5-Difluoro-2-methoxy-phenyl)-pyrido[2,3-b]pyrazin-6-yl]-3-ethyl

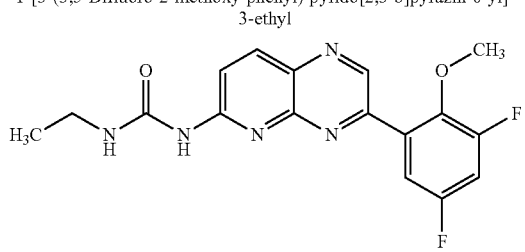

Compound 228
1-Ethyl-3-[3-(4-trifluoromethyl-phenyl)-pyrido[2,3-b]pyrazin-6-yl]-urea

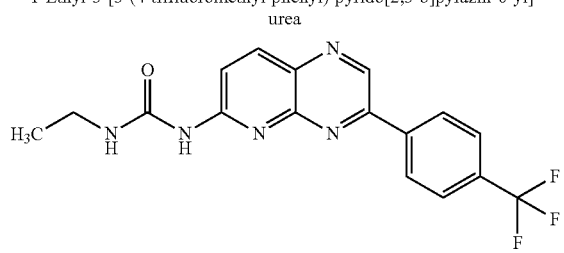

Compound 229

1-Ethyl-3-[3-(2,3,4-trimethoxy-phenyl)-pyrido[2,3-b]pyrazin-6-yl]-urea

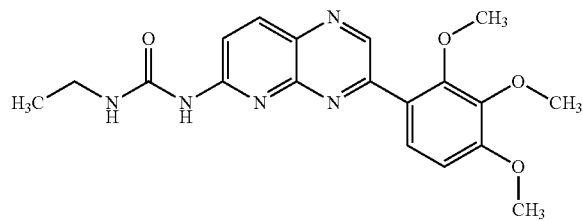

Compound 230

1-[3-(3-Chloro-4-methoxy-phenyl)-pyrido[2,3-b]pyrazin-6-yl]-3-ethyl-urea

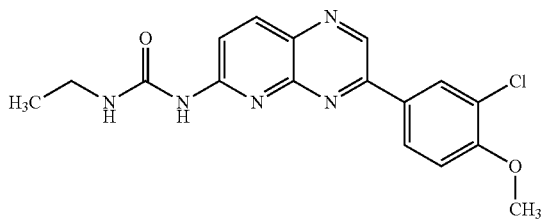

Compound 231

1-Ethyl-3-[3-(3-fluoro-4-hydroxy-phenyl)-pyrido[2,3-b]pyrazin-6-yl]-urea

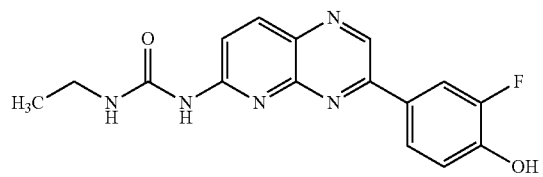

Compound 232

1-Ethyl-3-[3-(6-fluoro-pyridin-3-yl)-pyrido[2,3-b]pyrazin-6-yl]-urea

Compound 233

1-[3-(2,4-Dimethyl-thiazol-5-yl)-pyrido-[2,3-b]pyrazin-6-yl]-3-ethyl-urea

Compound 234

1-Ethyl-3-[3-(2-methoxy-phenyl)-pyrido[2,3-b]pyrazin-6-yl]-urea

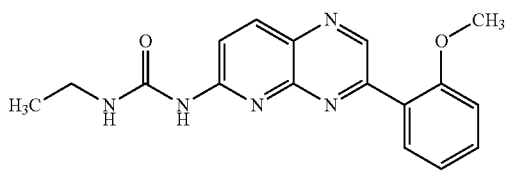

Compound 235

1-[3-(2-Chloro-pyridin-4-yl)-pyrido[2,3-b]pyrazin-6-yl]-3-ethyl-urea

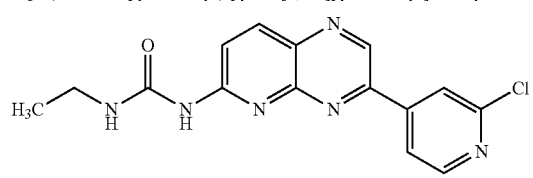

Compound 236

1-[3-(5-Acetyl-thiophen-2-yl)-pyrido[2,3-b]pyrazin-6-yl]-3-ethyl-urea

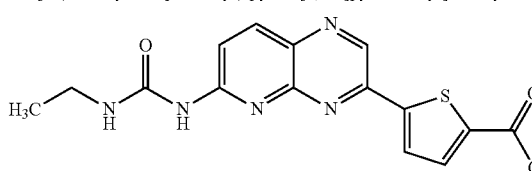

Compound 237

1-[3-(5-Chloro-thiophen-2-yl)-pyrido[2,3-b]pyrazin-6-yl]-3-ethyl-urea

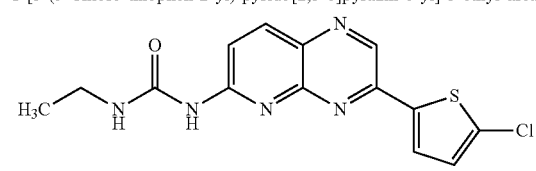

Compound 238

1-Ethyl-3-[3-(3-methoxy-phenyl)-pyrido[2,3-b]pyrazin-6-yl]-urea

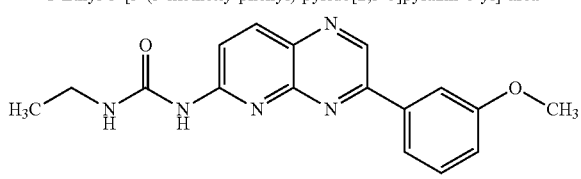

Compound 239

1-[3-(3-Bromo-5-methoxy-phenyl)-pyrido[2,3-b]pyrazin-6-yl]-3-ethyl-urea

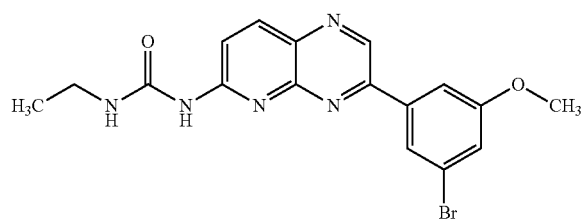

Compound 240

1-[3-(Benzothiazol-6-ylamino)-pyrido[2,3-b]pyrazin-6-yl]-3-ethyl-urea

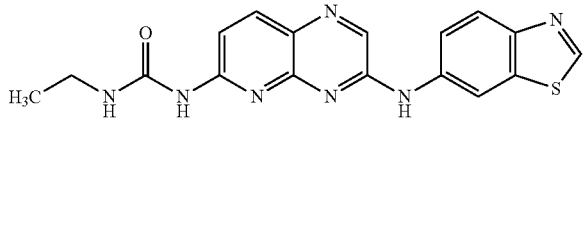

-continued

Compound 241

1-Ethyl-3-[3-(4-methyl-3-trifluoroomethyl-phenylamino)-pyrido[2,3-b]pyrazin-6-yl]-urea

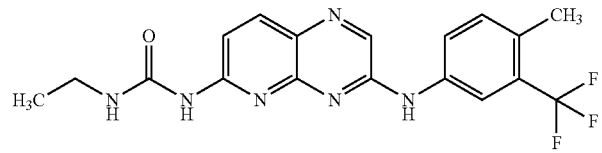

Compound 242

1-[3-(3-Cyano-4-methyl-phenylamino)-pyridol[2,3-b]pyrazin-6-yl]-3-ethyl-urea

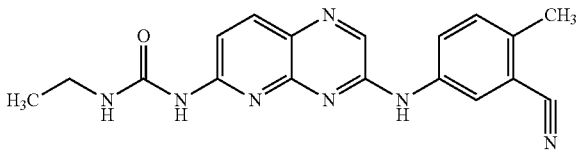

Compound 243

1-Ethyl-3-[3-(4-phenoxy-phenylamino)-pyrido[2,3-b]pyrazin-6-yl]-urea

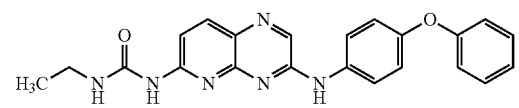

Compound 244

1-[3-(4-Chloro-3-methyl-phenylamino)-pyrido[2,3-b]pyrazin-6-yl]-3-ethyl-urea

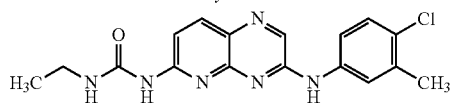

Compound 245

1-[3-(2-Chloro-4-methyl-phenylamino)-pyrido[2,3-b]pyrazin-6-yl]-3-ethyl-urea

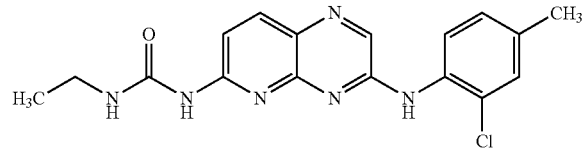

Compound 246

1-Ethyl-3-[3-(3-trifluoromethyl-phenylamino)-pyrido[2,3-b]pyrazin-6-yl]-urea

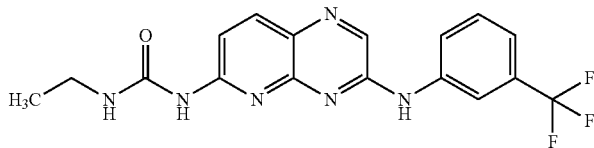

Compound 247

1-[3-(2-Chloro-4-trifluoromethoxy-phenylamino)-pyrido[2,3-b]pyrazin-6-yl]-3-ethyl-urea

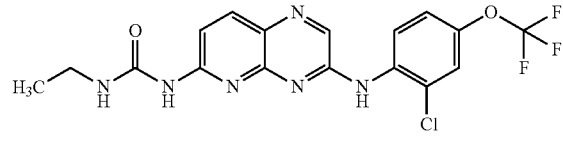

Compound 248

1-[3-(4-Chloro-2-methoxy-5-methyl-phenylamino)-pyrido[2,3-b]pyrazin-6-yl]-3-ethyl-urea

Compound 249

1-Ethyl-3-[3-(4-methylsulfanyl-phenyl)-pyrido[2,3-b]pyrazin-6-yl]-urea

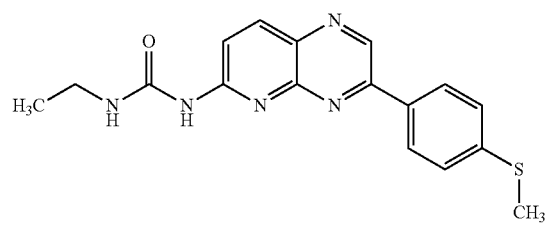

Compound 250

3-[6-(3-Ethyl-ureido)-pyrido[2,3-b]pyrazin-3-yl]-benzenesulfonamide

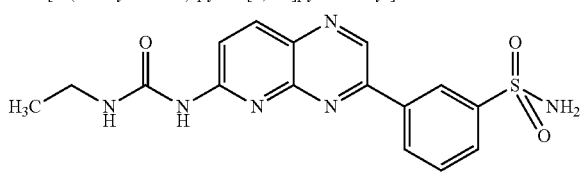

Compound 251

N-{4-[3-(3-Phenyl-pyrido[2,3-b]pyrazin-6-yl)-ureido]-butyl}-methansulfonamide

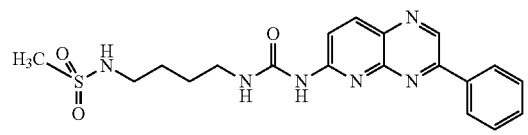

Compound 252

1-[3-(Benzo[1,3]dioxol-5-ylamino)-pyrido[2,3-b]pyrazin-6-yl]-3-ethyl-urea

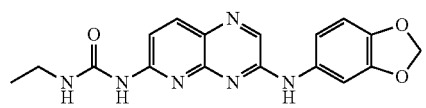

-continued

Compound 253

3-[6-(3-Ethyl-ureido)-pyrido[2,3-b]pyrazin-3-ylamino]-benzoic acid

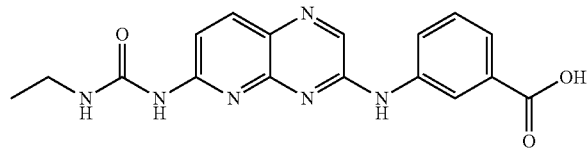

Compound 254

2-Chloro-4-[6-(3-ethyl-ureido)-pyrido[2,3-b]pyrazin-3-ylamino]-benzoic acid

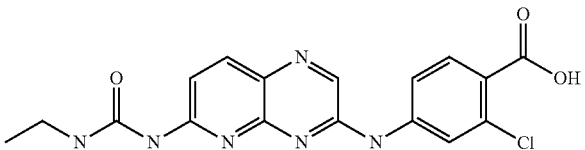

Compound 255

1-Ethyl-3-[3-(3-methoxy-5-trifluoromethyl-phenylamino)-pyrido[2,3-b]pyrazin-6-yl]-urea

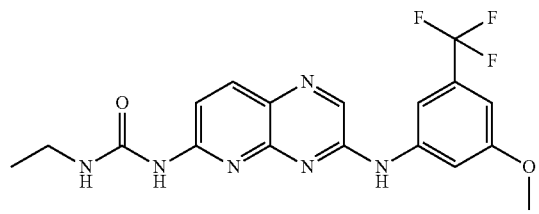

Compound 256

1-Ethyl-3-[3-(pyrimidin-2-ylamino)-pyrido[2,3-b]pyrazin-6-yl]-urea

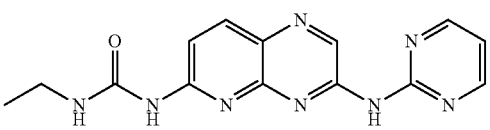

Compound 257

6-[6-(3-Ethyl-ureido)-pyrido[2,3-b]pyrazin-3-ylamino]-naphthalin-2-carbonic acid

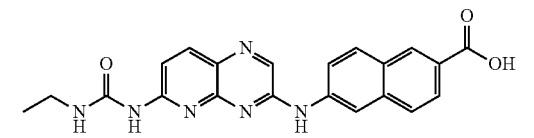

Compound 258

1-Ethyl-3-[3-(4-hydroxy-quinolin-2-ylamino)-pyrido[2,3-b]pyrazin-6-yl]-urea

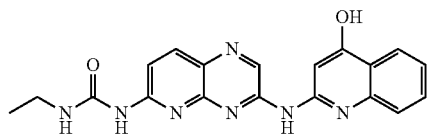

Compound 259

1-Ethyl-3-[3-(quinolin-6-ylamino)-pyrido[2,3-b]pyrazin-6-yl]-urea

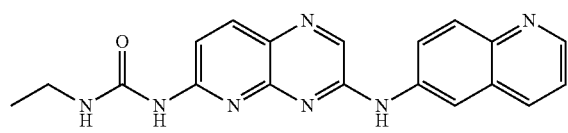

Compound 260

1-Ethyl-3-[3-(3,4,5-trimethoxy-phenylamino)-pyrido[2,3-b]pyrazin-6-yl]-urea

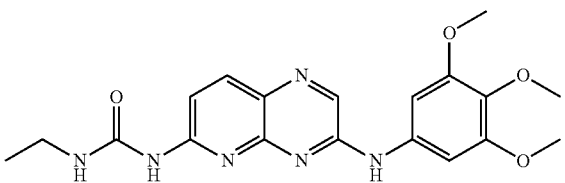

Compound 261

1-Ethyl-3-[3-(1H-indol-6-ylamino)-pyrido[2,3-b]pyrazin-6-yl]-urea

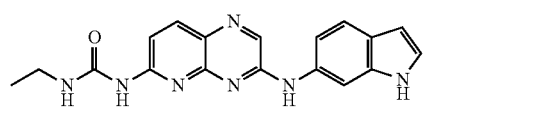

Compound 262

1-Ethyl-3-[3-(3-oxo-3,4-dihydro-2H-benzo[1,4]oxazin-7-ylamino)-pyrido[2,3-b]pyrazin-6-yl]urea

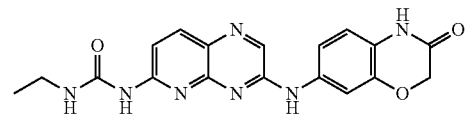

Compound 263

1-Ethyl-3-[3-(quinoxalin-6-ylamino)-pyrido[2,3-b]pyrazin-6-yl]-urea

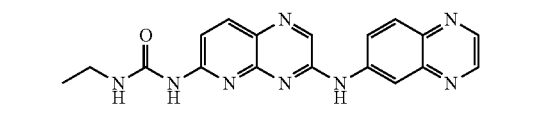

Compound 264

1-Ethyl-3-[3-(3-trifluoromethoxy-phenylamino)-pyrido[2,3-b]pyrazin-6-yl]-urea

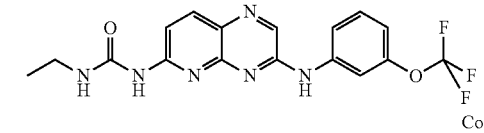

Compound 267

1-(6-Dimethylamino-hexyl)-3-[3-(4-hydroxy-3-methoxy-phenyl)-pyrido[2,3-b]pyrazin-6-yl]-urea

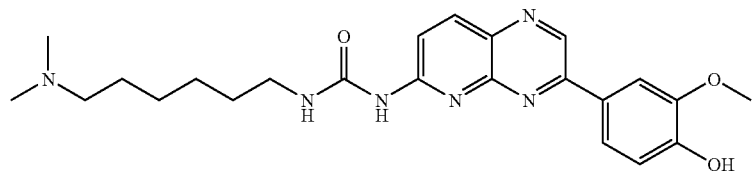

Compound 265

1-Ethyl-3-[3-(4-isopropoxy-phenylamino)-pyrido[2,3-b]pyrazin-6-yl]-urea

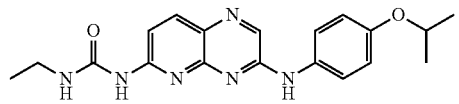

Compound 266

1-[3-(Dibenzofuran-2-ylamino)-pyrido[2,3-b]pyrazin-6-yl]-3-ethyl-urea

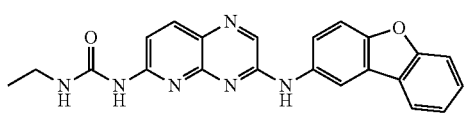

Compound 267

1-(6-Dimethylamino-hexyl)-3-[3-(4-hydroxy-3-methoxy-phenyl)-pyrido[2,3-b]pyrazin-6-yl]-urea

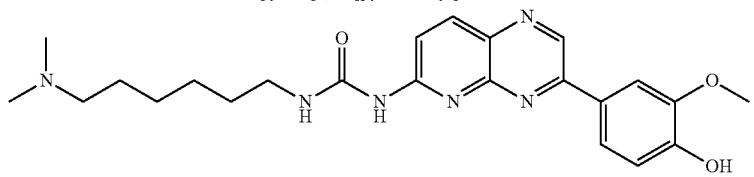

Compound 268

1-(4-Dimethylamino-butyl)-3-[3-(4-hydroxy-3-methoxy-phenyl)-pyrido[2,3-b]pyrazin-6-yl]-urea

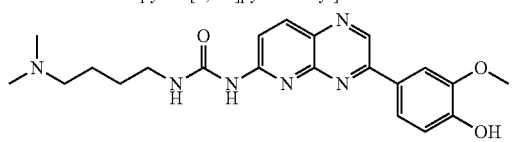

Compound 269

1-[3-(4-Hydroxy-3-methoxy-phenyl)-pyrido[2,3-b]pyrazin-6-yl]-3-(5-morpholin-4-yl-pentyl)-urea

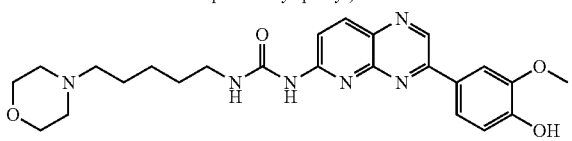

Oral administration can take place, for example, in solid form as tablet, capsule, gel capsule, dragee, granule or powder but also in the form of a potable solution. For oral administration, the new compounds according to the invention, as defined hereinbefore, can be combined with known physiologically compatible adjuvants and excipients usually used, such as gum Arabic, talc, starch, sugar such as, for example, mannite, methyl cellulose, lactose, gelatine, surfactants, magnesium stearate, cyclodextrin, aqueous or non-aqueous excipients, diluents, dispersants, emulsifiers, lubricants, preservatives and flavourings (e.g. ether oils). The compounds according to the invention can also be dispersed in a microparticle, e.g. nanoparticle composition.

Non-oral administration can be effected, for example, by intravenous, subcutaneous or intramuscular injection of sterile aqueous or oily solutions, suspensions or emulsions, by means of implants or by ointments, creams or suppositories. Optionally, administration can be effected as a retard form. Implants can contain inert materials, e.g. biologically degradable polymers or synthetic silicones such as, for example, silicone rubber. Intravaginal administration can be effected by means of vaginal rings, for example. Intrauterine administration can take place, for example, by means of diaphragms or other suitable intrauterine devices. In addition, transdermal administration can be provided, in particular by means of a formulation suitable for this purpose and/or suitable means such as plasters, for example.

As has already been explained, the new compounds according to the invention can also be combined with further pharmaceutically active substances. Within the framework of a combination therapy, the individual active constituents can be administered simultaneously or separately and either by the same pathway (e.g. oral) or by separate pathways (e.g. oral and as injection). They can be present or administered in the same or different quantities in a unit dose. A certain dosage regime can be applied insofar as this seems appropriate. In this way, a plurality of the new compounds according to the invention can be combined with one another.

The dosage can vary according to the type of indication, the severity of the disease, the type of administration, the age, sex, body weight and sensitivity of the subject to be treated over a wide range. It is within the capabilities of a person skilled in the art to determine a "pharmacologically effective quantity" of the combined pharmaceutical composition. The administration can be made in a single dose or a plurality of separate doses.

A suitable unit dose is 0.001 mg to 100 mg of the active substance, i.e. at least one compound according to the invention and optionally a further pharmaceutically active substance, per kg body weight of a patient.

In a further aspect of the present invention, accordingly pharmaceutical compositions comprising a pharmacologically active quantity of at least one compound selected from the group consisting of: "compound 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268 and/or compound 269" and optionally pharmaceutically compatible excipients and/or adjuvants are covered by the present invention.

Preferred and particularly preferred pharmaceutical compositions are those which comprise at least one of the aforesaid preferred compounds according to the invention. Pharmaceutical compositions according to the present invention can also contain, in addition to at least one compound according to the invention, as defined previously, at least one further pharmaceutically active substance, as has been described in detail hereinbefore.

The pharmaceutical compositions according to the invention contain at least one of the new compounds according to the invention, as defined hereinbefore, in a pharmacologically active quantity, preferably in a unit dose, e.g. the aforesaid unit dose and preferably in an administration form which allows oral administration.

With regard to pharmaceutical compositions comprising compounds according to the invention and with regard to the use of the compounds according to the invention as medicaments, reference is made to the statements made in connection with the use of the new compounds according to the invention themselves with regard to the possibilities for usage and administration.

In a further aspect of the present invention, the inventive object was surprisingly solved by preparing a kit comprising a pharmacologically active quantity of at least one preferred compound according to the invention as presented above and a pharmacologically active quantity of at least one further pharmacologically active substance as defined hereinbefore.

The naming of the compounds according to the invention having the general formula (I) together with preferred exemplary embodiments and in particular compounds 1 to 269 was made using AutoNom 2000-Software (ISIS™/Draw 2.5; MDL).

General Synthetic Regulations for the Compounds According to the Invention

The procedures for manufacturing substituted pyrido[2,3-b]pyrazine according to the invention are explained below.

The compounds according to the invention can be obtained according to the diagrams below (diagrams 1-7) or the corresponding procedures known to the person skilled in the art. In addition, refer to patent specifications WO2004/104002 and WO 2004/104003 or to the corresponding methods known in the literature to manufacture the compounds in accordance with the invention.

The residues X1 to X21 listed in the diagrams below correspond in their importance to the substituents defined above in conjunction with the general formula (I), for example, R-residues etc. The particular coordination is simple for the person skilled in the art to manage based on the average knowledge of the person skilled in the art.

Diagram 1

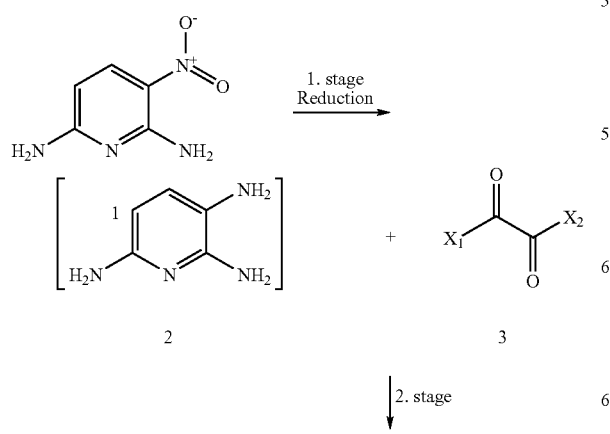

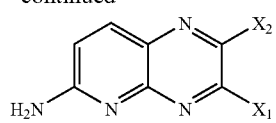

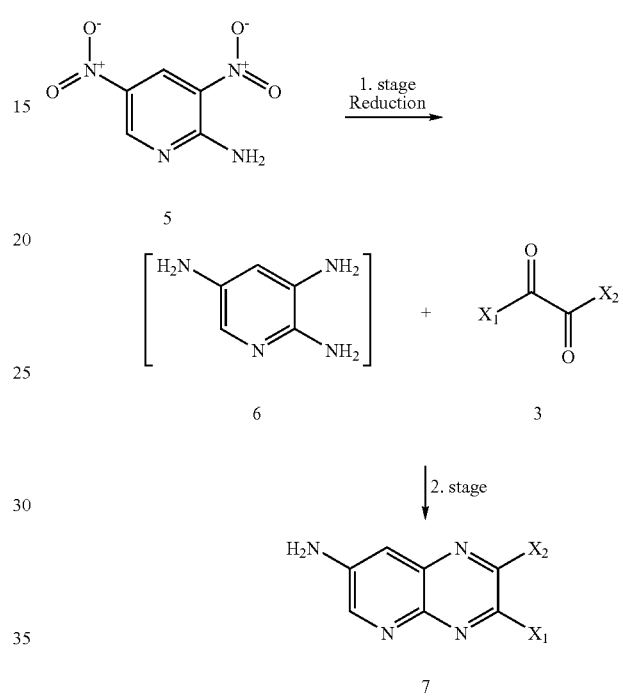

Initial stages for selected examples of the pyrido[2,3-b]pyrazine according to the invention where the substituents R2 and R4 are to be replaced by hydrogen, can for example, be obtained according to the procedure in diagram 2 or a corresponding procedure known to the person skilled in the art.

Diagram 2

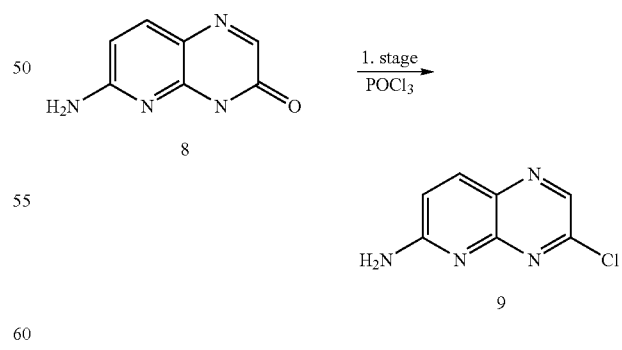

Initial stages for selected examples of the pyrido[2,3-b]pyrazine according to the invention, where the substituents R3 and/or R4 are to be the residues $OX_3$, $SX_4$, $NX_5X_6$, can for example, be obtained according to the procedure in diagram 3 or a corresponding procedure known to the person skilled in the art.

Diagram 3
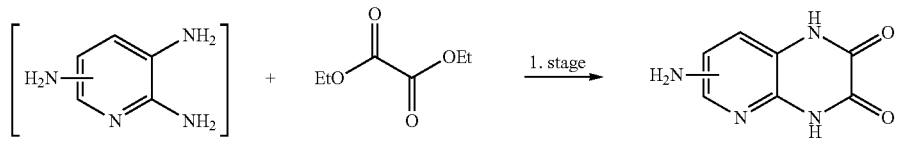
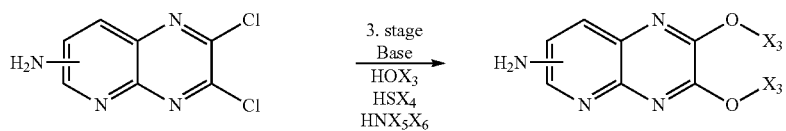
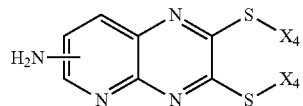
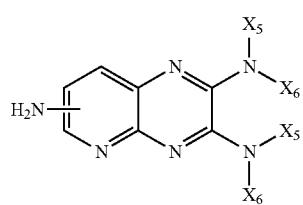

For the initial stage shown above 11 the intermediate product 9 in diagram 2 or the intermediate product 21 also in diagram 6 or an appropriate substituted intermediate product can be used.

Substituted initial stages for selected examples of the pyrido[2,3-b]pyrazine according to the invention can, for example, be obtained according to the procedure in diagram 4 or a corresponding procedure known to the person skilled in the art.

Diagram 4

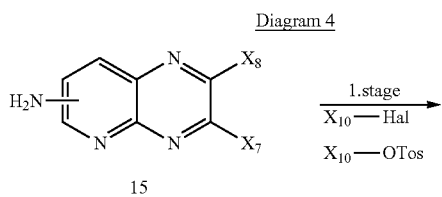

15

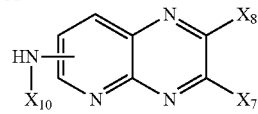

16

Translation of initial stage 16 in diagram 4 into the pyrido[2,3-b]pyrazines substituted according to the invention, can, for example, take place according to the procedure in diagram 5 or a corresponding procedure known to the person skilled in the art.

Diagram 5

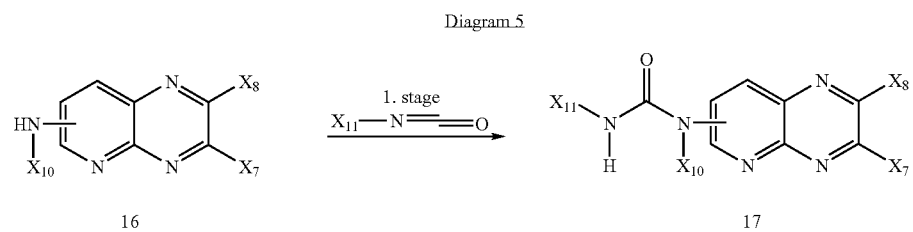

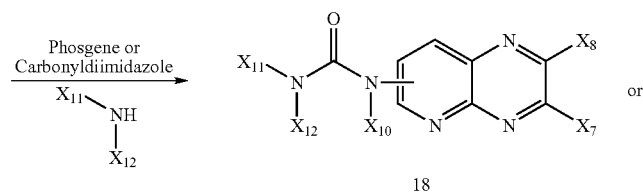

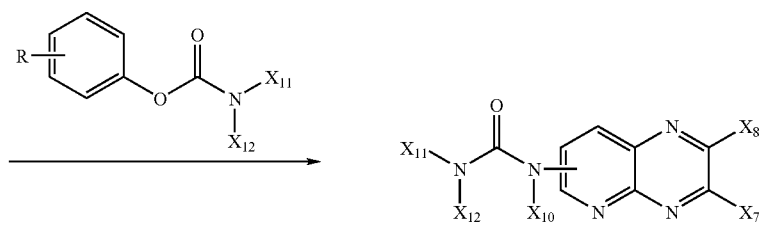

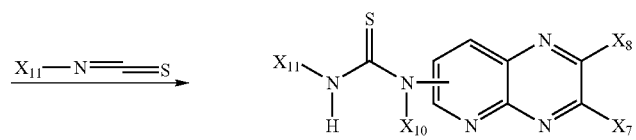

For the initial stage shown above 16 the intermediate product 15 in diagram 4 can be used.

Selected examples of the pyrido[2,3-b]pyrazine according to the invention where the substituents R3 and/or R4 can be selected alkyl, aryl or hetero-aryl residues, can be obtained, for example, according to the procedure in diagram 6 or corresponding procedures known to the person skilled in the art.

Diagram 6

X = -B(OR)$_2$, -SnR$_3$
Y = Alkyl

When manufacturing the pyridopyrazine substituted for aryl, hetero-aryl according to the invention, for the initial phase shown above 21 the intermediate product 9 in diagram 2 or the intermediate product 11 in diagram 3 can be used or an appropriate substituted intermediate product.

Selected examples of the pyrido[2,3-b]pyrazine according to the invention, where the substituents R3 and/or R4 can be selected O, S, or N substituted residues, can for instance, be obtained according to the procedure in diagram 7 or appropriate procedures known to the person skilled in the art.

Diagram 7

Y = O, S, NX19

Y = O, S, NX19

The cleavage of the corresponding phosphoric ester can be carried out according to procedures known or known to the person skilled in the art using methods known in the literature.

The initial compounds and intermediate stages can either be obtained on the market or manufactured according to procedures known to the person skilled in the art. The feed materials 4, 7, 9-16, 21, 24 and 26 represent valuable intermediate compounds for manufacturing pyridopyrazine according to the invention.

In order to manufacture the initial compounds, intermediate compounds and the pyridopyrazine according to the invention, refer amongst other things, to the primary literature below, the content of which is herewith to become an integral part of the disclosure of the present filing application:

1) Houben-Weyl, Methods of Organic Chemistry, Volume 4/1a, pp. 343-350
2) Houben-Weyl, Methods of Organic Chemistry, 4th edition, Volume E 7b (Part 2), p. 579; Degussa GB 1184848 (1970); p. Seko, et al. EP 735025 (1996)
3) D. Catarzi, et al.; *J. Med. Chem.* 1996, 1330-1336; J. K. Seydel, et al.; *J. Med. Chem.* 1994, 3016-3022
4) Houben-Weyl, Methods of Organic Chemistry, Volume E 9c, pp. 231-235
5) Houben-Weyl/Science of Synthesis, Volume 16, p. 1269
6) C. L. Leese, H. N. Rydon *J. Chem. Soc.* 1955, 303-309; T. S. Osdene, G. M. Timmis *J. Chem. Soc.* 1955, 2033-2035
7) W. He, et al. *Bioorg. Med. Chem. Lett.* 2003, 13, 3097-3100
8) M. S. A. El-Gaby, et al. *Indian J. Chem. Sect. B* 2001, 40, 195-200; M. R. Myers, et al. *Bioorg. Med. Chem. Lett.*

2003, 13, 3091-3096; A. R. Renslo, et al. *J. Amer. Chem. Soc.* 1999, 121, 7459-7460; C. O. Okafor, et al. *J. Heterocyclic Chem.* 1983, 20, 199-203; C. R. Hopkins, et al. *Tet. Lett.* 2004, 45, 8631-8633

9) J. Yin, et al. *Org. Lett.* 2002, 4, 3481-3484; O. A. El-Sayed, et al. *Arch. Pharm.* 2002, 335, 403-410; C. Temple, et al. *J. Med. Chem.* 1992, 35, 988-993

10) A. M. Thompson, et al. *J. Med. Chem.* 2000, 43, 4200-4211; N. A. Dales, et al. *Org. Lett.* 2001, 2313-2316; G. Dannhardt, et al. *Arch. Pharm.* 2000, 267-274; G. S. Poindexter, et al. *Bioorg. Med. Chem.* 2004, 12, 507-521; J.-M. Receveur, et al. *Bioorg. Med. Chem. Lett.* 2004, 14, 5075-5080

11) G. Heinisch, et al. *Arch. Pharm.* 1997, 207-210; K. Matsuno, et al. *J. Med. Chem.* 2002, 45, 4513-4523; A. M. Papini, et al. *J. Med. Chem.* 2004, 47, 5224-5229

12) L. Mao, et al. *Synthesis* 2004, 15, 2535-2539; M. Darabantu, et al. *Tetrahedron* 2005, 61, 2897-2905; E. Ford, et al. *Tet. Lett.* 2000, 41, 3197-3198; T. Shiota, et al. *J. Org. Chem.* 1999, 64, 453-457

13) J. F. Miravet, et al. *Org. Lett.* 2005, 7, 4791-4794; A. L. Castelhano, et al. *Bioorg. Med. Chem. Lett.* 2005, 15, 1501-1504.

14) J. W. Huffmann, et al. *Bioorg. Med. Chem.* 2006, 14, 247-262; T. Liu, et al. *Org. & Biomolecular Chem.* 2005, 3, 1525-1533

General Regulations Setting Out the Compounds According to the Invention:

Diagram 1: Stage 1

2,6-diamino-3-nitropyridine or 2-amino-3,5-dinitro-pyridine is dissolved in a suitable inert solvent, such as methanol, ethanol, dimethylformamide or dioxan, for instance. After adding a catalyst, Raney nickel. palladium on carbon or platinum(IV) oxide, the reaction mass is placed in a hydrogen atmosphere with pressure of between 1 and 5 bar being set. The reaction mass is allowed to react for several hours, 1-16 hours, for example, in a temperature range between 20° C. and 60° C. When conversion is finished, the insoluble residues are filtered out, the filter medium can, for example, consist of silica gel, celite or normal glass fibre filters and rewashed using the corresponding solvent. The raw product present in solution is used for the next conversion without additional purification.

Stage 2

The 1,2-dione derivative is placed in a suitable, inert solvent, methanol, ethanol, dioxan, toluene or dimethylformamide. Immediately after reduction 2,3,6-triaminopyridine or 2,3,5-triaminopyridine is added as solution of the raw products in one of the solvents referred to above to the presented 1,2-dione, if necessary adding an acid, such as for example, acetic acid or a base, potassium hydroxide. The reaction mass is allowed to react for a period, between 20 minutes and 40 hours in a temperature range of between 20° C. and 80° C. Once conversion is finished, a possible precipitate which has separated is filtered out, the filter medium can, for instance, consist of filter paper on the market, rewashed with the corresponding solvent and the remaining solid is dried in vacuum or rather the reaction mass is released from the solvent in vacuum. Where dimethylformamide is used, the reaction mass is stirred into a large quantity of water and the precipitate separated is filtered out or rather the aqueous phase is extracted using a suitable organic solvent, such as, for example, dichloromethane or ethyl acetate and the organic phases concentrated in vacuum. Cleaning of the remaining raw product takes place by recrystallisation from a suitable solvent, dioxan, for example, or using column or rather flash chromatography on silica gel or aluminium oxide. A mixture of methanol and dichloromethane, for example, can serve as solvent.

Diagram 2: Stage 1

The pyrido-pyrazine on derivate 8 is presented in a suitable, inert solvent, dimethylformamide, dioxan or toluene or without a solvent. A chlorinating agent, phosphoryl chloride or thionyl chloride, for instance, is added at room temperature and the reaction amount is allowed to react in a temperature range of between 20° C. and 100° C. for a period, between 1 hour and 24 hours for example. When conversion is finished, the reaction mass is poured on to water and neutralised using a suitable aqueous base, caustic soda solution, for instance. A possible precipitate separated is filtered out, the filter medium can consist, for instance of filter paper on the market, is rewashed with the corresponding solvent and the remaining solid dried in vacuum or the aqueous phase is extracted in a suitable organic solvent, such as dichloromethane or ethyl acetate, for example, and the organic phases are concentrated. Cleaning of the remaining raw product takes place by recrystallisation from a suitable solvent, dioxan or toluene, for example, or using column or rather flash chromatography on silica gel or aluminium oxide. A mixture of methanol and dichloromethane, for example, can serve as solvent.

Diagram 3: Stage 1

2,3,6-triaminopyridine or 2,3,5-triaminopyridine are presented directly after reduction as a solution of the raw products in one of the solvents referred to above. Having added an oxalic acid derivative, such as oxalic acid diethylester or oxalyl chloride, for example, the reaction mass is allowed to react, if necessary by adding an acid, such as hydrochloric acid, sulphuric acid or crystalline acid for a period of time, between 10 minutes and 24 hours, for instance, in a temperature range of between 20° C. and 150° C. Once conversion is finished, a possible precipitate which has separated is filtered out, the filter medium can, for instance, consist of filter paper on the market, rewashed with the corresponding solvent and the remaining solid is dried in vacuum or rather the reaction mass is released from the solvent in vacuum. Alternatively, the reaction mass can be stirred into a large quantity of water and the precipitate separated filtered out or rather the aqueous phase, following neutralisation using an appropriate aqueous base, such as for instance, caustic soda solution, extracted using a suitable organic solvent, such as for instance, dichloromethane or ethyl acetate, and the organic phase concentrated in vacuum. Cleaning of the remaining raw product takes place by recrystallisation from a suitable solvent, dioxan or toluene, for example, or using column or rather flash chromatography on silica gel or aluminium oxide. A mixture of methanol and dichloromethane, for example, can serve as solvent.

Stage 2

The diketone derivative 10 is presented in a suitable, inert solvent, dimethylformamide, dioxan or toluene, for instance, or without a solvent. A chlorinating agent, phosphoryl chloride or thionyl chloride, for instance, is added at room temperature and the reaction amount is allowed to react in a temperature range of between 20° C. and 100° C. for a period, between 1 hour and 24 hours, for example. When conversion is finished, the reaction mass is poured on to water and neutralised using a suitable aqueous base, caustic soda solution, for instance. A possible precipitate separated is filtered out, the filter medium can consist, for instance of filter paper on the market, is rewashed with the corresponding solvent and the remaining solid dried in vacuum or the aqueous phase is extracted in a suitable organic solvent, such as dichloromethane or ethyl acetate, for example, and the organic phases are concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as a solvent.

Stage 3

The intermediate stage 11 can be converted using a corresponding alcohol, thiol or amine and if necessary using a suitable base, preferably sodium hydride, pyridine, triethylamine, potassium carbonate or sodium methanolate in methanol, in a suitable, inert solvent, such as dimethylformamide, dimethyl sulfoxide, methanol, toluene or in a base as solvent, such as for example, pyridine or triethylamine without solvent. The reaction mass is allowed to react for a period, between 30 minutes and 2 days, for example, in a temperature range between 20° C. and 140° C. Alternatively, the intermediate stage 11 can be converted using a corresponding amine and a suitable catalyst, such as for instance, tris(dibenzalacetone) palladium(0) or tetrakis(triphenylphosphine) palladium(0) and a suitable ligand, such as for instance, 2-(dicyclohexylphosphanyl) biphenyl or BINAP, and a suitable base, sodium tert butanolate or potassium carbonate, in a suitable solvent, such as toluene, dioxan or dimethylformamide, for instance. The reaction mass is allowed to react for a period, between 2 hours and 30 hours, for example, in a temperature range of between 60° C. and 120° C. Once conversion is finished, a possible precipitate which has separated is filtered out, the filter medium can, for instance, consist of filter paper on the market, rewashed with the corresponding solvent and the remaining solid is dried in vacuum or the reaction mass is released from the solvent in vacuum. Alternatively, the reaction mass can be stirred into a large quantity of water and the separated precipitate filtered out or the aqueous phase, following neutralisation using a suitable aqueous acid, such as for instance, caustic soda solution, extracted using a suitable organic solvent, such as for example, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Diagram 4: Stage 1

The intermediate stage 15 can be converted in the corresponding suitable chloride, bromide, Iodide or tosylate and if necessary using a suitable base, preferably sodium hydride, pyridine, triethylamine, sodium carbonate or sodium methanolate in methanol in a suitable, inert solvent, such as, dimethylformamide, dimethyl sulfoxide, methanol or in a base as solvent, such as, for example, pyridine or triethylamine without a solvent. The reaction mass is allowed to react for a period, between 1 hour and 24 hours for example, in a temperature range between 20° C. and 150° C. Alternatively, the intermediate stage 15 can be converted using a corresponding aryl bromide or aryl Iodide and a suitable catalyst, such as, for example, tris(dibenzalacetone)palladium(0) or tetrakis(triphenylphosphine) palladium(0) and a suitable ligand, such as for example, 2-(dicyclohexylphosphanyl) biphenyl or BINAP, and a suitable base, for example, potassium carbonate or sodium tert butanolate or in a suitable solvent, such as toluene, dioxan or dimethylformamide, for instance. The reaction mass is allowed to react for a period, between 10 hours and 30 hours, for example, in a temperature range of between 60° C. and 120° C. Once conversion is finished, a possible precipitate separated is filtered out, the filter medium can, for instance, consist of filter paper on the market, rewashed with the corresponding solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using an suitable aqueous acid, such as for example, caustic soda solution, extracted using a suitable organic solvent, such as, for example, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Diagram 5: Stage 1

After the basic procedure, the products which have come about according to the basic procedure can be translated in consecutive reactions into resultant products according to the invention in a procedure known to the person skilled in the art.

Thus, if the product is to be a derivative of compound 17 according to diagram 5, then the reaction product 16 can be converted using a corresponding isocyanate and if necessary a suitable base, preferably sodium hydride, potassium hexamethyldisalzide, pyridine, triethylamine or potassium carbonate, in a suitable, inert solvent, such as dimethylformamide, dimethyl sulfoxide, acetonitrile, dichloromethane, 1,2-dichloroethane or dioxan or in a base as solvent, such as for example, pyridine or triethylamine without solvent. The reaction mass is allowed to react for several hours, between 1 and 24 hours, for instance, in a temperature range between 0 and 80° C. Once conversion is finished, a possible precipitate which has separated is filtered out, the filter medium can, for instance, consist of filter paper on the market, rewashed with the appropriate solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using an appropriate aqueous acid, such as for example, caustic soda solution, extracted using a suitable organic solvent, such as, for instance, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as a solvent.

Or alternatively, if the product is to be a derivative of the compound 18 according to diagram 5, the reaction product 16 can be converted using phosgene or carbonyldiimidazole and a corresponding amine in a suitable, inert solvent, such as, for example, dimethylformamide, tetrahydrofuran, toluene, dichloromethane or acetonitrile. If necessary, a suitable base is used, preferably pyridine, sodium hyrdogencarbonate, triethylamine, N-methylmorpholine or sodium acetate. The reaction mass is allowed to react for a period, for example between 15 minutes and 24 hours, in a temperature range between 0 and 60° C. Alternatively, the reaction product 16 can be converted using a corresponding amine phenyl carbamate reagent and if necessary using a suitable base, preferably pyridine, sodium carbonate, triethylamine or sodium hydride, in a suitable, inert solvent, such as, for example, pyridine or triethylamine or without solvent. The reaction mass is allowed to react for a period, between 1 hour and 18 hours for example, in a temperature range between 0° C. and 120° C. Once conversion is finished, a possible precipitate which has separated is filtered out, the filter medium can, for instance, consist of filter paper on the market, rewashed with the corresponding solvent and the remaining solid is dried in vacuum or the reaction mass is released from the solvent in vacuum. Alternatively, the reaction mass can be stirred into a large quantity of water and the precipitate separated is filtered out or the aqueous phase, following neutralisation using a suitable aqueous acid, such as for example, caustic soda solution, extracted using a suitable organic solvent, such as, for instance, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Thus if the product is to be a derivative of the compound 19 according to diagram 5, the reaction product 16 can be translated using a corresponding isothiocyanate, and if necessary, a suitable base, preferably sodium hydride, triethylamine, potassium carbonate or pyridine, in a suitable, inert solvent, such as for instance dimethylformamide, tetrahydrofuran, acetone or toluene, or in a base as solvent, such as, for instance, pyridine or triethylamine or without solvent. The reaction mass is allowed to react for a period, for example between 30 minutes and 90 hours, in a temperature range between 0 and 115° C., Once conversion is finished, a possible precipitate which has separated is filtered out, the filter medium can, for instance, consist of filter paper on the market, rewashed with the corresponding solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using a suitable aqueous acid, such as for example, caustic soda solution, extracted using a suitable organic solvent, such as, for instance, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as a solvent.

Or alternatively, if the product is to be a derivative of the compound 20 according to diagram 5, the reaction product 16 can be translated using thiophosgene or thiocarbonyl diimidazole and a corresponding amine in a suitable, inert solvent, such as dimethylformamide, tetrahydrofuran, toluene, dichloromethane, ethanol or acetonitrile. If necessary, a suitable base, preferably pyridine, sodium hydrogencarbonate, potassium carbonate, triethylamine or imidazole is used. The reaction mixture is allowed to react for several hours, between 1 and 24 hours for example, in a temperature range between −10 and 80° C. Once conversion is finished, a possible precipitate which has separated is filtered out, the filter medium can, for instance, consist of filter paper on the market, rewashed with the appropriate solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using an appropriate aqueous acid, such as for example, caustic soda solution, extracted using a suitable organic solvent, such as, for instance, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Diagram 6: Stage 1

After the basic procedure, the products which have come about according to the basic procedure can be translated in consecutive reactions into resultant products according to the invention in a procedure known to the person skilled in the art.

Thus, if the product is to be a derivative of the compound 22 according to diagram 6, the reaction product 21 can be translated using the corresponding aryl/heteroaryl boronic acid derivatives or aryl/heteroaryl organotin compounds and a suitable catalyst, such as, for example, $Pd(PPh_3)_4$, [1,1'-bis(diphenylphosphino)ferrocene]dichloro palladium(II) or $Pd_2(dba)_3$ and a suitable base, for example, sodium carbonate, cesium carbonate or triethylamine, in a suitable solvent, such as for instance, dimethylformamide, dimethylformamide/water, toluene, acetonitrile, dimethoxyethane or dioxan. The reaction mixture is allowed to react for a period, for instance between 6 hours and several days, in a temperature range between 60° C. and 120° C. Once conversion is finished, a possible precipitate which has separated is filtered out, the filter medium can, for instance, consist of filter paper on the market, rewashed with the corresponding solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using a suitable aqueous acid, such as for example, caustic soda solution, extracted using a suitable organic solvent, such as, for instance, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as a solvent.

Thus if the product is to be a derivative of the compound 23 according to diagram 6, the reaction product 21 can be converted using corresponding alkyl zinc halogenides and a suitable catalyst, such as, for example, $Pd(PPh_3)_4$, [1,1'-bis(diphenylphosphino)ferrocene]dichloro palladium(II) or $PdCl_2(PPh_3)_2$ in a suitable solvent, such as for instance, dimethylformamide, tetrahydrofuran, toluene, dimethoxyethane or dioxan. The reaction mixture is allowed to react for a period, for example between 30 minutes and 48 hours, in a temperature range between room temperature and 120° C. Once conversion is finished, a possible precipitate which has separated is filtered out, the filter medium can, for instance, consist of filter paper on the market, rewashed with the appropriate solvent and the remaining solid is dried in vacuum or the reaction mass is released from the solvent in vacuum. Alternatively, the reaction mass can be stirred into a large quantity of water and the perpetrate separated is filtered out or the aqueous phase, following neutralisation using an appropriate aqueous acid, such as for example, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Diagram 7: Stage 1

After the basic procedure, the products which have come about according to the basic procedure can be translated in consecutive reactions into resultant products according to the invention in a procedure known to the person skilled in the art.

Thus, if the product is to be a derivative of the compound 25 according to diagram 7, the reaction product 24 can be converted, for example, using a corresponding chloride, bromide, Iodide and if necessary using a suitable base, preferably sodium hydride, pyridine, triethylamine, sodium carbonate or sodium methanolate in methanol in a suitable, inert solvent, such as, dimethylformamide, dimethyl sulfoxide, methanol, dioxan, tetrahydrofuran, toluene or in a base as solvent, such as, for instance, pyridine or triethylamine or without solvent. The reaction mass is allowed to react for a period, between 30 minutes and 2 days, for example, in a temperature range between 0° C. and 140° C. Alternatively, an amino substituted intermediate stage 24, for example, can be used, using a corresponding chloride, bromide or Iodide and a suitable catalyst, such as, for instance, tris(dibenzalacetone)palladium(0) or tetrakis(triphenylphosphine) palladium(0) and a suitable ligand, such as, for instance, 2-(dicyclohexylphosphanyl) biphenyl or BINAP, and a suitable base, sodium tert butanolate or potassium carbonate, in a suitable solvent, such as toluene, dioxan or dimethylformamide, for instance. The reaction mass is allowed to react for a period, between 2 hours and 30 hours, for example, in a temperature range of between 60° C. and 120° C. Once conversion is finished, a possible precipitate separated is filtered out, the filter medium can, for instance, consist of filter paper on the market, rewashed with the suitable solvent and the remaining solid is dried in vacuum or the reaction mass is released from the solvent in vacuum. Alternatively, the reaction mass can be stirred into a large quantity of water and the perpetrate separated filtered out or the aqueous phase, following neutralisation using a suitable aqueous acid, such as for instance, caustic soda solution, extracted using a suitable organic solvent, such as, for example, dichloromethane or ethyl acetate, and the organic phase concentrated in vacuum. Cleaning of the remaining raw product takes place by recrystallisation from a suitable solvent, dioxan or toluene, for example, or using column or flash chromatography on silica gel or aluminium oxide. A mixture of methanol and dichloromethane, for example, can serve as solvent.

Thus, if the product is to be a derivative of the compound 27 according to diagram 7, the reaction product 26 can be converted, for example, using a corresponding chloro-phosphoric ester and if necessary using a suitable base, preferably sodium hydride, pyridine, triethylamine, potassium carbonate or lithium diisopropylamide in a suitable, inert solvent, such as for example, dimethylformamide, dimethyl sulfoxide, methanol, dioxan, tetrahydrofuran, toluene or in a base as solvent, such as for example, pyridine or triethylamine or without solvent. The reaction mass is allowed to react for a period, between 1 hour and 24 hours for example, in a temperature range between 0° C. and 100° C. Once conversion is finished, a possible precipitate separated is filtered out, the filter medium can, for instance, consist of filter paper on the market, rewashed with the suitable solvent and the remaining solid is dried in vacuum or the reaction mass is released from the solvent in vacuum. Alternatively, the reaction mass can be stirred into a large quantity of water and the precipitate separated filtered out or the aqueous phase, following neutralisation using a suitable aqueous acid, such as for example, caustic soda solution, extracted using a suitable organic solvent, such as, for example, dichloromethane or ethyl acetate, and the organic phase concentrated in vacuum. Cleaning of the remaining raw product takes place by recrystallisation from a suitable solvent, dioxan or toluene, for example, or using column or rather flash chromatography on silica gel or aluminium oxide. A mixture of methanol and dichloromethane, for example, can serve as solvent.

Under the reaction conditions mentioned, OH, SH and $NH_2$ groups can possibly undergo unwanted secondary reactions. It is therefore preferable to provide them with protective groups or in the case of $NH_2$ to replace with $NO_2$ and subsequently to split the protective group off or to reduce the $NO_2$ group. Thus varying the procedures described above, in the initial compounds at least one OH group, for example, can be replaced by a benzyl oxy group and/or at least one SH group, for example, by an S-benzyl group and/or at least one $NH_2$ group by a NH-benzyl group or by an $NO_2$group. Subsequently at least one—preferably all—benzyl oxy group(s) or NH benzyl group(s) can be split off, for instance, using hydrogen and palladium on carbon and/or at least one—preferably all—S-benzyl group(s), for example, using sodium in ammonia and/or at least one—preferably all $NO_2$ group(s) are reduced, for instance using hydrogen and Raney nickel to $NH_2$ Under some of the reaction conditions mentioned OH, $NH_2$ and COOH groups can possibly undergo unwanted secondary reactions. It is therefore preferable to convert initial compounds and intermediate stages containing at least one OH and/or at least one $NH_2$ and/or at least one COOH group into corresponding carbonic ester and carboxamide derivatives. Thus varying the procedures described above, in the initial compounds and intermediate stages with at least one OH group and/or at least one $NH_2$group can be converted into carboxamide derivatives by transformation using an active carboxamide group. Thus varying the procedures described above the initial compounds and intermediate stages with at least one COOH group can be converted into carbonic ester or carboxamide derivatives by transformation using an activator, such as thionyl chloride or carbonyldiimidazole and a subsequent transformation using a suitable alcohol or amine. Subsequently at least one—preferably all—carbonic ester or carboxamide group(s) in the initial compounds and intermediate stages can be split, for instance using diluted aqueous acids or bases to free at least one—preferably all —OH group(s) and/or $NH_2$ group(s) and/or COOH groups.

The invention will be explained in detail with reference to the following examples without being restricted to these examples.

EXAMPLES

I. Manufacture of Compounds According to the Invention

According to the general synthesis regulations on which the synthesis diagrams 1-7 are based, the following compounds according to the invention were synthesised.

The initial stages for the manufacture of the compounds according to the invention can be synthesised according to procedures known to the person skilled in the art—unless otherwise described.

The chemicals and solvents used were purchased commercially from the usual suppliers (Acros, Aldrich, Fluka, Lancaster, Maybridge, Merck, Sigma, TCI, etc.) or synthesised.

Example 1

1-ethyl-3-[3-(3-hydroxy-phenyl)-pyrido[2,3-b]pyrazine-6-yl]-urea (Compound 151)

Manufacture of 1-(3-chloropyrido[2,3-b]pyrazine-6-yl)-3-ethyl-urea (Conversion According to Diagram 5)

100 mg 3-chloropyrido[2,3-b]pyrazine-6-yl-amine (0.55 mmol) was presented in 5 ml predried pyridine and add 44 µL ethyl isocyanate (0.55 mmol) at room temperature. The mixture was stirred at 75° C. and then a total of 132 μL ethyl isocyanate (1.65 mmol) was added again over 18 hours to the reaction mixture in small amounts. Then the volatile components were removed in vacuum. The resulting solid was cleaned through column chromatography on silica gel (solvent dichloromethane/methanol). A light yellow solid was obtained.

Refer to the following literature and the procedures known to the person skilled in the art to manufacture 3-chloropyrido [2,3-b]pyrazine-6-yl-amine:
1) T. S. Osdene, et al. *J. Chem. Soc.* 1955, 2033-2035; C. L. Leese, et al. *J. Chem. Soc.* 1955, 303-309
2) C. M. Atkinson, et al. *J. Chem. Soc.* 1956, 26-30; S. Goswami, et al. *Molecules* 2005, 10, 929-936

Manufacture of 1-ethyl-3-[3-(3-hydroxy-phenyl)-pyrido[2,3-b]pyrazine-6-yl]-urea (Conversion According to Diagram 6)

100 mg 1-(3-chloropyrido[2,3-b]pyrazine-6-yl)-3-ethyl-urea (0.40 mmol) was presented in a dimethylformamide/water mixture under nitrogen as protective gas. Then 60.3 mg 3-hydroxyphenyl boronic acid (0.44 mmol), 126 mg sodium carbonate (1.19 mmol) and 23 mg tetrakis(triphenylphosphine) palladium(0) (0.02 mmol) were added. The reaction mixture was stirred at 90° C. for 4 hours. The mixture was filled with water for reprocessing and the deposited solid rewashed with dichloromethane. The resulting raw product was stirred again in warm DCM, filtered off and dried. A yellow solid was obtained.

Additional compounds according to the invention were produced according to this regulation: For example, the compounds 152, 153, 154, 208, 209 and 210.

Example 2

1-ethyl-3-(3-o-tolylamino-pyrido[2,3-b]-pyrazine-6-yl)-urea (Compound 160)

Manufacture of 1-ethyl-3-(3-o-tolylamino-pyrido[2,3-b]-pyrazine-6-yl)-urea (Conversion According to Diagram 3)

55 mg 1-(3-chlor-pyrido[2,3-b]pyrazine-6-yl)-3-ethyl-urea (0.22 mmol), 60 mg o-toluidine (0.56 mmol), 33 mg sodium-tert.-butylate(0.33 mmol), 29 mg tris(dibenzalacetone)palladium(0) (0.03 mmol) and 78 mg 2-(dicyclohexylphosphanyl)biphenyl (0.22 mmol) were presented in 1.5 ml predried toluene in a microwave reaction vessel under nitrogen as protective gas. The reaction mass was heated in the microwave at 100° C. (100 watt) for 30 minutes. Then the volatile components were removed in vacuum and the raw product was cleaned using column chromatography on silica gel (solvent dichloromethane/methanol). A yellow solid was obtained.

Additional compounds according to the invention were produced according to this regulation: For example, the compounds 161, 180, 211, 212 and 213.

Example 3

1-ethyl-3-(3-phenoxy-pyrido[2,3-b]pyrazine-6-yl)-urea (Compound 64)

Manufacture of 1-ethyl-3-(3-phenoxy-pyrido[2,3-b] pyrazine-6-yl)-urea (Conversion According to Diagram 3)

19 mg sodium hydride (0.48 mmol) (60% suspension in mineral oil) was presented in 10 ml predried dimethylformamide. 37 mg phenol (0.40 mmol) was added dissolved in a little predried dimethylformamide at 0° C. The mixture was stirred for 1 hour at 0° C. Then 100 mg 1-(3-chloro-pyrido[2,3-b]pyrazine-6-yl)-3-ethyl-urea (0.40 mmol) was dissolved in a little predried dimethylformamide and dropped in at 0° C. The reaction mixture was stirred overnight at room temperature. When the reaction was finished the reaction solution was poured on iced water and neutralised using 1N HCl. The raw product deposited was cleaned using column chromatography on silica gel (dichloromethane/methanol). A white solid was obtained.

Additional compounds according to the invention were produced according to this regulation: For example, the compounds 67, 69, 73, 80 and 87.

Conversion using amines can be undertaken using triethylamine as a base in dioxan or without a base in dioxan. Additional compounds according to the invention were produced according to this method: For example, the compounds 59, 62, 65, 81 and 88.

II. Physico-Chemical Characterisation

II.1 ESI MS Data for Selected Compounds

TABLE 1

New pyrido[2,3-b]pyrazine derivatives with relevant MS data according to the general formula (I)

| Comp. | Pyridopyrazine derivative | MS m/z (M + H$^+$) |
|---|---|---|
| 1 | 1-Allyl-3-(3-phenyl-pyrido[2,3-b]pyrazin-6-yl)-thiourea | 322.0 |
| 17 | 1-(2-Morpholin-4-yl-ethyl)-3-(3-phenyl-pyrido[2,3-b]pyrazin-6-yl)-urea | 379.1 |
| 29 | 1-[3-(4-Hydroxy-phenyl)-pyrido[2,3-b]pyrazin-6-yl]-3-prop-2-inyl-thiourea | 336.2 |
| 31 | 1-[3-(4-Hydroxy-phenyl)-pyrido[2,3-b]pyrazin-6-yl]-3-((E)-propenyl)-thiourea | 338.3 |
| 35 | 1-Phenethyl-3-(3-phenyl-pyrido[2,3-b]pyrazin-6-yl)-urea | 370.2 |
| 36 | 1-(2,3-Di-pyridin-2-yl-pyrido[2,3-b]pyrazin-6-yl)-3-ethyl-urea | 372.1 |
| 37 | 1-(2,3-Dimethyl-pyrido[2,3-b]pyrazin-6-yl)-3-ethyl-urea | 246.2 |
| 38 | 1-[3-(4-Hydroxy-phenyl)-pyrido[2,3-b]pyrazin-6-yl]-3-methyl-urea | 296.1 |
| 39 | 1-Allyl-3-[3-(4-phenoxy-phenyl)-pyrido[2,3-b]pyrazin-6-yl]-urea | 398.1 |
| 40 | Methansulfonic acid-4-[6-(3-allyl-ureido)-pyrido[2,3-b]pyrazin-3-yl]-phenyl-ester | 400.0 |
| 41 | 4-Dimethylamino-benzoic acid-4-[6-(3-allyl-ureido)-pyrido[2,3-b]pyrazin-3-yl]-phenyl-ester | 469.3 |
| 42 | Acetic acid-4-[6-(3-allyl-ureido)-pyrido[2,3-b]pyrazin-3-yl]-phenyl-ester | 364.1 |

TABLE 1-continued

New pyrido[2,3-b]pyrazine derivatives with relevant MS data according to the general formula (I)

| Comp. | Pyridopyrazine derivative | MS m/z (M + H$^+$) |
|---|---|---|
| 43 | 1-Ethyl-3-[3-(4-hydroxy-phenyl)-pyrido[2,3-b]pyrazin-6-yl]-urea | 310.2 |
| 44 | 1-[3-(4-Amino-phenyl)-pyrido[2,3-b]pyrazin-6-yl]-3-methyl-thiourea | 311.1 |
| 45 | 1-Ethyl-3-(3-phenyl-pyrido[2,3-b]pyrazin-6-yl)-urea | 294.2 |
| 46 | 1-Acetyl-1-ethyl-3-(3-phenyl-pyrido[2,3-b]pyrazin-6-yl)-urea | 336.3 |
| 47 | 1-Allyl-3-[3-(4-fluoroo-phenyl)-pyrido[2,3-b]pyrazin-6-yl]-urea | 324.0 |
| 48 | 1,1-Diethyl-3-(3-phenyl-pyrido[2,3-b]pyrazin-6-yl)-urea | 322.0 |
| 49 | 1-(2-Chloro-ethyl)-3-[3-(4-fluoro-phenyl)-pyrido[2,3-b]pyrazin-6-yl]-urea | 346.3 |
| 50 | 1-Ethyl-3-[3-(4-methoxy-phenyl)-pyrido[2,3-b]pyrazin-6-yl]-urea | 324.2 |
| 51 | 1-(3-Phenyl-pyrido[2,3-b]pyrazin-6-yl)-3-propyl-urea | 308.0 |
| 52 | [3-(3-Phenyl-pyrido[2,3-b]pyrazin-6-yl)-ureido]-acetic acid-ethyl-ester | 352.0 |
| 53 | 1-(3-Chloro-pyrido[2,3-b]pyrazin-6-yl)-3-ethyl-urea | 252.1 |
| 54 | 1-Ethyl-3-[3-(4-fluoro-phenyl)-pyrido[2,3-b]pyrazin-6-yl]-urea | 312.2 |
| 55 | 1-[3-(3-Chloro-4-fluoro-phenyl)-pyrido[2,3-b]pyrazin-6-yl]-3-ethyl-urea | 346.2 |
| 56 | 4-[6-(3-Ethyl-ureido)-pyrido[2,3-b]pyrazin-3-yl]-benzoic acid | 338.1 |
| 57 | N-{4-[6-(3-Ethyl-ureido)-pyrido[2,3-b]pyrazin-3-yl]-phenyl}-acetamide | 350.9 |
| 58 | 1-[3-(2,4-Difluoro-phenyl)-pyrido[2,3-b]pyrazin-6-yl]-3-ethyl-urea | 329.9 |
| 59 | 1-Ethyl-3-(3-morpholin-4-yl-pyrido[2,3-b]pyrazin-6-yl)-urea | 303.1 |
| 60 | 1-Ethyl-3-[3-(4-methyl-piperazin-1-yl)-pyrido[2,3-b]pyrazin-6-yl]-urea | 316.3 |
| 61 | 1-Ethyl-3-[3-(2-hydroxy-phenyl)-pyrido[2,3-b]pyrazin-6-yl]-urea | 310.2 |
| 62 | 1-Ethyl-3-[3-(2-methoxy-ethylamino)-pyrido[2,3-b]pyrazin-6-yl]-urea | 291.2 |
| 63 | 1-[3-(4-Chloro-3-trifluoromethyl-phenyl)-pyrido[2,3-b]pyrazin-6-yl]-3-ethyl-urea | 294.9 |
| 64 | 1-Ethyl-3-(3-phenoxy-pyrido[2,3-b]pyrazin-6-yl)-urea | 310.2 |
| 65 | 1-[3-(Cyclopropylmethyl-amino)-pyrido[2,3-b]pyrazin-6-yl]-3-ethyl-urea | 287.2 |
| 66 | 1-Ethyl-3-{3-[(pyridin-4-ylmethyl)-amino]-pyrido[2,3-b]pyrazin-6-yl}-urea | 324.2 |
| 67 | 1-Ethyl-3-[3-(4-fluoro-benzyloxy)-pyrido[2,3-b]pyrazin-6-yl]-urea | 341.9 |
| 68 | 1-Ethyl-3-(3-pyridin-4-yl-pyrido[2,3-b]pyrazin-6-yl)-urea | 295.3 |
| 69 | 1-Ethyl-3-[3-(pyridin-3-yloxy)-pyrido[2,3-b]pyrazin-6-yl]-urea | 311.3 |
| 70 | 1-Ethyl-3-[3-(tetrahydro-furan-2-ylmethoxy)-pyrido[2,3-b]pyrazin-6-yl]-urea | 318.2 |
| 71 | 1-Ethyl-3-[3-(4-morpholin-4-yl-phenyl)-pyrido[2,3-b]pyrazin-6-yl]-urea | 379.4 |
| 72 | 1-Ethyl-3-(3-hydroxy-pyrido[2,3-b]pyrazin-6-yl)-urea | 234.3 |
| 73 | 1-Ethyl-3-[3-(3-methoxy-phenylsulfanyl)-pyrido[2,3-b]pyrazin-6-yl]-urea | 355.9 |
| 74 | 1-Ethyl-3-(3-quinolin-3-yl-pyrido[2,3-b]pyrazin-6-yl)-urea | 345.1 |
| 75 | 1-(3-Benzo[b]thiophen-3-yl-pyrido[2,3-b]pyrazin-6-yl)-3-ethyl-urea | 350.1 |
| 76 | 1-Ethyl-3-[3-(pyridin-2-ylsulfanyl)-pyrido[2,3-b]pyrazin-6-yl]-urea | 327.3 |
| 77 | 1-[3-(4-Dimethylamino-phenyl)-pyrido[2,3-b]pyrazin-6-yl]-3-ethyl-urea | 337.2 |
| 78 | N-{4-[6-(3-Ethyl-ureido)-pyrido[2,3-b]pyrazin-3-yl]-phenyl}-methansulfonamide | 387.3 |
| 79 | 1-Ethyl-3-[3-(1H-pyrazol-4-yl)-pyrido[2,3-b]pyrazin-6-yl]-urea | 284.2 |
| 80 | 1-(3-Benzylsulfanyl-pyrido[2,3-b]pyrazin-6-yl)-3-ethyl-urea | 340.0 |
| 81 | 1-Ethyl-3-[3-(4-methyl-[1,4]diazepan-1-yl)-pyrido[2,3-b]pyrazin-6-yl]-urea | 330.5 |
| 82 | 1-[3-(4-Amino-phenyl)-pyrido[2,3-b]pyrazin-6-yl]-3-ethyl-urea | 309.4 |
| 83 | 1-(3-Amino-pyrido[2,3-b]pyrazin-6-yl)-3-ethyl-urea | 233.3 |
| 84 | 1-Ethyl-3-pyrido[2,3-b]pyrazin-6-yl-urea | 218.3 |
| 86 | 1-Ethyl-3-[3-(4-fluoro-2-hydroxy-phenyl)-pyrido[2,3-b]pyrazin-6-yl]-urea | 328.2 |
| 87 | 1-(3-Cyclopentyloxy-pyrido[2,3-b]pyrazin-6-yl)-3-ethyl-urea | 302.3 |
| 88 | 1-Ethyl-3-[3-(4-hydroxy-piperidin-1-yl)-pyrido[2,3-b]pyrazin-6-yl]-urea | 317.2 |
| 89 | (3-Phenyl-pyrido[2,3-b]pyrazin-6-yl)-urea | 266.2 |
| 90 | 1-Ethyl-3-(3-pyrimidin-5-yl-pyrido[2,3-b]pyrazin-6-yl)-urea | 296.3 |
| 91 | 1-Ethyl-3-(3-pyridin-3-yl-pyrido[2,3-b]pyrazin-6-yl)-urea | 295.3 |
| 92 | 1-Allyl-3-(3-phenyl-pyrido[2,3-b]pyrazin-6-yl)-urea | 306.3 |
| 93 | 1-Ethyl-3-(3-piperazin-1-yl-pyrido[2,3-b]pyrazin-6-yl)-urea | 302.3 |
| 94 | 1-[3-(3-Chloro-pyridin-4-ylmethyl)-pyrido[2,3-b]pyrazin-6-yl]-3-ethyl-urea | 329.3 |
| 95 | 1-Ethyl-3-[3-(6-methoxy-pyridin-3-yl)-pyrido[2,3-b]pyrazin-6-yl]-urea | 325.3 |
| 96 | 1-[3-(3,5-Dimethyl-isoxazol-4-yl)-pyrido[2,3-b]pyrazin-6-yl]-3-ethyl-urea | 313.3 |
| 97 | 1-Ethyl-3-[3-(4-trifluoromethoxy-phenyl)-pyrido[2,3-b]pyrazin-6-yl]-urea | 378.3 |
| 98 | 1-Ethyl-3-(3-furan-2-yl-pyrido[2,3-b]pyrazin-6-yl)-urea | 284.2 |
| 99 | 1-Ethyl-3-[3-(2-methoxy-pyridin-3-yl)-pyrido[2,3-b]pyrazin-6-yl]-urea | 325.3 |
| 100 | 1-[3-(2,4-Dimethoxy-phenyl)-pyrido[2,3-b]pyrazin-6-yl]-3-ethyl-urea | 353.9 |
| 101 | 1-Ethyl-3-[3-(1H-pyrrol-2-yl)-pyrido[2,3-b]pyrazin-6-yl]-urea | 383.3 |

TABLE 1-continued

New pyrido[2,3-b]pyrazine derivatives with relevant MS data according to the general formula (I)

| Comp. | Pyridopyrazine derivative | MS m/z (M + H+) |
|---|---|---|
| 102 | 1-Ethyl-3-[3-(6-morpholin-4-yl-pyridin-3-yl)-pyrido[2,3-b]pyrazin-6-yl]-urea | 380.3 |
| 103 | 1-Benzyl-3-ethyl-1-(3-phenyl-pyrido[2,3-b]pyrazin-6-yl)-urea | 384.0 |
| 104 | 1-[3-(2-Amino-phenyl)-pyrido[2,3-b]pyrazin-6-yl]-3-ethyl-urea | 309.2 |
| 105 | 1-Ethyl-3-[3-(4-hydroxymethyl-phenyl)-pyrido[2,3-b]pyrazin-6-yl]-urea | 324.2 |
| 106 | 1-[3-(3-Amino-phenyl)-pyrido[2,3-b]pyrazin-6-yl]-3-ethyl-urea | 309.2 |
| 107 | 1-[3-(4-Acetyl-phenyl)-pyrido[2,3-b]pyrazin-6-yl]-3-ethyl-urea | 336.1 |
| 108 | 1-[3-(2,3-Dihydro-benzofuran-5-yl)-pyrido[2,3-b]pyrazin-6-yl]-3-ethyl-urea | 336.2 |
| 109 | 1-[3-(4-Benzyloxy-3-fluoro-phenyl)-pyrido[2,3-b]pyrazin-6-yl]-3-ethyl-urea | 418.3 |
| 110 | 1-(2,3-Dihydroxy-propyl)-3-(3-phenyl-pyrido[2,3-b]pyrazin-6-yl)-urea | 340.0 |
| 111 | 1-Ethyl-3-[3-(3-formyl-4-methoxy-phenyl)-pyrido[2,3-b]pyrazin-6-yl]-urea | 352.1 |
| 112 | 1-Ethyl-3-[3-(4-methansulfonyl-phenyl)-pyrido[2,3-b]pyrazin-6-yl]-urea | 372.1 |
| 113 | N-{4-[6-(3-Ethyl-ureido)-pyrido[2,3-b]pyrazin-3-yl]-phenyl}-succinamid acid | 409.3 |
| 114 | 1-Ethyl-3-(3-pyridin-4-yl-pyrido[2,3-b]pyrazin-6-yl)-urea Methansulfonic acid salt | 295.3 |
| 115 | 1-[3-(2,6-Dimethoxy-pyridin-3-yl)-pyrido[2,3-b]pyrazin-6-yl]-3-ethyl-urea | 354.9 |
| 116 | 1-[3-(2,6-Dimethoxy-pyrimidin-4-yl)-pyrido[2,3-b]pyrazin-6-yl]-3-ethyl-urea | 356.1 |
| 117 | 1-[3-(2,4-Dioxo-1,2,3,4-tetrahydro-pyrimidin-5-yl)-pyrido[2,3-b]pyrazin-6-yl]-3-ethyl-urea | 328.4 |
| 118 | 1-Ethyl-3-[3-(1H-indol-5-yl)-pyrido[2,3-b]pyrazin-6-yl]-urea | 333.0 |
| 119 | 1-(3-Chlorooo-pyrido[2,3-b]pyrazin-6-yl)-3-ethyl-thiourea | 268.0 |
| 120 | 1-Ethyl-3-{3-[4-(2-methoxy-ethoxy)-phenyl]-pyrido[2,3-b]pyrazin-6-yl}-urea | 368.4 |
| 121 | Acrylic acid-4-[6-(3-ethyl-ureido)-pyrido[2,3-b]-pyrazin-3-yl]-phenyl-ester | 364.1 |
| 122 | 1-[3-(4-Cyano-phenyl)-pyrido[2,3-b]pyrazin-6-yl]-3-ethyl-urea | 319.1 |
| 123 | 1-(3-Benzo[1,2,5]oxadiazol-4-yl-pyrido[2,3-b]pyrazin-6-yl)-3-ethyl-urea | 336.0 |
| 124 | 1-Ethyl-3-[3-(4-hydroxy-3-methoxy-phenyl)-pyrido[2,3-b]pyrazin-6-yl]-urea | 340.0 |
| 125 | 1-[3-(2,6-Dimethoxy-phenyl)-pyrido[2,3-b]pyrazin-6-yl]-3-ethyl-urea | 354.2 |
| 126 | 1-[3-(3-Acetyl-phenyl)-pyrido[2,3-b]pyrazin-6-yl]-3-ethyl-urea | 336.2 |
| 127 | 1-Ethyl-3-[3-(3-morpholin-4-yl-phenyl)-pyrido[2,3-b]pyrazin-6-yl]-urea | 379.2 |
| 128 | 1-[3-(6-Amino-pyridin-3-yl)-pyrido[2,3-b]pyrazin-6-yl]-3-ethyl-urea | 310.2 |
| 129 | 3-{4-[6-(3-Ethyl-ureido)-pyrido[2,3-b]-pyrazin-3-yl]-phenoxy}-propionic acid | 382.3 |
| 130 | 1-Isopropyl-3-(3-phenyl-pyrido[2,3-b]pyrazin-6-yl)-urea | 308.2 |
| 131 | 1-Cyclopentyl-3-(3-phenyl-pyrido[2,3-b]pyrazin-6-yl)-urea | 333.9 |
| 132 | 1-Pentyl-3-(3-phenyl-pyrido[2,3-b]pyrazin-6-yl)-urea | 336.2 |
| 133 | N-{4-[6-(3-Ethyl-ureido)-pyrido[2,3-b]pyrazin-3-yl]-phenyl}-acrylamide | 363.2 |
| 134 | 1-tert-Butyl-3-(3-phenyl-pyrido[2,3-b]pyrazin-6-yl)-urea | 322.1 |
| 135 | 1-(2-Hydroxy-ethyl)-3-(3-phenyl-pyrido[2,3-b]pyrazin-6-yl)-urea | 310.2 |
| 136 | 1-Cyclobutyl-3-(3-phenyl-pyrido[2,3-b]pyrazin-6-yl)-urea | 319.8 |
| 137 | 1-Allyl-3-[3-(4-nitro-phenyl)-pyrido[2,3-b]pyrazin-7-yl]-thiourea | 367.1 |
| 138 | 1-Ethyl-1-(Ethylcarbamoyl)-3-(3-phenyl-pyrido[2,3-b]pyrazin-6-yl)-urea | 365.1 |
| 139 | [3-(4-Hydroxy-phenyl)-pyrido[2,3-b]pyrazin-6-yl]-carbamic acid-allyl-ester | 323.0 |
| 140 | (3-Phenyl-pyrido[2,3-b]pyrazin-6-yl)-carbamic acid-ethyl-ester | 295.3 |
| 141 | 1-Ethyl-3-[3-(4-phenyl-piperazin-1-yl)-pyrido[2,3-b]pyrazin-6-yl]-urea | 378.3 |
| 142 | 1-(2,2-Dimethyl-[1,3]dioxolan-4-ylmethyl)-3-(3-phenyl-pyrido[2,3-b]pyrazin-6-yl)-urea | 380.2 |
| 143 | 1,3-Bis-(3-phenyl-pyrido[2,3-b]pyrazin-6-yl)-urea | 471.3 |
| 144 | N-(3-Phenyl-pyrido[2,3-b]pyrazin-6-yl)-acetamidine | 264.8 |
| 145 | 1-Ethyl-3-[3-(2-methoxy-pyridin-3-yl)-pyrido[2,3-b]pyrazin-6-yl]-thiourea | 341.2 |
| 146 | 1-(4-Hydroxy-butyl)-3-(3-phenyl-pyrido[2,3-b]pyrazin-6-yl)-urea | 338.2 |
| 147 | 1-(3-Hydroxy-propyl)-3-(3-phenyl-pyrido[2,3-b]pyrazin-6-yl)-urea | 324.2 |
| 148 | 1-Ethyl-3-{3-[4-(3-morpholin-4-yl-propoxy)-phenyl]-pyrido[2,3-b]pyrazin-6-yl}-urea | 437.3 |
| 149 | 1-Ethyl-3-[3-(4-hydroxy-phenyl)-pyrido[2,3-b]pyrazin-6-yl]-thiourea | 326.1 |
| 150 | 1-Ethyl-3-(3-p-tolylamino-pyrido[2,3-b]pyrazin-6-yl)-urea | 323.2 |
| 151 | 1-Ethyl-3-[3-(3-hydroxy-phenyl)-pyrido[2,3-b]pyrazin-6-yl]-urea | 310.2 |
| 152 | 3-[6-(3-Ethyl-ureido)-pyrido[2,3-b]pyrazin-3-yl]-benzoic acid | 338.2 |

TABLE 1-continued

New pyrido[2,3-b]pyrazine derivatives with relevant MS data according to the general formula (I)

| Comp. | Pyridopyrazine derivative | MS m/z (M + H+) |
|---|---|---|
| 153 | 1-[3-(3,4-Dimethoxy-phenyl)-pyrido[2,3-b]pyrazin-6-yl]-3-ethyl-urea | 354.1 |
| 154 | 1-[3-(4-Amino-3-methoxy-phenyl)-pyrido[2,3-b]pyrazin-6-yl]-3-ethyl-urea | 339.1 |
| 155 | 3-[6-(3-Ethyl-ureido)-pyrido[2,3-b]-pyrazin-3-yl]-benzamide | 337.1 |
| 156 | 1-[3-(3-Chloro-4-hydroxy-5-methoxy-phenyl)-pyrido[2,3-b]pyrazin-6-yl]-3-ethyl-urea | 374.2 |
| 157 | 1-Ethyl-3-(3-m-tolylamino-pyrido-[2,3-b]pyrazin-6-yl)-urea | 323.3 |
| 158 | 1-Ethyl-3-[3-(4-methoxy-phenylamino)-pyrido[2,3-b]pyrazin-6-yl]-urea | 339.0 |
| 159 | 1-[3-(4-Chloroo-phenylamino)-pyrido-[2,3-b]pyrazin-6-yl]-3-ethyl-urea | 343.1 |
| 160 | 1-Ethyl-3-(3-o-tolylamino-pyrido[2,3-b]-pyrazin-6-yl)-urea | 323.2 |
| 161 | 1-Ethyl-3-[3-(pyridin-3-ylamino)-pyrido-[2,3-b]pyrazin-6-yl]-urea | 310.2 |
| 162 | 1-Ethyl-3-[3-(4-ethyl-phenylamino)-pyrido[2,3-b]pyrazin-6-yl]-urea | 337.2 |
| 163 | 1-Ethyl-3-[3-(3-methoxy-4-methyl-phenylamino)-pyrido[2,3-b]pyrazin-6-yl]-urea | 353.3 |
| 164 | 1-Ethyl-3-[3-(4-hydroxy-phenylamino)-pyrido[2,3-b]pyrazin-6-yl]-urea | 325.3 |
| 165 | 1-Ethyl-3-[3-(5-methyl-pyridin-2-yl-amino)-pyrido[2,3-b]pyrazin-6-yl]-urea | 324.3 |
| 166 | 1-Ethyl-3-[3-(1-methyl-1H-pyrazol-3-ylamino)-pyrido[2,3-b]pyrazin-6-yl]-urea | 313.4 |
| 167 | 1-Ethyl-3-[3-(4-fluoro-phenylamino)-pyrido[2,3-b]pyrazin-6-yl]-urea | 327.4 |
| 168 | 1-(4-Hydroxy-butyl)-3-[3-(4-hydroxy-3-methoxy-phenyl)-pyrido[2,3-b]pyrazin-6-yl]-urea | 384.3 |
| 169 | Phosphoric acid-mono-{4-[6-(3-ethyl-ureido)-pyrido-[2,3-b]pyrazin-3-yl]-2-methoxy-phenyl}-ester | 420.2 |
| 170 | 1-[3-(2-Chloro-4-hydroxy-phenyl)-pyrido[2,3-b]pyrazin-6-yl]-3-ethyl-urea | 344.3 |
| 171 | 1-[3-(4-Chloro-2-methoxy-phenyl)-pyrido[2,3-b]pyrazin-6-yl]-3-ethyl-urea | 358.1 |
| 172 | 1-[3-(3,5-Dimethyl-1H-pyrazol-4-yl)-pyrido[2,3-b]pyrazin-6-yl]-3-ethyl-urea | 312.2 |
| 173 | 1-Ethyl-3-[3-(1-methyl-1H-pyrazol-4-yl)-pyrido[2,3-b]pyrazin-6-yl]-urea | 298.4 |
| 174 | 1-[3-(5-Cyano-thiophen-2-yl)-pyrido[2,3-b]pyrazin-6-yl]-3-ethyl-urea | 325.3 |
| 176 | 1-[3-(4-Hydroxy-3-methoxy-phenyl)-pyrido[2,3-b]pyrazin-6-yl]-3-(4-morpholin-4-yl-butyl)-urea | 453.4 |
| 177 | 1-[3-(3-Chloro-4-methoxy-phenylamino)-pyrido[2,3-b]pyrazin-6-yl]-3-ethyl-urea | 373.4 |
| 178 | 1-Ethyl-3-[3-(naphthalin-2-ylamino)-pyrido[2,3-b]pyrazin-6-yl]-urea | 359.3 |
| 179 | 1-Ethyl-3-[3-(chinolin-3-ylamino)-pyrido[2,3-b]pyrazin-6-yl]-urea | 360.3 |
| 180 | 1-[3-(3,5-Dimethoxy-phenylamino)-pyrido[2,3-b]pyrazin-6-yl]-3-ethyl-urea | 369.3 |
| 181 | 1-Ethyl-3-[3-(pyrazin-2-ylamino)-pyrido[2,3-b]pyrazin-6-yl]-urea | 311.3 |
| 182 | 1-Ethyl-3-[3-(3-isopropoxy-phenylamino)-pyrido[2,3-b]pyrazin-6-yl]-urea | 367.2 |
| 183 | 1-Ethyl-3-[3-(4-hydroxy-3-methoxy-phenyl)-pyrido[2,3-b]pyrazin-6-yl]-urea p-Toluolsulfonate | 340.3 (free base) |
| 184 | 1-[3-(2-Chloro-pyridin-4-ylamino)-pyrido[2,3-b]pyrazin-6-yl]-3-ethyl-urea | 344.3 |
| 185 | 1-[3-(3,5-Dichloro-4-hydroxy-phenylamino)-pyrido[2,3-b]pyrazin-6-yl]-3-ethyl-urea | 393.2 |
| 186 | 1-[3-(3,5-Dichloro-4-hydroxy-phenyl)-pyrido[2,3-b]pyrazin-6-yl]-3-ethyl-urea | 369.2 |
| 187 | 1-[3-(3,4-Dimethoxy-phenylamino)-pyrido[2,3-b]pyrazin-6-yl]-3-ethyl-urea | 369.2 |
| 188 | 1-Ethyl-3-[3-(3-hydroxy-4-methyl-phenylamino)-pyrido[2,3-b]pyrazin-6-yl]-urea | 339.1 |
| 189 | 3-[6-(3-Ethyl-ureido)-pyrido[2,3-b]-pyrazin-3-ylamino]-5-trifluoromethyl-benzoic acid | 421.3 |
| 190 | 1-Ethyl-3-[3-(6-methoxy-pyridin-3-ylamino)-pyrido[2,3-b]pyrazin-6-yl]-urea | 340.3 |
| 191 | 1-[3-(3,5-Dimethyl-phenylamino)-pyrido[2,3-b]pyrazin-6-yl]-3-ethyl-urea | 337.3 |
| 192 | 1-[3-(4-Cyano-phenylamino)-pyrido-[2,3-b]pyrazin-6-yl]-3-ethyl-urea | 334.1 |
| 194 | 1-Ethyl-3-[3-(4-hydroxy-3-methoxy-phenyl)-pyrido[2,3-b]pyrazin-6-yl]-urea Hydrochloride | 340.1 (free base) |
| 195 | 1-Ethyl-3-(3-phenyl-pyrido[2,3-b]pyrazin-6-yl)-thiourea | 310.2 |
| 196 | 1-(3-Chloro-pyrido[2,3-b]pyrazin-6-yl)-3-cyclohexyl-urea | 306.2 |
| 197 | 1-Ethyl-3-[3-(4-hydroxy-3-methoxy-phenylamino)-pyrido[2,3-b]pyrazin-6-yl]-urea | 355.3 |
| 198 | 1-Ethyl-3-[3-(4-hydroxy-3,5-dimethyl-phenyl)-pyrido[2,3-b]pyrazin-6-yl]-urea | 338.3 |
| 199 | 3-Ethyl-1-phenethyl-1-(3-phenyl-pyrido[2,3-b]pyrazin-6-yl)-urea | 398.2 |
| 200 | 1-Allyl-3-{3-[4-(tetrahydro-pyran-2-yloxy)-phenyl]-pyrido[2,3-b]pyrazin-6-yl}-thiourea | 422.2 |

TABLE 1-continued

New pyrido[2,3-b]pyrazine derivatives with relevant MS data according to the general formula (I)

| Comp. | Pyridopyrazine derivative | MS m/z (M + H⁺) |
|---|---|---|
| 201 | 3-Ethyl-1-[3-(4-methoxy-phenyl)-pyrido[2,3-b]pyrazin-6-yl]-1-propyl-urea | 366.3 |
| 202 | 3-Ethyl-1-(3-phenyl-pyrido[2,3-b]pyrazin-6-yl)-1-(2-piperidin-1-yl-ethyl)-urea Hydrochloride | 405.4 (free base) |
| 203 | N-{4-[6-(3-Ethyl-ureido)-pyrido[2,3-b]-pyrazin-3-yl]-phenyl}-2-phenyl-acetamide | 427.3 |
| 204 | 1-(4-Hydroxy-butyl)-3-(3-phenyl-pyrido[2,3-b]pyrazin-6-yl)-urea Hydrochloride | 338.3 (free base) |
| 205 | Acetic acid-4-[3-(3-phenyl-pyrido[2,3-b]pyrazin-6-yl)-ureido]-butyl ester | 380.4 |
| 206 | 1-(4-Amino-butyl)-3-(3-phenyl-pyrido[2,3-b]pyrazin-6-yl)-urea | 337.3 |
| 207 | 1-(5-Hydroxy-pentyl)-3-(3-phenyl-pyrido[2,3-b]pyrazin-6-yl)-urea | 352.3 |
| 208 | 3-[6-(3-Ethyl-ureido)-pyrido[2,3-b]-pyrazin-3-yl]-N-methyl-benzamide | 351.2 |
| 209 | 1-Ethyl-3-[3-(2-methoxy-5-methyl-phenyl)-pyrido[2,3-b]pyrazin-6-yl]-urea | 338.1 |
| 210 | 1-Ethyl-3-(3-p-tolyl-pyrido[2,3-b] pyrazin-6-yl)-urea | 308.2 |
| 211 | 1-Ethyl-3-[3-(methyl-p-tolyl-amino)-pyrido[2,3-b]pyrazin-6-yl]-urea | 337.1 |
| 212 | 1-Ethyl-3-[3-(2-p-tolyl-ethylamino)-pyrido[2,3-b]pyrazin-6-yl]-urea | 351.1 |
| 213 | 1-Ethyl-3-[3-(4-methyl-benzylamino)-pyrido[2,3-b]pyrazin-6-yl]-urea | 337.2 |
| 214 | 1-Ethyl-3-[3-(3-fluoro-4-methyl-phenyl-amino)-pyrido[2,3-b]pyrazin-6-yl]-urea | 341.2 |
| 215 | 1-[3-(3,4-Dimethyl-phenylamino)-pyrido[2,3-b]pyrazin-6-yl]-3-ethyl-urea | 337.1 |
| 216 | 1-Ethyl-3-[3-(4-isopropyl-phenylamino)-pyrido[2,3-b]pyrazin-6-yl]-urea | 351.1 |
| 217 | 1-(4-Morpholin-4-yl-butyl)-3-(3-phenyl-pyrido[2,3-b]pyrazin-6-yl)-urea | 407.3 |
| 218 | N-{4-[3-(3-Phenyl-pyrido[2,3-b]pyrazin-6-yl)-ureido]-butyl}-acetamide | 379.3 |
| 219 | 1-[3-(3-Amino-4-methyl-phenyl)-pyrido[2,3-b]pyrazin-6-yl]-3-ethyl-urea | 323.3 |
| 220 | 1-[3-(3-Acetyl-2-fluoro-phenyl)-pyrido[2,3-b]pyrazin-6-yl]-3-ethyl-urea | 354.2 |
| 221 | 1-Ethyl-3-[3-(4-methoxy-3-methyl-phenyl)-pyrido[2,3-b]pyrazin-6-yl]-urea | 338.3 |
| 222 | 1-[3-(6-Ethoxy-pyridin-3-yl)-pyrido[2,3-b]pyrazin-6-yl]-3-ethyl-urea | 339.3 |
| 223 | 1-Ethyl-3-[3-(2-fluoro-4-methyl-phenyl)-pyrido[2,3-b]pyrazin-6-yl]-urea | 326.2 |
| 224 | 1-Ethyl-3-[3-(3-fluoro-4-methoxy-phenyl)-pyrido[2,3-b]pyrazin-6-yl]-urea | 342.1 |
| 225 | 1-Ethyl-3-[3-(2-fluoro-3-methoxy-phenyl)-pyrido[2,3-b]pyrazin-6-yl]-urea | 342.1 |
| 226 | 1-Ethyl-3-[3-(3,4,5-trimethoxy-phenyl)-pyrido[2,3-b]pyrazin-6-yl]-urea | 384.2 |
| 227 | 1-[3-(3,5-Difluoro-2-methoxy-phenyl)-pyrido[2,3-b]pyrazin-6-yl]-3-ethyl-urea | 360.3 |
| 228 | 1-Ethyl-3-[3-(4-trifluoromethyl-phenyl)-pyrido[2,3-b]pyrazin-6-yl]-urea | 362.3 |
| 229 | 1-Ethyl-3-[3-(2,3,4-trimethoxy-phenyl)-pyrido[2,3-b]pyrazin-6-yl]-urea | 384.3 |
| 230 | 1-[3-(3-Chloro-4-methoxy-phenyl)-pyrido[2,3-b]pyrazin-6-yl]-3-ethyl-urea | 358.2 |
| 231 | 1-Ethyl-3-[3-(3-fluoro-4-hydroxy-phenyl)-pyrido[2,3-b]pyrazin-6-yl]-urea | 328.3 |
| 232 | 1-Ethyl-3-[3-(6-fluoro-pyridin-3-yl)-pyrido[2,3-b]pyrazin-6-yl]-urea | 313.3 |
| 233 | 1-[3-(2,4-Dimethyl-thiazol-5-yl)-pyrido-[2,3-b]-pyrazin-6-yl]-3-ethyl-urea | 329.4 |
| 234 | 1-Ethyl-3-[3-(2-methoxy-phenyl)-pyrido[2,3-b]pyrazin-6-yl]-urea | 324.3 |
| 235 | 1-[3-(2-Chloro-pyridin-4-yl)-pyrido[2,3-b]pyrazin-6-yl]-3-ethyl-urea | 329.3 |
| 236 | 1-[3-(5-Acetyl-thiophen-2-yl)-pyrido[2,3-b]pyrazin-6-yl]-3-ethyl-urea | 342.3 |
| 237 | 1-[3-(5-Chloro-thiophen-2-yl)-pyrido[2,3-b]pyrazin-6-yl]-3-ethyl-urea | 334.1 |
| 238 | 1-Ethyl-3-[3-(3-methoxy-phenyl)-pyrido[2,3-b]pyrazin-6-yl]-urea | 324.1 |
| 239 | 1-[3-(3-Bromo-5-methoxy-phenyl)-pyrido[2,3-b]pyrazin-6-yl]-3-ethyl-urea | 402.3 |
| 240 | 1-[3-(Benzothiazol-6-ylamino)-pyrido[2,3-b]pyrazin-6-yl]-3-ethyl-urea | 366.3 |
| 241 | 1-Ethyl-3-[3-(4-methyl-3-trifluoromethyl-phenylamino)-pyrido[2,3-b]pyrazin-6-yl]-urea | 391.4 |
| 242 | 1-[3-(3-Cyano-4-methyl-phenylamino)-pyrido[2,3-b]pyrazin-6-yl]-3-ethyl-urea | 348.3 |
| 243 | 1-Ethyl-3-[3-(4-phenoxy-phenylamino)-pyrido[2,3-b]pyrazin-6-yl]-urea | 401.3 |
| 244 | 1-[3-(4-Chloro-3-methyl-phenylamino)-pyrido[2,3-b]pyrazin-6-yl]-3-ethyl-urea | 357.3 |
| 245 | 1-[3-(2-Chloro-4-methyl-phenylamino)-pyrido[2,3-b]pyrazin-6-yl]-3-ethyl-urea | 357.1 |
| 246 | 1-Ethyl-3-[3-(3-trifluoromethyl-phenylamino)-pyrido[2,3-b]pyrazin-6-yl]-urea | 377.4 |

TABLE 1-continued

New pyrido[2,3-b]pyrazine derivatives with relevant MS data according to the general formula (I)

| Comp. | Pyridopyrazine derivative | MS m/z (M + H$^+$) |
|---|---|---|
| 247 | 1-[3-(2-Chloro-4-trifluoromethoxy-phenylamino)-pyrido[2,3-b]pyrazin-6-yl]-3-ethyl-urea | 427.3 |
| 248 | 1-[3-(4-Chloro-2-methoxy-5-methyl-phenylamino)-pyrido[2,3-b]pyrazin-6-yl]-3-ethyl-urea | 387.4 |
| 249 | 1-Ethyl-3-[3-(4-methylsulfanyl-phenyl)-pyrido[2,3-b]pyrazin-6-yl]-urea | 340.3 |
| 250 | 3-[6-(3-Ethyl-ureido)-pyrido[2,3-b]pyrazin-3-yl]-benzolsulfonamide | 373.3 |
| 251 | N-{4-[3-(3-Phenyl-pyrido[2,3-b]pyrazin-6-yl)-ureido]-butyl}-methansulfonamide | 415.3 |

II.2 NMR Spectroscopic Data and Melting Points for Selected Compounds

Compound 1: 1-allyl-3-(3-phenyl-pyrido[2,3-b]pyrazin-6-yl)-thiourea

Melting point: 239-240° C. (Decomp.)
$^1$H-NMR (d$_6$-DMSO): δ=4.40 (m, 2H), 5.30 (d, 1H), 5.60 (d, 1H), 6.07-6.17 (m, 1H), 7.55-7.70 (m, 4H), 8.35 (d, 2H), 8.45 (d, 1H), 9.50 (s, 1H), 11.35 (s, 1H), 12.55 (m, 1H).

Compound 2: 1-(2-methyl-allyl)-3-(3-naphth-2-yl-pyrido[2,3-b]pyrazin-6-yl)-thiohurea Mp.: 239-240° C. (Decomp.)
$^1$H-NMR (d$_6$-DMSO): δ=1.94 (s, 3H), 4.32 (m, 2H), 5.07 (s, 1H), 5.28 (s, 1H), 7.60-7.69 (m, 3H), 8.00-8.05 (m, 1H), 8.07-8.12 (m, 1H), 8.14 (d, 1H), 8.42-8.51 (m, 2H), 8.98 (s, 1H), 9.68 (s, 1H), 11.32 (s, 1H), 12.78 (m, 1H).

Compound 3: 1-[3-(4-methoxy-phenyl)-pyrido[2,3-b]pyrazin-6-yl]-3-(2-methyl-allyl)-thiourea Mp.: 251-252° C. (Decomp.)
$^1$H-NMR (d$_6$-DMSO): δ=1.92 (s, 3H), 3.85 (s, 3H), 4.27-4.35 (m, 2H), 5.02 (s, 1H), 5.24 (s, 1H), 7.15 (d, 2H), 7.58 (d, 1H), 8.31 (d, 2H), 8.41 (d, 1H), 9.46 (s, 1H), 11.29 (s, 1H), 12.68 (m, 1H).

Compound 4: 1-(2-methyl-allyl)-3-(3-phenyl-pyrido[2,3-b]pyrazin-6-yl)-thiourea

Mp.: 225-226° C. (Decomp.)
$^1$H-NMR (d$_6$-DMSO): δ=1.90 (s, 3H), 4.30-4.35 (m, 2H), 5.01 (s, 1H), 5.22 (s, 1H), 7.55-7.80 (m, 4H), 8.30-8.38 (m, 2H), 8.45 (d, 1H), 9.52 (s, 1H), 11.32 (s, 1H), 12.65 (m, 1H).

Compound 5: 1-allyl-3-(3-naphth-2-yl-pyrido[2,3-b]pyrazin-6-yl)-thiourea

Mp.: 242-243° C. (Decomp.)
$^1$H-NMR (d$_6$-DMSO): δ=4.42 (m, 2H), 5.37 (d, 1H), 5.65 (d, 1H), 6.07-6.19 (m, 1H), 7.57-7.68 (m, 3H), 7.97-8.05 (m, 1H), 8.07-8.19 (m, 2H), 8.40-8.52 (m, 2H), 8.99 (s, 1H), 9.70 (s, 1H), 11.36 (s, 1H), 12.56 (t, 1H).

Compound 6: 1-allyl-3-[3-(4-methoxy-phenyl)-pyrido[2,3-b]pyrazin-6-yl]-thiourea

Mp.: 240-241° C. (Decomp.)
$^1$H-NMR (d$_6$-DMSO): δ=3.87 (s, 3H), 4.36-4.42 (m, 2H), 5.32 (d, 1H), 5.60 (d, 1H), 6.06-6.16 (m, 1H), 7.16 (d, 2H), 7.60 (d, 1H), 8.32 (d, 2H), 8.42 (d, 1H), 9.56 (s, 1H), 11.29 (s, 1H), 12.56 (m, 1H).

Compound 7: 1-allyl-3-[3-(4-hydroxy-phenyl)-pyrido[2,3-b]pyrazin-6-yl]-thiourea-hydrochloride Mp.: 160-161° C. (Decomp.)
$^1$H-NMR (d$_6$-DMSO): δ=4.36-4.43 (m, 2H), 5.31 (d, 1H), 5.59 (d, 1H), 6.05-6.16 (m, 1H), 6.97 (d, 2H), 7.57 (d, 1H), 8.20 (d, 2H), 8.40 (d, 1H), 9.41 (s, 1H), 10.17 (bs, 1H), 11.24 (s, 1H), 12.56 (m, 1H).

Compound 8: 1-(3-naphth-2-yl-pyrido[2,3-b]pyrazin-6-yl)-3-(4-nitro-phenyl)-thiourea Mp.: 260-261° C. (Decomp.)
$^1$H-NMR (d$_6$-DMSO): δ=7.61-7.68 (m, 3H), 7.72 (d, 2H), 7.75 (d, 1H), 8.01-8.06 (m, 1H), 8.16 (m, 2H), 8.26 (d, 2H), 8.53 (d, 1H), 8.58 (d, 1H), 9.04 (s, 1H), 9.62 (s, 1H), 9.76 (s, 1H), 11.81 (s, 1H).

Compound 9: 1-[3-(4-methoxy-phenyl)-pyrido[2,3-b]pyrazin-6-yl]-3-(4-nitro-phenyl)-thiourea Mp.: 250-251° C. (Decomp.)
$^1$H-NMR (d$_6$-DMSO): δ=3.85 (s, 3H), 7.17 (d, 2H), 7.71 (d, 2H), 8.21 (d, 2H), 8.22-8.27 (m, 1H), 8.36-8.42 (m, 3H), 9.53 (s, 1H), 9.65 (s, 1H), 11.77 (s, 1H).

Compound 10: 1-tert.butyl-3-(3-phenyl-pyrido[2,3-b]pyrazin-6-yl)-thiourea

Mp.: 227° C. (Decomp.)
$^1$H-NMR (d$_6$-DMSO): δ=1.65 (s, 9H), 7.53-7.69 (m, 4H), 8.34 (d, 2H), 8.41 (d, 1H), 9.51 (s, 1H), 10.98 (s, 1H), 12.75 (s, 1H).

Compound 11: 1-cyclopropyl-3-(3-phenyl-pyrido[2,3-b]pyrazin-6-yl)-thiourea

Mp.: 233-234° C.
$^1$H-NMR (d$_6$-DMSO): δ=0.70-0.80 (m, 2H), 0.91-1.00 (m, 2H), 3.20-3.28 (m, 1H), 7.51-7.72 (m, 4H), 8.36 (d, 2H), 8.45 (d, 1H), 9.52 (s, 1H), 11.31 (s, 1H), 12.45 (s, 1H).

Compound 12: 1-methyl-3-(3-phenyl-pyrido[2,3-b]pyrazin-6-yl)-thiourea

Mp.: 253-254° C.
$^1$H-NMR (d$_6$-DMSO): δ=3.25 (s, 3H), 7.59-7.67 (m, 4H), 8.38 (d, 2H), 8.46 (d, 1H), 9.52 (s, 1H), 11.31 (s, 1H), 12.10 (s, 1H).

Compound 13: 1-benzyl-3-(3-phenyl-pyrido[2,3-b]pyrazin-6-yl)-thiourea

Mp.: 232-233° C.
$^1$H-NMR (d$_6$-DMSO): δ=4.96 (m, 2H), 7.37-7.48 (m, 3H), 7.54-7.67 (m, 6H), 8.32 (d, 2H), 8.47 (d, 1H), 9.52 (s, 1H), 11.43 (s, 1H), 12.91 (s, 1H).

Compound 14: 1-(4-fluoro-phenyl)-3-(3-phenyl-pyrido[2,3-b]pyrazin-6-yl)-thiourea Mp.: 225-226° C.
$^1$H-NMR (d$_6$-DMSO): δ=7.33 (m, 2H), 7.57-7.65 (m, 3H), 7.70-7.81 (m, 3H), 8.34 (d, 2H), 8.54 (d, 1H), 9.57 (s, 1H), 11.62 (s, 1H).

Compound 15: 1-(3-phenyl-pyrido[2,3-b]pyrazin-6-yl)-3-p-tolyl-urea

Mp.: 298-299° C.
$^1$H-NMR (d$_6$-DMSO): δ=2.29 (s, 3H), 7.20 (d, 2H), 7.52 (d, 2H), 7.59-7.67 (m, 3H), 7.80 (d, 2H), 8.38 (d, 2H), 8.44 (d, 1H), 9.59 (s, 1H), 10.36 (s, 1H), 11.46 (s, 1H).

Compound 16: 1-(4-chloro-3-trifluoromethyl-phenyl)-3-(3-phenyl-pyrido[2,3-b]pyrazin-6-yl)-urea Mp.: 250° C.
$^1$H-NMR (d$_6$-DMSO): δ=7.58-7.67 (m, 3H), 7.74 (d, 1H), 7.80 (d, 1H), 7.87 (d, 1H), 8.21 (s, 1H), 8.39 (d, 2H), 8.48 (d, 1H), 9.53 (s, 1H), 10.55 (s, 1H), 11.82 (s, 1H).

Compound 17: 1-(2-morpholin-4-yl-ethyl)-3-(3-phenyl-pyrido[2,3-b]pyrazin-6-yl)-urea Mp.: 226° C.
$^1$H-NMR (d$_6$-DMSO): δ=2.45-2.67 (m, 6H), 3.40-3.48 (m, 2H), 3.60-3.69 (m, 4H), 7.55-7.70 (m, 4H), 8.30-8.40 (m, 3H), 9.29 (s, 1H), 9.42 (s, 1H), 10.18 (s, 1H).

Compound 18: 1-cyclohexyl-3-(3-phenyl-pyrido[2,3-b]pyrazin-6-yl)-thiourea

Mp.: 230-232° C.
$^1$H-NMR (d$_6$-DMSO): δ=1.50-1.75 (m, 6H), 1.80-2.00 (m, 4H), 7.55-7.70 (m, 4H), 8.37 (d, 2H), 8.45 (d, 1H), 9.55 (s, 1H), 11.20 (s, 1H), 12.80 (s, 1H).

Compound 19: 1-isopropyl-3-(3-phenyl-pyrido[2,3-b]pyrazin-6-yl)-thiourea

Mp.: 229-230° C.
$^1$H-NMR (d$_6$-DMSO): δ=1.40 (d, 6H), 4.40-4.50 (m, 1H), 7.58-7.66 (m, 4H), 8.36 (d, 2H), 8.44 (d, 1H), 9.52 (s, 1H), 11.20 (s, 1H), 12.48 (s, 1H).

Compound 20: 1-furan-2-ylmethyl-3-(3-phenyl-pyrido[2,3-b]pyrazin-6-yl)-thiourea Mp.: 250° C. (Decomp.)
$^1$H-NMR (d$_6$-DMSO): δ=4.95 (s, 2H), 6.55 (m, 1H), 6.68 (d, 1H), 7.59-7.68 (m, 4H), 7.74 (d, 1H), 8.37 (d, 2H), 8.48 (d, 1H), 9.55 (s, 1H), 11.45 (s, 1H), 12.83 (s, 1H).

Compound 21: 1-cyclopropyl-3-(3-phenyl-pyrido[2,3-b]pyrazin-6-yl)-urea

Mp.: 158-160° C.
$^1$H-NMR (d$_6$-DMSO): δ=0.52-0.60 (m, 2H), 0.72-0.82 (m, 2H), 2.70-2.79 (m, 1H), 7.57-7.65 (m, 3H), 7.71 (d, 1H), 8.34 (d, 2H), 8.38 (d, 1H), 9.21 (s, 1H), 9.46 (s, 1H), 10.12 (s, 1H).

Compound 22: 1-methyl-3-[3-(4-nitro-phenyl)-pyrido[2,3-b]pyrazin-6-yl]-thiourea Mp.: 270° C.
$^1$H-NMR (d$_6$-DMSO): δ=3.25 (s, 3H), 7.70 (d, 1H), 8.44 (d, 2H), 8.50 (d, 1H), 8.64 (d, 2H), 9.64 (s, 1H), 11.38 (s, 1H), 12.03 (s, 1H).

Compound 23: 1-[3-(4-hydroxy-phenyl)-pyrido[2,3-]pyrazin-6-yl]-3-methyl-thiourea Mp.: 282° C.
$^1$H-NMR (d$_6$-DMSO): δ=3.25 (s, 3H), 6.98 (d, 2H), 7.57 (d, 1H), 8.26 (d, 2H), 8.40 (d, 1H), 9.45 (s, 1H), 10.18 (s, 1H), 11.25 (s, 1H), 12.10 (s, 1H).

Compound 24: 1-allyl-3-[3-(4-nitro-phenyl)-pyrido[2,3-b]pyrazin-6-yl]-thiourea Mp.: 244° C. (Decomp.)
$^1$H-NMR (d$_6$-DMSO): δ=4.40 (s, 2H), 5.36 (d, 1H), 5.59 (d, 1H), 6.08-6.15 (m, 1H), 7.71 (d, 1H), 8.46 (d, 2H), 8.51 (d, 1H), 8.60 (d, 2H), 9.64 (s, 1H), 11.45 (s, 1H), 12.51 (t, 1H).

Compound 25: 1-allyl-3-[3-(4-hydroxy-phenyl)-pyrido[2,3-b]pyrazin-6-yl]-urea Mp.: 240° C. (Decomp.)
$^1$H-NMR (d$_6$-DMSO): δ=3.98 (s, 2H), 5.19 (d, 1H), 5.37 (d, 1H), 5.96-6.05 (m, 1H), 6.97 (d, 2H), 7.59 (d, 1H), 8.22 (d, 2H), 8.33 (d, 1H), 9.38 (s, 1H), 9.45 (s, 1H), 10.13 (s, 1H), 10.18 (s, 1H).

Compound 26: 4-[6-(3-allyl-thioureido)-pyrido[2,3-b]pyrazin-3-yl]-benzoic acid ethyl ester Mp.: 223-224° C.
$^1$H-NMR (d$_6$-DMSO): δ=1.39 (t, 3H), 4.35-4.42 (m, 4H), 5.35 (d, 1H), 5.60 (d, 1H), 6.08-6.15 (m, 1H), 7.68 (d, 1H), 8.17 (d, 2H), 8.47 (d, 2H), 8.50 (d, 1H), 9.60 (s, 1H), 11.40 (s, 1H), 12.52 (t, 1H).

Compound 27: 1-allyl-3-[3-(3-hydroxy-phenyl)-pyrido[2,3-b]pyrazin-6-yl]-thiourea Mp.: 205° C. (Decomp.)
$^1$H-NMR (d$_6$-DMSO): δ=4.41 (s, 2H), 5.33 (d, 1H), 5.58 (d, 1H), 6.07-6.15 (m, 1H), 6.99 (d, 1H), 7.42 (t, 1H), 7.64 (d, 1H), 7.72 (s, 1H), 7.77 (d, 1H), 8.46 (d, 1H), 9.45 (s, 1H), 9.80 (s, 1H), 11.37 (s, 1H), 12.55 (s, 1H).

Compound 28: 1-allyl-3-(3-benzo[1,3]dioxol-5-yl-pyrido[2,3-b]pyrazin-6-yl)-thiourea Mp.: 218-220° C. (Decomp.)
$^1$H-NMR (d$_6$-DMSO): δ=4.40 (s, 2H), 5.31 (d, 1H), 5.60 (d, 1H), 6.08-6.20 (m, 3H), 7.16 (d, 1H), 7.61 (d, 1H), 7.90 (s, 1H), 7.96 (d, 1H), 8.43 (d, 1H), 9.49 (s, 1H), 11.34 (s, 1H), 12.58 (s, 1H).

Compound 29: 1-[3-(4-hydroxy-phenyl)-pyrido[2,3-b]pyrazin-6-yl]-3-prop-2-inyl-thiourea Mp.: 350° C. (Decomp.)
$^1$H-NMR (d$_6$-DMSO): δ=2.09 (s, 1H), 2.44 (s, 2H), 6.99 (d, 2H), 7.19 (s, 1H), 7.44 (s, 1H), 8.24 (d, 2H), 8.26 (d, 1H), 9.29 (s, 1H), 10.08 (s, 1H), 11.81 (s, 1H).

Compound 30: 1-allyl-3-[3-(4-hydroxy-phenyl)-pyrido[2,3-b]pyrazin-6-yl]-thiourea Mp.: 230° C. (Decomp.)
$^1$H-NMR (d$_6$-DMSO): δ=4.40 (s, 2H), 5.34 (d, 1H), 5.60 (d, 1H), 6.07-6.15 (m, 1H), 6.98 (d, 2H), 7.58 (d, 1H), 8.24 (d, 2H), 8.42 (d, 1H), 9.45 (s, 1H), 10.19 (s, 1H), 11.34 (s, 1H), 12.60 (s, 1H).

Compound 31: 1-[3-(4-hydroxy-phenyl)-pyrido[2,3-b]pyrazin-6-yl]-3-((E)-propenyl)-thiourea $^1$H-NMR (d$_6$-DMSO): δ=2.12 (d, 3H), 5.17 (m, 1H), 6.96 (d, 2H), 7.22-7.26 (m, 1H), 7.59 (d, 1H), 8.25 (d, 2H), 8.45 (d, 1H), 9.48 (s, 1H), 10.20 (s, 1H), 11.56 (s, 1H), 14.67 (s, 1H).

Compound 32: 1-allyl-3-[2,3-bis-(4-hydroxy-phenyl)-pyrido[2,3-b]pyrazin-6-yl]-thiourea Mp.: 270° C. (Decomp.)
$^1$H-NMR (d$_6$-DMSO): δ=4.40 (s, 2H), 5.25 (d, 1H), 5.50 (d, 1H), 6.02-6.13 (m, 1H), 6.74 (d, 2H), 6.76 (d, 2H), 7.31 (d, 2H), 7.36 (d, 2H), 7.62 (d, 1H), 8.42 (d, 1H), 9.78 (s, 1H), 9.85 (s, 1H), 11.30 (s, 1H), 12.47 (s, 1H).

Compound 33: 1-[2,3-bis-(4-hydroxy-phenyl)-pyrido[2,3-b]pyrazin-6-yl]-3-((E)-propenyl)-thiourea Mp.: 240° C. (Decomp.)
$^1$H-NMR (d$_6$-DMSO): δ=2.05 (d, 3H), 5.10-5.18 (m, 1H), 6.74 (d, 2H), 6.76 (d, 2H), 7.20-7.26 (m, 1H), 7.34 (d, 2H), 7.39 (d, 2H), 7.63 (d, 1H), 8.45 (d, 1H), 9.79 (s, 1H), 9.89 (s, 1H), 11.55 (s, 1H), 14.56 (d, 1H).

Compound 34: 1-allyl-3-[2-(4-hydroxy-phenyl)-pyrido[2,3-b]pyrazin-6-yl]-thiourea Mp.: 260° C. (Decomp.)
$^1$H-NMR (d$_6$-DMSO): δ=4.40 (s, 2H), 5.28 (d, 1H), 5.48 (d, 1H), 6.03-6.12 (m, 1H), 6.96 (d, 2H), 7.66 (d, 1H), 8.16 (d, 2H), 8.43 (d, 1H), 9.52 (s, 1H), 10.06 (s, 1H), 11.31 (s, 1H), 12.40 (s, 1H).

Compound 35: 1-phenethyl-3-(3-phenyl-pyrido[2,3-]pyrazin-6-yl)-urea

Mp.: 250° C. (Decomp.)
$^1$H-NMR (d$_6$-DMSO): δ=2.88-2.95 (m, 2H), 3.52-3.60 (m, 2H), 7.18 (t, 1H), 7.28 (t, 2H), 7.42 (d, 1H), 7.58-7.68 (m, 4H), 8.37 (d, 3H), 9.25 (s, 1H), 9.48 (s, 1H), 10.18 (s, 1H).

Compound 36: 1-(2,3-di-pyridin-2-yl-pyrido[2,3-b]pyrazin-6-yl)-3-ethyl-urea

Mp.: 236-237° C.
$^1$H-NMR (d$_6$-DMSO): δ=1.13-1.22 (m, 3H), 3.28-3.39 (m, 2H), 3.60-3.69 (m, 4H), 7.31-7.39 (m, 2H), 7.79 (d, 1H), 7.91-7.99 (m, 4H), 8.26 (d, 1H), 8.29 (d, 1H), 8.47 (d, 1H), 9.08 (s, 1H), 10.20 (s, 1H).

Compound 37: 1-(2,3-dimethyl-pyrido[2,3-b]pyrazin-6-yl)-3-ethyl-urea

Mp.: 246-248° C.
$^1$H-NMR (d$_6$-DMSO): δ=1.17 (t, 3H), 2.64 (s, 3H), 2.67 (s, 3H), 3.24-3.40 (m, 2H), 7.55 (d, 1H), 8.24 (d, 1H), 9.14 (s, 1H), 9.91 (s, 1H).

Compound 85: 1-ethyl-3-(3-imidazol-1-yl-pyrido[2,3-b]pyrazin-6-yl)-urea $^1$H-NMR (d$_6$-DMSO): δ=1.20 (t, 3H), 3.26-3.32 (m, 2H), 7.26 (s, 1H), 7.75 (d, 1H), 8.20 (s, 1H), 8.40 (d, 1H), 8.79 (s, 1H), 8.84 (s, 1H), 9.39 (s, 1H), 10.16 (s, 1H) ppm.

Compound 137: 1-allyl-3-[3-(4-nitro-phenyl)-pyrido[2,3-b]pyrazin-7-yl]-thiourea Mp.: 250° C. (Decomp.)
$^1$H-NMR (d$_6$-DMSO): δ=4.23 (s, 2H), 5.19 (d, 1H), 5.29 (d, 1H), 5.90-6.00 (m, 1H), 8.46 (d, 2H), 8.55 (s, 1H), 8.64 (d, 2H), 8.92 (s, 1H), 9.23 (s, 1H), 9.77 (s, 1H), 10.35 (s, 1H).

III. Evidence of the Kinase Inhibition of Compounds According to the Invention

III.1 Cell-Free Kinase Assays (Using ALPHA Technology)

The inhibitory effect of the compounds according to the invention was tested on various serine/threonine, tyrosine and lipid kinases in enzymatic assays. Recombinant human kinases such as, for example, Erk2, PI3Kalpha, -beta, -gamma, -delta, p38alpha, p38gamma, Jnk1, Jnk2 and others were used in this case, partly as full-length kinases, partly as shortened fragments, but at least consisting of the functional kinase domains. The commercial kinase proteins (Proqinase, Upstate) were used as recombinant fusion proteins with GST (glutathion-S-transferase) or His-Tag. Depending on the type of substrate, the various kinase reactions were quantified by means of suitable ALPHA™ beads (Perkin-Elmer).

Testing

The substance testing is described in detail hereinafter for the Erk assay. Selected test results of the Erk2, PD3Kalpha, p38alpha and Jnk2 assays are given below. To determine the IC$_{50}$ value, the potential inhibitor substances were investigated in 10 semi-logarithmically graded concentrations of 3.16 nM-100 µM.

a) MAPK-ALPHAs (e.g. Erk2): the test substance, 0.625 ng Erk2 (#14-173, Upstate), 10 µM ATP and 15 nM biotinylated MBP (myelin basic protein) substrate were incubated on a 384-well Optiplate (Perkin-Elmer) in a volume of 15 µl for 1 h in 25 mM Tris, 10 mM MgCl$_2$, 0.1% Tween-20, 100 µM NaVO$_4$, 2 mM DTT at pH 7.5. The kinase reaction was then stopped by adding 10 µl of the ALPHA bead mixes (10 µg/ml, #6760617/Perkin-Elmer) pre-incubated with anti-phospho MBP antibody (320 pM, #05-429/Upstate) in 25 mM Tris, 200 mM NaCl, 110 nM EDTA and 0.3% BSA and left to stand overnight.

b) PI3K-ALPHAs (e.g. PI3Kalpha): the test substance, 1 ng PI3Kalpha (#14-602, Upstate), 100 µM ATP and 20 µM PIP$_2$ substrate (#P4508, Echelon) were incubated on a 384-well Optiplate (Perkin-Elmer) for 1 h in 50 mM Hepes, 50 mM NaCl, 5 mM MgCl$_2$, 0.05% Chaps, 5 mM DTT at pH 7.4. The kinase reaction was then stopped by adding ALPHA bead mixes (10 µg/ml, #6760603/Perkin-Elmer) pre-incubated with 1 nM GST:Grp1 fusion protein (Upstate) and 15 nM biotinylated PIP3 (#C-39B6/Echelon) in 50 mM Hepes, 50 mM NaCl, 50 mM EDTA and 0.1% BSA and left to stand overnight.

The fluorescence was detected the following morning in a Fusion™$^a$α-system (Perkin-Elmer).

Evaluation

The %-inhibition values per substance concentration were calculated by means of the following formula from the raw data determined in the Fusion™ □:

$$\% \text{ Kinase } inhibition_{(Sample)} = 100 - \left(100 \times \frac{Mean_{(Sample)} - Mean_{(0\% \, Control)}}{Mean_{(100\% \, Control)} - Mean_{(0\% \, Control)}}\right)$$

Eight determinations were made for each control and two for the substance samples. The 0% control either contains no ATP or no substrate, the 100% control (fully active kinase) contains no test substance. The IC$_{50}$ values were determined using GraphPadPrism.

The compounds according to the invention showed effective inhibition of Erk, PI3K, p38alpha and Jnk1+Jnk2 with IC$_{50}$ values of up to 6 nM (see Table 2).

TABLE 2

MAPK and PI3Kalpha kinase assay test results (IC50 [µM] bei 10 µM bzw. 100 µM* ATP)

| Compound | Erk2 | PI3Kalpha | p38alpha | Jnk1 + Jnk2 |
|---|---|---|---|---|
| 1 | 1 | 0.9 | >31.6 | >31.6 |
| 25 | 0.076 | 1.5 | >100 | >31.6 |
| 30 | 0.392 | 0.37 | >100 | 21.8 |
| 43 | 0.006 | 6.2 | >100 | 5.5 |
| 44 | 2.5 | 3.8 | >100 | 1.5 |
| 46 | 9.5 | >100 | 0.495 | >100 |
| 82 | 0.944 | 6.4 | >31.6 | 1.1 |
| 124 | 0.062 | 0.49 | >100 | 1.0 |
| 146 | 0.155 | 1.1 | >100 | 3.3 |
| 147 | 0.711 | 4.1 | >100 | 14.2 |
| 148 | 1.8 | 1.4 | >100 | 13.7 |
| 149 | 0.954 | 3.5 | >100 | >31.6 |
| 150 | 18.7 | 0.129 | 18.1 | >100 |
| 151 | 0.104 | 1.5 | >100 | 2.9 |
| 152 | 1.9 | 5.3 | >100 | 12.1 |
| 153 | 0.939 | 0.612 | >100 | 6.7 |
| 154 | 0.592 | 0.984 | >31.6 | 2.8 |
| 155 | >100 | 5 | >100 | 7.8 |
| 156 | 0.138 | 0.425 | >100 | 2.1 |
| 157 | >100 | 0.348 | >100 | 28.5 |
| 158 | >100 | 0.186 | >100 | >31.6 |
| 159 | >100 | 0.147 | >100 | 12.6 |
| 160 | 5.8 | 2.9 | >31.6 | >31.6 |
| 161 | >100 | 1.1 | >100 | >100 |
| 162 | >100 | 0.19 | >100 | >31.6 |
| 163 | 26.9 | 0.096 | >100 | >31.6 |
| 164 | 19.6 | 0.444 | >100 | 24.3 |
| 165 | 19.4 | 1.2 | >100 | 27.1 |
| 166 | 13.7 | 1.3 | >100 | 21.9 |
| 167 | >100 | 1.1 | >100 | 27.3 |
| 168 | 0.15 | 0.612 | >100 | 2.5 |
| 169 | 2.7 | 3.7 | >100 | 9.5 |
| 170 | 0.103 | 2.4 | >31.6 | 1.1 |
| 171 | 0.084 | 3 | >100 | 1.4 |
| 172 | 0.41 | 4 | >100 | 4 |
| 173 | 0.107 | 2.4 | >100 | 2.9 |
| 174 | 4.9 | 3 | >31.6 | 4.6 |
| 175 | 0.191 | 0.458 | >100 | 2.5 |
| 177 | >31.6 | 0.295 | >100 | 3.9 |
| 178 | >100 | 0.164 | >31.6 | 2.3 |
| 179 | 8 | 0.202 | 1.4 | 8.1 |
| 180 | 15.7 | 1.1 | >100 | 8.6 |
| 181 | 1.7 | 0.739 | >100 | 4.3 |
| 182 | >31.6 | 1.1 | >100 | 21 |
| 183 | 0.203 | 2.8 | >100 | 4.7 |
| 184 | >100 | 0.133 | >100 | 6.3 |
| 185 | >31.6 | 0.154 | >100 | 4.3 |
| 186 | 0.223 | 3.8 | >100 | 2.5 |
| 187 | 16.6 | 0.712 | >31.6 | >100 |
| 188 | >100 | 2.8 | >100 | >31.6 |
| 189 | 20.3 | 0.237 | >100 | 6.2 |
| 190 | >100 | 0.271 | >100 | 31 |
| 192 | 31.6 | 0.422 | >100 | 1.8 |
| 193 | 0.212 | 2.2 | >100 | 1.5 |

III.2A Cellular Assay: Testing for Anti-Proliferative Effect (XTT Assay)

The principle of this test is based on the intracellular reduction of the tetrazolium dye XTT (sodium 3'-[1-(phenylaminocarbonyl)-3,4-tetrazolium]-bis(4-methoxy-6-nitro)benzene sulfonic acid, Sigma) to a formazan dye by mitochondrial dehydrogenases. The dye is only formed by metabolically active cells and its photometrically measurable intensity is a quantitative indicator for the presence of living cells. The reduction of dye formation by incubation of the cells with substances serves as a parameter for the anti-proliferative effect.

Testing

The tumour cell lines (ATCC) were injected into 96-well microtitre plates in a defined cell number (5000 cells/well for BxPC3 and Hct116; 10000 cells/well for MDA MB468) and then incubated overnight in an incubator at 37° C., 5% CO$_2$ and 95% air humidity. The test substances were prepared as stock solutions (10 mM) in DMSO. To determine the EC$_{50}$ values the potential inhibitor substances were added to the cells in quarter-logarithmically graded dilutions, resulting in final concentrations of 0.28 µM-50 µM. The cell plates were then incubated for 45 h in an incubator at 37° C., 5% CO$_2$ and 95% air humidity.

For the detection reaction the substrate XTT was mixed with PMS (N-Methyl dibenzopyrazine methylsulfate, Sigma) and added to the cells so that a final concentration of 325 µg XTT/ml and 2.5 µg PMS/ml was obtained. It was then incubated for 3 h at 37° C., 95% air humidity. The formazan salt formed by the cellular dehydrogenases could then be quantified by adsorption at 490 nm.

Evaluation

The % inhibition value was evaluated by means of the following formula from the values for the optical densities measured in each case at 490 nm:

$$\% \text{ Inhibition of cell } proliferation_{(Sample)} = 100 - \left(100 \times \frac{Mean_{(Sample)} - Mean_{(0\% \, Control)}}{Mean_{(100\% \, Control)} - Mean_{(0\% \, Control)}}\right)$$

Eight determinations were made for each control and two for the substance samples. The 0% control contains no cells, the 100% control (proliferation control) contains no test substance. The $EC_{50}$ values were determined using GraphPad-Prism.

The compounds according to the invention showed partly effective inhibition of the cell proliferation with $EC_{50}$ values of to <1 µM (see Table 3).

TABLE 3

XTT assay test results (EC50 [µM])

| Compound | BxPC3 | MDA-MB468 | Hct116 |
|---|---|---|---|
| 30 | 12 | 4 | 6 |
| 124 | 10 | 10 | 1.5 |
| 146 | >50 | ca. 20 | 9.3 |
| 150 | 0.9 | 4.3 | 2.3 |
| 153 | >25 | 24 | 6 |
| 156 | 8.9 | 15 | 1.4 |
| 157 | >25 | 3.5 | 4.4 |
| 164 | >50 | 5.2 | >25 |
| 169 | nicht getestet | 5.7 | 2.8 |
| 173 | nicht getestet | >25 | 9 |
| 175 | nicht getestet | >50 | 4.4 |
| 176 | nicht getestet | 17 | 11.8 |
| 183 | nicht getestet | 4.3 | 2.1 |
| 191 | nicht getestet | 8.5 | 5.5 |
| 193 | nicht getestet | 4.4 | 2.1 |
| Ly294002 | 25 | 20 | 17 |

It was surprisingly found that the PI3K inhibitor Ly294002 known from the literature only showed weak anti-proliferative effects on the cell lines used compared to the Exemplary Embodiments.

III.2B Cellular Assay: Testing for Substrate Inhibition (Western Blotting)

This method can be used to predict whether the kinase modulator under study also achieves the desired effect in a cellular context, i.e. in this case, a substrate protein downstream of the target kinase is investigated for its phosphorylation status. For this purpose, the cells incubated with substance are lysed and the total protein separated on a reducing polyacrylamide gel. The proteins are then transferred to a PVDF membrane by means of Western Blotting and the substrate bands sought are made visible with specific antibodies and a suitable detection method. The substrate proteins downstream of the target kinases are detected simultaneously with a respectively special anti-phospho-antibody and at the same time a total antibody which recognizes the substrate total protein. This simultaneous measurement can be made using the duplex technology of the ODYSSEY imagers (LiCOR). The intensity of the total substrate bands is used for normalising or quantifying the phosphorylation inhibition or activation.

Testing

Suitable tumour cell lines (e.g. BxPC3, Hct116 or MDA MB468) were injected into six-well microtitre plates in a defined cell number (e.g. 350 000 cells/well for BxPC3 and Hct116) in the respective standard complete medium and then incubated overnight at 37° C., 5% $CO_2$ and 95% air humidity. The cells were then incubated for a further 24 h under serum-reduced conditions i.e. in the respective medium but with only 0.25% serum. The test substances were prepared as stock solutions (10 mM) in DMSO and incubated with the cells in final concentrations of 5, 15.8 and 50 µM for 5 h. This was followed by cell lysis in 25 mM Tris, 150 mM NaCl, 10 mM Na-pyrophosphate, 2 mM EGTA, 25 mM β-glycerophosphate, 25 mM NaF, 10% glycerine, 0.75% NP-40, 100 µM $NaVO_4$ buffer. Following protein quantification by means of BCA (bicinchonic acid protein assay kit, Sigma) Assay, protein quantities of about 20 µg per track were separated on a Lämmli polyacrylamide gel and then transferred to a PVDF membrane (Millipore) by means of Semi-Dry Western-Blotting at 0.8 $mA/cm^2$ for 1 h. This was followed by pre-hybridisation of the membrane for 1 hour in I-block reagent (Applied Biosystems) and incubation overnight with the specific antibodies. To determine the Erk and PI3K inhibition, the respectively downstream substrates Rsk1 were detected with the total antibody (Rsk #sc-231g C-21, Santa Cruz) and the phospho-antibody (Phospho-p90RSK (S380) #9341, NEB Cell Signalling) and Akt was detected with the total antibody (Akt1 #sc-1618 C-20, Santa Cruz) and the phospho-antibody (Phospho-Akt (Ser 473) #9271, NEB Cell Signaling). After washing the membrane, secondary antibody incubation was carried out with anti-rabbit IR Dye 800 (#611-732-127, Rockland) for the phospho-antibody and anti-goat Alexa Fluor 680 (#A-21081, Molecular Probes) for the total protein-antibody. After incubating for 30 min at room temperature in the dark, the hybridisation of the detection antibody on the membrane was detected by scanning in the ODYSSEY imager (LiCOR).

Evaluation

At concentrations of 5-50 µM, the compounds according to the invention exhibited dual inhibition of Erk (MAPK1/2) and PI3K (see Table 4) which are indicated by inhibition of the band intensity of both corresponding phospho-substrate proteins Rsk1 and Akt. The reduction of the fluorescence intensity of the phospho-substrate bands (pRsk and pAkt) is given in the table below as % inhibition and relates to the following formula:

$$\% \text{ Inhibition of Substrate } phosphorylation_{(Sample)} = 100 - \left(100 \times \frac{\text{Sample}}{100\% \text{ Control}}\right)$$

The band intensity (fluorescence intensity) of the respective non-inhibited (without substance) phospho-substrates was used as 100% control.

TABLE 4

Inhibition of cellular substrate phosphorylation by selected substances (bei 50 µM)

| Compound | Erk → pRsk | PI3K → pAkt |
|---|---|---|
| 30 | 90% | 100% |
| 124 | 90% | 90% |
| 146 | 100% | 10% |
| 150 | 0% | 90% |
| 173 | 90% | 50% |
| 183 | 80% | 80% |
| Ly294002 | 0% | 40% |
| Wortmannin | 0% | 100% |

The PI3K inhibitor Ly294002 known from the literature showed only weak PI3K inhibition compared to the pyridopyrazine derivatives, i.e. inhibition of the PI3K substrate p-Akt and as predicted, no Erk inhibition or inhibition of the Erk substrate p-Rsk. Wortmannin—a further PI3K inhibitor known from the literature—showed complete inhibition of the PI3K substrate pAkt, but no Erk or p-RSK inhibition.

In contrast to Exemplary Embodiments both reference substances used here showed no dual inhibition, i.e. of Erk and PI3K simultaneously but only a PI3K inhibition.

ABBREVIATIONS

Akt of: murine Akt8 retrovirus or protein kinase B (PKB)
Ask1 apoptosis signal-regulating kinase
ATR ataxia-telangiectasia and Rad3-related
ATM Ataxia-telangiectasia mutated
Bag1 Bcl-2 associated athanogene-1
Bcl-2 B-cell leukemia/lymphoma-2 gene
DNA-PK DNA-dependent protein kinase
Erk extracellular signal-regulated kinase
Flt-3 fms like tyrosine kinase 3
GSK-3 Glycogen synthase kinase-3
hSMG-1 human ortholog of product of seven nematode gene-1
JAK-3 Janus kinase 3
JNK c-jun N-terminal kinase
MAPK mitogen activated protein kinase
Mek MAP or Erk kinase
mTOR mammalian target of rapamycin
PDGFR platelet derived growth factor receptor
PI3K phosphoinositol 3-kinase
PIKK phosphoinositol 3-kinase related kinase
$PIP_2$ phosphatidylinositol-biphosphate
$PIP_3$ phosphatidylinositol-triphosphate
PtdIns phosphatidylinositol
Raf rapid accelerated fibrosarcoma
Ras rat sarcoma
RTK receptor tyrosine kinase
SAPK stress-activated protein kinase
Ser Serine
Syk spleen tyrosine kinase
Thr Threonine
Tyr Tyrosine
VEGFR vascular endothelial growth factor receptor

REFERENCES

1. Alessi D R, Andjelkovic M, Caudwell B, Cron P, Morrice N, Cohen P, Hemmings B A. Mechanism of activation of protein kinase B by insulin and IGF-1. EMBO J. 1996 Dec. 2; 15(23):6541-51.
2. Ali K, Bilancio A, Thomas M, Pearce W, Gilfillan A M, Tkaczyk C, Kuehn N, Gray A, Giddings J, Peskett E, Fox R, Bruce I, Walker C, Sawyer C, Okkenhaug K, Finan P, Vanhaesebroeck B. Essential role for the p110delta phosphoinositide 3-kinase in the allergic response. Nature. 2004 Oct. 21; 431(7011):1007-11.
3. Bennett B L, Sasaki D T, Murray B W, O'Leary E C, Sakata S T, Xu W, Leisten J C, Motiwala A, Pierce S, Satoh Y, Bhagwat S S, Manning A M, Anderson D W. SP600125, an anthrapyrazolone inhibitor of Jun N-terminal kinase. Proc Natl Acad Sci USA. 2001 Nov. 20; 98(24):13681-6.
4. Bondev A, Rubio I, Wetzker R. Differential regulation of lipid and protein kinase activities of phosphoinositide 3-kinase gamma in vitro. Biol. Chem. 1999 November; 380 (11):1337-40.
5. Bondeva T, Pirola L, Bulgarelli-Leva G, Rubio I, Wetzker R, Wymann M P. Bifurcation of lipid and protein kinase signals of PI3Kgamma to the protein kinases PKB and MAPK. Science. 1998 Oct. 9; 282(5387):293-6.
6. Campbell I G, Russell S E, Choong D Y, Montgomery K G, Ciavarella M L, Hooi C S, Cristiano B E, Pearson R B, Phillips W A. Mutation of the PIK3CA gene in ovarian and breast cancer. Cancer Res. 2004 Nov. 1; 64(21):7678-81.
7. Chang F, Lee J T, Navolanic P M, Steelman L S, Shelton J G, Blalock W L, Franklin R A, McCubrey J A. Involvement of PI3K/Akt pathway in cell cycle progression, apoptosis, and neoplastic transformation: a target for cancer chemotherapy. Leukemia. 2003 March; 17(3):590-603. Review
8. Chang F, Steelman L S, Lee J T, Shelton J G, Navolanic P M, Blalock W L, Franklin R A, McCubrey J A. Signal transduction mediated by the Ras/Raf/MEK/ERK pathway from cytokine receptors to transcription factors: potential targeting for therapeutic intervention. Leukemia. 2003 July; 17(7):1263-93. Review.
9. Chang H W, Aoki M, Fruman D, Auger K R, Bellacosa A, Tsichlis P N, Cantley L C, Roberts T M, Vogt P K. Transformation of chicken cells by the gene encoding the catalytic subunit of PI 3-kinase. Science. 1997 Jun. 20; 276 (5320):1848-50.
10. Chen J, Fujii K, Zhang L, Roberts T, Fu H. Raf-1 promotes cell survival by antagonizing apoptosis signal-regulating kinase 1 through a MEK-ERK independent mechanism. Proc Natl Acad Sci USA. 2001 Jul. 3; 98(14):7783-8.
11. Chiang G G, Abraham R T. Determination of the catalytic activities of mTOR and other members of the phosphoinositide-3-kinase-related kinase family. Methods Mol Biol. 2004; 281:125-41.
12. Crackower M A, Oudit G Y, Kozieradzki I, Sarao R, Sun H, Sasaki T, Hirsch E, Suzuki A, Shioi T, Irie-Sasaki J, Sah R, Cheng H Y, Rybin V O, Lembo G, Fratta L, Oliveirados-Santos A J, Benovic J L, Kahn C R, Izumo S, Steinberg S F, Wymann M P, Backx P H, Penninger J M. Regulation of myocardial contractility and cell size by distinct PI3K-PTEN signaling pathways. Cell. 2002 Sep. 20; 110(6):737-49.
13. Davies H, Bignell G R, Cox C, Stephens P, Edkins S, Clegg S, Teague J, Woffendin H, Garnett M J, Bottomley W, Davis N, Dicks E, Ewing R, Floyd Y, Gray K, Hall S, Hawes R, Hughes J, Kosmidou V, Menzies A, Mould C, Parker A, Stevens C, Watt S, Hooper S, Wilson R, Jayatilake H, Gusterson B A, Cooper C, Shipley J, Hargrave D, Pritchard-Jones K, Maitland N, Chenevix-Trench G, Riggins G J, Bigner D D, Palmieri G, Cossu A, Flanagan A, Nicholson A, Ho J W, Leung S Y, Yuen S T, Weber B L, Seigler H F, Darrow T L, Paterson H, Marais R, Marshall C J, Wooster R, Stratton M R, Futreal P A. Mutations of the BRAF gene in human cancer. Nature. 2002 Jun. 27; 417 (6892):949-54.
14. Davies S P, Reddy H, Caivano M, Cohen P. Specificity and mechanism of action of some commonly used protein kinase inhibitors. Biochem J. 2000 Oct. 1; 351 (Pt 1):95-105.
15. Dhand R, Hiles I, Panayotou G, Roche S, Fry M J, Gout I, Totty N F, Truong O, Vicendo P, Yonezawa K, et al. PI 3-kinase is a dual specificity enzyme: autoregulation by an intrinsic protein-serine kinase activity. EMBO J. 1994 Feb. 1; 13(3):522-33.
16. Elliott R D, Temple C Jr, Montgomery J A. Potential folic acid antagonists. 3. Deaza analogs of methotrexate. 3. 1- and 3-Deaza analogs of 2,4-diamino-6-[(n-methylanilino) methyl]pteridine. J Org Chem. 1968 February; 33(2):533-6.
17. Friess H, Berberat P, Schilling M, Kunz J, Korc M, Buchler M W. Pancreatic cancer: the potential clinical relevance of alterations in growth factors and their receptors. J Mol Med. 1996 January; 74(1):35-42. Review.
18. Gotz R, Wiese S, Takayama S, Camarero G C, Rossoll W, Schweizer U, Troppmair J, Jablonka S, Holtmann B, Reed J C, Rapp U R, Sendtner M. Bag1 is essential for differentiation and survival of hematopoietic and neuronal cells. Nat. Neurosci. 2005 September; 8(9): 1169-78.
19. Gum R J, McLaughlin M M, Kumar S, Wang Z, Bower M J, Lee J C, Adams J L, Livi G P, Goldsmith E J, Young P R.

Acquisition of sensitivity of stress-activated protein kinases to the p38 inhibitor, SB 203580, by alteration of one or more amino acids within the ATP binding pocket. J Biol Chem. 1998 Jun. 19; 273(25):15605-10.

20. Hoshino R, Chatani Y, Yamori T, Tsuruo T, Oka H, Yoshida O, Shimada Y, Ari-i S, Wada H, Fujimoto J, Kohno M. Constitutive activation of the 41-/43-kDa mitogen-activated protein kinase signaling pathway in human tumors. Oncogene. 1999 Jan. 21; 18(3):813-22.

21. Katso R, Okkenhaug K, Ahmadi K, White S, Timms J, Waterfield M D. Cellular function of phosphoinositide 3-kinases: implications for development, homeostasis, and cancer. Annu Rev Cell Dev Biol. 2001; 17:615-75. Review.

22. Khleif S N, Abrams S I, Hamilton J M, Bergmann-Leitner E, Chen A, Bastian A, Bernstein S, Chung Y, Allegra C J, Schlom J. A phase I vaccine trial with peptides reflecting ras oncogene mutations of solid tumors. J Immunother. 1999 March; 22(2): 155-65.

23. Levine D A, Bogomolniy F, Yee C J, Lash A, Barakat R R, Borgen P I, Boyd J. Frequent mutation of the PIK3CA gene in ovarian and breast cancers. Clin Cancer Res. 2005 Apr. 15; 11(8):2875-8.

24. Lewis T S, Shapiro P S, Ahn N G. Signal transduction through MAP kinase cascades. Adv Cancer Res. 1998; 74:49-139. Review.

25. Li J, Yen C, Liaw D, Podsypanina K, Bose S, Wang S I, Puc J, Miliaresis C, Rodgers L, McCombie R, Bigner S H, Giovanella B C, Ittmann M, Tycko B, Hibshoosh H, Wigler M H, Parsons R. PTEN, a putative protein tyrosine phosphatase gene mutated in human brain, breast, and prostate cancer. Science. 1997 Mar. 28; 275(5308):1943-7.

26. Lu Y, Wang H, Mills G B. Targeting PI3K-AKT pathway for cancer therapy. Rev Clin Exp Hematol. 2003 June; 7(2):205-28. Review.

27. Ma Y Y, Wei S J, Lin Y C, Lung J C, Chang T C, Whang-Peng J, Liu J M, Yang D M, Yang W K, Shen C Y. PIK3CA as an oncogene in cervical cancer. Oncogene. 2000 May 25; 19(23):2739-44.

28. Marshall C. How do small GTPase signal transduction pathways regulate cell cycle entry? Curr Opin Cell Biol. 1999 December; 11(6):732-6. Review.

29. McPhillips F, Mullen P, Monia B P, Ritchie A A, Dorr F A, Smyth J F, Langdon S P. Association of c-Raf expression with survival and its targeting with antisense oligonucleotides in ovarian cancer. Br J Cancer. 2001 Nov. 30; 85(11): 1753-8.

30. Mendelsohn J, Baselga J. The EGF receptor family as targets for cancer therapy. Oncogene. 2000 Dec. 27; 19(56):6550-65. Review.

31. Moore S M, Rintoul R C, Walker T R, Chilvers E R, Haslett C, Sethi T. The presence of a constitutively active phosphoinositide 3-kinase in small cell lung cancer cells mediates anchorage-independent proliferation via a protein kinase B and p70s6k-dependent pathway. Cancer Res. 1998 Nov. 15; 58(22):5239-47.

32. Okkenhaug K, Vanhaesebroeck B. PI3K in lymphocyte development, differentiation and activation. Nat Rev Immunol. 2003 April; 3(4):317-30. Review.

33. Patrucco E, Notte A, Barberis L, Selvetella G, Maffei A, Brancaccio M, Marengo S, Russo G, Azzolino O, Rybalkin S D, Silengo L, Altruda F, Wetzker R, Wymann M P, Lembo G, Hirsch E. PI3Kgamma modulates the cardiac response to chronic pressure overload by distinct kinase-dependent and -independent effects. Cell. 2004 Aug. 6; 118(3):375-87.

34. Rapp U R, Rennefahrt U, Troppmair J. Bcl-2 proteins: master switches at the intersection of death signaling and the survival control by Raf kinases. Biochim Biophys Acta. 2004 Mar. 1; 1644(2-3):149-58. Review.

35. Rodriguez-Viciana P, Warne P H, Dhand R, Vanhaesebroeck B, Gout I, Fry M J, Waterfield M D, Downward J. Phosphatidylinositol-3-OH kinase as a direct target of Ras. Nature. 1994 Aug. 18; 370(6490):527-32.

36. Samuels Y, Wang Z, Bardelli A, Silliman N, Ptak J, Szabo S, Yan H, Gazdar A, Powell S M, Riggins G J, Willson J K, Markowitz S, Kinzler K W, Vogelstein B, Velculescu V E. High frequency of mutations of the PIK3CA gene in human cancers, Science. 2004 Apr. 23; 304(5670):554.

37. Sebolt-Leopold J S, Herrera R. Targeting the mitogen-activated protein kinase cascade to treat cancer. Nat Rev Cancer. 2004 December; 4(12):937-47. Review.

38. Shayesteh L, Lu Y, Kuo W L, Baldocchi R, Godfrey T, Collins C, Pinkel D, Powell B, Mills G B, Gray J W. PIK3CA is implicated as an oncogene in ovarian cancer Nat Genet. 1999 January; 21(1):99-102.

39. Sirivatanauksorn V, Sirivatanauksorn Y, Lemoine N R. Molecular pattern of ductal pancreatic cancer. Langenbecks Arch Surg. 1998 April; 383(2):105-15. Review.

40. Steck P A, Pershouse M A, Jasser S A, Yung W K, Lin H, Ligon A H, Langford L A, Baumgard M L, Hattier T, Davis T, Frye C, Hu R, Swedlund B, Teng D H, Tavtigian S V. Identification of a candidate tumour suppressor gene, MMAC 1, at chromosome 10q23.3 that is mutated in multiple advanced cancers. Nat Genet. 1997 April; 15(4):356-62.

41. Sujobert P, Bardet V, Cornillet-Lefebvre P, Hayflick J S, Prie N, Verdier F, Vanhaesebroeck B, Muller O, Pesce F, Ifrah N, Hunault-Berger M, Berthou C, Villemagne B, Jourdan E, Audhuy B, Solary E, Witz B, Harousseau J L, Himberlin C, Lamy T, Lioure B, Cahn J Y, Dreyfus F, Mayeux P, Lacombe C, Bouscary D. Essential role for the p110delta isoform in phosphoinositide 3-kinase activation and cell proliferation in acute myeloid leukemia. Blood. 2005 Aug. 1; 106(3):1063-6.

42. Temple C Jr, Rener G A. Potential antimitotic agents. Synthesis of some ethyl benzopyrazin-7-ylcarbamates, ethyl pyrido[3,4-b]pyrazin-7-ylcarbamates, and ethyl pyrido[3,4-e]-as-triazin-7-ylcarbamates. J Med Chem. 1990 November; 33(11):3044-50.

43. Troppmair J, Rapp U R. Raf and the road to cell survival: a tale of bad spells, ring bearers and detours. Biochem Pharmacol. 2003 Oct. 15; 66(8):1341-5. Review.

44. Vanhaesebroeck B, Higashi K, Raven C, Welham M, Anderson S, Brennan P, Ward S G, Waterfield M D. Autophosphorylation of p110delta phosphoinositide 3-kinase: a new paradigm for the regulation of lipid kinases in vitro and in vivo. EMBO J. 1999 Mar. 1; 18(5):1292-302.

45. Vanhaesebroeck B, Leevers S J, Ahmadi K, Timms J, Katso R, Driscoll P C, Woscholski R, Parker P J, Waterfield M D. Synthesis and function of 3-phosphorylated inositol lipids. Annu Rev Biochem. 2001; 70:535-602. Review.

46. Weinstein-Oppenheimer C R, Blalock W L, Steelman L S, Chang F, McCubrey J A. The Raf signal transduction cascade as a target for chemotherapeutic intervention in growth factor-responsive tumors. Pharmacol Ther. 2000 December; 88(3):229-79. Review.

47. Wetzker R, Rommel C. Phosphoinositide 3-kinases as targets for therapeutic intervention. Curr Pharm Des. 2004; 10(16):1915-22. Review.

48. Wymann M P, Pirola L. Structure and function of phosphoinositide 3-kinases. Biochim Biophys Acta. 1998 Dec. 8; 1436(1-2):127-50. Review.

The invention claimed is:
1. A method for treating a mammal having a malignant tumor comprising:
administering to a mammal in need thereof an effective amount of at least one compound according to general formula (I):

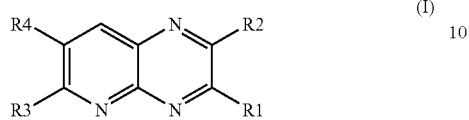

wherein the substituents R1, R2, R3, R4 have the following meanings:
R1 is NR7R8,
wherein R7 and R8 independently of each other are hydrogen, alkyl, cycloalkyl, aryl, heteroaryl, alkyl-cycloalkyl, alkyl-heterocyclyl, alkyl-aryl or alkyl-heteroaryl; wherein said alkyl-, cycloalkyl-, aryl- and heteroaryl-, alkyl-cycloalkyl, alkyl-heterocyclyl, alkyl-aryl or alkyl-heteroaryl substituents are independently of each other optionally substituted by F, Cl, Br, I, CN, $CF_3$, $NH_2$, NH-alkyl, NH-aryl, N(alkyl)$_2$, $NO_2$, SH, S-alkyl, OH, $OCF_3$, O-alkyl, O-aryl, $OSO_2H$, $OP(O)(OH)_2$, CHO, $CO_2H$, $SO_3H$ or alkyl, and wherein R7 and R8 do not together form a heterocycle,
R2 is hydrogen,
R3 is —NR9R10,
wherein R9 is hydrogen or alkyl and R10 is —C(Y)NR11R12, wherein Y=O or S and R11 and R12 are independently of each other
(i) hydrogen,
(ii) unsubstituted or substituted alkyl, wherein the alkyl group is optionally substituted with one or more substitutents selected from the group consisting of F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)cycloalkyl, OC(O)-heterocyclyl, OC(O)-aryl, OC(O)-heteroaryl, OC(O)-alkyl-aryl, OC(O)alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, $OP(O)(OH)_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, cycloalkyl, heterocyclyl, aryl and heteroaryl, which may be the same or different from each other;
(iii) unsubstituted or substituted cycloalkyl, wherein the cycloalkyl group is optionally substituted with one or more substituents selected from the group consisting of F, Cl, Br, I, $NH_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, OH, O-alkyl, O-cycloalkyl, O-heterocyclyl, O-aryl, O-heteroaryl, O-alkyl-aryl, O-alkyl-heteroaryl, OC(O)alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, $OP(O)(OH)_2$, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, alkyl, and aryl, which may be the same or different from each other;
(iv) unsubstituted or substituted heterocyclyl, wherein the heterocyclyl group is optionally substituted with one or more substituents selected from the group consisting of OH, O-alkyl, O-aryl, $NH_2$, NH-alkyl, NH-aryl, alkyl, alkyl-aryl or and aryl, which may be the same or different from each other;
(v) unsubstituted or substituted aryl, wherein the aryl group is optionally substituted with one or more substituents selected from the group consisting of F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, $O(CH_2)_n$—O, OC(O)-alkyl, OC(O)-cycloalkyl, OC(O)-heterocyclyl, OC(O)-aryl, OC(O)heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, $OP(O)(OH)_2$, C(O)-alkyl, C(O)-aryl, C(O)-heteroaryl, $CO_2H$, $CO_2$-alkyl, $CO_2$-cycloalkyl, $CO_2$-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO-alkyl, SO-aryl, SO₂-alkyl, SO₂-aryl, SO₂NH₂, SO₂NH-alkyl, SO₂NH-aryl, SO₂NH-heteroaryl, SO₂NH-alkyl-aryl, SO₃H, SO₂O-alkyl, SO₂O-aryl, SO₂O-alkyl-aryl, alkyl, cycloalkyl, heterocyclyl, aryl and heteroaryl, which may be the same or different from each other, and n can have the value 1, 2 or 3;

(vi) unsubstituted or substituted heteroaryl, wherein the heteroaryl group is optionally substituted with one or more substituents selected from the group consisting of F, Cl, Br, I, CF₃, CN, NH₂, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-NH₂, NH-alkyl-OH, N(alkyl)₂, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, NHSO₂-alkyl, NHSO₂-cycloalkyl, NHSO₂-heterocyclyl, NHSO₂-aryl, NHSO₂-heteroaryl, NHSO₂-alkyl-aryl, NHSO₂-alkyl-heteroaryl, NO₂, SH, S-alkyl, S-aryl, S-heteroaryl, OH, OCF₃, O-alkyl, O-cycloalkyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OSO₃H, OSO₂-alkyl, OSO₂-cycloalkyl, OSO₂-heterocyclyl, OSO₂-aryl, OSO₂-heteroaryl, OSO₂-alkyl-aryl, OSO₂-alkyl-heteroaryl, OP(O)(OH)₂, C(O)-alkyl, C(O)-aryl, C(O)-heteroaryl, CO₂H, CO₂-alkyl, CO₂-cycloalkyl, CO₂-heterocyclyl, CO₂-aryl, CO₂-heteroaryl, CO₂-alkyl-cycloalkyl, CO₂-alkyl-heterocyclyl, CO₂-alkyl-aryl, CO₂-alkyl-heteroaryl, C(O)—NH₂, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)₂, C(O)N(cycloalkyl)₂, C(O)N(aryl)₂, C(O)N(heteroaryl)₂, SO₂NH₂, SO₂NH-alkyl, SO₂NH-aryl, SO₂NH-heteroaryl, SO₂NH-alkyl-aryl, SO₃H, SO₂O-alkyl, SO₂O-aryl, SO₂O-alkyl-aryl, alkyl, cycloalkyl, heterocyclyl, aryl and heteroaryl, which may be the same or different from each other;

(vii) —C(O)—R17, wherein R17 is alkyl, aryl or heteroaryl, wherein the alkyl and aryl substituents are optionally substituted by F, Cl, Br, I, CN, CF₃, NH₂, NH-alkyl, NH-aryl, N(alkyl)₂, NO₂, SH, S-alkyl, OH, OCF₃, O-alkyl, O-aryl, OSO₂H, OP(O)(OH)₂, CHO, CO₂H, SO₃H or alkyl; and (viii) or R11 and R12 together form heterocyclyl, and R4 is hydrogen;

wherein said compound inhibits PI3K alpha, PI3K beta, PI3K gamma, and PI3K delta in the PI3K-Akt signal transduction pathway; and wherein said malignant tumor is selected from the group consisting of a colon tumor, a gastric tumor, an intestinal tumor, a pulmonary tumor, a pancreatic tumor, an ovarian tumor, a prostatic tumor, melanoma, a hepatic tumor, a renal tumor, a head tumor, glioma, a breast tumor, cervico-uterine carcinoma, adeno-acanthoma, an endometrial cancer, a colorectal tumor, esophageal cancer, thyroid cancer, lymphoma, and leukemia.

2. The method according to claim 1, wherein R7, R8, R9, R11, or R12 is an alkyl group that is selected from the group consisting of methyl, ethyl, n-propyl, 2-propyl, n-butyl, sec-butyl, tert-butyl, n-pentyl, iso-pentyl, neo-pentyl, n-hexyl, 2-hexyl, n-octyl, ethylenyl (vinyl), ethynyl, propenyl, propynyl, butenyl, butynyl, pentenyl, pentynyl, hexenyl, hexynyl, heptenyl, heptynyl, octenyl and octynyl.

3. The method according to claim 1, wherein R7, R8, R11, or R12 is a heteroaryl group that is selected from the group consisting of pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl and acridinyl.

4. The method according to claim 1, wherein R11 or R12 is a heterocyclyl group or R11 and R12 together form heterocyclyl group that is selected from the group consisting of tetrahydrofuryl, tetrahydropyranyl, pyrrolidinyl, piperidinyl, piperazinyl and morpholinyl.

5. The method according to claim 1, wherein said compound is selected from the group consisting of

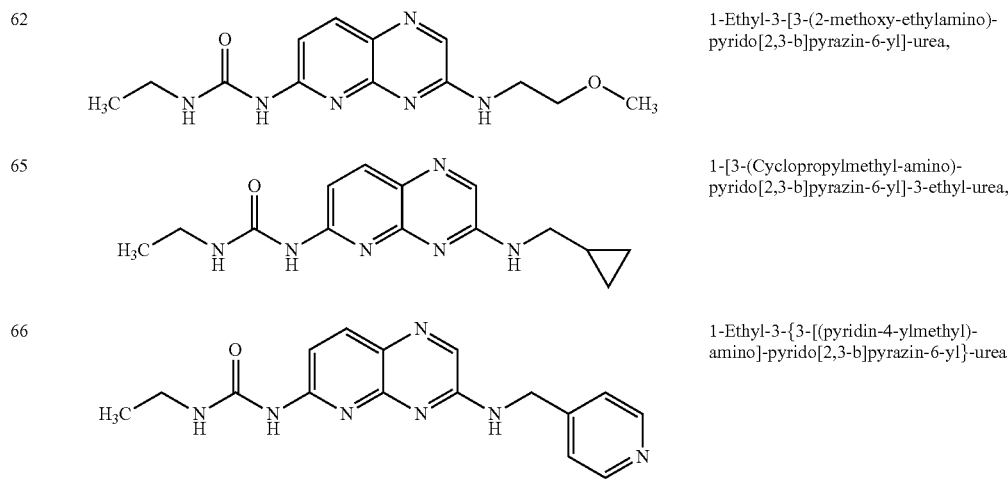

| 62 | | 1-Ethyl-3-[3-(2-methoxy-ethylamino)-pyrido[2,3-b]pyrazin-6-yl]-urea, |
| 65 | | 1-[3-(Cyclopropylmethyl-amino)-pyrido[2,3-b]pyrazin-6-yl]-3-ethyl-urea, |
| 66 | | 1-Ethyl-3-{3-[(pyridin-4-ylmethyl)-amino]-pyrido[2,3-b]pyrazin-6-yl}-urea, |

| | | |
|---|---|---|
| 83 | 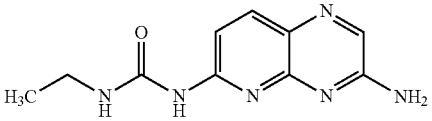 | 1-(3-Amino-pyrido[2,3-b]pyrazin-6-yl)-3-ethyl-urea, |
| 150 | 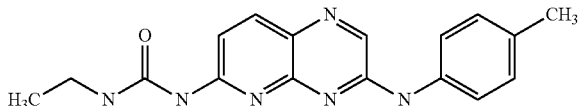 | 1-Ethyl-3-(3-p-tolylamino-pyrido[2,3-b]pyrazin-6-yl)-urea, |
| 157 | 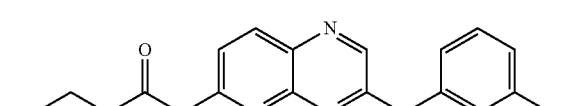 | 1-Ethyl-3-(3-m-tolylamino-pyrido-[2,3-b]pyrazin-6-yl)-urea, |
| 158 | 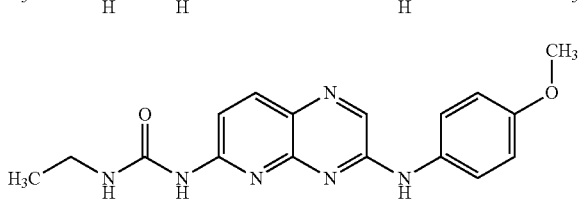 | 1-Ethyl-3-[3-(4-methoxy-phenylamino)-pyrido[2,3-b]pyrazin-6-yl]-urea, |
| 159 | 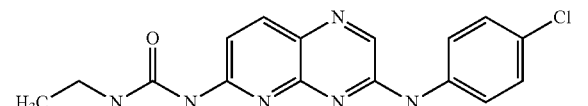 | 1-[3-(4-Chloro-phenylamino)-pyrido-[2,3-b]pyrazin-6-yl]-3-ethyl-urea, |
| 160 | 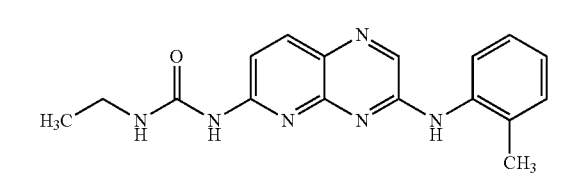 | 1-Ethyl-3-(3-o-tolylamino-pyrido[2,3-b]-pyrazin-6-yl)-urea, |
| 161 | 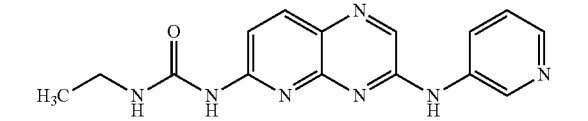 | 1-Ethyl-3-[3-(pyridin-3-ylamino)-pyrido-[2,3-b]pyrazin-6-yl]-urea, |
| 162 | 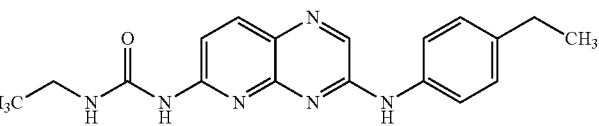 | 1-Ethyl-3-[3-(4-ethyl-phenylamino)-pyrido[2,3-b]pyrazin-6-yl]-urea, |
| 163 | 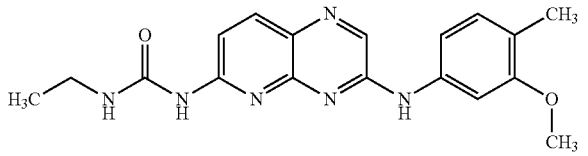 [SMILES: CCNC(=O)Nc1ccc2ncc(Nc3ccc(O)c(OC)c3)nc2n1] | 1-Ethyl-3-[3-(3-methoxy-4-methyl-phenylamino)-pyrido[2,3-b]pyrazin-6-yl]-urea, |
| 164 | 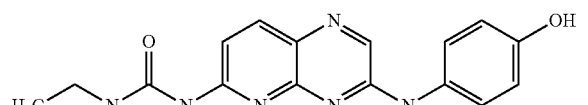 | 1-Ethyl-3-[3-(4-hydroxy-phenylamino)-pyrido[2,3-b]pyrazin-6-yl]-urea, |
| 165 | 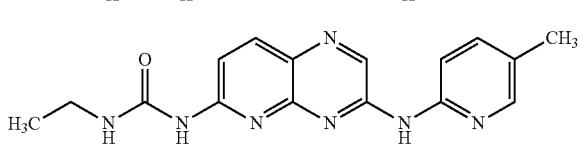 | 1-Ethyl-3-[3-(5-methyl-pyridin-2-yl-amino)-pyrido[2,3-b]pyrazin-6-yl]-urea, |

| # | Name |
|---|---|
| 166 | 1-Ethyl-3-[3-(1-methyl-1H-pyrazol-3-ylamino)-pyrido[2,3-b]pyrazin-6-yl]-urea, |
| 167 | 1-Ethyl-3-[3-(4-fluoro-phenylamino)-pyrido[2,3-b]pyrazin-6-yl]-urea, |
| 177 | 1-[3-(3-Chloro-4-methoxy-phenylamino)-pyrido[2,3-b]pyrazin-6-yl]-3-ethyl-urea, |
| 178 | 1-Ethyl-3-[3-(naphthalin-2-ylamino)-pyrido[2,3-b]pyrazin-6-yl]-urea, |
| 179 | 1-Ethyl-3-[3-(quinolin-3-ylamino)-pyrido[2,3-b]pyrazin-6-yl]-urea, |
| 180 | 1-[3-(3,5-Dimethoxy-phenylamino)-pyrido[2,3-b]pyrazin-6-yl]-3-ethyl-urea, |
| 181 | 1-Ethyl-3-[3-(pyrazin-2-ylamino)-pyrido[2,3-b]pyrazin-6-yl]-urea, |
| 182 | 1-Ethyl-3-[3-(3-isopropoxy-phenylamino)-pyrido[2,3-b]pyrazin-6-yl]-urea, |
| 184 | 1-[3-(2-Chloro-pyridin-4-ylamino)-pyrido[2,3-b]pyrazin-6-yl]-3-ethyl-urea, |
| 185 | 1-[3-(3,5-Dichloro-4-hydroxy-phenylamino)-pyrido[2,3-b]pyrazin-6-yl]-3-ethyl-urea, |

| # | | Name |
|---|---|---|
| 187 | | 1-[3-(3,4-Dimethoxy-phenylamino)-pyrido[2,3-b]pyrazin-6-yl]-3-ethyl-urea, |
| 188 | | 1-Ethyl-3-[3-(3-hydroxy-4-methyl-phenylamino)-pyrido[2,3-b]pyrazin-6-yl]-urea, |
| 189 | | 3-[6-(3-Ethyl-ureido)-pyrido[2,3-b]-pyrazin-3-ylamino]-5-trifluoromethyl-benzoic acid, |
| 190 | | 1-Ethyl-3-[3-(6-methoxy-pyridin-3-ylamino)-pyrido[2,3-b]pyrazin-6-yl]-urea, |
| 191 | | 1-[3-(3,5-Dimethyl-phenylamino)-pyrido[2,3-b]pyrazin-6-yl]-3-ethyl-urea, |
| 192 | | 1-[3-(4-Cyano-phenylamino)-pyrido-[2,3-b]pyrazin-6-yl]-3-ethyl-urea, |
| 197 | | 1-Ethyl-3-[3-(4-hydroxy-3-methoxy-phenylamino)-pyrido[2,3-b]pyrazin-6-yl]-urea, |
| 211 | | 1-Ethyl-3-[3-(methyl-p-tolyl-amino)-pyrido[2,3-b]pyrazin-6-yl]-urea, |
| 212 | | 1-Ethyl-3-[3-(2-p-tolyl-ethylamino)-pyrido[2,3-b]pyrazin-6-yl]-urea, |
| 213 | | 1-Ethyl-3-[3-(4-methyl-benzylamino)-pyrido[2,3-b]pyrazin-6-yl]-urea, |

| | | |
|---|---|---|
| 214 | 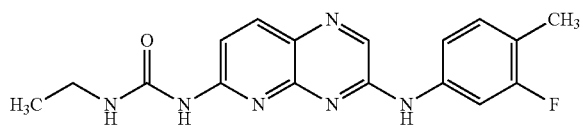 [SMILES: CCNC(=O)Nc1ccc2ncc(Nc3ccc(C)c(F)c3)nc2n1] | 1-Ethyl-3-[3-(3-fluoro-4-methyl-phenyl-amino)-pyrido[2,3-b]pyrazin-6-yl]-urea, |
| 215 | 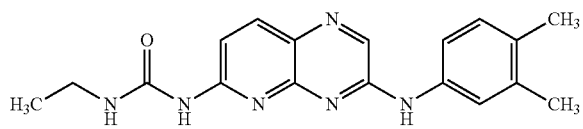 [SMILES: CCNC(=O)Nc1ccc2ncc(Nc3ccc(C)c(C)c3)nc2n1] | 1-[3-(3,4-Dimethyl-phenylamino)-pyrido[2,3-b]pyrazin-6-yl]-3-ethyl-urea, |
| 216 | 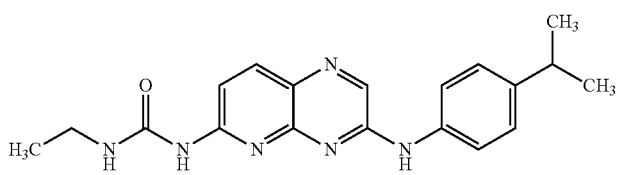 [SMILES: CCNC(=O)Nc1ccc2ncc(Nc3ccc(C(C)C)cc3)nc2n1] | 1-Ethyl-3-[3-(4-isopropyl-phenylamino)-pyrido[2,3-b]pyrazin-6-yl]-urea, |
| 240 | 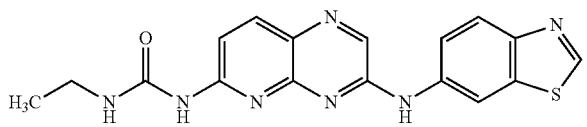 [SMILES: CCNC(=O)Nc1ccc2ncc(Nc3ccc4ncsc4c3)nc2n1] | 1-[3-(Benzothiazol-6-ylamino)-pyrido[2,3-b]pyrazin-6-yl]-3-ethyl-urea, |
| 241 | 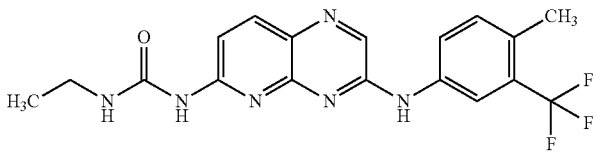 [SMILES: CCNC(=O)Nc1ccc2ncc(Nc3ccc(C)c(C(F)(F)F)c3)nc2n1] | 1-Ethyl-3-[3-(4-methyl-3-trifluoromethyl-phenylamino)-pyrido[2,3-b]pyrazin-6-yl]-urea, |
| 242 | 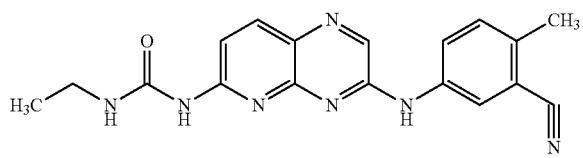 [SMILES: CCNC(=O)Nc1ccc2ncc(Nc3ccc(C)c(C#N)c3)nc2n1] | 1-[3-(3-Cyano-4-methyl-phenylamino)-pyrido[2,3-b]pyrazin-6-yl]-3-ethyl-urea, |
| 243 | 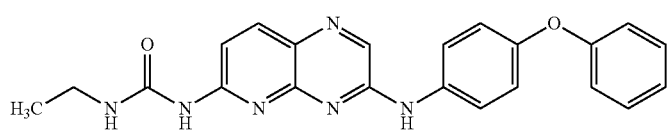 [SMILES: CCNC(=O)Nc1ccc2ncc(Nc3ccc(Oc4ccccc4)cc3)nc2n1] | 1-Ethyl-3-[3-(4-phenoxy-phenylamino)-pyrido[2,3-b]pyrazin-6-yl]-urea, |
| 244 | 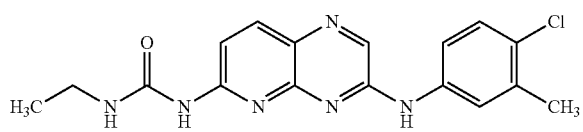 [SMILES: CCNC(=O)Nc1ccc2ncc(Nc3ccc(Cl)c(C)c3)nc2n1] | 1-[3-(4-Chloro-3-methyl-phenylamino)-pyrido[2,3-b]pyrazin-6-yl]-3-ethyl-urea, |
| 245 | 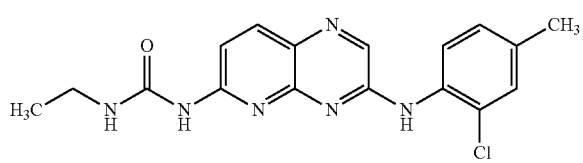 [SMILES: CCNC(=O)Nc1ccc2ncc(Nc3ccc(C)cc3Cl)nc2n1] | 1-[3-(2-Chloro-4-methyl-phenylamino)-pyrido[2,3-b]pyrazin-6-yl]-3-ethyl-urea, |
| 246 | 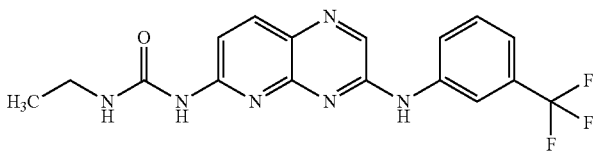 [SMILES: CCNC(=O)Nc1ccc2ncc(Nc3cccc(C(F)(F)F)c3)nc2n1] | 1-Ethyl-3-[3-(3-trifluoromethyl-phenylamino)-pyrido[2,3-b]pyrazin-6-yl]-urea, |

| | | |
|---|---|---|
| 247 | | 1-[3-(2-Chloro-4-trifluoromethoxy-phenylamino)-pyrido[2,3-b]pyrazin-6-yl]-3-ethyl-urea, |
| 248 | | 1-[3-(4-Chloro-2-methoxy-5-methyl-phenylamino)-pyrido[2,3-b]pyrazin-6-yl]-3-ethyl-urea, |
| 252 | | 1-[3-(Benzo[1,3]-dioxol-5-ylamino)-pyrido[2,3-b]pyrazin-6-yl]-3-ethyl-urea, |
| 253 | | 3-[6-(3-Ethyl-ureido)-pyrido[2,3-b]pyrazin-3-ylamino]-benzoic acid, |
| 254 | | 2-Chloro-4-[6-(3-ethyl-ureido)-pyrido[2,3-b]pyrazin-3-ylamino]-benzoic acid, |
| 255 | | 1-Ethyl-3-[3-(3-methoxy-5-trifluoromethyl-phenylamino)-pyrido[2,3-b]pyrazin-6-yl]-urea, |
| 256 | | 1-Ethyl-3-[3-(pyrimidin-2-ylamino)-pyrido[2,3-b]pyrazin-6-yl]-urea, |
| 257 | | 6-[6-(3-Ethyl-ureido)-pyrido[2,3-b]pyrazin-3-ylamino]-naphthalin-2-carbonic acid, |
| 258 | | 1-Ethyl-3-[3-(4-hydroxy-quinolin-2-ylamino)-pyrido[2,3-b]pyrazin-6-yl]-urea, |

| | | |
|---|---|---|
| 259 | 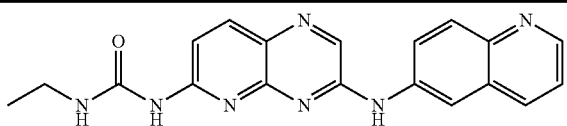 | 1-Ethyl-3-[3-(quinolin-6-ylamino)-pyrido[2,3-b]pyrazin-6-yl]-urea, |
| 260 | 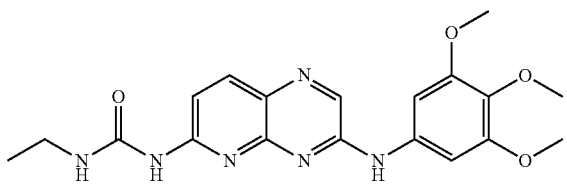 [SMILES: CCNC(=O)Nc1ccc2ncc(Nc3cc(OC)c(OC)c(OC)c3)nc2n1] | 1-Ethyl-3-[3-(3,4,5-trimethoxy-phenylamino)-pyrido[2,3-b]pyrazin-6-yl]-urea, |
| 261 | 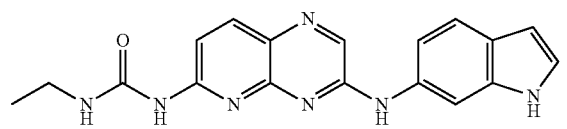 [SMILES: CCNC(=O)Nc1ccc2ncc(Nc3ccc4cc[nH]c4c3)nc2n1] | 1-Ethyl-3-[3-(1H-indol-6-ylamino)-pyrido[2,3-b]pyrazin-6-yl]-urea, |
| 263 | 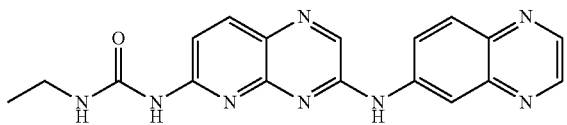 | 1-Ethyl-3-[3-(quinoxalin-6-ylamino)-pyrido[2,3-b]pyrazin-6-yl]-urea, |
| 264 | 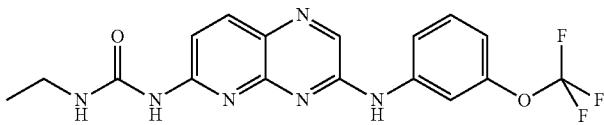 [SMILES: CCNC(=O)Nc1ccc2ncc(Nc3cccc(OC(F)(F)F)c3)nc2n1] | 1-Ethyl-3-[3-(3-trifluoromethoxy-phenylamino)-pyrido[2,3-b]pyrazin-6-yl]-urea, |
| 265 | 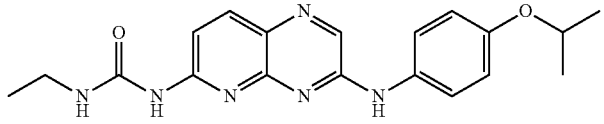 [SMILES: CCNC(=O)Nc1ccc2ncc(Nc3ccc(OC(C)C)cc3)nc2n1] | 1-Ethyl-3-[3-(4-isopropoxy-phenylamino)-pyrido[2,3-b]pyrazin-6-yl]-urea, |
| and | | |
| 266 | 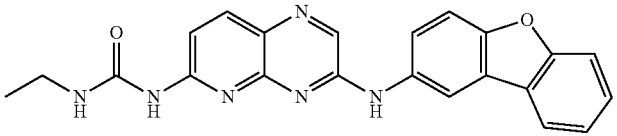 [SMILES: CCNC(=O)Nc1ccc2ncc(Nc3ccc4oc5ccccc5c4c3)nc2n1] | 1-[3-(Dibenzofuran-2-ylamino)-pyrido[2,3-b]pyrazin-6-yl]-3-ethyl-urea. |

6. The method according to claim 1, wherein the mammal is selected from the group consisting of a human, beef cattle, cow, sheep, pig, goat, horse, pony, donkey, hinny, mule, hare, rabbit, cat, dog, guinea pig, hamster, rat, and mouse.

7. The method according to claim 1, wherein said compound is administered as a pharmaceutical composition comprising a pharmacologically active quantity of said compound.

8. The method according to claim 1, wherein said compound is administered in a unit dose of 0.001 mg to 100 mg per kg body weight of a patient.

9. The method according to claim 1, wherein said compound is administered as a composition that contains at least one pharmaceutically compatible excipient and/or adjuvant.

10. The method of claim 1, wherein said mammal is human.

11. A method for reducing growth or proliferation of a mammalian tumor via inhibition of enzymes of the PI3K-Akt signal transduction pathway comprising administering to a mammal at least one compound of formula (I):

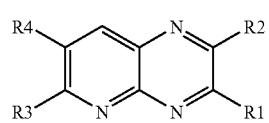

wherein the substituents R1, R2, R3, R4 have the following meanings:

R1 is NR7R8, wherein R7 and R8 independently of each other are hydrogen, alkyl, cycloalkyl, aryl, heteroaryl, alkyl-cycloalkyl, alkyl-heterocyclyl, alkyl-aryl or alkyl-heteroaryl; wherein said alkyl-, cycloalkyl-, aryl- and heteroaryl-, alkyl-cycloalkyl, alkyl-heterocyclyl, alkyl-aryl or alkyl-heteroaryl substituents are independent of each other optionally substituted by F, Cl, Br, I, CN, $CF_3$, $NH_2$, NH-alkyl, NH-aryl, $N(alkyl)_2$, $NO_2$, SH, S-alkyl, OH, $OCF_3$, O-alkyl, O-aryl, $OSO_2H$, $OP(O)(OH)_2$, CHO, $CO_2H$, $SO_3H$ or alkyl, and wherein R7 and R8 do not together form a heterocycle;

R2 is hydrogen,

R3 is —NR9R10, wherein R9 is hydrogen or alkyl and R10 is —C(Y)NR11R12, wherein Y=O or S and R11 and R12 are, independently, (i) hydrogen, (ii) unsubstituted or substituted alkyl, wherein the alkyl group is optionally substituted with one or more substitutents selected from the group consisting of F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, NHSOr aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)cycloalkyl, OC(O)-heterocyclyl, OC(O)-aryl, OC(O)-heteroaryl, OC(O)-alkyl-aryl, OC(O)alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, cycloalkyl, heterocyclyl, aryl and heteroaryl, which may be the same or different from each other;

(iii) unsubstituted or substituted cycloalkyl, wherein the cycloalkyl group is optionally substituted with one or more substituents selected from the group consisting of F, Cl, Br, I, $NH_2$, NH-alkyl, NH-cycloalkyl, NH-heterocyclyl, NH-aryl, NH-heteroaryl, NH-alkyl-aryl, NH-alkyl-heteroaryl, N(alkyl)$_2$, NHC(O)-alkyl, NHC(O)cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, OH, O-alkyl, O-cycloalkyl, O-heterocyclyl, O-aryl, O-heteroaryl, O-alkyl-aryl, O-alkyl-heteroaryl, OC(O)alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, alkyl, and aryl, which may be the same or different from each other;

(iv) unsubstituted or substituted heterocyclyl, wherein the heterocyclyl group is optionally substituted with one or more substituents selected from the group consisting of OH, O-alkyl, O-aryl, $NH_2$, NH-alkyl, NH-aryl, alkyl, alkyl-aryl and aryl, which may be the same or different from each other;

(v) unsubstituted or substituted aryl, wherein the aryl group is optionally substituted with one or more substituents selected from the group consisting of F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl $NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O(CH$_2$)$_n$—O, OC(O)-alkyl, OC(O)-cycloalkyl, OC(O)-heterocyclyl, OC(O)-aryl, OC(O)heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, aryl and heteroaryl, which may be the same or different from each other, and n can have the value 1, 2 or 3;

(vi) unsubstituted or substituted heteroaryl, wherein the heteroaryl group is optionally substituted with one or more substituents selected from the group consisting of F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkly-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-aryl, S-heteroaryl, OH, $OCF_3$, O-alkyl, O-cycloalkyl, O-aryl, O-heteroaryl, O-alkyl-cycloalkyl, O-alkyl-heterocyclyl, O-alkylaryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, aryl and heteroaryl, which may be the same or different from each other;

(vii) —C(O)—R17, wherein R17 is alkyl, aryl or heteroaryl, and the alkyl and aryl substituents are optionally substituted by F, Cl, Br, I, CN, $CF_3$, $NH_2$, NH-alkyl, NH-aryl, N(alkyl)$_2$, $NO_2$, SH, S-alkyl, OH, $OCF_3$, O-alkyl, O-aryl, $OSO_2H$, OP(O)(OH)$_2$, CHO, $CO_2H$, $SO_3H$ or alkyl;

(viii) or R11 and R12 together form heterocyclyl, and R4 is hydrogen;

wherein said compound inhibits PI3K alpha, PI3K beta, PI3K gamma, and PI3K delta in the PI3K-Akt signal transduction pathway; and wherein said malignant tumor is selected from the group consisting of a colon tumor, a gastric tumor, an intestinal tumor, a pulmonary tumor, a pancreatic tumor, an ovarian tumor, a prostatic tumor, melanoma, a hepatic tumor, a renal tumor, a head tumor, glioma, a breast tumor, cervico-uterine carcinoma, adeno-acanthoma, an endometrial cancer, a colorectal tumor, esophageal cancer, thyroid cancer, lymphoma, and leukemia.

12. The method of claim 11, wherein said compound is Compound 150:

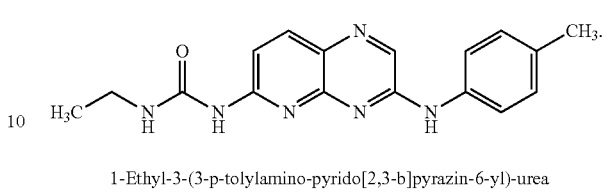

1-Ethyl-3-(3-p-tolylamino-pyrido[2,3-b]pyrazin-6-yl)-urea

13. The method of claim 11, wherein the administration of said compound increases apoptosis of said mammalian tumor.

14. The method according to claim 11, wherein R7, R8, R9, R11, or R12 is an alkyl group that is selected from the group consisting of methyl, ethyl, n-propyl, 2-propyl, n-butyl, sec-butyl, tert-butyl, n-pentyl, iso-pentyl, neo-pentyl, n-hexyl, 2-hexyl, n-octyl, ethylenyl (vinyl), ethynyl, propenyl, propynyl, butenyl, butynyl, pentenyl, pentynyl, hexenyl, hexynyl, heptenyl, heptynyl, octenyl and octynyl.

15. The method according to claim 11, wherein R7, R8, R11, or R12 is a heteroaryl group that is selected from the group consisting of pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, quinolinyl, isoquinolinyl, quinoxalinyl, quinazolinyl, carbazolyl, phenazinyl, phenothiazinyl and acridinyl.

16. The method according to claim 11, wherein R11 or R12 is a heterocyclyl group or R11 and R12 together form heterocyclyl that is selected from the group consisting of tetrahydrofuryl, tetrahydropyranyl, pyrrolidinyl, piperidinyl, piperazinyl and morpholinyl.

17. The method according to claim 11, wherein said compound is selected from the group consisting of:

62 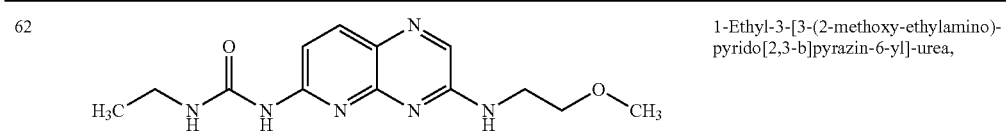 1-Ethyl-3-[3-(2-methoxy-ethylamino)-pyrido[2,3-b]pyrazin-6-yl]-urea, 65 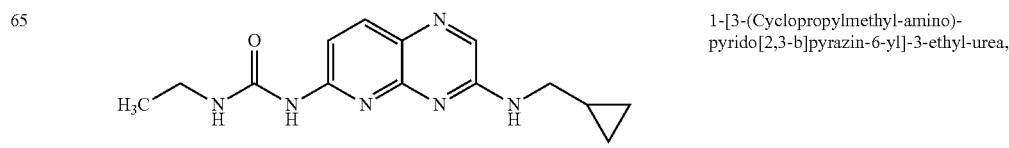 1-[3-(Cyclopropylmethyl-amino)-pyrido[2,3-b]pyrazin-6-yl]-3-ethyl-urea, 66 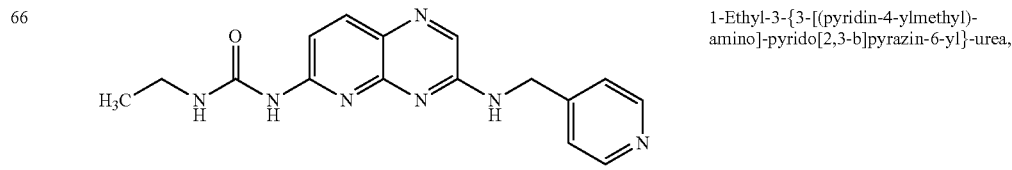 1-Ethyl-3-{3-[(pyridin-4-ylmethyl)-amino]-pyrido[2,3-b]pyrazin-6-yl}-urea, 83 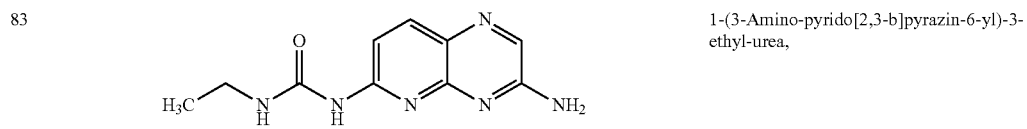 1-(3-Amino-pyrido[2,3-b]pyrazin-6-yl)-3-ethyl-urea, -continued

| | | |
|---|---|---|
| 150 | | 1-Ethyl-3-(3-p-tolylamino-pyrido[2,3-b]pyrazin-6-yl)-urea, |
| 157 | | 1-Ethyl-3-(3-m-tolylamino-pyrido-[2,3-b]pyrazin-6-yl)-urea, |
| 158 | | 1-Ethyl-3-[3-(4-methoxy-phenylamino)-pyrido[2,3-b]pyrazin-6-yl]-urea, |
| 159 | | 1-[3-(4-Chloro-phenylamino)-pyrido-[2,3-b]pyrazin-6-yl]-3-ethyl-urea, |
| 160 | | 1-Ethyl-3-(3-o-tolylamino-pyrido[2,3-b]-pyrazin-6-yl)-urea, |
| 161 | | 1-Ethyl-3-[3-(pyridin-3-ylamino)-pyrido-[2,3-b]pyrazin-6-yl]-urea, |
| 162 | | 1-Ethyl-3-[3-(4-ethyl-phenylamino)-pyrido[2,3-b]pyrazin-6-yl]-urea, |
| 163 | | 1-Ethyl-3-[3-(3-methoxy-4-methyl-phenylamino)-pyrido[2,3-b]pyrazin-6-yl]-urea, |
| 164 | | 1-Ethyl-3-[3-(4-hydroxy-phenylamino)-pyrido[2,3-b]pyrazin-6-yl]-urea, |
| 165 | | 1-Ethyl-3-[3-(5-methyl-pyridin-2-yl-amino)-pyrido[2,3-b]pyrazin-6-yl]-urea, |
| 166 | | 1-Ethyl-3-[3-(1-methyl-1H-pyrazol-3-ylamino)-pyrido[2,3-b]pyrazin-6-yl]-urea, |

| # | | Name |
|---|---|---|
| 167 | | 1-Ethyl-3-[3-(4-fluoro-phenylamino)-pyrido[2,3-b]pyrazin-6-yl]-urea, |
| 177 | | 1-[3-(3-Chloro-4-methoxy-phenylamino)-pyrido[2,3-b]pyrazin-6-yl]-3-ethyl-urea, |
| 178 | | 1-Ethyl-3-[3-(naphthalin-2-ylamino)-pyrido[2,3-b]pyrazin-6-yl]-urea, |
| 179 | | 1-Ethyl-3-[3-(quinolin-3-ylamino)-pyrido[2,3-b]pyrazin-6-yl]-urea, |
| 180 | | 1-[3-(3,5-Dimethoxy-phenylamino)-pyrido[2,3-b]pyrazin-6-yl]-3-ethyl-urea, |
| 181 | | 1-Ethyl-3-[3-(pyrazin-2-ylamino)-pyrido[2,3-b]pyrazin-6-yl]-urea, |
| 182 | | 1-Ethyl-3-[3-(3-isopropoxy-phenylamino)-pyrido[2,3-b]pyrazin-6-yl]-urea, |
| 184 | | 1-[3-(2-Chloro-pyridin-4-ylamino)-pyrido[2,3-b]pyrazin-6-yl]-3-ethyl-urea, |
| 185 | | 1-[3-(3,5-Dichloro-4-hydroxy-phenylamino)-pyrido[2,3-b]pyrazin-6-yl]-3-ethyl-urea, |
| 187 | | 1-[3-(3,4-Dimethoxy-phenylamino)-pyrido[2,3-b]pyrazin-6-yl]-3-ethyl-urea, |

-continued

| | | |
|---|---|---|
| 188 | 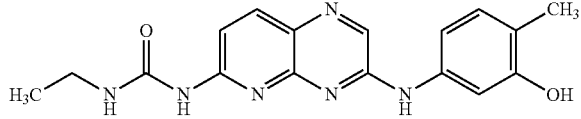 | 1-Ethyl-3-[3-(3-hydroxy-4-methyl-phenylamino)-pyrido[2,3-b]pyrazin-6-yl]-urea, |
| 189 | 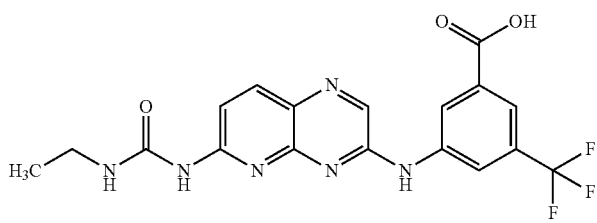 | 3-[6-(3-Ethyl-ureido)-pyrido[2,3-b]-pyrazin-3-ylamino]-5-trifluoromethyl-benzoic acid, |
| 190 | 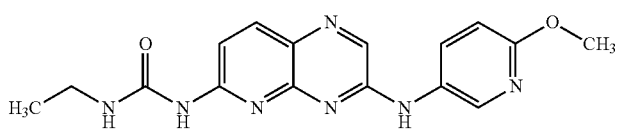 [SMILES: CCNC(=O)Nc1ccc2ncc(Nc3ccc(CC)cc3)nc2n1] | 1-Ethyl-3-[3-(6-methoxy-pyridin-3-ylamino)-pyrido[2,3-b]pyrazin-6-yl]-urea, |
| 191 | 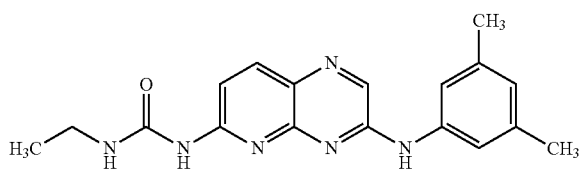 [SMILES: CCNC(=O)Nc1ccc2ncc(Nc3cc(C)cc(C)c3)nc2n1] | 1-[3-(3,5-Dimethyl-phenylamino)-pyrido[2,3-b]pyrazin-6-yl]-3-ethyl-urea, |
| 192 | 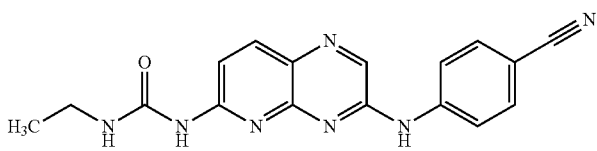 [SMILES: CCNC(=O)Nc1ccc2ncc(Nc3ccc(C#N)cc3)nc2n1] | 1-[3-(4-Cyano-phenylamino)-pyrido-[2,3-b]pyrazin-6-yl]-3-ethyl-urea, |
| 197 | 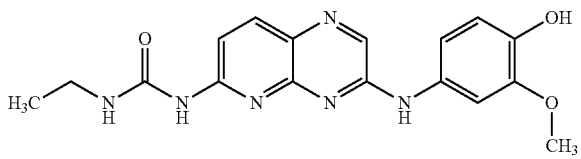 [SMILES: CCNC(=O)Nc1ccc2ncc(Nc3ccc(O)c(OC)c3)nc2n1] | 1-Ethyl-3-[3-(4-hydroxy-3-methoxy-phenylamino)-pyrido[2,3-b]pyrazin-6-yl]-urea, |
| 211 | 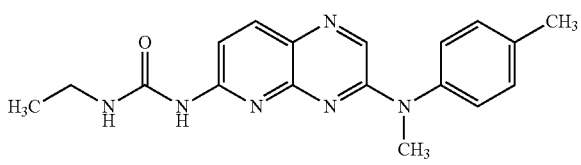 [SMILES: CCNC(=O)Nc1ccc2ncc(N(C)c3ccc(C)cc3)nc2n1] | 1-Ethyl-3-[3-(methyl-p-tolyl-amino)-pyrido[2,3-b]pyrazin-6-yl]-urea, |
| 212 | 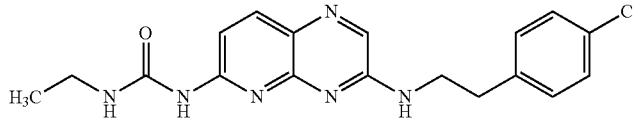 | 1-Ethyl-3-[3-(2-p-tolyl-ethylamino)-pyrido[2,3-b]pyrazin-6-yl]-urea, |
| 213 | 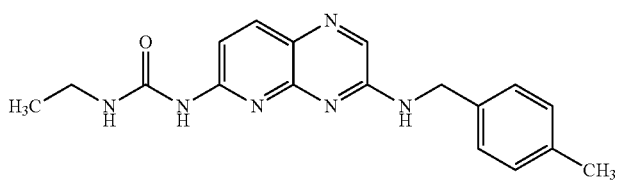 [SMILES: CCNC(=O)Nc1ccc2ncc(NCc3ccc(C)cc3)nc2n1] | 1-Ethyl-3-[3-(4-methyl-benzylamino)-pyrido[2,3-b]pyrazin-6-yl]-urea, |
| 214 | 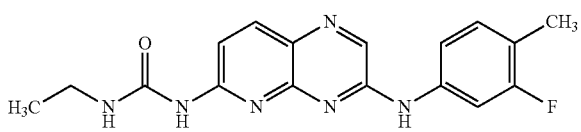 [SMILES: CCNC(=O)Nc1ccc2ncc(Nc3ccc(C)c(F)c3)nc2n1] | 1-Ethyl-3-[3-(3-fluoro-4-methyl-phenyl-amino)-pyrido[2,3-b]pyrazin-6-yl]-urea, |

| | | |
|---|---|---|
| 215 | 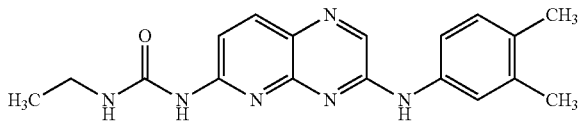 [SMILES: CCNC(=O)Nc1ccc2ncc(Nc3ccc(C)c(C)c3)nc2n1] | 1-[3-(3,4-Dimethyl-phenylamino)-pyrido[2,3-b]pyrazin-6-yl]-3-ethyl-urea, |
| 216 | 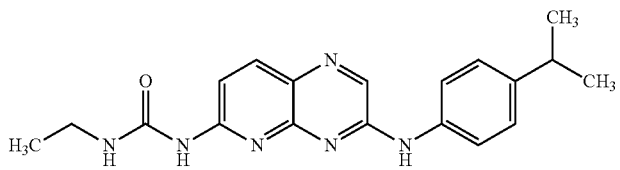 [SMILES: CCNC(=O)Nc1ccc2ncc(Nc3ccc(C(C)C)cc3)nc2n1] | 1-Ethyl-3-[3-(4-isopropyl-phenylamino)-pyrido[2,3-b]pyrazin-6-yl]-urea, |
| 240 | 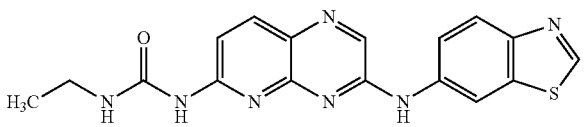 [SMILES: CCNC(=O)Nc1ccc2ncc(Nc3ccc4ncsc4c3)nc2n1] | 1-[3-(Benzothiazol-6-ylamino)-pyrido[2,3-b]pyrazin-6-yl]-3-ethyl-urea, |
| 241 | 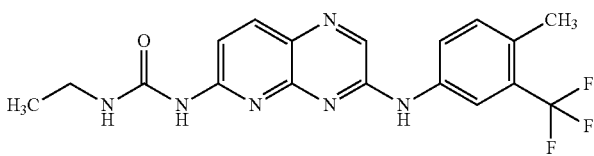 [SMILES: CCNC(=O)Nc1ccc2ncc(Nc3ccc(C)c(C(F)(F)F)c3)nc2n1] | 1-Ethyl-3-[3-(4-methyl-3-trifluoromethyl-phenylamino)-pyrido[2,3-b]pyrazin-6-yl]-urea, |
| 242 | 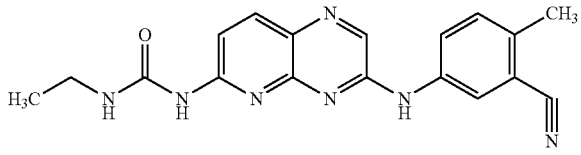 [SMILES: CCNC(=O)Nc1ccc2ncc(Nc3ccc(C)c(C#N)c3)nc2n1] | 1-[3-(3-Cyano-4-methyl-phenylamino)-pyrido[2,3-b]pyrazin-6-yl]-3-ethyl-urea, |
| 243 | 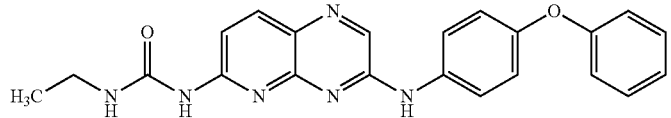 [SMILES: CCNC(=O)Nc1ccc2ncc(Nc3ccc(Oc4ccccc4)cc3)nc2n1] | 1-Ethyl-3-[3-(4-phenoxy-phenylamino)-pyrido[2,3-b]pyrazin-6-yl]-urea, |
| 244 | 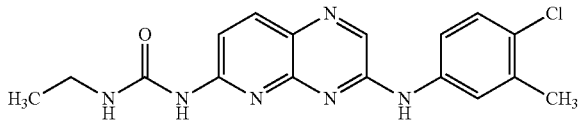 [SMILES: CCNC(=O)Nc1ccc2ncc(Nc3ccc(Cl)c(C)c3)nc2n1] | 1-[3-(4-Chloro-3-methyl-phenylamino)-pyrido[2,3-b]pyrazin-6-yl]-3-ethyl-urea, |
| 245 | 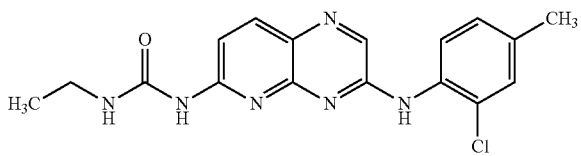 [SMILES: CCNC(=O)Nc1ccc2ncc(Nc3ccc(C)cc3Cl)nc2n1] | 1-[3-(2-Chloro-4-methyl-phenylamino)-pyrido[2,3-b]pyrazin-6-yl]-3-ethyl-urea, |
| 246 | 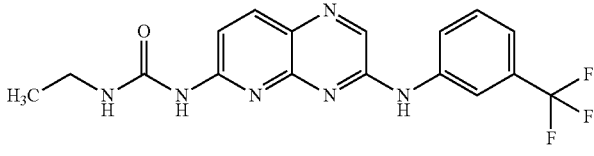 [SMILES: CCNC(=O)Nc1ccc2ncc(Nc3cccc(C(F)(F)F)c3)nc2n1] | 1-Ethyl-3-[3-(3-trifluoromethyl-phenylamino)-pyrido[2,3-b]pyrazin-6-yl]-urea, |
| 247 | 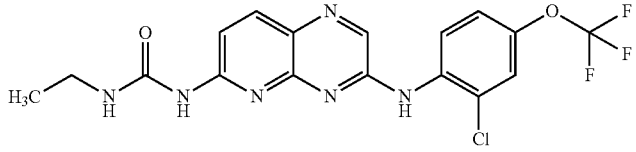 [SMILES: CCNC(=O)Nc1ccc2ncc(Nc3ccc(OC(F)(F)F)cc3Cl)nc2n1] | 1-[3-(2-Chloro-4-trifluoromethoxy-phenylamino)-pyrido[2,3-b]pyrazin-6-yl]-3-ethyl-urea, |

| | | |
|---|---|---|
| 248 | 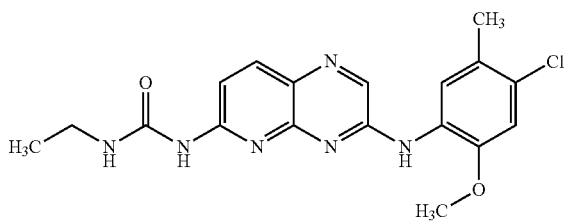 [SMILES: CCNC(=O)Nc1ccc2ncc(Nc3cc(C)c(Cl)cc3OC)nc2n1] | 1-[3-(4-Chloro-2-methoxy-5-methyl-phenylamino)-pyrido[2,3-b]pyrazin-6-yl]-3-ethyl-urea, |
| 252 | 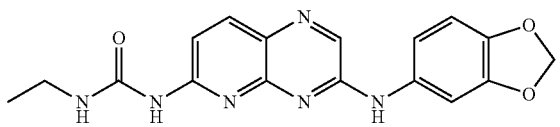 [SMILES: CCNC(=O)Nc1ccc2ncc(Nc3ccc4c(c3)OCO4)nc2n1] | 1-[3-(Benzo[1,3]-dioxol-5-ylamino)-pyrido[2,3-b]pyrazin-6-yl]-3-ethyl-urea, |
| 253 | 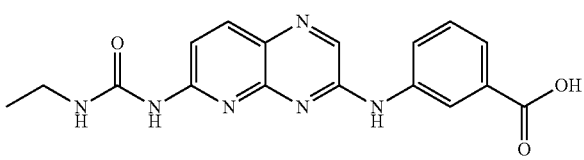 [SMILES: CCNC(=O)Nc1ccc2ncc(Nc3cccc(C(=O)O)c3)nc2n1] | 3-[6-(3-Ethyl-ureido)-pyrido[2,3-b]pyrazin-3-ylamino]-benzoic acid, |
| 254 | 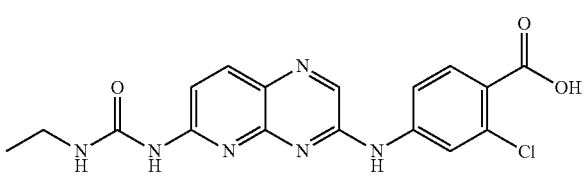 [SMILES: CCNC(=O)Nc1ccc2ncc(Nc3ccc(C(=O)O)c(Cl)c3)nc2n1] | 2-Chloro-4-[6-(3-ethyl-ureido)-pyrido[2,3-b]pyrazin-3-ylamino]-benzoic acid, |
| 255 | 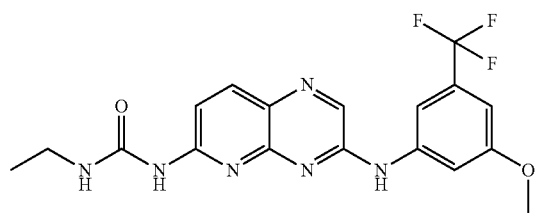 [SMILES: CCNC(=O)Nc1ccc2ncc(Nc3cc(OC)cc(C(F)(F)F)c3)nc2n1] | 1-Ethyl-3-[3-(3-methoxy-5-trifluoromethyl-phenylamino)-pyrido[2,3-b]pyrazin-6-yl]-urea, |
| 256 | 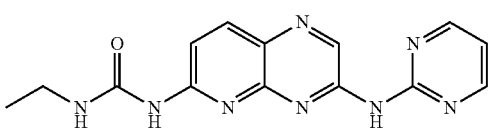 [SMILES: CCNC(=O)Nc1ccc2ncc(Nc3ncccn3)nc2n1] | 1-Ethyl-3-[3-(pyrimidin-2-ylamino)-pyrido[2,3-b]pyrazin-6-yl]-urea, |
| 257 | 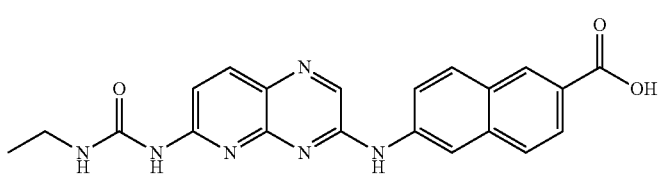 [SMILES: CCNC(=O)Nc1ccc2ncc(Nc3ccc4cc(C(=O)O)ccc4c3)nc2n1] | 6-[6-(3-Ethyl-ureido)-pyrido[2,3-b]pyrazin-3-ylamino]-naphthalin-2-carbonic acid, |
| 258 | 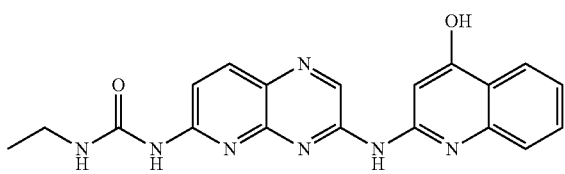 [SMILES: CCNC(=O)Nc1ccc2ncc(Nc3cc(O)c4ccccc4n3)nc2n1] | 1-Ethyl-3-[3-(4-hydroxy-quinolin-2-ylamino)-pyrido[2,3-b]pyrazin-6-yl]-urea, |
| 259 | 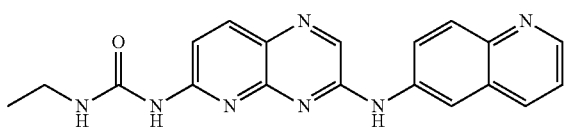 [SMILES: CCNC(=O)Nc1ccc2ncc(Nc3ccc4ncccc4c3)nc2n1] | 1-Ethyl-3-[3-(quinolin-6-ylamino)-pyrido[2,3-b]pyrazin-6-yl]-urea, |

-continued

| | | |
|---|---|---|
| 260 | 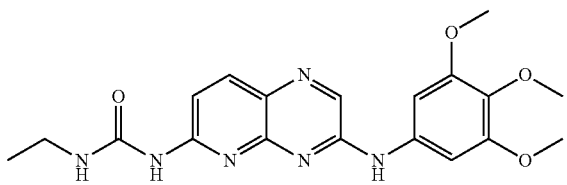 [SMILES: CCNC(=O)Nc1ccc2ncc(Nc3cc(OC)c(OC)c(OC)c3)nc2n1] | 1-Ethyl-3-[3-(3,4,5-trimethoxy-phenylamino)-pyrido[2,3-b]pyrazin-6-yl]-urea, |
| 261 | 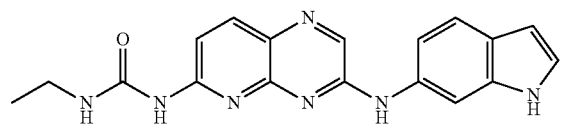 [SMILES: CCNC(=O)Nc1ccc2ncc(Nc3ccc4cc[nH]c4c3)nc2n1] | 1-Ethyl-3-[3-(1H-indol-6-ylamino)-pyrido[2,3-b]pyrazin-6-yl]-urea, |
| 263 | 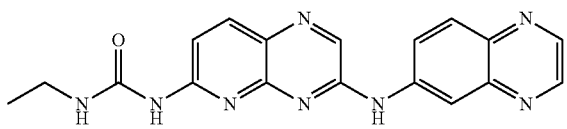 | 1-Ethyl-3-[3-(quinoxalin-6-ylamino)-pyrido[2,3-b]pyrazin-6-yl]-urea, |
| 264 | 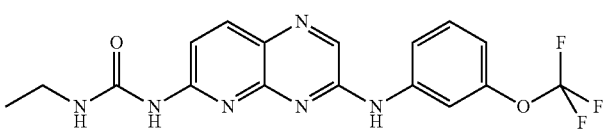 [SMILES: CCNC(=O)Nc1ccc2ncc(Nc3cccc(OC(F)(F)F)c3)nc2n1] | 1-Ethyl-3-[3-(3-trifluoromethoxy-phenylamino)-pyrido[2,3-b]pyrazin-6-yl]-urea, |
| 265 | 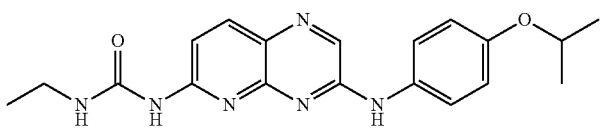 [SMILES: CCNC(=O)Nc1ccc2ncc(Nc3ccc(OC(C)C)cc3)nc2n1] | 1-Ethyl-3-[3-(4-isopropoxy-phenylamino)-pyrido[2,3-b]pyrazin-6-yl]-urea, | and

| | | |
|---|---|---|
| 266 | 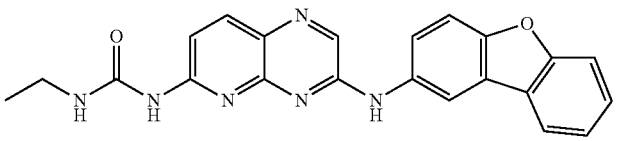 [SMILES: CCNC(=O)Nc1ccc2ncc(Nc3ccc4oc5ccccc5c4c3)nc2n1] | 1-[3-(Dibenzofuran-2-ylamino)-pyrido[2,3-b]pyrazin-6-yl]-3-ethyl-urea. |

18. The method according to claim 11, wherein the mammal is selected from the group consisting of a human, beef cattle, cow, sheep, pig, goat, horse, pony, donkey, hinny, mule, hare, rabbit, cat, dog, guinea pig, hamster, rat, and mouse.

19. The method according to claim 11, wherein said compound is administered as a pharmaceutical composition comprising a pharmacologically active quantity of said compound.

20. The method according to claim 11, wherein said compound is administered in a unit dose of 0.001 mg to 100 mg per kg body weight of a patient.

21. The method according to claim 11, wherein said compound is administered as a composition that contains at least one pharmaceutically compatible excipient and/or adjuvant.

22. The method of claim 11, wherein said mammal is human.

* * * * *